(12) United States Patent
Grossi et al.

(10) Patent No.: US 11,040,107 B2
(45) Date of Patent: Jun. 22, 2021

(54) DOSING REGIMENS AND RELATED COMPOSITIONS AND METHODS

(71) Applicant: Apellis Pharmaceuticals, Inc., Crestwood, KY (US)

(72) Inventors: Federico Grossi, Newton, MA (US); Pascal Deschatelets, Lexington, MA (US); Cedric Francois, Prospect, KY (US); Patrick Johnson, Zurich (CH); Carolina Vega, Berkeley, CA (US)

(73) Assignee: Apellis Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 16/500,994

(22) PCT Filed: Apr. 9, 2018

(86) PCT No.: PCT/US2018/026753
§ 371 (c)(1),
(2) Date: Oct. 4, 2019

(87) PCT Pub. No.: WO2018/187813
PCT Pub. Date: Oct. 11, 2018

(65) Prior Publication Data
US 2020/0038516 A1 Feb. 6, 2020

Related U.S. Application Data

(60) Provisional application No. 62/485,343, filed on Apr. 13, 2017, provisional application No. 62/483,295, filed on Apr. 7, 2017.

(51) Int. Cl.
| | | |
|---|---|---|
| *A61K 47/60* | (2017.01) | |
| *A61K 47/64* | (2017.01) | |
| *A61K 47/69* | (2017.01) | |
| *A61P 7/00* | (2006.01) | |
| *A61P 37/06* | (2006.01) | |
| *A01N 1/02* | (2006.01) | |
| *A61K 9/00* | (2006.01) | |
| *A61M 5/142* | (2006.01) | |
| *A61M 5/145* | (2006.01) | |
| *A61M 5/152* | (2006.01) | |
| *C07K 7/08* | (2006.01) | |
| *A61K 38/00* | (2006.01) | |

(52) U.S. Cl.
CPC ............ *A61K 47/60* (2017.08); *A01N 1/0226* (2013.01); *A61K 9/0019* (2013.01); *A61K 47/643* (2017.08); *A61K 47/6901* (2017.08); *A61M 5/1452* (2013.01); *A61M 5/14248* (2013.01); *A61M 5/152* (2013.01); *A61P 7/00* (2018.01); *A61P 37/06* (2018.01); *C07K 7/08* (2013.01); *A61K 38/00* (2013.01)

(58) Field of Classification Search
CPC ........ C07K 7/08; A61K 38/00; A61K 9/0019; A61K 47/60; A61K 47/643; A61K 47/6901; A61K 9/0021; A61K 9/0048; A61P 27/02; A61P 37/06; A61P 7/06; A61P 9/10; A61P 7/00; A01N 1/0226; A61M 5/14248; A61M 5/1452; A61M 5/152
See application file for complete search history.

(56) References Cited

U.S. PATENT DOCUMENTS

| | | |
|---|---|---|
| 4,299,838 A | 11/1981 | Durlach |
| 4,576,750 A | 3/1986 | Pitzenberger |
| 4,816,567 A | 3/1989 | Cabilly et al. |
| 4,870,097 A | 9/1989 | Makovec et al. |
| 5,157,110 A | 10/1992 | Kotwal et al. |
| 5,482,135 A | 1/1996 | Phillips et al. |
| 5,492,135 A | 2/1996 | Hubbell |
| 5,632,984 A | 5/1997 | Wong et al. |
| 5,770,589 A | 6/1998 | Billson et al. |
| 5,776,970 A | 7/1998 | Shechter et al. |
| 5,797,898 A | 8/1998 | Santini, Jr. et al. |
| 5,824,072 A | 10/1998 | Wong |
| 5,844,099 A | 12/1998 | Stahl et al. |

(Continued)

FOREIGN PATENT DOCUMENTS

| | | |
|---|---|---|
| BR | 112013028816 A2 | 11/2016 |
| EP | 0422681 A1 | 4/1991 |

(Continued)

OTHER PUBLICATIONS

Mastellos et al. Compstatin: a C3-targeted complement inhibitor reaching its prime for bedside intervention. Eur J Clin Invest. Apr. 2015 ; vol. 45, No. 4, pp. 423-440. (Year: 2015).*

(Continued)

*Primary Examiner* — Marcela M Cordero Garcia
(74) *Attorney, Agent, or Firm* — Choate, Hall & Stewart LLP; Brenda Herschbach Jarrell; Rolando Medina

(57) ABSTRACT

In some aspects, the present invention provides cell-reactive compstatin analogs and compositions comprising cell-reactive compstatin analogs. In some aspects, the invention further provides methods of using cell-reactive compstatin analogs, e.g., treat a complement-mediated disorder, e.g., to inhibit complement-mediated damage to a cell, tissue, or organ. In some aspects, the invention provides long-acting compstatin analogs and compositions comprising long-acting compstatin analogs. In some aspects, the invention further provides methods of using long-acting compstatin analogs, e.g., to treat a complement-mediated disorder, e.g., to inhibit complement-mediated damage to a cell, tissue, or organ. In some aspects, the invention provides targeted compstatin analogs and compositions comprising targeted compstatin analogs. In some aspects, the invention further provides methods of using targeted compstatin analogs, e.g., to treat a complement-mediated disorder, e.g., to inhibit complement-mediated damage to a cell, tissue, or organ.

24 Claims, 29 Drawing Sheets
Specification includes a Sequence Listing.

(56) References Cited

U.S. PATENT DOCUMENTS

| | | |
|---|---|---|
| 5,861,486 A | 1/1999 | Devore et al. |
| 5,869,079 A | 2/1999 | Wong et al. |
| 5,942,405 A | 8/1999 | Ames et al. |
| 6,051,698 A | 4/2000 | Janjic et al. |
| 6,129,761 A | 10/2000 | Hubbell |
| 6,140,472 A | 10/2000 | Rosengard et al. |
| 6,169,057 B1 | 1/2001 | Lovatt |
| 6,197,934 B1 | 3/2001 | DeVore et al. |
| 6,204,365 B1 | 3/2001 | Devore et al. |
| 6,214,790 B1 | 4/2001 | Richelson et al. |
| 6,319,897 B1 | 11/2001 | Lambris et al. |
| 6,331,313 B1 | 12/2001 | Wong et al. |
| 6,378,526 B1 | 4/2002 | Bowman et al. |
| 6,436,427 B1 | 8/2002 | Hammang et al. |
| 6,534,058 B2 | 3/2003 | Fung et al. |
| 6,551,595 B1 | 4/2003 | Rosengard et al. |
| 6,582,959 B2 | 6/2003 | Kim |
| 6,692,759 B1 | 2/2004 | Wong et al. |
| 6,818,447 B1 | 11/2004 | Pavco et al. |
| 6,821,950 B1 | 11/2004 | Fairlie et al. |
| 6,897,290 B1 | 5/2005 | Atkinson et al. |
| 6,976,982 B2 | 12/2005 | Santini, Jr. et al. |
| 7,084,106 B1 | 8/2006 | Kotwal et al. |
| 7,108,982 B1 | 9/2006 | Hageman |
| 7,112,327 B2 | 9/2006 | Fung et al. |
| 7,745,389 B2 | 6/2010 | Hageman |
| 7,888,323 B2 | 2/2011 | Lambris et al. |
| 7,947,267 B2 | 5/2011 | Francois et al. |
| 7,989,589 B2 | 8/2011 | Lambris |
| 8,043,609 B2 | 10/2011 | Deschatelets et al. |
| 8,168,584 B2 | 5/2012 | Deschatelets et al. |
| 8,521,273 B2 | 8/2013 | Kliman |
| 8,580,735 B2 | 11/2013 | Francois et al. |
| 8,753,625 B2 | 6/2014 | Fung et al. |
| 8,840,893 B2 | 9/2014 | Schwaeble et al. |
| 8,871,230 B2 | 10/2014 | Rudolph et al. |
| 9,056,076 B2 | 6/2015 | Deschatelets et al. |
| 9,107,861 B1* | 8/2015 | Andrien, Jr. ............... A61P 3/10 |
| 9,421,240 B2 | 8/2016 | Francois et al. |
| 9,512,180 B2 | 12/2016 | Morikis et al. |
| 10,035,822 B2* | 7/2018 | Francois ............... A61K 47/542 |
| 10,125,171 B2 | 11/2018 | Francois et al. |
| 10,308,687 B2 | 6/2019 | Francois et al. |
| 10,407,466 B2 | 9/2019 | Deschatelets et al. |
| 10,875,893 B2* | 12/2020 | Francois ............... A61K 47/60 |
| 2002/0086356 A1 | 7/2002 | Tuschl et al. |
| 2002/0102581 A1 | 8/2002 | Hageman et al. |
| 2002/0164667 A1 | 11/2002 | Alitalo et al. |
| 2003/0017501 A1 | 1/2003 | Hageman et al. |
| 2003/0171320 A1 | 9/2003 | Guyer |
| 2003/0175950 A1 | 9/2003 | McSwiggen |
| 2003/0191084 A1 | 10/2003 | Biesecker et al. |
| 2003/0207309 A1 | 11/2003 | Hageman et al. |
| 2004/0018176 A1 | 1/2004 | Tolentino et al. |
| 2004/0038869 A1 | 2/2004 | Finney et al. |
| 2004/0092470 A1 | 5/2004 | Leonard et al. |
| 2004/0115774 A1 | 6/2004 | Kochendoerfer et al. |
| 2004/0177387 A1 | 9/2004 | Jayakrishna |
| 2004/0210041 A1 | 10/2004 | Arbogast et al. |
| 2004/0229266 A1 | 11/2004 | Tuschl et al. |
| 2005/0020525 A1 | 1/2005 | McSwiggen et al. |
| 2005/0032733 A1 | 2/2005 | McSwiggen et al. |
| 2005/0048099 A1 | 3/2005 | Shiah et al. |
| 2005/0054596 A1 | 3/2005 | McSwiggen et al. |
| 2005/0090448 A1 | 4/2005 | Johnson et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0260198 A1 | 11/2005 | Holers et al. |
| 2005/0281861 A1 | 12/2005 | Hughes et al. |
| 2005/0287601 A1 | 12/2005 | Hageman et al. |
| 2006/0002852 A1 | 1/2006 | Saltzman et al. |
| 2006/0002971 A1 | 1/2006 | Saltzman et al. |
| 2006/0105980 A1 | 5/2006 | Benedict et al. |
| 2006/0115476 A1 | 6/2006 | Tedesco et al. |
| 2006/0140939 A1 | 6/2006 | Fung |
| 2006/0142191 A1 | 6/2006 | Francois et al. |
| 2006/0257359 A1 | 11/2006 | Francois et al. |
| 2006/0263819 A1 | 11/2006 | Hageman et al. |
| 2007/0020647 A1 | 1/2007 | Hageman et al. |
| 2007/0065433 A1 | 3/2007 | Mollnes et al. |
| 2007/0134244 A1 | 6/2007 | Slakter et al. |
| 2007/0149616 A1 | 6/2007 | Clark et al. |
| 2007/0196367 A1 | 8/2007 | Dinu |
| 2007/0238654 A1 | 10/2007 | Deschatelets et al. |
| 2008/0075755 A1 | 3/2008 | Deschatelets et al. |
| 2008/0227717 A1 | 9/2008 | Lambris et al. |
| 2009/0196903 A1 | 8/2009 | Kliman |
| 2009/0214538 A1 | 8/2009 | Fung et al. |
| 2009/0220572 A1 | 9/2009 | Deschatelets et al. |
| 2010/0015136 A1 | 1/2010 | Michel et al. |
| 2010/0166862 A1 | 7/2010 | Francois et al. |
| 2010/0222550 A1 | 9/2010 | Lambris |
| 2010/0239659 A1 | 9/2010 | Diwan et al. |
| 2011/0092446 A1 | 4/2011 | Francois et al. |
| 2011/0182877 A1 | 7/2011 | Francois et al. |
| 2011/0311549 A1 | 12/2011 | Schwaeble et al. |
| 2013/0072442 A1 | 3/2013 | Deschatelets et al. |
| 2013/0296254 A1 | 11/2013 | Deschatelets et al. |
| 2013/0324482 A1 | 12/2013 | Francois et al. |
| 2014/0050739 A1 | 2/2014 | Francois et al. |
| 2014/0113874 A1 | 4/2014 | Lambris et al. |
| 2014/0323407 A1 | 10/2014 | Francois et al. |
| 2014/0371133 A1 | 12/2014 | Francois et al. |
| 2015/0064176 A1 | 3/2015 | Schwaeble et al. |
| 2015/0158915 A1 | 6/2015 | Lambris et al. |
| 2016/0015810 A1 | 1/2016 | Deschatelets et al. |
| 2016/0060297 A1 | 3/2016 | Deschatelets et al. |
| 2016/0067357 A1 | 3/2016 | Francois et al. |
| 2016/0166862 A1 | 6/2016 | Qui et al. |
| 2016/0194359 A1* | 7/2016 | Francois ............... A61K 47/60 424/278.1 |
| 2016/0215020 A1 | 7/2016 | Francois et al. |
| 2016/0215022 A1 | 7/2016 | Francois et al. |
| 2017/0283461 A1* | 10/2017 | Francois ............... A61K 38/10 |
| 2017/0349631 A1 | 12/2017 | Deschatelets et al. |
| 2019/0194254 A1* | 6/2019 | Francois ............... C07K 14/472 |
| 2019/0241617 A1 | 8/2019 | Francois et al. |
| 2019/0248839 A1 | 8/2019 | Francois et al. |
| 2019/0381129 A1* | 12/2019 | Grossi ............... A61P 7/00 |
| 2020/0282012 A1* | 9/2020 | Francois ............... A61K 31/713 |
| 2020/0316163 A1* | 10/2020 | Grossi ............... A61K 38/12 |
| 2020/0325175 A1* | 10/2020 | Francois ............... A61K 47/60 |

FOREIGN PATENT DOCUMENTS

| | | |
|---|---|---|
| EP | 0737484 A2 | 10/1996 |
| EP | 2278987 A2 | 2/2011 |
| EP | 2311479 A1 | 4/2011 |
| EP | 1993673 B1 | 6/2017 |
| JP | 11-197234 A | 7/1999 |
| JP | 2003-535581 A | 12/2003 |
| JP | 2004-065461 A | 3/2004 |
| JP | 2006-505254 A | 2/2006 |
| JP | 2009-511496 A | 3/2009 |
| JP | 2009-517476 A | 4/2009 |
| JP | 2010-280688 A | 12/2010 |
| JP | 2012-525443 A | 10/2012 |
| RU | 2474586 C2 | 2/2013 |
| RU | 2505311 C2 | 1/2014 |
| WO | WO-96/030046 A1 | 10/1996 |
| WO | WO-97/33603 A1 | 9/1997 |
| WO | WO-99/013899 A1 | 3/1999 |
| WO | WO-00/47130 A1 | 8/2000 |
| WO | WO-00/71147 A1 | 11/2000 |
| WO | WO-01/84149 A2 | 11/2001 |
| WO | WO-2002/011793 A1 | 2/2002 |
| WO | WO-2003/047633 A2 | 6/2003 |
| WO | WO-2003/086448 A1 | 10/2003 |
| WO | WO-2004/026328 A1 | 4/2004 |
| WO | WO-2004/028635 A1 | 4/2004 |
| WO | WO-2004/037310 A2 | 5/2004 |
| WO | WO-2004/041160 A2 | 5/2004 |

(56) References Cited

FOREIGN PATENT DOCUMENTS

| | | |
|---|---|---|
| WO | WO-2005/023296 A1 | 3/2005 |
| WO | WO-2005/110435 A1 | 11/2005 |
| WO | WO-2005/110436 A2 | 11/2005 |
| WO | WO-2006/042329 A2 | 4/2006 |
| WO | WO-2006/062716 A2 | 6/2006 |
| WO | WO-2006/080951 A2 | 8/2006 |
| WO | WO-2006/099330 A2 | 9/2006 |
| WO | WO-2007/044668 A2 | 4/2007 |
| WO | WO-2007/056227 A2 | 5/2007 |
| WO | WO-2007/076437 A2 | 7/2007 |
| WO | WO-2007/084765 A2 | 7/2007 |
| WO | WO-2007/062249 A2 | 9/2007 |
| WO | WO-2009/015087 A2 | 1/2009 |
| WO | WO-2009/046198 A2 | 4/2009 |
| WO | WO-2010/127336 A1 | 11/2010 |
| WO | WO-2010/135717 A2 | 11/2010 |
| WO | WO-2011/076391 A1 | 6/2011 |
| WO | WO-2011/163394 A2 | 12/2011 |
| WO | WO-2012/006599 A2 | 1/2012 |
| WO | WO-2012/040259 A2 | 3/2012 |
| WO | WO-2012/155107 A1 | 11/2012 |
| WO | WO-2012/178083 A1 | 12/2012 |
| WO | WO-2013/036778 A2 | 3/2013 |
| WO | WO-2014/078731 A2 | 5/2014 |
| WO | WO-2014/078734 A2 | 5/2014 |
| WO | WO-2014078734 A2 * | 5/2014 ............... C07K 7/08 |
| WO | WO-2014/152391 A1 | 9/2014 |
| WO | WO-2015/142701 A1 | 9/2015 |
| WO | WO-2016/049385 A1 | 3/2016 |
| WO | WO-2017/062879 A2 | 4/2017 |
| WO | WO-2018/075373 A1 | 4/2018 |
| WO | WO-2018/187813 A1 | 10/2018 |
| WO | WO-2019/118938 A1 | 6/2019 |

OTHER PUBLICATIONS

Acosta, J. et al., Complement and complement regulatory proteins as potential molecular targets for vascular diseases, Curr. Pharm. Des., 10(2):203-11 (2004).
Acosta, J. et al., Molecular basis for a link between complement and the vascular complications of diabetes, Proc. Nat. Acad. Sci., 97(10):5450 (2000).
Albrecht, J.C. and Fleckenstein, B., New Member of the Multigene Family of Complement Control Proteins in Herpes Saimiri, Journal of Virology, 66(6):3937-3940 (1992).
Albrecht, J.C. et al., Herpesvirus Saimiri Has a Gene Specifying a Homologue of the Cellular Membrane Glycoprotein CD59, Virology, 190(1):527-530 (1992).
Aldrich, ChemFiles, Peptide Synthesis, 7(2): 20 pages (2007).
Allen, T.M., Ligand-Targeted Therapeutics in Anticancer Therapy, Nature Reviews Cancer, 2(10):750-765 (2002).
Altschul, S.F. et al., Basic local alignment search tool, Journal of Molecular Biology, 215(3):403-410 (1990).
Altschul, S.F., Gapped BLAST and PSI-BLAST: a New Generation of Protein Database Search Programs, Nucleic Acids Research, 25(17):3389-3402 (1997).
Ambati, J. et al., Age-related macular degeneration: etiology, pathogenesis, and therapeutic strategies, Survey of Ophthalmology, 48(3):257-293 (2003).
Ambati, J. et al., An Animal Model of Age-Related Macular Degeneration in Senescent Ccl-2- or Ccr-2-Deficient Mice, Nature Medicine, 9(11):1390-1397 (2003).
American Academy of Ophthalmology, Age-Related Macular Degeneration, Preferred Practice Pattern, American Academy of Ophthalmology, San Francisco, CA (2006).
Anderson, Amy C., The Process of Structure-Based Drug Design, Chemistry & Biology, 10:787-797 (2003).
Anderson, DH, et al., A role for local inflammation in the formation of drusen in the aging eye, Am. J. Ophthalmol, 134: 411-431 (2002).
Author Not Known, Peptide User Guide: A brief introduction into synthesis methods, handling and design of peptides, Bachem Brochure, 24 pages (2009).
Babitzke, P. and Yanofsky, C., Structural Features of L-Tryptophan Required for Activation of TRAP, the trp RNA-Binding Attenuation Protein of Bacillus subtilis, Journal of Biological Chemistry, 270(21):12452-12456 (1995).
Barlett, J.B. et al., The Evolution of Thalidomide and its IMiD Derivatives as Anticancer Agents, Nature Reviews Cancer, 4 (4):314-322 (2004).
Bartz, R. et al., Effective siRNA delivery and target mRNA degradation using an amphipathic peptide to facilitate pH-dependent endosomal escape, Biochem J., 435:475-487 (2011).
Beene, D.L. et al., Cation-π Interactions in Ligand Recognition by Serotonergic (5-HT3A) and Nicotinic Acetylcholine Receptors: The Anomalous Binding Properties of Nicotine, Biochemistry, 41(32):10262-10269 (2002).
Bora, P.S. et al., Immunotherapy for Choroidal Neovascularization in a Laser-Induced Mouse Model Simulating Exudative (Wet) Macular Degeneration, Proceedings of the National Academy of Science, 100(5):2679-2684 (2003).
Bora, PS et al., Complement activation by alternative pathway is critical in the development of laser-induced choroidal neovascularization, Invest Ophthalmol Vis Sci, 47: E-Abstract 4167 (2006).
Bora, PS et al., Neovascularization in a mouse model that simulates exudative macular degeneration is complement dependent, Invest. Ophthalmol. Vis. Sci. 45: E-Abstract 1871 (2004).
Bora, PS et al., Role of complement and complement membrane attack complex in neovascularization, Journal of Immunology, 174 (1): 491-497 (2005).
Bora, PS, et al., Complement Activation is Required in the Murine Model of Laser-induced Choroidal Neovascularization, Invest. Ophthalmol. Vis. Sci., 44: E-Abstract 3940 (2003).
Bourges, J-L. et al., Ocular drug delivery targeting the retina and retinal pigment epithelium using polylactide nanoparticles, Investigative Ophthalmology and Visual Sciences, 44(8):3562-3569 (2003).
Braun, J., UCSB Studies Link Alzheimer's Disease, Macular Degeneration, The Daily Nexus, University of California, Santa Barbara, 83(135): 1-5 (Published May 28, 2003).
Chapple, J.P. et al., Unfolding retinal dystrophies: a role for molecular chaperones?, Trends in Mol. Med., 7: 414-421 (2001).
Charkravarthy, U. et al., Year 2 Efficacy Results of 2 Randomized Controlled Clinical Trials of Pegaptanib for Neovascular Age-Related Macular Degeneration, Ophthalmology, 113:1508-1521 (2006).
Chauhan, A. et al., The Taming of the Cell Penetrating Domain of the HIV Tat: Myths and Realities, J. Control Release, 117(2):148-162 (2007).
Conley YP, et al., Candidate gene analysis suggests a role for fatty acid biosynthesis and regulation of the complement system in the etiology of age-related maculopathy, Hum. Mol. Genet., 14:1991-2002 (2005).
Corrales, L. et al., Anaphylatoxin C5a Creates a Favorable Microenvironment for Lung Cancer Progression, The Journal of Immunology, 4674-4683 (2012).
D'Amico, D. et al., Pegaptanib Sodium for Neovascular Age-Related Macular Degeneration, Ophthalmology, 113:992-1001 (2006).
Daniel, R. et al., Compstatin: A Complement Inhibitor on its Way to Clinical Application, Adv. Exp. Med. Biol., 632:273-292 (2008).
Database BIOSIS on STN, BIOSIS, (Philadelphila, PA, USA), DN: PREV200600053073, & Raisler, B.J. et al., Drusen Complement Components C3a and C5a Promote Choroidal Neovascularization, IOVS, 2005, vol. 46, No. Suppl, p. 1214.
Davenport, R.J., Tarnished Vision, Sci. Aging Knowl. Environ., 2004(37): nf85 (2004).
Debets, M. et al., Aza-dibenzocyclooctynes for fast and efficient enzyme PEGylation via copper-free (3+2) cycloaddition, Chem. Commun., 46:97-99 (2010).
Deshayes, S. et al., Cell-penetrating peptides: tools for intracellular delivery of therapeutics, CMLS Cellular and Molecular Life Sciences, 62:1839-1849 (2005).
Donoso, L. et al., The role of inflammation in the pathogenesis of age-related macular degeneration, Survey of Ophthalmology, 51(2):137-152 (2006).
Edwards, AO et al., Complement Factor H Polymorphism and Age-Related Macular Degeneration, Science, 308(5720):421-424 (2005).

(56) References Cited

OTHER PUBLICATIONS

Eguchi, M. and Kahn, M., Design, Synthesis, and Application of Peptide Secondary Structure Mimetics, Mini Reviews in Medicinal Chemistry, 2(5):447-462 (2002).
Einmahl, S. et al., Evaluation of a Novel Biomaterial in the Suprachoroidal Space of the Rabbit Eye, Investigative Ophthalmology and Visual Science, 43(5):1533-1539 (2002).
Ferrara, N., Vascular Endothelial Growth Factor: Basic Science and Clinical Progress, Endocrine Reviews, 25(4):581-611 (2004).
Fish et al., Anti-vascular Endothelial Growth Factor Therapy for Subfoveal Choroidal Neovascularization Secondary to Age-related Macular Degeneration, Phase II Study Results, The Eyetech Study Group, Ophthalmology, 110: 978-986 (2003).
Frankel, A. et al., Characterization of diphtheria fusion proteins targeted to the human interleukin-3 receptor, Protein Eng, 13(8):575-81 (2000).
Fung, A.E. et al., An Optical Coherence Tomography-Guided, Variable Dosing Regimen with Intravitreal Ranibizumab (Lucentis) for Neovascular Age-related Macular Degeneration, Am. J. Ophthalmol., 143:566-583 (2007).
Futaki, S. et al., An Abundant Source of Membrane-Permeable Peptides Having Potential as Carriers for Intracellular Protein Delivery, The Journal of Biological Chemistry, 276(8):5836-5840 (2001).
Gaudreault, J. et al., Preclinical pharmacokinetics of Ranibizumab (rhuFabV2) after a single intravitreal administration, Investigative Ophthalmology and Visual Science, 46(2):726-733 (2005).
Gautam, A. et al., CPPsite: a curated database of cell penetrating peptides, Database, 7 pages (2012).
Gerl, V et al., Extensive Deposits of Complement C3d and C5b-9 in the Choriocapillaris of Eyes of Patients with Diabetic Retinopathy, Investigative Ophthalmology and Visual Sciences, 43(4):1104-1108 (2002).
Gold, B. et al., Variation in factor B (BF) and complement component 2 (C2) genes is associated with age-related macular degeneration, Nature Genetics, 38: 458-462 (2006).
Gonzales, N.R. et al., Minimizing the Immunogenicity of Antibodies for Clinical Application, Tumour Biology, 26(1):31-43 (2005).
Gragoudas, E. et al., Pegaptanib for Neovascular Age-Related Macular Degeneration, The New England Journal of Medicine, 351:2805-2516 (2004).
Haas, A. K. et al., Human protein derived peptides for intracellular delivery of biomolecules, Biochemical Journal Immediate Publication, 25 pages (2011).
Hageman, GS et al., A common haplotype in the complement regulatory gene factor H (HF1/CFH) predisposes individuals to age-related macular degeneration, Proceedings of the National Academy of Sciences, 102(20):7053-7054 (2005).
Hageman, GS et al., An integrated hypothesis that considers drusen as biomarkers of immune-mediated processes at the RPE-Bruch's membrane interface in aging and age-related macular degeneration, Progress in Retinal and Eye Research, 20(6):705-732 (2001).
Haines, JL et al., Complement factor H variant increases the risk of age-related macular degeneration, Science, 308(5720):419-421 (2005).
Hanes, J. and Plückthun, A., In Vitro Selection and Evolution of Functional Proteins by Using Ribosome Display, Proceedings of the National Academy of Science, 94(10):4937-4947 (1997).
Ho, A. et al., Synthetic Protein Transduction Domains: Enhanced Transduction Potential in Vitro and in Vivo, Cancer Research, 61:474-477 (2001).
Holland, MCH, et al., Synthetic small-molecule complement inhibitors, Curr. Op. Invest. Drugs, 5(11) 1164-1173 (2004).
Hrynchak, PK, et al., Optical coherence tomography: an introduction to the technique and its use, Optometry and Vision Science, 77(7): 347-356 (2000).
Hughes et al., A common CFH haplotype, with deletion of CFHR1 and CFHR3, is associated with lower risk of age-related macular degeneration, Nature Genetics, 38(10):1173-1177 (2006).
International Search Report for PCT/US05/036547, 5 pages (dated Jun. 10, 2006).
International Search Report for PCT/US06/039397, 6 pages (dated Oct. 24, 2007).
International Search Report for PCT/US18/65870 (Dosing Regimens and Related Compositions and Methods, filed Dec. 14, 2018), issued by ISA/US, 7 pages (dated May 17, 2019).
International Search Report for PCT/US2012/037648, (Cell-Reactive, Long-Acting, or Targeted Compstatin Analogs and Uses Thereof, filed May 11, 2012) issued by ISA, 3 pages (dated Sep. 20, 2012).
International Search Report for PCT/US2013/070417, 3 pages (dated Jun. 5, 2014).
International Search Report for PCT/US2013/070424, 3 pages (dated Jun. 5, 2014).
International Search Report for PCT/US2014/27289, 4 pages (dated Aug. 19, 2014).
International Search Report for PCT/US2016/56144, 6 pages (dated Apr. 27, 2017).
International Search Report for PCT/US2018/026753 (Dosing Regimens and Related Compositions and Methods, filed Apr. 9, 2018), issued by ISA/US, 6 pages (dated Sep. 13, 2018).
International Search Report from PCT/US2007/001649 (dated Mar. 31, 2008).
Internet Citation: URL: www.rsinewsrxreportingfrom.com/ content.asp?myid+40&tid=365> Anti-VEGF Agents Useful in Age-Related Macular Degeneration, Am Acad of Ophthalm, (Oct. 15, 2005).
Ishida, T. et al., A Combinational Approach to Producing Sterically Stabilized (Stealth) Immunoliposomal Drugs, FEBS Letters, 460(1):129-133 (1999).
Jaffe, G. Safety and pharmacokinetics of an intraocular fluocinolone acetonide sustained delivery device, Investigative Ophthalmology and Visual Sciences, 41(11):3569-3575 (2000).
Jager et al., Age-related Macular Degeneration, N. Engl. J. Med., 358(24): 2606-2617 (2008).
Jha, P. et al., The complement system plays a critical role in the development of experimental autoimmune anterior uveitis, Investigative Ophthalmology and Visual Sciences, 47(3):1030-1038 (2006).
Johnson, L.V. et al., Complement activation and inflammatory processes in drusen formation and age related macular degeneration, Experimental Eye Research, 73(6):887-896, Academic Press Ltd., London, GB (2001).
Kabouridis, Panagiotis S., Biological applications of protein transduction technology, Trends Biotechnol., 21(11):498-503 (2003).
Kalayoglu, M.V., Emerging Treatment Strategies for Age-related Macular Degeneration, Internet Citation, URL: <www.medcompare.com/spotlight.asp?spotlightid=62> (Retrieved Jun. 30, 2004).
Karlin, S. and Altschul, S.F., Applications and Statistics for Multiple High-Scoring Segments in Molecular Sequences, Proceedings of the National Academy of Science, 90(12):5873-5877 (1993).
Karlin, S. and Altschul, S.F., Methods for Assessing the Statistical Significance of Molecular Sequence Features by Using General Scoring Schemes, Proceedings of the National Academy of Science, 87(6):2264-2268 (1990).
Katragadda et al., Thermodynamic studies on the interaction of the third complement component and its inhibitor, compstatin, Journal of Biological Chemistry, 279(53): 54987-54995 (2004).
Katragadda et al., Expression of compstatin in *Escherichia coli*: Incorporation of unnatural amino acids enhances its activity, Protein Expression and Purification, 47(1):289-295 (2006).
Katragadda et al., Structure-activity-based design of potent compstatin analogs, Molecular Immunology, 44(103): 192 (2007).
Katragadda, M. et al., Hydrophobic effect and hydrogen bonds account for the improved activity of a complement inhibitor, compstatin, Journal of Medicinal Chemistry, 49(15):4616-4622 (2006).
Keam, S. J. et al., Verteporfin, A Review of its Use in the Management of Subfoveal Choroidal Neovascularisation, Drugs, 63: 2521-2554 (2003).
Kent, S., Total Chemical Synthesis of Enzymes, Journal of Peptide Science, 9(9):574-593 (2003).
Klein, RJ et al., Complement Factor H Polymorphism in Age-Related Macular Degeneration, Science, 308(5720):385-389 (2005).
Kohler, G. and Milstein, C., Continuous Cultures of Fused Cells Secreting Antibody of Predetermined Specificity, Nature, 256(5517): 495-497 (1975).

(56) References Cited

OTHER PUBLICATIONS

Kourlas, H. et al., Pegaptanib Sodium for the Treatment of Neovascular Age-Related Macular Degeneration: A Review, Clinical Therapeutics, 28(1):36-44 (2006).
Kozlowski, A. et al., Development of Pegylated Interferons for the Treatment of Chronic Hepatitis C, BioDrugs, 15(7):419-429 (2001).
Lattig-Tunnemann, G. et al., Backbone rigidity and static presentation of guanidinum groups increases cellular uptake or arginine-rich cell-penetrating peptides, Nature Communications, 2:453, 6 pages (2011).
Li, M. et al., CFH haplotypes without the Y402H coding variant show strong association with susceptibility to age-related macular degeneration, Nature Genetics, 38(9):1049-1054 (2006).
Lippinvott Co., Anti-Vascular Endothelial Growth Factor Therapy for Subfoveal choroidal Neovascularization Secondary to Age-Related Macular Degeneration: Phase II Study Results, Opthal., 110(5): 979-986 (2003).
Liszewski, K. et al., Cleavage of intracellular C3 into C3a and C3b by cathepsin L is required for human TH1 induction, Abstract #61, Immunobiology, 217, p. 1150 (2012).
Liu, D. et al., Suppression of Acute Lung Inflammation by Intracellular Peptide Delivery of a Nuclear Import Inhibitor, The American Society of Gene Therapy, 17(5):796-802 (2009).
Liu, X. Y. et al., Peptide-directed Suppression of a Pro-inflammatory Cytokine Response, The Journal of Biological Chemistry, 275(22):16774-16778 (2000).
Lopes, L. et al., Cell Permeant Peptide Analogues of the Small Heat Shock Protein, HSP20, Reduce TGF-β1-Induced CTGF Expression in Keloid Fibroblasts, Journal of Investigative Dermatology, 129:590-598 (2009).
Magnusson, KP, et al., CFH Y402H Confers Similar Risk of Soft Drusen and Both Forms of Advanced AMD, PLoS Med, 3:e5 (2006).
Makrides, S.C. et al., Therapeutic inhibition of the complement system, Pharmacological Reviews, 50(1):59-87, American Society for Pharmacology and Experimental Therapeutics, Bethesda, MD (1998).
Maller, J. et al., Common variation in three genes, including a noncoding variant in CFH, strongly influences risk of age-related macular degeneration, Nature Genetics, 38(9):1055-1059 (2006).
Mallik, B et al.,: Design and NMR characterization of active analogues of compstatin containing non-natural amino acids, Journal of Medicinal Chemistry, 48 (1):274-286 (2005).
McCusker, C. et al., Inhibition of Experimental Allergic Airways Disease by Local Application of a Cell-Penetrating Dominant-Negative STAT-6 Peptide, The Journal of Immunology, 179:2556-2564 (2007).
Michels, S. and Rosenfeld, P.J., Treatment of Neovascular Age-Related Macular Degeneration With Ranibizumab/Lucentis, Klin Monbl Augenheikd, 222(6): 480-484 (2005).
Midena, E., et al., Macular function impairment in eyes with early age-related macular degeneration, Invest. Ophthalmol. Vis. Sci., 38: 467-477 (1997).
Miller, C.G., The Cowpox Virus-Encoded Homolog of the Vaccinia Virus Complement Control Protein Is an Inflammation Modulatory Protein, Virology,229(1):129-133 (1997).
Mishra, Ritu, Biological evaluation of novel peptidic vectors for transmembrane delivery of intracellularly targeted probes for molecular imaging, Dissertation, 103 pages (2009).
Morikis, D. et al., Improvement of the anti-C3 activity of compstatin using rational and combinatorial approaches, Biochemical Society Transactions, 32(1):28-32, Biochemical Society, London, UK (2004).
Morikis, D. et al., Solution structure of Compstatin, a potent complement inhibitor, Protein Science, 7(3):619-627 (1998).
Morikis, D. et al., The Structural Basis of Compstatin Activity Examined by Structure-Function-based Design of Peptide Analogs and NMR, J. Biol. Chem., 277(17):14942-14953 (2002).
Nektar Advanced Pegylation, 34 pages (2005-2006 Product Catalog, Nektar Therapeutics, San Carlos, CA).

Ng et al., Targeting Angiogenesis, the Underlying Disorder in Neovascular Age-Related Macular Degeneration, Canadian Journal of Ophthalmology, 40(3): 352-368 (2005).
Nielsen, M. et al., MHC Class II epitope predictive algorithms, Immunology, 130:319-328 (2010).
No Author Listed, Copper-free Click Chemistry from https://web.archive.org/III0110228014635/http://www.jenabioscience.com/1b94dca880/Newsletter_Copper-Free-ClickChem_Feb11.html, pp. 1-2, published online Feb. 28, 2011.
Novina, C.D. and Sharp, P.A., The RNAi Revolution, Nature, 430(6996):161-164 (2004).
Nozaki, M. et al., Drusen complement components C3a and C5a promote choroidal neovascularization, Proc. Natl. Acad. Sci. USA, 103:2328-2333 (2006).
Nwe, K. and Brechbiel, M. et al., Growing Applications of "Click Chemistry" for Bioconjugation in Contemporary Biomedical Research, Cancer Biotherapy and Radiopharmaceuticals, 24:289-302 (2009).
Pakula, A. and Sauer, R., Genetic analysis of protein stability and function, Annu Rev Genet, 23:289-310 (1989).
Peptide Modifications, Designer Bioscience, created on Jun. 25, 2009, accessed on Jun. 9, 2016, 2 pages.
Pio, R. et al., The Role of Complement in Tumor Growth, C. Koumenis et al. (eds.), Tumor Microenvironment and Cellular Stress, Advances, Experimental Medicine and Biology, 772, Chapter 11, 229-262 (2014).
Rakoczy, P.E. et al., Progressive Age-Related Changes Similar to Age-Related Macular Degeneration in a Transgenic Mouse Model, American Journal of Pathology,161(4):1515-1524 (2002).
Reid, K.B. and Day, A.J., Structure-Function Relationships of the Complement Components, Immunology Today, 10(6):177-180 (1989).
Ricklin, D. et al., Complement—a key system for immune surveillance and homeostasis, Nat. Immunol., 11(9):785-797 (2010).
Rosenfeld et al., URL: www.revophth.com/index.asp?page+1_857.htm> An Update on Bevacizumab (Dec. 1, 2005).
Rosengard, A.M. et al., Variola Virus Immune Evasion Design: Expression of a Highly Efficient Inhibitor of Human Complement, Proceedings of the National Academy of Science, 99(13):8803-8813 (2002).
Sahu, A, et al., Compstatin, a peptide inhibitor of complement, exhibits species-specific binding to complement component C3, Mol. Immunol., 39(10):557-66 (2003).
Sahu, A. et al., Interaction of Vaccinia Virus Complement Control Protein with Human Complement Proteins: Factor I-Mediated Degradation of C3b to iC3b1 Inactivates the Alternative Complement Pathway, Journal of Immunology, 160(11): 5596-5604 (1998).
Sahu, A., et al., Binding kinetics, structure-activity relationship, and biotransformation of the complement inhibitor compstatin, J. Immunol., 165(5):2491-9 (2000).
Sanders, W. et al., Prediction of Cell Penetrating Peptides by Support Vector Machines, PLoS Computational Biology, 7(7):e1002101, 12 pages (2011).
Scullica, L. and Benedetto, F., Diagnosis and classification of macular degenerations: an approach based on retinal function testings, Documenta Ophthalmologica, 102: 237-250 (2001).
Sepp, T. et al., Complement Factor H Variant Y402H Is a Major Risk Determinant for Geographic Atrophy and Choroidal Neovascularization in Smokers and Nonsmokers, Invest. Ophthalmol. Vis. Sci., 47:536-540 (2006).
Siddiqui, M. and Keating, G., Pegaptanib—In Exudative Age-Related Macular Degeneration, Drugs, 65(11):1571-1577 (2005).
Sivaprasad, S. and Chong, NV. The complement system and age-related macular degeneration, Eye, 20: 867-872 (2006).
Smith, S.S. et al., Conserved Surface-Exposed K/R-X-K/R Motifs and Net Positive Charge on Provirus Complement Control Proteins Serve as Putative Heparin Binding Sites and Contribute to Inhibition of Molecular Interactions with Human Endothelial Cells: a Novel Mechanism for Evasion of Host Defense, Journal of Virology, 74(12):5659-5666 (2000).
Soulika, AM, et al., Studies of structure-activity relations of complement inhibitor compstatin, J. Immunol., 171(4):1881-90 (2003).
Soulika, et al., Compstatin Inhibits Complement Activation by Binding to the Beta-Chain of Complement Factor 3, Mol. Immunol., 43:2023-2029 (2006).

(56) References Cited

OTHER PUBLICATIONS

Subasinghe, N. et al., Design and synthesis of polyethylene glycol-modified biphenylsulfonyl-thiop-hene-carboxamidine inhibitors of the complement component C1s, Bioorganic & Medicinal Chemistry Letters, 22:5303-5307 (2012).

Sugita, T. et al., Comparative study on transduction and toxicity of protein transduction domains, British Journal of Pharmacology, 153:1143-1152 (2008).

Suhorutsenko, J. et al., Cell-Penetrating Peptides, PepFects, Show No Evidence of Toxicity and Immunogenicity in Vitro and In Vivo, Bioconjugate Chemistry, 22:2255-2262 (2011).

Supplemental Partial European Search Report for EP13854990, 6 pages (dated Jun. 6, 2016).

Tamai, K. et al., Lipid Hydroperoxide Stimulates Subretinal Choroidal Neovascularization in the Rabbit, Experimental Eye Research, 74(2):301-308 (2002).

Tezel, T.H. et al., Pathogenesis of Age-Related Macular Degeneration, Trends in Molecular Medicine, 10(9):417-420 (2004).

Torchilin, V.P. et al., p-Nitrophenylcarbonyl-PEG-PE-Liposomes: Fast and Simple Attachment of Specific Ligands, Including Monoclonal Antibodies, to Distal Ends of PEG Chains Via p-Nitrophenylcarbonyl Groups, Biochimica Biophysica Acta, 1511(2):497-522 (2001).

Tunnemann, G. et al,. Cargo-dependent mode of uptake and bioavailability of TAT-containing proteins and peptides in living cells, The FASEB Journal, 20:1775-1784 (2006).

Uvarova, E.A. and Shchelkunov, S.N., Species-specific Differences in the Structure of Orthopoxvirus Complement-Binding Protein, Virus Research, 81(1-2):39-45 (2001).

Viegas, T. et al., Polyoxazoline: Chemistry, Properties, and Applications in Drug Delivery, Bioconjugate Chemistry, 22:976-986 (2011).

Wang, F. et al., AAV-Mediated Expression of Vascular Endothelial Growth Factor Induces Choroidal Neovascularization in Rat, Investigative Ophthalmology and Visual Science, 44(2):781-790 (2003).

Ward, B. et al., Design of a bioactive cell-penetrating, peptide: when a transduction domain does more than transduce, J. Pept. Sci., 15(10):668-674 (2009).

Wender, P. et al., The design, synthesis, and evaluation of molecules that enable or enhance cellular update: Peptoid molecular transporters, PNAS, 97(24):13003-13008 (2000).

Winter, G. et al., Making Antibody by Phage Display Technology, Annual Reviews in Immunology,12:433-455 (1994).

Written Opinion for PCT/US05/036547, 7 pages (dated Jun. 10, 2006).

Written Opinion for PCT/US18/65870 (Dosing Regimens and Related Compositions and Methods, filed Dec. 14, 2018), issued by ISA/US, 16 pages (dated May 17, 2019).

Written Opinion for PCT/US2007/001649, 9 pages (dated Mar. 31, 2008).

Written Opinion for PCT/US2012/037648, (Cell-Reactive, Long-Acting, or Targeted Compstatin Analogs and Uses Thereof, filed May 11, 2012) issued by ISA, 7 pages (dated Sep. 20, 2012).

Written Opinion for PCT/US2013/070417, 6 pages (dated Jun. 5, 2014).

Written Opinion for PCT/US2013/070424, 6 pages (dated Jun. 5, 2014).

Written Opinion for PCT/US2014/27289, 4 pages (dated Aug. 19, 2014).

Written Opinion for PCT/US2016/56144, 15 pages (dated Apr. 27, 2017).

Written Opinion for PCT/US2018/026753 (Dosing Regimens and Related Compositions and Methods, filed Apr. 9, 2018), issued by ISA/US, 17 pages (dated Sep. 13, 2018).

Written Opinion of PCT/US06/039397, 8 pages (dated Aug. 11, 2007).

Yannuzzi, L. et al., Retinal angiomatous proliferation in age-related macular degeneration, Retina, 21(5): 416-34 (2001).

Yates J.R.W. et al.,, Complement C3 variant and the risk of age-related macular degeneration, N. Engl. J. Med., 357(6):553-61 (2007).

Zacks, D.N. et al., Verteporfin Photodynamic Therapy in the Rat Model of Choroidal Neovascularization: Angiographic and HIstologic Characterization, Investigative Ophthalmology and Visual Science, 43(7):2384-2391 (2002).

Zareparsi, S, et al., Strong association of the Y402H variant in complement factor H at 1q32 with susceptibility to age-related macular degeneration, Am. J. Hum. Genet., 77:149-153 (2005).

Zhang et al, Early complement activation and decreased levels of glycosylphosphatidylinositol-anchored complement inhibitors in human and experimental diabetic retinopathy, Diabetes, 51(12):3499-3504 (2002).

Zhang, L. et al., TEPITOPEpan: Extending TEPITOPE for Peptide Binding Prediction Covering over 700 HLA-DR Molecules, PLoS One, 7(2):e30483, 10 pages (2012).

Zhou et al., Complement Activation by Bisretinoid Constituents of RPE Lipofuscin, Invest. Ophthalmol. Vis. Sci., 50: 1392-1399 (2009).

Zhou, J, et al., Complement activation by photooxidation products of A2E, a lipofuscin constituent of the retinal pigment epithelium, Proc. Natl. Acad. Sci. USA, 103:16182-16187 (2006).

Clinical Trial NCT02461771, posted Jun. 3, 2015, downloaded from clinicaltrials.gov, 3 pages (2015).

BD, Subcutaneous Injection Guidelines for Needle Length and Gauge Selection, available from www.bd.com, 2 pages (2012).

ChemIDplus record for Pegcetacoplan, available from chem.nim.nih.gov/chemidplus/m/2019171-69-6, 2 pages (2019).

Clinical Trial NCT02503332, available from clinicaltrials.gov on Jul. 17, 2015, 3 pages.

Ricklin, D. and Lambris, J., Therapeutic control of complement activation at the level of the central component C3, Immunobiology, 221:740-746 (2016).

Siegmund, T. et al., Comparison of usability and patient preference for insulin pen needles produced with different production techniques: "thin-wall" needles compared to "regular-wall" needles: an open-label study, Diabetes Technol. Ther., 11(8):523-528, Abstract Only (2009).

* cited by examiner

PK prediction: Cohorts 1, 2 & 3

PK prediction: Cohorts 1 & 2 (up to Day 35)

Observed PK data: Cohorts 1 & 2 (up to Day 35)

Observed PK data vs prediction: Cohort 1

Observed PK data vs prediction: Cohort 2

Observed PK data vs prediction: Cohorts 1 & 2

Observed PK data vs cohort 3 prediction

SEQUENCE LISTING

```
<160> NUMBER OF SEQ ID NOS: 74

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond

<400> SEQUENCE: 1

Ile Cys Val Val Gln Asp Trp Gly His His Arg Cys Thr
1               5                   10

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(19)
<223> OTHER INFORMATION: Any independently selected amino acid or amino
      acid analog
<220> FEATURE:
<221> NAME/KEY: misc_feature
<222> LOCATION: (1)..(19)
<223> OTHER INFORMATION: This region may encompass 2 to 19 residues,
      wherein some residues may be absent
<220> FEATURE:
<221> NAME/KEY: MOD_RES
<222> LOCATION: (22)..(22)
<223> OTHER INFORMATION: Trp or an analog of Trp
<220> FEATURE:
<221> NAME/KEY: MOD_RES
<222> LOCATION: (24)..(42)
<223> OTHER INFORMATION: Any independently selected amino acid or amino
      acid analog
<220> FEATURE:
<221> NAME/KEY: misc_feature
<222> LOCATION: (24)..(42)
<223> OTHER INFORMATION: This region may encompass 2 to 19 residues,
      wherein some residues may be absent
```

```
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Gln Asp Xaa Gly Xaa Xaa Xaa Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, an analog of Trp, or other amino acid or
      amino acid analog comprising at least one aromatic ring
<220> FEATURE:
<221> NAME/KEY: MOD_RES
<222> LOCATION: (4)..(4)
<223> OTHER INFORMATION: Trp, an analog of Trp, or other amino acid or
      amino acid analog comprising at least one aromatic ring
<220> FEATURE:
<223> OTHER INFORMATION: See specification as filed for detailed
      description of substitutions and preferred embodiments

<400> SEQUENCE: 3

Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, an analog of Trp, or other amino acid or
      amino acid analog comprising at least one aromatic side chain
<220> FEATURE:
<221> NAME/KEY: MOD_RES
<222> LOCATION: (4)..(4)
<223> OTHER INFORMATION: Trp, an analog of Trp, or other amino acid or
      amino acid analog comprising at least one aromatic side chain
<220> FEATURE:
<221> NAME/KEY: MOD_RES
<222> LOCATION: (6)..(6)
<223> OTHER INFORMATION: His, Ala, analog of Ala, Phe, Trp or analog of
      Trp
<220> FEATURE:
<223> OTHER INFORMATION: See specification as filed for detailed
      description of substitutions and preferred embodiments

<400> SEQUENCE: 4

Xaa Gln Asp Xaa Gly Xaa
1               5

<210> SEQ ID NO 5
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any independently selected amino acid or amino
      acid analog
<220> FEATURE:
<221> NAME/KEY: MOD_RES
<222> LOCATION: (4)..(4)
<223> OTHER INFORMATION: Trp or analog of Trp
<220> FEATURE:
<221> NAME/KEY: MOD_RES
<222> LOCATION: (7)..(7)
<223> OTHER INFORMATION: Trp or analog of Trp
<220> FEATURE:
<221> NAME/KEY: MOD_RES
<222> LOCATION: (9)..(13)
<223> OTHER INFORMATION: Any independently selected amino acid or amino
      acid analog
<220> FEATURE:
<223> OTHER INFORMATION: See specification as filed for detailed
      description of substitutions and preferred embodiments

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of the L-Thr, D-Thr, Ile,
      Val, Gly, Ala or Asn is optionally replaced by a second blocking
      moiety
```

```
<220> FEATURE:
<221> NAME/KEY: misc_feature
<222> LOCATION: (14)..(16)
<223> OTHER INFORMATION: This region may encompass 1 to 3 residues,
      wherein some positions may be absent
<220> FEATURE:
<223> OTHER INFORMATION: See specification as filed for detailed
      description of substitutions and preferred embodiments

<400> SEQUENCE: 6

Xaa Xaa Cys Val Xaa Gln Asp Xaa Gly Xaa His Arg Cys Xaa Xaa Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, Ac-Ile, Ac-Val, Ac-Leu or a
      dipeptide comprising Gly-Ile or Ac-Gly-Ile
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of L-Thr, D-Thr, Ile,
      Val, Gly, Ala, or Asn is optionally replaced by -NH2
<220> FEATURE:
<221> NAME/KEY: misc_feature
<222> LOCATION: (14)..(16)
<223> OTHER INFORMATION: This region may encompass 1 to 3 residues,
      wherein some positions may be absent
<220> FEATURE:
<223> OTHER INFORMATION: See specification as filed for detailed
      description of substitutions and preferred embodiments

<400> SEQUENCE: 7

Xaa Xaa Cys Val Xaa Gln Asp Xaa Gly Xaa His Arg Cys Xaa Xaa Xaa
1               5                   10                  15

<210> SEQ ID NO 8
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term CONH2

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 10

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term COOH

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2
```

```
<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (13)..(13)
<223> OTHER INFORMATION: d-Thr
<220> FEATURE:
<223> OTHER INFORMATION: C-term COOH

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term CONH2

<400> SEQUENCE: 14

Ile Cys Val Ala Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term COOH

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-Nal
<220> FEATURE:
<223> OTHER INFORMATION: C-term COOH

<400> SEQUENCE: 16

Ile Cys Val Ala Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term CONH2

<400> SEQUENCE: 17

Ile Cys Val Gly Gln Asp Trp Gly Ala His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term COOH

<400> SEQUENCE: 18

Ile Cys Val Gly Gln Asp Trp Gly Ala His Arg Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Dht
<220> FEATURE:
<223> OTHER INFORMATION: C-term COOH

<400> SEQUENCE: 19

Ile Cys Val Trp Gln Asp Trp Gly Ala His Arg Cys Thr
1               5                   10
```

```
<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term COOH

<400> SEQUENCE: 20

Ile Cys Val Phe Gln Asp Trp Gly Ala His Arg Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term CONH2

<400> SEQUENCE: 21

Ile Cys Val Phe Gln Asp Trp Gly Ala His Arg Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term COOH

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
```

```
<220> FEATURE:
<223> OTHER INFORMATION: C-term CONH2

<400> SEQUENCE: 23

Ile Cys Val Xaa Gln Asp Trp Gly Ala His Arg Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: 2-Abu
<220> FEATURE:
<223> OTHER INFORMATION: C-term CONH2

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term COOH

<400> SEQUENCE: 25

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<223> OTHER INFORMATION: C-term CONH2

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<223> OTHER INFORMATION: C-term CONH2

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<223> OTHER INFORMATION: C-term CONH2

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2
```

```
<400> SEQUENCE: 30

Ile Cys Val Trp Gln Asp Trp Gly Ala His Arg Cys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 32

Ile Cys Val Trp Gln Asp Trp Gly Ala His Arg Cys Thr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 6f-Trp
<220> FEATURE:
<221> NAME/KEY: MOD_RES
<222> LOCATION: (8)..(8)
<223> OTHER INFORMATION: 6f-Trp
<220> FEATURE:
<223> OTHER INFORMATION: C-term COOH
```

```
<400> SEQUENCE: 33

Gly Ile Cys Val Trp Gln Asp Trp Gly Ala His Arg Cys Thr Asn
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-formyl-Trp
<220> FEATURE:
<223> OTHER INFORMATION: C-term CONH2

<400> SEQUENCE: 34

Ile Cys Val Trp Gln Asp Trp Gly Ala His Arg Cys Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methoxy-Trp
<220> FEATURE:
<223> OTHER INFORMATION: C-term CONH2

<400> SEQUENCE: 35

Ile Cys Val Trp Gln Asp Trp Gly Ala His Arg Cys Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 5f-Trp
<220> FEATURE:
<221> NAME/KEY: MOD_RES
<222> LOCATION: (8)..(8)
<223> OTHER INFORMATION: 5f-Trp
<220> FEATURE:
<223> OTHER INFORMATION: C-term COOH

<400> SEQUENCE: 36

Gly Ile Cys Val Trp Gln Asp Trp Gly Ala His Arg Cys Thr Asn
1               5                   10                  15
```

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp

<400> SEQUENCE: 37

Ile Cys Val Trp Gln Asp Trp Gly Ala His Arg Cys Thr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 38

Ile Cys Val Trp Gln Asp Trp Gly Ala His Arg Cys Thr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term (C=O)-(CH2)5-maleimide

<400> SEQUENCE: 39

Ile Cys Val Trp Gln Asp Trp Gly Ala His Arg Cys Thr
1               5                   10

<210> SEQ ID NO 40
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Maleimide-(CH2)2-C(=O)-NH-CH2CH2OCH2CH2O
      CH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 40

Ile Cys Val Trp Gln Asp Trp Gly Ala His Arg Cys Thr
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)2-C(=O)-NH-
      CH2CH2OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 41

Ile Cys Val Trp Gln Asp Trp Gly Ala His Arg Cys Thr
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)3-C(=O)-NH-CH2CH2OCH2CH2
      OCH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 42

Ile Cys Val Trp Gln Asp Trp Gly Ala His Arg Cys Thr
1               5                   10
```

```
<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)-NH-CH2CH2OCH2CH2
      OCH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 43

Ile Cys Val Trp Gln Asp Trp Gly Ala His Arg Cys Thr
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)4-C(=O)-NH-CH2CH2OCH2CH2
      OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 44

Ile Cys Val Trp Gln Asp Trp Gly Ala His Arg Cys Thr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)2-C(=O)-NH-CH2CH2OCH2CH2
      OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 45

Ile Cys Val Trp Gln Asp Trp Gly Ala His Arg Cys Thr
1               5                   10
```

```
<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)-NH-CH2CH2OCH2CH2
      OCH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 46

Ile Cys Val Trp Gln Asp Trp Gly Ala His Arg Cys Thr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 47

Ile Cys Val Trp Gln Asp Trp Gly Ala His Arg Cys Thr Lys
1               5                   10

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 48

Ile Cys Val Trp Gln Asp Trp Gly Ala His Arg Cys Thr Gly Gly Gly
1               5                   10                  15

Gly Gly Lys
```

```
<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 49

Ile Cys Val Trp Gln Asp Trp Gly Ala His Arg Cys Thr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 50

Ile Cys Val Trp Gln Asp Trp Gly Ala His Arg Cys Thr
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys
<220> FEATURE:
<223> OTHER INFORMATION: C-term NH2

<400> SEQUENCE: 51

Ile Cys Val Trp Gln Asp Trp Gly Ala His Arg Cys Thr Lys
1               5                   10

<210> SEQ ID NO 52
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-(C(=O)-(CH2)5-Mal)
<220> FEATURE:
<223> OTHER INFORMATION: C-term NH2

<400> SEQUENCE: 52

Ile Cys Val Trp Gln Asp Trp Gly Ala His Arg Cys Thr Lys
1               5                   10

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (19)..(19)
<223> OTHER INFORMATION: Lys-(C(=O)-(CH2)5-Mal)
<220> FEATURE:
<223> OTHER INFORMATION: C-term NH2

<400> SEQUENCE: 53

Ile Cys Val Trp Gln Asp Trp Gly Ala His Arg Cys Thr Gly Gly Gly
1               5                   10                  15

Gly Gly Lys

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mal-(CH2)5-(C(=O)-NH(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 54

Ile Cys Val Trp Gln Asp Trp Gly Ala His Arg Cys Thr
1               5                   10
```

```
<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mal-(CH2)5-(C(=O)NH(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 55

Ile Cys Val Trp Gln Asp Trp Gly Ala His Arg Cys Thr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2)5-Mal)
<220> FEATURE:
<223> OTHER INFORMATION: C-term NH2

<400> SEQUENCE: 56

Ile Cys Val Trp Gln Asp Trp Gly Ala His Arg Cys Thr Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-CH2(OCH2CH2)2NH(C(=O)-(CH2)5-Mal)
<220> FEATURE:
<223> OTHER INFORMATION: C-term NH2
```

```
<400> SEQUENCE: 57

Ile Cys Val Trp Gln Asp Trp Gly Ala His Arg Cys Thr Lys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (CH2CH2O)nC(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 58

Ile Cys Val Trp Gln Asp Trp Gly Ala His Arg Cys Thr
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-C(=O)-(CH2CH2O)n
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 59

Ile Cys Val Trp Gln Asp Trp Gly Ala His Arg Cys Thr Lys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
```

```
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 60

Ile Cys Val Trp Gln Asp Trp Gly Ala His Arg Cys Thr Lys
1               5                   10

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (19)..(19)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 61

Ile Cys Val Trp Gln Asp Trp Gly Ala His Arg Cys Thr Gly Gly
1               5                   10                  15

Gly Gly Lys

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (8)..(18)
<223> OTHER INFORMATION: Disulfide bond
<220> FEATURE:
<221> NAME/KEY: MOD_RES
<222> LOCATION: (10)..(10)
<223> OTHER INFORMATION: (1Me)Trp
<220> FEATURE:
<223> OTHER INFORMATION: C-term NH2
```

```
<220> FEATURE:
<223> OTHER INFORMATION: See specification as filed for detailed
      description of substitutions and preferred embodiments

<400> SEQUENCE: 62

Lys Gly Gly Gly Gly Ile Cys Val Trp Gln Asp Trp Gly Ala His
1               5                   10                  15

Arg Cys Thr

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: (1Me)Trp
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 63

Lys Ile Cys Val Trp Gln Asp Trp Gly Ala His Arg Cys Thr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2CH2O)n-R)
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 64

Ile Cys Val Trp Gln Asp Trp Gly Ala His Arg Cys Thr Lys
1               5                   10
```

```
<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      (CH2CH2O)n-R)
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 65

Ile Cys Val Trp Gln Asp Trp Gly Ala His Arg Cys Thr Lys
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2)m-C(=O)-(CH2CH2O)n-R)
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 66

Ile Cys Val Trp Gln Asp Trp Gly Ala His Arg Cys Thr Lys
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2)m-C(=O)-(CH2)j(CH2CH2O)n-R)
<220> FEATURE:
<223> OTHER INFORMATION: C-term NH2

<400> SEQUENCE: 67

Ile Cys Val Trp Gln Asp Trp Gly Ala His Arg Cys Thr Lys
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: misc_feature
<222> LOCATION: (13)..(14)
<223> OTHER INFORMATION: Residues at these positions are linked by an
      AEEAc moiety
<220> FEATURE:
<221> NAME/KEY: MOD_RES
<222> LOCATION: (14)..(14)
<223> OTHER INFORMATION: Lys-(C(=O)-(CH2)5-Mal)
<220> FEATURE:
<223> OTHER INFORMATION: C-term NH2

<400> SEQUENCE: 68

Ile Cys Val Trp Gln Asp Trp Gly Ala His Arg Cys Thr Lys
1               5                   10

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 69

His His His His His His
1               5

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(4)
<223> OTHER INFORMATION: Any independently selected amino acid or amino
      acid analog
<220> FEATURE:
<221> NAME/KEY: MOD_RES
<222> LOCATION: (5)..(5)
<223> OTHER INFORMATION: Trp or analog of Trp
<220> FEATURE:
<221> NAME/KEY: MOD_RES
<222> LOCATION: (8)..(8)
<223> OTHER INFORMATION: Trp or analog of Trp
<220> FEATURE:
<221> NAME/KEY: MOD_RES
<222> LOCATION: (10)..(14)
<223> OTHER INFORMATION: Any independently selected amino acid or amino
      acid analog
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 70

Xaa Xaa Xaa Xaa Xaa Gln Asp Xaa Gly Xaa Xaa Xaa Xaa Xaa Xaa
1               5                   10                  15

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (2)..(3)
<223> OTHER INFORMATION: This region may encompass 1 to 2 residues,
      wherein some positions may be absent
<220> FEATURE:
<221> NAME/KEY: misc_feature
<222> LOCATION: (4)..(14)
<223> OTHER INFORMATION: Disulfide bond
<220> FEATURE:
<221> NAME/KEY: MOD_RES
<222> LOCATION: (6)..(6)
<223> OTHER INFORMATION: Independently selected from Trp or analogs of
      Trp
<220> FEATURE:
<221> NAME/KEY: MOD_RES
<222> LOCATION: (9)..(9)
<223> OTHER INFORMATION: Independently selected from Trp or analogs of
      Trp
<220> FEATURE:
<221> NAME/KEY: MOD_RES
<222> LOCATION: (11)..(11)
<223> OTHER INFORMATION: His, Ala or an analog of Ala, Phe, Trp or an
      analog of Trp
```

<220> FEATURE:
<221> NAME/KEY: MOD_RES
<222> LOCATION: (15)..(17)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a C-term -OH of any of the L-Thr, D-Thr,
      Ile, Val, Gly, Ala or Asn is optionally replaced by a second
      blocking moiety
<220> FEATURE:
<221> NAME/KEY: misc_feature
<222> LOCATION: (15)..(17)
<223> OTHER INFORMATION: This region may encompass 1 to 3 residues,
      wherein some positions may be absent
<220> FEATURE:
<221> NAME/KEY: MOD_RES
<222> LOCATION: (18)..(18)
<223> OTHER INFORMATION: Any amino acid
<220> FEATURE:
<223> OTHER INFORMATION: See specification as filed for detailed
      description of substitutions and preferred embodiments

<400> SEQUENCE: 71

Xaa Xaa Xaa Cys Val Xaa Gln Asp Xaa Gly Xaa His Arg Cys Xaa Xaa
1               5                   10                  15

Xaa Xaa

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Ile or Gly
<220> FEATURE:
<221> NAME/KEY: MOD_RES
<222> LOCATION: (3)..(3)
<223> OTHER INFORMATION: Ile or Cys
<220> FEATURE:
<221> NAME/KEY: MOD_RES
<222> LOCATION: (4)..(4)
<223> OTHER INFORMATION: Val or Cys
<220> FEATURE:
<221> NAME/KEY: MOD_RES
<222> LOCATION: (5)..(5)
<223> OTHER INFORMATION: Val, Tyr, Trp, 2-Nal, 1-Nal, 2-Igl, Dht, Bpa,
      Bta, 5f-Trp, 5-methyl-Trp, 1-methyl-Trp, 1-formyl-Trp or
      1-methyoxy-Trp
<220> FEATURE:
<221> NAME/KEY: MOD_RES
<222> LOCATION: (6)..(6)
<223> OTHER INFORMATION: Gln, Trp, 6f-Trp or 5f-Trp
<220> FEATURE:
<221> NAME/KEY: MOD_RES
<222> LOCATION: (7)..(7)
<223> OTHER INFORMATION: Asp or Gln
<220> FEATURE:
<221> NAME/KEY: MOD_RES
<222> LOCATION: (8)..(8)
<223> OTHER INFORMATION: Trp, Asp or 5f-Trp
<220> FEATURE:
<221> NAME/KEY: MOD_RES
<222> LOCATION: (9)..(9)
<223> OTHER INFORMATION: Gly, Trp, 6f-Trp or 5f-Trp
<220> FEATURE:
<221> NAME/KEY: MOD_RES
<222> LOCATION: (10)..(10)
<223> OTHER INFORMATION: His, Ala, 2-Abu or Gly

```
<220> FEATURE:
<221> NAME/KEY: MOD_RES
<222> LOCATION: (11)..(11)
<223> OTHER INFORMATION: His or Ala
<220> FEATURE:
<221> NAME/KEY: MOD_RES
<222> LOCATION: (12)..(12)
<223> OTHER INFORMATION: Arg or His
<220> FEATURE:
<221> NAME/KEY: MOD_RES
<222> LOCATION: (13)..(13)
<223> OTHER INFORMATION: Cys or Arg
<220> FEATURE:
<221> NAME/KEY: MOD_RES
<222> LOCATION: (14)..(14)
<223> OTHER INFORMATION: Thr, D-Thr or Cys
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 72

Xaa Xaa Xaa Xaa Xaa Xaa Xaa Xaa Xaa Xaa Xaa Xaa Xaa Xaa Xaa
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 73

Xaa Ile Cys Val Trp Gln Asp Trp Gly Ala His Arg Cys Ile Xaa
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 74

Xaa Ile Cys Val Trp Gln Asp Trp Gly Ala His Arg Cys Ile Xaa
1               5                   10                  15
```

DOSING REGIMENS AND RELATED COMPOSITIONS AND METHODS

CROSS REFERENCE TO RELATED APPLICATIONS

The present application is the National Stage of International Application No. PCT/US18/26753, filed Apr. 9, 2018, which claims priority to U.S. Provisional Application No. 62/485,343 filed Apr. 13, 2017, and to U.S. Provisional Application No. 62/483,295 filed Apr. 7, 2017, the entire contents of all of which are hereby incorporated by reference in their entirety.

SEQUENCE LISTING

The present specification makes reference to a Sequence Listing (submitted electronically as a .txt file named 2008575-0384_Sequence_Listing.txt) on Apr. 23, 2021. The .txt file was generated on May 18, 2018, and is 40,760 bytes in size. The entire contents of the Sequence Listing are herein incorporated by reference.

BACKGROUND

Complement is a system consisting of more than 30 plasma and cell-bound proteins that plays a significant role in both innate and adaptive immunity. The proteins of the complement system act in a series of enzymatic cascades through a variety of protein interactions and cleavage events. Complement activation occurs via three main pathways: the antibody-dependent classical pathway, the alternative pathway, and the mannose-binding lectin (MBL) pathway. Inappropriate or excessive complement activation is an underlying cause or contributing factor to a number of serious diseases and conditions, and considerable effort has been devoted over the past several decades to exploring various complement inhibitors as therapeutic agents.

SUMMARY

In some aspects, the invention provides and/or relates to certain long-acting compstatin analogs. For example, the invention provides and/or relates to such long-acting compstatin analogs, compositions comprising them, and methods of making, identifying, characterizing, and/or using them. In some aspects, the invention provides and/or relates to a physiologically acceptable composition comprising a long-acting compstatin analog. In some aspects, the invention provides and/or relates to a pharmaceutical grade composition comprising a long-acting compstatin analog. Among other things, in some aspects, the present disclosure describes particularly useful long-acting compstatin analogs and, furthermore provides particular doses, dose formats, dosing regimens, unit dose compositions, and other technologies relating to administration of long-acting compstatin analogs to human subjects, for example to particular human subjects e.g., suffering from and/or susceptible to one or more certain diseases, disorders or conditions.

In some aspects, the invention provides methods of treating a subject in need of treatment for a complement-mediated disorder, which methods may comprise administering a long-acting compstatin analog to the subject using particular doses, dose formats (e.g., unit dose compositions and/or particular formulations) and/or dosing regimens (e.g., routes of administration, timing of doses, etc., in some embodiments as determined to be particularly desirable for treatment of certain diseases, disorders, or conditions).

In some embodiments, a complement-mediated disorder to be treated in accordance with the present disclosure is paroxysmal nocturnal hemoglobinuria (PNH), atypical hemolytic uremic syndrome (aHUS), or another disorder associated with complement-mediated hemolysis. In some embodiments the disorder is ischemia/reperfusion (I/R) injury (e.g., due to myocardial infarction, thromboembolic stroke, or surgery. In some embodiments, the disorder is trauma. In some embodiments, the disorder is transplant rejection. In some embodiments the disorder is a chronic respiratory disorder, e.g., asthma or COPD.

All articles, books, patent applications, patents, other publications, websites, and databases mentioned in this application are incorporated herein by reference. In the event of a conflict between the specification and any of the incorporated references the specification (including any amendments thereto) shall control. Unless otherwise indicated, art-accepted meanings of terms and abbreviations are used herein. The practice of certain aspects described herein may employ conventional techniques of molecular biology, cell culture, recombinant nucleic acid (e.g., DNA) technology, immunology, and/or nucleic acid and polypeptide synthesis, detection, manipulation, and quantification, etc., that are within the ordinary skill of the art. See, e.g., Ausubel, F., et al., (eds.), Current Protocols in Molecular Biology, Current Protocols in Immunology, Current Protocols in Protein Science, and Current Protocols in Cell Biology, all John Wiley & Sons, N.Y., e.g., edition current as of January 2010 or later; Sambrook, Russell, and Sambrook, Molecular Cloning: A Laboratory Manual, $3^{rd}$ ed., Cold Spring Harbor Laboratory Press, Cold Spring Harbor, 2001 or $4^{th}$ ed, 2012.

DETAILED DESCRIPTION OF CERTAIN EMBODIMENTS

I. Definitions

Figure 1:
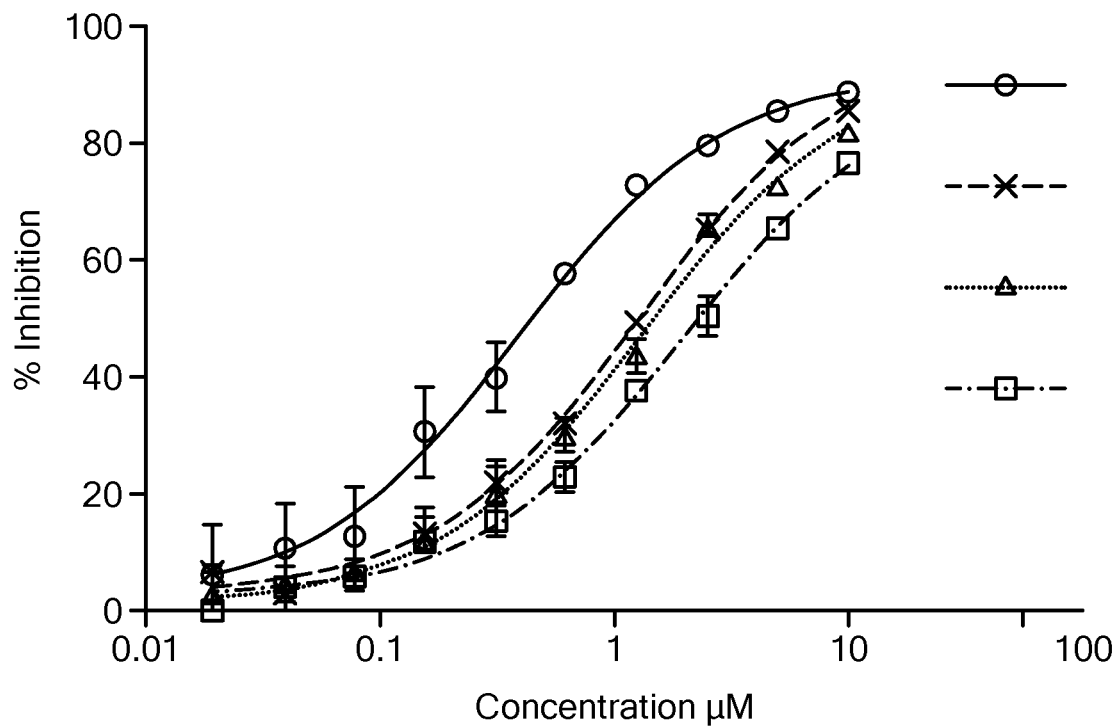
FIG. 1 is a plot that shows percent complement activation inhibiting activity of compstatin analog CA28 (SEQ ID NO: 28) and three long-acting compstatin analogs (CA28-1, CA28-2, CA28-3), as a function of peptide concentration (μM). Inhibition of complement activation was tested in vitro using a classical complement inhibition assay. The plot shows values obtained by averaging the results of two sets of measurements. CA28 (circles; red), CA28-1 (crosses (x); blue); CA28-2 (triangles, green), CA28-3 (squares (purple).

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value).

A "complement component" or "complement protein" is a protein that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, and properdin. Components of the lectin pathway include, e.g., MBL2, MASP-1, and MASP-2. Complement components also include cell-bound receptors for soluble complement components, wherein such receptor mediates one or more biological activities of such soluble complement component following binding of the soluble complement component. Such receptors include, e.g., C5a receptor (C5aR), C3a receptor (C3aR), Complement Receptor 1 (CR1), Complement Receptor 2 (CR2), Complement Receptor 3 (CR3, also known as CD45), etc. It will be appreciated that the term "complement component" is not intended to include those molecules and molecular structures that serve as "triggers" for complement activation, e.g., antigen-antibody complexes, foreign structures found on microbial or artificial surfaces, etc.

A "complement-mediated disorder" is any disorder in which complement activation is known or suspected of being a contributing and/or at least partially causative factor in at least some subjects suffering from the disorder, e.g., disorders in which complement activation results in tissue damage. Non-limiting examples of complement-mediated disorders include, but are not limited to, (i) various disorders characterized by hemolysis or hemolytic anemia such as atypical hemolytic uremic syndrome, warm antibody autoimmune hemolytic anemia, cold agglutinin disease, paroxysmal nocturnal hemoglobinuria, transfusion reactions; (ii) transplant rejection (e.g., hyperacute or acute transplant rejection) or transplant dysfunction; (iii) disorders involving ischemia/reperfusion injury such as trauma, surgery (e.g., aneurysm repair), myocardial infarction, ischemic stroke; (iv) disorders of the respiratory system such as asthma and chronic obstructive pulmonary disease (COPD); (v) arthritis, e.g., rheumatoid arthritis; (vi) ocular disorders such as age-related macular degeneration (AMD), diabetic retinopathy, glaucoma, and uveitis. "Disorder" is used interchangeably herein with "disease", "condition", and similar words to refer to any impairment of health or state of abnormal functioning of an organism, e.g., any state in which medical and/or surgical management is indicated or for which a subject appropriately seeks medical and/or surgical attention. It should also be understood that the listing of a particular disorder within a particular category is for convenience and is not intended to limit the invention. It will be understood that certain disorders could appropriately be listed in multiple categories.

A "complement regulatory protein" (CRP) is a protein involved in regulating complement activity. A complement regulatory protein may down-regulate complement activity by, e.g., inhibiting complement activation or by inactivating or accelerating decay of one or more activated complement proteins. Examples of complement regulatory proteins include C1 inhibitor, C4 binding protein, clusterin, vitronectin, CFH, factor I, and the cell-bound proteins CD46, CD55, CD59, CR1, CR2, and CR3.

"Isolated", as used herein, means 1) separated from at least some of the components with which it is usually associated in nature; 2) prepared or purified by a process that involves the hand of man; and/or 3) not occurring in nature, e.g., present in an artificial environment. In general, unless otherwise indicated or clearly evident, any entity, product, agent, composition, etc., may be deemed "isolated", if desired.

"Linked", as used herein with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linking moiety" or "linking portion", the linkage between the two linked moieties is indirect, and typically each of the linked moieties is covalently bonded to the linking moiety. Two moieties may be linked using a "linker". A linker can be any suitable moiety that reacts with the entities to be linked within a reasonable period of time, under conditions consistent with stability of the entities (portions of which may be protected as appropriate, depending upon the conditions), and in sufficient amount, to produce a reasonable yield. Typically the linker will contain at least two functional groups, one of which reacts with a first entity and the other of which reacts with a second entity. It will be appreciated that after the linker has reacted with the entities to be linked, the term "linker" may refer to the part of the resulting structure that originated from the linker, or at least the portion that does not include the reacted functional groups. A linking moiety may comprise a portion that does not participate in a bond with the entities being linked, and whose main purpose may be to spatially separate the entities from each other. Such portion may be referred to as a "spacer".

As used herein, "physiological conditions" refers to a set of conditions such as temperature, salt concentration, pH that at least in part mimic those conditions as typically found in a living subject, e.g., a mammalian subject. In some aspects, physiological conditions refer to conditions in an aqueous medium, e.g., a medium comprising at least 90%, 95%, 96%, 97%, 97%, 99%, or about 100% water on a volume/volume basis. In some embodiments other liquids, if present, do not substantially affect protein secondary or tertiary structure. In some embodiments physiological conditions at least in part mimic those found in a body fluid such as blood or extracellular fluid, e.g., interstitial fluid, e.g., of a mammalian subject. A variety of physiological conditions useful for, e.g., in vitro assays, are known in the art. Generally, a medium under physiological conditions contains a physiological concentration of salt, e.g., sodium chloride. In some embodiments a physiological concentration of salt refers to a concentration ranging from about 250 mOsm/L to about 350 mOsm/L, e.g., about 275 mOsm/L to about 325 mOsm/L, e.g., about 300 mOsm/L. In some embodiments physiological conditions are approximately isotonic to a body fluid, e.g., blood or extracellular fluid, e.g., interstitial fluid. In some embodiments physiological conditions include a pH ranging from about 6.5 to about 7.8, e.g., about 7.0 to about 7.5. In some embodiments a physiological medium comprises a buffer substance that helps maintain the pH of the medium within a physiological range. In some embodiments physiological conditions comprise conditions such that a typical mammalian protein, e.g., a protein typically found in a body fluid, such as blood or extracellular fluid, substantially retains the secondary and, if applicable, tertiary structure that such protein has in the body fluid in which it is normally found. In some embodiments components of a physiological medium are typically substantially non-toxic to mammalian cells at the concentration at which they are present in the physiological medium. A variety of physiological media (sometimes termed "buffers") are listed in various standard references, such as those cited above (e.g., Sambrook, et al., Protocols series). In some embodiments a physiological temperature ranges from about 25 degrees C. to about 38 degrees C., e.g., from about 30 degrees C. to about 37 degrees C., e.g., 35 degrees C. to 37 degrees C.

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328 and/or below. The polypeptide may be acetylated, e.g., at the N-terminus and/or amidated, e.g., at the C-terminus.

The term "purified", as used herein, refers to substances that have been separated from at least some or most of the components with which they are associated in nature or when originally generated or with which they were associated prior to purification. In general, such purification involves action of the hand of man. Purified agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate.

"Recombinant host cells", "host cells", and other such terms, denote prokaryotic or eukaryotic cells or cell lines that contain an exogenous nucleic acid (typically DNA) such as an expression vector comprising a nucleic acid that encodes a polypeptide of interest. It will be understood that such terms include the descendants of the original cell(s) into which the vector or other nucleic acid has been introduced. Appropriate host cells include any of those routinely used in the art for expressing polynucleotides (e.g., for purposes of producing polypeptide(s) encoded by such polynucleotides) including, for example, prokaryotes, such as *E. coli* or other bacteria such as species of *Escherichia; Lactobacillus, Bacillus* (e.g., *B subtilis*), *Salmonella Pseudomonas, Streptomyces, Staphylococcus*, etc.; and eukaryotes, including for example, fungi, such as yeast (e.g., *Pichia* (e.g., *Pichia pastoris*), *Kluyveromyces*, such as *K. lactis, Hansenula*, e.g. *H. polymorpha*). Examples of other fungal cells are cells of filamentous fungi, e.g. *Aspergillus* spp., *Neurospora* spp., *Fusarium* spp. or *Trichoderma* spp., e.g., strains of *A. oryzae, A. nidulans* or *A. niger*; insect cells (e.g., Sf9), plant cells, and animal cells, e.g., mammalian cells such as CHO, R1.1, B-W, L-M, African Green Monkey Kidney cells (e.g. COS-1, COS-7, BSC-1, BSC-40 and BMT-10), and cultured human cells. Also encompassed are genetically modified cells in genetically modified (e.g., transgenic) plants or animals, wherein a recombinant polypeptide is produced by at least some such cells. A polypeptide may be secreted in milk, harvested from plant material, etc. The exogenous nucleic acid may be stably maintained as an episome such as a plasmid or may at least in part be integrated into the host cell's genome, optionally after being copied or reverse transcribed. Terms such as "host cells", etc., are also used to refer to cells or cell lines that can be used as recipients for an exogenous nucleic acid, prior to introduction of the nucleic acid. A "recombinant polynucleotide" generally is a polynucleotide that contains nucleic acid sequences that are not found joined directly to one another in nature. For example, the nucleic acid sequences may occur in different genes or different species or one or more of the sequence(s) may be a variant of a naturally occurring sequence or may at least in part be an artificial sequence that is not homologous to a naturally occurring sequence. A "recombinant polypeptide" generally is a polypeptide that is at least in part produced by transcription and translation of an exogenous nucleic acid by a recombinant host cell or by a cell-free in vitro expression system and/or that contains amino acid sequences that are not found joined directly to one another in nature. In the latter case, the recombinant polypeptide may be referred to as a "chimeric polypeptide". The amino acid sequences in a chimeric polypeptide may, for example, occur in different genes or in different species or one or more of the sequence(s) may be a variant of a naturally occurring sequence or may at least in part be an artificial sequence that is not identical or in some embodiments is not homologous to a naturally occurring sequence over a substantial portion of the length. It will be understood that a chimeric polypeptide may comprise two or more polypeptides. For example, first and second polypeptides A and B of a chimeric polypeptide may be directly linked (A-B or B-A) or may be separated by a third polypeptide portion C (A-C-B or B-C-A). In some embodiments, portion C represents a polypeptide linker which may, for example, comprise multiple glycine and/or serine residues or any of a variety of other amino acids. In some embodiments, two or more polypeptides may be linked by non-polypeptide linker(s). "Recombinant" as used herein encompasses in certain embodiments polypeptides produced by joining (e.g., chemically conjugating, enzymatically conjugating), shorter recombinant polypeptides that may be produced in recombinant host cells. In some embodiments a recombinant polypeptide may comprise a signal sequence that directs secretion of the polypeptide or a sequence that directs the expressed polypeptide to a specific compartment or organelle. Suitable sequences are known in the art. Appropriate sequences for a host cell type of interest (e.g., bacterial, fungal, mammalian, plant, etc.) may be selected. A signal sequence may be located at or near (e.g., within up to 10-50 amino acids of) the N-terminus or C-terminus in some embodiments. In some embodiments a polypeptide comprises a tag. A tag may be useful to facilitate detection and/or purification of a protein that contains it. Examples of tags include polyhistidine-tag (e.g., 6×-His tag (SEQ ID NO: 69)), glutathione-S-transferase, maltose binding protein, NUS tag, SNUT tag, Strep tag, epitope tags such as V5, HA, Myc, or FLAG. In some embodiments a protease cleavage site is located in the region between the tag and the polypeptide, allowing the polypeptide to be separated from the tag by exposure to the protease. In some embodiments a polynucleotide that encodes a recombinant polypeptide is at least in part codon optimized for expression in a host cell of interest (e.g., bacterial, fungal, mammalian, plant, etc.). A tag may be located at or near (e.g., within up to 10-50 amino acids of) the N- or C-terminus of a polypeptide in various embodiments. A recombinant polypeptide may be isolated, purified, etc., using any of a variety of methods. See, e.g., Sambrook, Protocols series, or other standard references. Methods of use may include, e.g., dialysis (e.g., using membranes having defined pore size), chromatography, precipitation, gel purification, or affinity-based methods that may, in some embodiments, utilize a tag or a specific binding reagent such as an antibody.

"Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds, N-hydroxysuccinimide esters, maleimides, sulfhydryls, and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989, and Hermanson, G., *Bioconjugate Techniques*, $2^{nd}$ ed., Academic Press, San Diego, 2008).

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant, epitope, binding pocket or cleft, recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc.). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. In some embodiments, the affinity (as measured by the equilibrium dissociation constant, Kd) of two molecules that exhibit specific binding is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions.

A "subject" treated according to the instant invention is typically a human, a non-human primate, or a lower animal (e.g., a mouse or rat), which expresses or contains at least some primate (e.g., human) complement component C3 and, optionally, one or more additional primate complement component(s). In some embodiments the subject is male. In some embodiments the subject is female. In some embodiments the subject is an adult, e.g., a human at least 18 years of age, e.g., between 18 and 100 years of age. In some embodiments, a human subject is at least 12 years of age. In some embodiments a subject is an adult, e.g., a human at least 18 years of age, e.g., between 18 and 100 years of age. In some embodiments a subject is at least 40, 45, 50, 55, 60, 65, 70, 75, or 80 years of age. In some embodiments the subject is a child, e.g., a human between 0 and 4 years of age, or between 5 and 11 years of age.

"Treating", as used herein in regard to treating a subject, refers to providing treatment, i.e., providing any type of medical or surgical management of a subject. The treatment can be provided in order to reverse, alleviate, inhibit the progression of, prevent or reduce the likelihood of a disease, or in order to reverse, alleviate, inhibit or prevent the progression of, prevent or reduce the likelihood of one or more symptoms or manifestations of a disease. "Prevent" refers to causing a disease or symptom or manifestation of a disease not to occur for at least a period of time in at least some individuals. Treating can include administering a compound or composition to the subject following the development of one or more symptoms or manifestations indicative of a disease, e.g., in order to reverse, alleviate, reduce the severity of, and/or inhibit or prevent the progression of the disease and/or to reverse, alleviate, reduce the severity of, and/or inhibit or one or more symptoms or manifestations of the disease. A compound or composition can be administered to a subject who has developed a disease, or is at increased risk of developing the disease relative to a member of the general population. A compound or composition can be administered to a subject who has developed a disease and is at increased risk of developing one or more particular symptoms or manifestations of the disease or an exacerbation of the disease relative to other individuals diagnosed with the disease, or relative to the subject's typical or average risk for such symptom or manifestation or exacerbation. For example, the subject may have been exposed to a "trigger" that places the subject at increased risk (e.g., temporarily increased risk) of experiencing an exacerbation. A compound or composition can be administered prophylactically, i.e., before development of any symptom or manifestation of the disease. Typically in this case the subject will be at risk of developing the disease, e.g., relative to a member of the general population, optionally matched in terms of age, sex, and/or other demographic variable(s).

A "vector" may be any of a variety of nucleic acid molecules, viruses, or portions thereof that are capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses, vaccinia virus and other poxviruses, herpesviruses (e.g., herpes simplex virus), and others. Baculovirus are of use, e.g., in insect cells. A wide range of plant viral vectors are known and include, e.g., those based on or comprising Cauliflower Mosaic Virus, Tobacco Mosaic Virus, or one or more genetic elements thereof (e.g., Cauliflower Mosaic Virus 35S promoter). Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a prokaryotic (bacterial) or eukaryotic (e.g., fungal, plant, mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1 alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), e.g., (a U6, H1, 7SK or tRNA promoter or a functional variant thereof) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), e.g., a promoter for transcription of ribosomal RNA (other than 5S rRNA) or a functional variant thereof is used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. In some embodiments, regulatable (e.g., inducible or repressible) expression control element(s), e.g., a regulatable promoter, is/are used so that expression can be regulated, e.g., turned on or increased or turned off or decreased. In some embodiments a vector may comprise a polynucleotide sequence that encodes a polypeptide, wherein the polynucleotide sequence is positioned in frame with a nucleic acid inserted into the vector so that an N- or C-terminal fusion is created. In some embodiments a polypeptide encoded by the polynucleotide sequence may comprise a signal sequence (which directs secretion of a protein) or a sequence that directs the expressed protein to a specific organelle or location in the cell such as the nucleus or mitochondria. In some embodiments a polypeptide comprises a tag. A tag may be useful to facilitate detection and/or purification of a protein that contains it. Examples of tags include polyhistidine-tag (e.g., 6×-His tag (SEQ ID NO: 69)), glutathione-S-transferase, maltose binding protein, NUS tag, SNUT tag, Strep tag, epitope tags such as V5, HA, Myc, or FLAG. In some embodiments a protease cleavage site is located in the region between the protein encoded by the inserted nucleic acid and the polypeptide, allowing the polypeptide to be removed by exposure to the protease. Vectors may be introduced into host cells using methods known in the art. One of ordinary skill will select an appropriate method based, e.g., on the vector, cell type, etc. Examples of suitable methods include, e.g., calcium phosphate-mediated transfection, transfection with any of a variety of commercially available reagents, e.g., lipid-based or non-lipid based, such as FuGENE, Lipofectamine, TurboFect; electroporation; microparticle bombardment, etc. Such methods are explained in detail in standard references such as Sambrook, Protocols series, and others.

As used herein the term "aliphatic" denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-30 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "alkanoyl" refers to an optionally substituted straight or branched aliphatic acyclic residue having about 1 to 10 carbon atoms (and all combinations and subcombinations of ranges and specific number of carbon atoms) therein, e.g., from about 1 to 7 carbon atoms which, as will be appreciated, is attached to a terminal C=O group with a single bond (and may also be referred to as an "acyl group"). Alkanoyl groups include, but are not limited to, formyl, acetyl, propionyl, butyryl, isobutyryl, pentanoyl, isopentanoyl, 2-methyl-butyryl, 2,2-dimethoxypropionyl, hexanoyl, heptanoyl, octanoyl, and the like, and for purposes of the present invention a formyl group is considered an alkanoyl group. "Lower alkanoyl" refers to an optionally substituted straight or branched aliphatic acyclic residue having about 1 to about 5 carbon atoms (and all combinations and subcombinations of ranges and specific number of carbon atoms). Such groups include, but are not limited to, formyl, acetyl, propionyl, butyryl, isobutyryl, pentanoyl, isopentanoyl, etc.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and having from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

The term "cyclic ring system" refers to an aromatic or non-aromatic, partially unsaturated or fully saturated, 3- to 10-membered ring system, which includes single rings of 3 to 8 atoms in size and bi- and tri-cyclic ring systems which may include aromatic 5- or 6-membered aryl or aromatic heterocyclic groups fused to a non-aromatic ring. These heterocyclic rings include those having from 1 to 3 heteroatoms independently selected from the group consisting of oxygen, sulfur, and nitrogen. In certain embodiments, the term heterocyclic refers to a non-aromatic 5-, 6-, or 7-membered ring or a polycyclic group wherein at least one ring atom is a heteroatom selected from the group consisting of O, S, and N, including, but not limited to, a bi- or tri-cyclic group, comprising fused six-membered rings having between one and three heteroatoms independently selected from the group consisting of the oxygen, sulfur, and nitrogen. In some embodiments, "cyclic ring system" refers to a cycloalkyl group which, as used herein, refers to groups having 3 to 10, e.g., 4 to 7 carbon atoms. Cycloalkyls include, but are not limited to cyclopropyl, cyclobutyl, cyclopentyl, cyclohexyl, cycloheptyl and the like, which, is optionally substituted. In some embodiments, "cyclic ring system" refers to a cycloalkenyl or cycloalkynyl moiety, which is optionally substituted.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

II. Complement System

In order to facilitate understanding of the invention, and without intending to limit the invention in any way, this section provides an overview of complement and its pathways of activation. Further details are found, e.g., in *Kuby Immunology*, 6$^{th}$ ed., 2006; Paul, W. E., *Fundamental Immunology*, Lippincott Williams & Wilkins; 6$^{th}$ ed., 2008; and Walport M J., Complement. First of two parts. *N Engl J Med.*, 344(14): 1058-66, 2001.

Complement is an arm of the innate immune system that plays an important role in defending the body against infectious agents. The complement system comprises more than 30 serum and cellular proteins that are involved in three major pathways, known as the classical, alternative, and lectin pathways. The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils.

The alternative pathway is initiated by and amplified at, e.g., microbial surfaces and various complex polysaccharides. In this pathway, hydrolysis of C3 to C3(H2O), which occurs spontaneously at a low level, leads to binding of factor B, which is cleaved by factor D, generating a fluid phase C3 convertase that activates complement by cleaving C3 into C3a and C3b. C3b binds to targets such as cell surfaces and forms a complex with factor B, which is later cleaved by factor D, resulting in a C3 convertase. Surface-bound C3 convertases cleave and activate additional C3 molecules, resulting in rapid C3b deposition in close proximity to the site of activation and leading to formation of additional C3 convertase, which in turn generates additional C3b. This process results in a cycle of C3 cleavage and C3 convertase formation that significantly amplifies the response. Cleavage of C3 and binding of another molecule of C3b to the C3 convertase gives rise to a C5 convertase. C3 and C5 convertases of this pathway are regulated by host cell molecules CR1, DAF, MCP, CD59, and fH. The mode of action of these proteins involves either decay accelerating activity (i.e., ability to dissociate convertases), ability to serve as cofactors in the degradation of C3b or C4b by factor I, or both. Normally the presence of complement regulatory proteins on host cell surfaces prevents significant complement activation from occurring thereon.

The C5 convertases produced in both pathways cleave C5 to produce C5a and C5b. C5b then binds to C6, C1, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The lectin complement pathway is initiated by binding of mannose-binding lectin (MBL) and MBL-associated serine protease (MASP) to carbohydrates. The MB 1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase described above.

Complement activity is regulated by various mammalian proteins referred to as complement control proteins (CCPs) or regulators of complement activation (RCA) proteins (U.S. Pat. No. 6,897,290). These proteins differ with respect to ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b:C4b receptor), complement receptor type 2 (CR2), membrane cofactor protein (MCP; CD46), decay-accelerating factor (DAF), complement factor H (fH), and C4b-binding protein (C4 bp). CD59 is a membrane-bound complement regulatory protein unrelated structurally to the CCPs. Complement regulatory proteins normally serve to limit complement activation that might otherwise occur on cells and tissues of the mammalian, e.g., human host. Thus, "self" cells are normally protected from the deleterious effects that would otherwise ensue were complement activation to proceed on these cells. Deficiencies or defects in complement regulatory protein(s) are involved in the pathogenesis of a variety of complement-mediated disorders, e.g., as discussed herein.

III. Compstatin Analogs

Compstatin is a cyclic peptide that binds to C3 and inhibits complement activation. U.S. Pat. No. 6,319,897 describes a peptide having the sequence Ile-[Cys-Val-Val-Gln-Asp-Trp-Gly-His-His-Arg-Cys]-Thr (SEQ ID NO: 1), with the disulfide bond between the two cysteines denoted by brackets. It will be understood that the name "compstatin" was not used in U.S. Pat. No. 6,319,897 but was subsequently adopted in the scientific and patent literature (see, e.g., Morikis, et al., *Protein Sci.*, 7(3):619-27, 1998) to refer to a peptide having the same sequence as SEQ ID NO: 2 disclosed in U.S. Pat. No. 6,319,897, but amidated at the C terminus as shown in Table 1 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32(Pt 1):28-32, 2004, Mallik, B., et al., *J. Med. Chem.*, 274-286, 2005; Katragadda, M., et al. *J. Med. Chem.*, 49: 4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 µM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

The $K_d$ of compstatin binding to C3 can be measured using isothermal titration calorimetry (Katragadda, et al., *J. Biol. Chem.*, 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra-, Katragadda 2006, supra). In certain embodiments of the invention the compstatin analog binds to C3 with a $K_d$ of between 0.1 µM and 1.0 µM, between 0.05 µM and 0.1 µM, between 0.025 µM and 0.05 µM, between 0.015 µM and 0.025 µM, between 0.01 µM and 0.015 µM, or between 0.001 µM and 0.01 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-Nal), 1-naphthylalanine (1-Nal), 2-indanylglycine carboxylic acid (2Ig1), dihydrotrpytophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH—W), 5-hydroxy-L-tryptophan (5OH—W), 6-hydroxy-L-tryptophan (6OH—W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, *J. Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyltryptophan. In certain embodiments of the invention a Trp analog (e.g., at position 4) comprising a 1-alkyl substituent, e.g., a lower alkyl (e.g., $C_1$-$C_5$) substituent is used. In certain embodiments, N($\alpha$) methyl tryptophan or 5-methyltryptophan is used. In some embodiments, an analog comprising a 1-alkanyol substituent, e.g., a lower alkanoyl (e.g., $C_1$-$C_5$) is used. Examples include 1-acetyl-L-tryptophan and L-β-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of $(X'aa)_n$-Gln-Asp-Xaa-Gly-$(X''aa)_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is (X'aa)$_n$ and the other of which is located within (X"aa)$_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used. In some embodiments a peptide is cyclized with a thioether bond, e.g., as described in PCT/US2011/052442 (WO/2012/040259). For example, in some embodiments a disulfide bond in any of the peptides is replaced with a thioether bond. In some embodiments, a cystathionine is formed. In some embodiments the cystathionine is a delta-cystathionine or a gamma-cystathionine. In some embodiments a modification comprises replacement of a Cys-Cys disulfide bond between cysteines at X'aa2 and X"aa4 in SEQ ID NO: 5 (or corresponding positions in other sequences) with addition of a $CH_2$, to form a homocysteine at X'aa2 or X"aa4, and introduction of a thioether bond, to form a cystathionine. In one embodiment, the cystathionine is a gamma-cystathionine. In another embodiment, the cystathionine is a delta-cystathionine. Another modification in accordance with the present invention comprises replacement of the disulfide bond with a thioether bond without the addition of a $CH_2$, thereby forming a lantithionine. In some embodiments a compstatin analog having a thioether in place of a disulfide bond has increased stability, at least under some conditions, as compared with the compstatin analog having the disulfide bond.

In certain embodiments, the compstatin analog is a compound that comprises a peptide having a sequence:
Xaa1-Cys-Val-Xaa2-Gln-Asp-Xaa2*-Gly-Xaa3-His-Arg-Cys-Xaa4 (SEQ ID NO: 6); wherein:
Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-NaI), 1-naphthylalanine (1-NaI), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—NH$_2$ or —NHR$^1$, wherein R is an organic moiety such as an alkyl group).

In certain embodiments of the invention blocking moiety $B^1$ is any moiety that neutralizes or reduces the positive charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:
xaa1-Cys-Val-Xaa2-Gln-Asp-Xaa2*-Gly-Xaa3-His-Arg-Cys-Xaa4 (SEQ ID NO: 7); wherein:
Xaa1 is Ile, Val, Leu, Ac-Ile, Ac-Val, Ac-Leu or a dipeptide comprising Gly-Ile or Ac-Gly-Ile;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH$_2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety B2; and the two Cys residues are joined by a disulfide bond.

In some embodiments, Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 1 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 1 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 1 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 1 contains at least one N-methyl glycine, e.g., at the position corresponding to position 8 of compstatin and/or at the position corresponding to position 13 of compstatin. In some embodiments, one or more of the compstatin analogs in Table 1 contains at least one N-methyl isoleucine, e.g., at the position corresponding to position 13 of compstatin. For example, a Thr at or near the C-terminal end of a peptide whose sequence is listed in Table 1 or any other compstatin analog sequence may be replaced by N-methyl Ile. As will be appreciated, in some embodiments the N-methylated amino acids comprise N-methyl Gly at position 8 and N-methyl Ile at position 13. In some embodiments the N-methylated amino acids comprise N-methyl Gly in a core sequence such as SEQ ID NO: 3 or SEQ ID NO: 4. In some embodiments the N-methylated amino acids comprise N-methyl Gly in a core sequence such as SEQ ID NO: 5, SEQ ID NO: 6, or SEQ ID NO: 7.

TABLE 1

| Peptide | Sequence | SEQ ID NO: | Activity over compstatin |
|---|---|---|---|
| Compstatin | H-ICVVQDWGHHRCT-CONH2 | 8 | * |
| Ac-compstatin | Ac-ICVVQDWGHHRCT-CONH2 | 9 | 3 x more |
| Ac-V4Y/H9A | Ac-ICVYQDWGAHRCT-CONH2 | 10 | 14 x more |
| Ac-V4W/H9A -OH | Ac-ICVWQDWGAHRCT-COOH | 11 | 27 x more |
| Ac-V4W/H9A | Ac-ICVWQDWGAHRCT-CONH2 | 12 | 45 x more |
| Ac-V4W/H9A/T13dT -OH | Ac-ICVWQDWGAHRCdT-COOH | 13 | 55 x more |
| Ac-V4(2-NaI)/H9A | Ac-ICV(2-NaI)QDWGAHRCT-CONH2 | 14 | 99 x more |
| Ac V4(2-NaI)/H9A -OH | Ac-ICV(2-NaI)QDWGAHRCT-COOH | 15 | 38 x more |
| Ac V4(1-NaI)/H9A -OH | Ac-ICV(1-NaI)QDWGAHRCT-COOH | 16 | 30 x more |
| Ac-V42IgI/H9A | Ac-ICV(2-IgI)QDWGAHRCT-CONH2 | 17 | 39 x more |
| Ac-V42IgI/H9A -OH | Ac-ICV(2-IgI)QDWGAHRCT-COOH | 18 | 37 x more |
| Ac-V4Dht/H9A -OH | Ac-ICVDhtQDWGAHRCT-COOH | 19 | 5 x more |
| Ac-V4(Bpa)/H9A -OH | Ac-ICV(Bpa)QDWGAHRCT-COOH | 20 | 49 x more |
| Ac-V4(Bpa)/H9A | Ac-ICV(Bpa)QDWGAHRCT-CONH2 | 21 | 86 x m0re |
| Ac-V4(Bta)/H9A -OH | Ac-ICV(Bta)QDWGAHRCT-COOH | 22 | 65 x more |
| Ac-V4(Bta)/H9A | Ac-ICV(Bta)QDWGAHRCT-CONH2 | 23 | 64 x more |
| Ac-V4W/H9(2-Abu) | Ac-ICVWQDWG(2-Abu)HRCT-CONH2 | 24 | 64 x more |
| +G/V4W/H9A +AN -OH | H-GICVWQDWGAHRCTAN-COOH | 25 | 38 x more |
| Ac-V4(5fW)/H9A | Ac-ICV(5fW)QDWGAHRCT-CONH$_2$ | 26 | 31 x more |
| Ac-V4(1-MeW)/H9A | Ac-ICV(5-methyl-W)QDWGAHRCT-CONH$_2$ | 27 | 67 x more |
| Ac-V4(1-MeW)/H9A | Ac-ICV(1-methyl-W)QDWGAHRCT-CONH$_2$ | 28 | 264 x more |
| Ac-V4W/W7(5fW)/H9A | Ac-ICVWQD(5fW)GAHRCT-CONH$_2$ | 29 | 121 x more |
| Ac-V4(5fW)/W7(5fW)/H9A | Ac-ICV(5fW)QD(5fW)GAHRCT-CONH$_2$ | 30 | NA |
| Ac-V4(5-MeW)/W7(5fW)H9A | Ac-ICV(5-methyl-W)QD(5fW)GAHRCT-CONH$_2$ | 31 | NA |
| Ac-V4(1MeW)/W7(5fW)/H9A | Ac-ICV(1-methyl-W)QD(5fW)GAHRCT-CONH$_2$ | 32 | 264 x more |
| +G/V4(6fW)/W7(6fW)H9A +N -OH | H-GICV(6fW)QD(6fW)GAHRCTN-COOH | 33 | 126 x more |
| Ac-V4(1-formyl-W)/H9A | Ac-ICV(1-formyl-W)QDWGAHRCT-CONH$_2$ | 34 | 264 x more |
| Ac-V4(5-methoxy-W)/H9A | Ac-ICV(1-methyoxy-W)QDWGAHRCT-CONH$_2$ | 35 | 76 x more |
| G/V4(5f-W)/W7(5fW)/H9A +N -OH | H-GICV(5fW)QD(5fW)GAHRCTN-COOH | 36 | 112 x more |

NA = not available

In certain embodiments of the compositions and methods of the invention the compstatin analog has a sequence selected from sequences 9-36. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In some embodiments a blocking moiety $B^1$ comprises an amino acid, which may be represented as Xaa0. In some embodiments blocking moiety $B^2$ comprises an amino acid, which may be represented as XaaN. In some embodiments blocking moiety $B^1$ and/or $B^2$ comprises a non-standard amino acid, such as a D-amino acid, N-alkyl amino acid (e.g., N-methyl amino acid). In some embodiments a blocking moiety $B^1$ and/or $B^2$ comprises a non-standard amino acid that is an analog of a standard amino acid. In some embodiments an amino acid analog comprises a lower alkyl, lower alkoxy, or halogen substituent, as compared with a standard amino acid of which it is an analog. In some embodiments a substituent is on a side chain. In some embodiments a substituent is on an alpha carbon atom. In some embodiments, a blocking moiety $B^1$ comprising an amino acid, e.g., a non-standard amino acid, further comprises a moiety $B^{1a}$. For example, blocking moiety $B^1$ may be represented as $B^{1a}$-Xaa0. In some embodiments $B^{1a}$ neutralizes or reduces a positive charge that may otherwise be present at the N-terminus at physiological pH. In some embodiments $B^{1a}$ comprises or consists of, e.g., an acyl group that, e.g., comprises between 1 and 12 carbons, e.g., between 1 and 6 carbons. In certain embodiments blocking moiety $B^{1a}$ is selected from the group consisting of: formyl, acetyl, proprionyl, butyryl, isobutyryl, valeryl, isovaleryl, etc. In some embodiments, a blocking moiety $B^2$ comprising an amino acid, e.g., a non-standard amino acid, may further comprise a moiety $B^{2a}$ For example, blocking moiety $B^2$ may be represented as XaaN-$B^{2a}$, where N represents the appropriate number for the amino acid (which will depend on the numbering used in the rest of the peptide). In some embodiments $B^{2a}$ neutralizes or reduces a negative charge that may otherwise be present at the C-terminus at physiological pH. In some embodiments $B^{2a}$ comprises or consists of a primary or secondary amine (e.g., $NH_2$). It will be understood that a blocking activity of moiety $B^{1a}$-Xaa0 and/or XaaN-$B^{2a}$ may be provided by either or both components of the moiety in various embodiments. In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid residue may be at least as important as a contribution to blocking activity. For example, in some embodiments Xaa0 and/or XaaN in $B^{1a}$-Xaa0 and/or XaaN-$B^{2a}$ may function mainly to increase affinity or activity of the compound, while $B^{1a}$ and/or $B^{2a}$ may inhibit digestion of and/or neutralize a charge of the peptide. In some embodiments a compstatin analog comprises the amino acid sequence of any of SEQ ID NOs: 5-36, wherein SEQ ID NOs: 5-36 is further extended at the N- and/or C-terminus. In some embodiments, the sequence may be represented as $B^{1a}$-Xaa0-SEQUENCE-XaaN-$B^{2a}$, where SEQUENCE represents any of SEQ ID NOs: 5-36, wherein $B^{1a}$ and $B^{2a}$ may independently be present or absent. For example, in some embodiments a compstatin analog comprises $B^{1a}$-Xaa0-X'aa1-X'aa2-X'aa3-X'aa4-Gln-Asp-Xaa-Gly-X"aa1-X"aa2-X"aa3-X"aa4-X"aa5-XaaN-$B^{2a}$ (SEQ ID NO: 70), where X'aa1-X'aa2-X'aa3-X'aa4, Xaa, X"aa1, X"aa2, X"aa3, X"aa4, and X"aa5 are as set forth above for SEQ ID NO: 5.

In some embodiments a compstatin analog comprises $B^{1a}$-Xaa0-Xaa1-Cys-Val-Xaa2-Gln-Asp-Xaa2*-Gly-Xaa3-His-Arg-Cys-Xaa4-XaaN-$B^{2a}$ (SEQ ID NO: 71), where Xaa1, Xaa2, Xaa2*, Xaa3, and Xaa4 are as set forth above for SEQ ID NO: 6 or wherein Xaa1, Xaa2, Xaa2*, Xaa3, and Xaa4 are as set forth for SEQ ID NO: 6 or SEQ ID NO: 7.

In some embodiments a compstatin analog comprises $B^{1a}$-Xaa0-Xaa1-Xaa2-Xaa3-Xaa4-Xaa5-Xaa6-Xaa7-Xaa8-Xaa9-Xaa10-Xaa11-Xaa12-Xaa13-XaaN-$B^{2a}$ (SEQ ID NO: 72) wherein Xaa1, Xaa2, Xaa3, Xaa4, Xaa5, Xaa6, Xaa7, Xaa8, Xaa9, Xaa10, Xaa11, Xaa12, and Xaa13 are identical to amino acids at positions 1-13 of any of SEQ ID NOs: 9-36.

In some embodiments Xaa0 and/or XaaN in any compstatin analog sequence comprises an amino acid that comprises an aromatic ring having an alkyl substituent at one or more positions. In some embodiments an alkyl substituent is a lower alkyl substituent. For example, in some embodiments an alkyl substituent is a methyl or ethyl group. In some embodiments a substituent is located at any position that does not destroy the aromatic character of the compound. In some embodiments a substituent is located at any position that does not destroy the aromatic character of a ring to which the substituent is attached. In some embodiments a substituent is located at position 1, 2, 3, 4, or 5. In some embodiments Xaa0 comprises an O-methyl analog of tyrosine, 2-hydroxyphenylalanine or 3-hydroxyphenylalanine. For purposes of the present disclosure, a lower case "m" followed by a three letter amino acid abbreviation may be used to specifically indicate that the amino acid is an N-methyl amino acid. For example, where the abbreviation "mGly" appears herein, it denotes N-methyl glycine (also sometimes referred to as sarcosine or Sar). In some embodiments Xaa0 is or comprises mGly, Tyr, Phe, Arg, Trp, Thr, Tyr(Me), Cha, mPhe, mVal, mIle, mAla, DTyr, DPhe, DArg, DTrp, DThr, DTyr(Me), mPhe, mVal, mIle, DAla, or DCha. For example, in some embodiments a compstatin analog comprises a peptide having a sequence $B^1$-Ile-[Cys-Val-Trp(Me)-Gln-Asp-Trp-mGly-Ala-His-Arg-Cys]-mIle-$B^2$ (SEQ ID NO: 73) or $B^1$Ile-[Cys-Val-Trp(Me)-Gln-Asp-Trp-mGly-Ala-His-Arg-Cys]-mIle-$B^2$ (SEQ ID NO: 74). The two Cys residues are joined by a disulfide bond in the active compounds. In some embodiments the peptide is acetylated at the N-terminus and/or amidated at the C-terminus. In some embodiments $B^1$ comprises $B^{1a}$-Xaa0 and/or $B^2$ comprises XaaN-$B^{2a}$, as described above. For example, in some embodiments $B^1$ comprises or consists of Gly, mGly, Tyr, Phe, Arg, Trp, Thr, Tyr(Me), mPhe, mVal, mIle, mAla, DTyr, DPhe, DTrp, DCha, DAla and $B^2$ comprises $NH_2$, e.g., a carboxy terminal —OH of mIle is replaced by $NH_2$. In some embodiments $B^1$ comprises or consists of mGly, Tyr, DTyr, or Tyr(Me) and $B^2$ comprises $NH_2$, e.g., a carboxy terminal —OH of mIle is replaced by $NH_2$. In some embodiments an Ile at position Xaa1 is replaced by Gly. Complement inhibition potency and/or C3b binding parameters of selected compstatin analogs are described in WO/2010/127336

(PCT/US2010/033345) and/or in Qu, et al., Immunobiology (2012), doi:10.1016/j.imbio.2012.06.003.

In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid or amino acid analog may be more significant than a blocking activity.

In certain embodiments of the compositions and methods of the invention the compstatin analog has a sequence as set forth in Table 1, but where the Ac— group is replaced by an alternate blocking moiety $B^1$, as described herein. In some embodiments the —$NH_2$ group is replaced by an alternate blocking moiety $B^2$, as described herein.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., Mol. Immunol., 35:160, 1998; Soulika, A. M., et al., Mol. Immunol. 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 1, e.g., SEQ ID NO: 14, 21, 28, 29, 32, 33, 34, or 36, 37, 70, 71, 72, 73, or 74 or another compstatin analog sequence disclosed herein in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, or 36, 37, 70, 71, 72, 73, or 74 or another compstatin analog sequence disclosed herein in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 1, e.g., SEQ ID NO: 14, 21, 28, 29, 32, 33, 34, or 36, or in some embodiments SEQ ID NO: 30 or 31, 37, 70, 71, 72, 73, or 74 or another compstatin analog sequence disclosed herein.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

In certain embodiments, a compstatin analog may be or comprise a cell-reactive compstatin analog. Cell-reactive compstatin analogs are compounds that comprise a compstatin analog moiety and a cell-reactive functional group that is capable of reacting with a functional group exposed at the surface of a cell, e.g., under physiological conditions, to form a covalent bond. The cell-reactive compstatin analog thus becomes covalently attached to the cell. Without wishing to be bound by any particular theory, a cell-tethered compstatin analog protects the cell from complement-mediated damage by, for example, binding to C3 (which may be in the form of $C3(H_2O)$) at the cell surface and/or in the vicinity of the cell and inhibiting C3 cleavage and activation, and/or by binding to C3b and inhibiting its deposition on the cell or participation in the complement activation cascade. In some aspects of the invention, isolated cells are contacted with a cell-reactive compstatin analog ex vivo (outside the body). In some aspects of the invention, the cells are present in an isolated tissue or organ, e.g., a tissue or organ to be transplanted into a subject. In some aspects of the invention, cells are contacted with a cell-reactive compstatin analog in vivo, by administering the cell-reactive compstatin analog to a subject. The cell-reactive compstatin analog becomes covalently attached to cells in vivo. In some aspects, the inventive approach protects cells, tissues, and/or organs from the deleterious effects of complement activation for at least two weeks, without need for retreatment during that time.

In some embodiments, the invention provides and/or utilizes compstatin analogs comprising a targeting moiety that binds non-covalently to a target molecule present at the surface of cells or tissues or to an extracellular substance not attached to cells or tissues. Such compstatin analogs are referred to herein as "targeted compstatin analogs"). Often the target molecule is a protein or carbohydrate attached to the cell membrane and exposed at the cell surface. The targeting moiety targets the compstatin analog to a cell, tissue, or location susceptible to complement activation. In some aspects of the invention, isolated cells are contacted with a targeted compstatin analog ex vivo (outside the body). In some aspects of the invention, the cells are present in an isolated tissue or organ, e.g., a tissue or organ to be transplanted into a subject. In some aspects of the invention, a targeted compstatin analog is administered to a subject and becomes non-covalently attached to a cell, tissue, or extracellular substance in vivo. In some aspects, the inventive approach protects cells, tissues, and/or organs from the deleterious effects of complement activation for at least two weeks, without need for retreatment during that time. In some embodiments, a targeted compstatin analog comprises both a targeting moiety and a cell-reactive moiety. The targeting moiety targets the compstatin analog, e.g., to a particular cell type, by binding non-covalently to a molecule on such cells. The cell-reactive moiety then binds covalently to the cell or extracellular substance. In other embodiments, a targeted compstatin analog does not comprise a cell-reactive moiety.

In some aspects, a compstatin analog may be or comprise a long-acting compstatin analog, wherein the long-acting compstatin analogs comprise a moiety such as polyethylene glycol (PEG) that prolongs the lifetime of the compound in the body (e.g., by reducing its clearance from the blood). In some embodiments, a long-acting compstatin analog does not comprise a targeting moiety or a cell-reactive moiety. In some embodiments, a long-acting compstatin analog comprises a targeting moiety and/or a cell-reactive moiety.

A compstatin analog, optionally linked to a cell-reactive moiety or targeting moiety, can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458, 2002); Hinds, K. D. & Kim, S. W. Adv. Drug Deliv. Rev. 54, 505-530 (2002; Roberts, M. J., Bentley, M. D. & Harris, J. M. Adv. Drug Deliv. Rev. 54, 459-476; 2002); Wang, Y. S. et al. Adv. Drug Deliv. Rev. 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. In another embodiment a compstatin analog is fused to the Fc domain of an immunoglobulin or a portion thereof. In some other embodiments a compstatin analog is conjugated to an albumin moiety or to an albumin binding peptide. Thus in some embodiments a compstatin analog is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a compstatin analog is a multivalent compound comprising a plurality of compstatin analog moieties covalently or noncovalently linked to a polymeric backbone or scaffold. The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two of more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In some embodiments, the compstatin analog comprises an amino acid having a side chain comprising a primary or secondary amine, e.g., a Lys residue. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. The spacer may, for example, comprise a substituted or unsubstituted, saturated or unsaturated alkyl chain, oligo (ethylene glycol) chain, and/or other moieties, e.g., as described in Section VI with regard to linkers. The length of the chain may be, e.g., between 2 and 20 carbon atoms. In other embodiments the spacer is a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

IV. Compstatin Mimetics

The structure of compstatin is known in the art, and NMR structures for a number of compstatin analogs having higher activity than compstatin are also known (Malik, supra). Structural information may be used to design compstatin mimetics.

In one embodiment, the compstatin mimetic is any compound that competes with compstatin or any compstatin analog (e.g., a compstatin analog whose sequence is set forth in Table 1) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 1, e.g., SEQ ID NO: 14, 21, 28, 29, 32, 33, 34, or 36 or in certain embodiments SEQ ID NO: 30 or 31 or other compstatin analog sequence, in a peptide-C3 structure. In certain embodiments the compstatin mimetic is a compound that could substitute for a peptide having a sequence set forth in Table 1, e.g., SEQ ID NO: 14, 21, 28, 29, 32, 33, 34, or 36 or in certain embodiments SEQ ID NO: 30 or 31 or other compstatin analog sequence, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far. It will be appreciated that compstatin mimetics could be used in the cell-reactive compounds of the invention, and the invention provides such cell-reactive compstatin mimetics.

V. Cell-Reactive or Long-Acting Compstatin Analogs

As noted above, in certain embodiments, the invention provides and/or utilizes a variety of cell-reactive compstatin analogs. In some aspects, a cell-reactive compstatin analog comprises a compound of formula A-L-M, wherein A is a moiety that comprises a cell-reactive functional group J, L is an optionally present linking portion, and M comprises a compstatin analog moiety. The compstatin analog moiety can comprise any compstatin analog, e.g., any compstatin analog described above, in various embodiments. Formula A-L-M encompasses embodiments in which A-L is present at the N-terminus of the compstatin analog moiety, embodiments in which A-L is present at the C-terminus of the compstatin analog moiety, embodiments in which A-L is attached to a side chain of an amino acid of the compstatin analog moiety, and embodiments where the same or different A-Ls are present at both ends of M. It will be appreciated that when certain compstatin analog(s) are present as a compstatin analog moiety in a compound of formula A-L-M, a functional group of the compstatin analog will have reacted with a functional group of L to form a covalent bond to A or L. For example, a cell-reactive compstatin analog in which the compstatin analog moiety comprises a compstatin analog that contains an amino acid with a side chain containing a primary amine ($NH_2$) group (which compstatin analog can be represented by formula $R^1$—($NH_2$)), can have a formula $R^1$—NH-L-A in which a new covalent bond to L (e.g., N—C) has been formed and a hydrogen lost. Thus the term "compstatin analog moiety" includes molecular structures in which at least one atom of a compstatin analog participates in a covalent bond with a second moiety, which may, e.g., modification of a side chain. Similar considerations apply to compstatin analog moieties present in multivalent compound described above. In some embodiments, a blocking moiety at the N-terminus or C-terminus of a compstatin analog, e.g., a compstatin analog described in Section IV above, is replaced by A-L in the structure of a cell-reactive compstatin analog. In some embodiments, A or L comprises a blocking moiety. In some embodiments, a cell-reactive compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a cell-reactive moiety. In some embodiments in which a cell-reactive compstatin analog comprises multiple compstatin analog moieties, the molar activity of the cell-reactive compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

Cell-reactive moiety A can comprise any of a variety of different cell-reactive functional groups J, in various embodiments. In general, a cell-reactive functional group may be selected based at least in part on factors such as (a) the particular functional group to be targeted; (b) the ability of the reactive functional group to react with the target functional group under physiologically acceptable ex vivo conditions (e.g., physiologically acceptable pH and osmolarity) and/or in vivo conditions (e.g., in blood); (c) the specificity of the reaction between the reactive functional group and the target functional group under physiologically acceptable ex vivo conditions and/or in vivo; (d) the stability (e.g., under in vivo conditions) of the covalent bond that would result from reaction of the reactive functional group with its target functional group; (e) the ease of synthesizing a cell-reactive compstatin analog comprising the reactive functional group, etc. In some embodiments, a reactive functional group that reacts with its target chemical group without releasing a leaving group is selected. In some embodiments, a reactive functional group that results in release of a leaving group upon reaction with a target is selected. Compounds containing such groups may be useful, e.g., to monitor progress and/or extent of a reaction. In some embodiments, a leaving group is physiologically acceptable to cells, tissues, or organs in the amount generated (e.g., based on concentration and/or absolute amount generated) and/or is medically acceptable to a subject in the amount generated in vivo (e.g., based on concentration in a relevant body fluid such as blood and/or based on the absolute amount generated). In some embodiments, a leaving group generated ex vivo is at least in part removed, e.g., by washing cells or by washing or perfusing a tissue or organ, e.g., with saline.

In many embodiments, a cell-reactive functional group of use in the invention reacts with a side chain of an amino acid residue and/or with an N-terminal amino group or C-terminal carboxyl group of a protein. In some embodiments, the cell-reactive functional group is reactive with sulfhydryl (—SH) groups, which are found in the side chains of cysteine residues. In some embodiments, a maleimide group is used. Maleimide groups react with sulfhydryl groups of cysteine residues of proteins at physiologic pH and form a stable thioether linkage. In some embodiments, a haloacetyl group, such as an iodoacetyl or a bromoacetyl group, is used. Haloacetyls react with sulfhydryl groups at physiologic pH. The reaction of the iodoacetyl group proceeds by nucleophilic substitution of iodine with a sulfur atom from a sulfhydryl group resulting in a stable thioether linkage. In other embodiments, an iodoacetamide group is used. In some embodiments, the cell-reactive functional group reacts with amino (—$NH_2$) groups, which are present at the N-termini of proteins and in the side chain of lysine residues (ε-amino group). In some embodiments an activated ester, e.g., a succinimidyl ester (i.e., NHS ester) is used. For example, N-hydroxysuccinimide (NHS) or its water-soluble analog (sulfo-NHS) can be used in the synthesis, whereby the resulting cell-reactive compstatin analog comprises an NHS ester. In some embodiments, the cell-reactive functional group reacts with carboxyl (—COOH) groups, which are present at the C-termini of proteins and in the side chains of various amino acid residues. In some embodiments, the cell-reactive compstatin analog is reactive with hydroxyl (—OH) groups, which are present in the side chains of various amino acids and in carbohydrate moieties of glycosylated proteins.

In general, linking portion L can comprise any one or more aliphatic and/or aromatic moieties consistent with the formation of a stable compound joining the linked moieties. The term "stable", as used herein, preferably refers to compounds which possess stability sufficient to allow manufacture and which maintain the integrity of the compound for a sufficient period of time, e.g., to be useful for one or more purposes described herein. In some embodiments, L comprises a saturated or unsaturated, substituted or unsubstituted, branched or unbranched, aliphatic chain having a length of between 1 and 30, between 1 and 20, between 1 and 10, between 1 and 6, or 5 or less carbon atoms, where length refers to the number of C atoms in the main (longest) chain. In some embodiments, the aliphatic chain comprises one or more heteroatoms (O, N, S), which may be independently selected. In some embodiments, at least 50% of the atoms in the main chain of L are carbon atoms. In some embodiments, L comprises a saturated alkyl moiety $(CH_2)_n$, wherein n is between 1 and 30.

In some embodiments, L comprises one or more heteroatoms and has a length of between 1 and 1000, between 1 and 800, between 1 and 600, between 1 and 400, between 1 and 300, between 1 and 200, between 1 and 100, between 1 and 50, between 1 and 30, or between 1 and 10 total carbon atoms in a chain. In some embodiments, L comprises an oligo(ethylene glycol) moiety (—(O—$CH_2$—$CH_2$-)$_n$) wherein n is between 1 and 500, between 1 and 400, between 1 and 300, between 1 and 200, between 1 and 100, between 10 and 200, between 200 and 300, between 100 and 200, between 40 and 500, between 30 and 500, between 20 and 500, between 10 and 500, between 1 and 40, between 1 and 30, between 1 and 20, or between 1 and 10.

In some embodiments, L comprises an unsaturated moiety such as —CH═CH— or —CH$_2$—CH═CH—; a moiety comprising a non-aromatic cyclic ring system (e.g., a cyclohexyl moiety), an aromatic moiety (e.g., an aromatic cyclic ring system such as a phenyl moiety); an ether moiety (—C—O—C—); an amide moiety (—C(═O)—N—); an ester moiety (—CO—O—); a carbonyl moiety (—C(═O)—); an imine moiety (—C═N—); a thioether moiety (—C—S—C—); an amino acid residue; and/or any moiety that can be formed by the reaction of two compatible reactive functional groups. In certain embodiments, one or more moieties of a linking portion or cell-reactive moiety is/are substituted by independent replacement of one or more of the hydrogen (or other) atoms thereon with one or more moieties including, but not limited to aliphatic; aromatic, aryl; alkyl, aralkyl, alkanoyl, aroyl, alkoxy; thio; F; Cl; Br; I; —NO2; —CN; —CF3; —CH2CF3; —CHCl2; —CH2OH; —CH2CH2OH; —CH2NH2; —CH2SO2CH3; - or -GRG1 wherein G is —O—, —S—, —NRG2-, —C(═O)—, —S(═O)—, —SO2-, —C(═O)O—, —C(═O)NRG2-, —OC(═O)—, —NRG2C(═O)—, —OC(═O)O—, —OC(═O)NRG2-, —NRG2C(═O)O—, —NRG2C(═O)NRG2-, —C(═S)—, —C(═S)S—, —SC(═S)—, —SC(═S)S—, —C(═NRG2)-, —C(═NRG2)O—, —C(═NRG2)NRG3-, —OC(═NRG2)-, —NRG2C(═NRG3)-, —NRG2SO2-, —NRG2SO2NRG3-, or —SO2NRG2-, wherein each occurrence of RG1, RG2 and RG3 independently includes, but is not limited to, hydrogen, halogen, or an optionally substituted aliphatic, aromatic, or aryl moiety. It will be appreciated that cyclic ring systems when present as substituents may optionally be attached via a linear moiety. Combinations of substituents and variables envisioned by this invention are preferably those that result in the formation of stable compounds useful in any one or more of the methods described herein, e.g., useful for the treatment of one or more disorders and/or for contacting a cell, tissue, or organ, as described herein, and/or useful as intermediates in the manufacture of one or more such compounds.

L can comprise one or more of any of the moieties described in the preceding paragraph, in various embodiments. In some embodiments, L comprises two or more different moieties linked to one another to form a structure typically having a length of between 1 to about 60 atoms, between 1 to about 50 atoms, e.g., between 1 and 40, between 1 and 30, between 1 and 20, between 1 and 10, or between 1 and 6 atoms, where length refers to the number of atoms in the main (longest) chain. In some embodiments, L comprises two or more different moieties linked to one another to form a structure typically having between 1 to about 40, e.g., between 1 and 30, e.g., between 1 and 20, between 1 and 10, or between 1 and 6 carbon atoms in the main (longest) chain. In general, the structure of such a cell-reactive compstatin analog can be represented by formula A-(L$^{Pj}$)j-M, wherein j is typically between 1 and 10, and each L$^{pj}$ is independently selected from among the moieties described in the preceding paragraph. In many embodiments, L comprises one or more carbon-containing chains such as —(CH$_2$)n- and/or —(O—CH$_2$—CH$_2$-)$_n$, which are joined covalently to each other and/or to a cell-reactive functional group or compstatin analog, e.g., by moieties (e.g., amide, ester, or ether moieties) that result from the reaction of two compatible reactive functional groups. In some embodiments, L comprises an oligo(ethylene glycol) moiety and/or a saturated alkyl chain. In some embodiments, L comprises —(CH$_2$)$_m$—C(═O)—NH—(CH$_2$CH2O)$_n$(CH$_2$)$_p$C(═O)— or —(CH$_2$)$_m$—C(═O)—NH—(CH$_2$)$_p$(OCH$_2$CH$_2$)$_n$C(═O)—. In some embodiments, m, n, and p are selected so that the number of carbons in the chain is between 1 and 500, e.g., between 2 and 400, between 2 and 300, between 2 and 200, between 2 and 100, between 2 and 50, between 4 and 40, between 6 and 30, or between 8 and 20. In some embodiments, m is between 2 and 10, n is between 1 and 500, and/or p is between 2 and 10. In some embodiments, m is between 2 and 10, n is between 1 and 400, and/or p is between 2 and 10. In some embodiments, m is between 2 and 10, n is between 1 and 300, and/or p is between 2 and 10. In some embodiments, m is between 2 and 10, n is between 1 and 200, and/or p is between 2 and 10. In some embodiments, m is between 2 and 10, n is between 1 and 100, and/or p is between 2 and 10. In some embodiments, m is between 2 and 10, n is between 1 and 50, and/or p is between 2 and 10. In some embodiments, m is between 2 and 10, n is between 1 and 25, and/or p is between 2 and 10. In some embodiments, m is between 2 and 10, n is between 1 and 8, and/or p is between 2 and 10. Optionally, at least one —CH$_2$— is replaced by CH—R, wherein R can be any substituent. Optionally, at least one —CH$_2$— is replaced by a heteroatom, cyclic ring system, amide, ester, or ether moiety. In some embodiments, L does not comprise an alkyl group having more than 3 carbon atoms in the longest chain. In some embodiments, L does not comprise an alkyl group having more than 4, 5, 6, 7, 8, 9, 10, or 11 carbon atoms in the longest chain.

In some embodiments of the invention, A comprises a cell-reactive functional group J and a linker L$^1$ comprising a linking portion L$^{P1}$ and a reactive functional group that reacts with the compstatin analog to generate A-M In some embodiments, a bifunctional linker L$^2$ comprising two reactive functional groups and a linking portion L$^{P2}$ is used. The reactive functional groups of L react with appropriate reactive functional groups of A and M to produce a cell-reactive compstatin analog A-L-M. In some embodiments, the compstatin analog comprises a linker L$^3$ comprising a linking portion L$^{P3}$. For example, as discussed below, a linker comprising a reactive functional group may be present at the N- or C-terminus or a moiety comprising a reactive functional group may be attached to the N- or C-terminus via a linker. Thus L may contain multiple linking portions L$^p$ contributed, e.g., by A, by linker(s) used to join A and M, and/or by the compstatin analog. It will be understood that, when present in the structure A-L-M, certain reactive functional group(s) present prior to reaction in L$^1$, L$^2$, L$^3$, etc., will have undergone reaction, so that only a portion of said reactive functional group(s) will be present in the final structure A-L-M, and the compound will contain moieties formed by reaction of said functional groups. In general, if a compound contains two or more linking portions, the linking portions can be the same or different, and can be independently selected in various embodiments. Multiple linking portions L$^p$ can be attached to one another to form a larger linking portion L, and at least some of such linking portions can have one or more compstatin analog(s) and/or cell-reactive functional group(s) attached thereto. In molecules comprising multiple compstatin analogs, the compstatin analogs can be the same or different and, if different, can be independently selected. The same applies to the linking portions and reactive functional groups. The invention encompasses the use of multivalent compstatin analogs comprising one or more cell-reactive functional group(s) and use of concatamers of compstatin analogs comprising one or more cell-reactive functional group(s). In some embodiments, at least one linkage is a stable non-covalent linkage such as a biotin/(strept)avidin linkage or other noncovalent linkage of approximately equivalent strength.

In some embodiments a cell-reactive compstatin analog comprises a compstatin analog in which any of SEQ ID NOs: 3-36, 70, 71, 72, 73, or 74 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring. In some embodiments, the amino acid(s) is/are L-amino acids. In some embodiments, any one or more of the amino acid(s) is a D-amino acid. If multiple amino acids are added, the amino acids can be independently selected. In some embodiments, the reactive functional group (e.g., a primary or secondary amine) is used as a target for addition of a moiety comprising a cell-reactive functional group. Amino acids having a side chain that comprises a primary or secondary amine include lysine (Lys) and diaminocarboxylic acids of general structure $NH_2(CH2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. In some embodiments at least one amino acid is cysteine, aspartic acid, glutamic acid, arginine, tyrosine, tryptophan, methionine, or histidine. Cysteine has a side chain comprising a sulfhydryl group. Aspartic acid and glutamic acid have a side chain comprising a carboxyl group (ionizable to a carboxylate group). Arginine has a side chain comprising a guanidino group. Tyrosine has a side chain comprising a phenol group (ionizable to a phenolate group). Tryptophan has a side chain comprising an indole ring include, e.g., tryptophan. Methionine has a side chain comprising a thioether group include, e.g., methionine. Histidine has a side chain comprising an imidazole ring. A wide variety of non-standard amino acids having side chains that comprise one or more such reactive functional group(s) are available, including naturally occurring amino acids and amino acids not found in nature. See, e.g., Hughes, B. (ed.), *Amino Acids, Peptides and Proteins in Organic Chemistry*, Volumes 1-4, Wiley-VCH (2009-2011); Blaskovich, M., Handbook on Syntheses of Amino Acids General Routes to Amino Acids, Oxford University Press, 2010. The invention encompasses embodiments in which one or more non-standard amino acid(s) is/are used to provide a target for addition of a moiety comprising a cell-reactive functional group. Any one or more of the amino acid(s) may be protected as appropriate during synthesis of the compound. For example, one or more amino acid(s) may be protected during reaction(s) involving the target amino acid side chain. In some embodiments, wherein a sulfhydryl-containing amino acid is used as a target for addition of a moiety comprising a cell-reactive functional group, the sulfhydryl is protected while the compound is being cyclized by formation of an intramolecular disulfide bond between other amino acids such as cysteines.

In the discussion in this paragraph, an amino acid having a side chain containing an amine group is used as an example. The invention encompasses analogous embodiments in which an amino acid having a side chain containing a different reactive functional group is used. In some embodiments, an amino acid having a side chain comprising a primary or secondary amine is attached directly to the N-terminus or C-terminus of any of SEQ ID NOs: 3-36, 37, 70, 71, 72, 73, or 74 or via a peptide bond. In some embodiments, an amino acid having a side chain comprising a primary or secondary amine is attached to the N- or C-terminus of any of SEQ ID NOs: 3-36, 37, 70, 71, 72, 73, or 74 or via a linking portion, which may contain any one or more of the linking moieties described above. In some embodiments, at least two amino acids are appended to either or both termini. The two or more appended amino acids may be joined to each other by peptide bonds or at least some of the appended amino acids may be joined to each other by a linking portion, which may contain any one or more of the linking moieties described herein. Thus in some embodiments, a cell-reactive compstatin analog comprises a compstatin analog moiety M of formula $B1-R1-M_1-R2-B2$, wherein Mt represents any of SEQ ID NOs: 3-36, 37, 70, 71, 72, 73, or 74, either R1 or R2 may be absent, at least one of R1 and R2 comprises an amino acid having a side chain that contains a primary or secondary amine, and B1 and B2 are optionally present blocking moieties. R1 and/or R2 may be joined to $M_1$ by a peptide bond or a non-peptide bond. R1 and/or R2 may comprise a linking portion $L^{P3}$. For example, R1 can have formula $M_2-L^{P3}$ and/or R2 can have formula $L^{P3}-M_2$ wherein $L^{P3}$ is a linking portion, and $M_2$ comprises at least one amino acid having a side chain comprising a primary or secondary amine. For example, $M_2$ can be Lys or an amino acid chain comprising Lys. In some embodiments, $L^{P3}$ comprises of consists of one or more amino acids. For example, $L^{P3}$ can be between 1 and about 20 amino acids in length, e.g., between 4 and 20 amino acids in length. In some embodiments, $L^{P3}$ comprises or consist of multiple Gly, Ser, and/or Ala residues. In some embodiments, $L^{P3}$ does not comprise an amino acid that comprises a reactive SH group, such as Cys. In some embodiments, $L^{P3}$ comprises an oligo(ethylene glycol) moiety and/or a saturated alkyl chain. In some embodiments, $L^{P3}$ is attached to the N-terminal amino acid of $M_1$ via an amide bond. In some embodiments, $L^{P3}$ is attached to the C-terminal amino acid of $M_1$ via an amide bond. The compound may be further extended at either or both termini by addition of further linking portion(s) and/or amino acid(s). The amino acids can the same or different and, if different, can be independently selected. In some embodiments, two or more amino acids having side chains comprising reactive functional groups are used, wherein the reactive functional groups can be the same or different. The two or more reactive functional groups can be used as targets for addition of two or more moieties. In some embodiments, two or more cell-reactive moieties are added. In some embodiments, a cell-reactive moiety and a targeting moiety are added. In some embodiments, a linker and/or cell-reactive moiety is attached to an amino acid side chain after incorporation of the amino acid into a peptide chain. In some embodiments, a linker and/or cell-reactive moiety is already attached to the amino acid side chain prior to use of the amino acid in the synthesis of a cell-reactive compstatin analog. For example, a Lys derivative having a linker attached to its side chain can be used. The linker may comprise a cell-reactive functional group or may subsequently be modified to comprise a cell-reactive functional group.

Certain cell-reactive compstatin analogs are described in further detail below. In the following discussion, a peptide having the amino acid sequence Ile-Cys*-Val-(1Me)Trp-Gln-Asp-Trp-Gly-Ala-His-Arg-Cys*-Thr (SEQ ID NO: 37) (corresponding to the compstatin analog of SEQ ID NO: 28, wherein asterisks in SEQ ID NO: 37 represent cysteines joined by a disulfide bond in the active compound, and (1Me)Trp represents 1-methyl-tryptophan)), is used as an exemplary compstatin analog moiety; maleimide (abbreviated Mai) is used as an example of a cell-reactive functional group; $(CH2)_n$ and $(O\text{-}CH2\text{-}CH2)_n$ are used as examples of linking portions; lysine is used as an example of an amino acid comprising a reactive functional group (in some compounds), and acetylation and amidation of the N- and C-termini, respectively, are used as optionally present exemplary blocking moieties in some compounds and are represented in italics, i.e., as Ac and $NH_2$ respectively. It will be appreciated that the compounds can be prepared using a variety of synthetic approaches and using a variety of precursors. The discussion of various synthetic approaches and precursors below is not intended to limit the invention. In general, any of the features of any of the compounds described below or herein can be freely combined with feature(s) of other compounds described below or elsewhere herein, and the invention encompasses such embodiments.

In some embodiments, the cell-reactive moiety is provided by a cell-reactive compound comprising a maleimide group (as a cell-reactive functional group) and an alkanoic acid (RCOOH), where R is an alkyl group. For example, 6-malemeidocaproic acid (Mal-$(CH_2)_5$—COOH), depicted below, can be used.

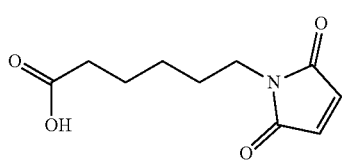

Compound I

In some embodiments, the cell-reactive moiety is provided by a derivative of an alkanoic acid in which the carboxylic acid moiety has been activated, e.g., the OH moiety has been converted to a better leaving group. For example, the carboxyl group of compound I may be reacted with EDC, followed by reaction with NHS (which can optionally be provided as water-soluble sulfo-NHS), resulting in an N-hydroxysuccinimide ester derivative of 6-malemeidocaproic acid, i.e., 6-maleimidohexanoic acid N-hydroxysuccinimide (NHS) ester (depicted below).

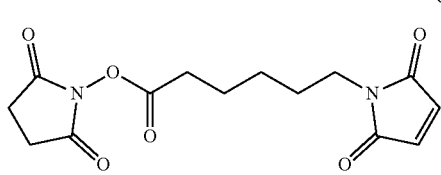

Compound II

The compound of SEQ ID NO: 37 can be modified at the N- and/or C-terminus to generate a cell-reactive compstatin analog. For example, compound II can be used to generate the following cell-reactive compstatin analog by reaction with the N-terminal amino group of Ile.

Maleimide-$(CH_2)_5$—C(=O)—Ile-Cys*-Val-(1Me)Trp-Gln-Asp-Trp-Gly-Ala-His-Arg-Cys*-Thr-$NH_2$ (SEQ ID NO: 38). It will be appreciated that in SEQ ID NO: 38 the —C(=O) moiety is attached to the immediately C-terminal amino acid (Ile), via a C—N bond, wherein the N is part of the amino acid and is not shown.

In other embodiments, a maleimide group is linked to Thr at the C-terminus, resulting in the following cell-reactive compstatin analog:

```
                                        (SEQ ID NO: 39)
Ac-Ile-Cys*-Val-(1Me)Trp-Gln-Asp-Trp-Gly-Ala-His-

Arg-Cys*-Thr-(C=O)-(CH2)5-maleimide.
```

In some embodiments, a cell-reactive compstatin analog can be synthesized using bifunctional linker (e.g., a heterobifunctional linker). An exemplary heterobifunctional linker comprising $(CH_2$—$CH_2$—$O)_n$ and $(CH_2)_m$ (where m=2) moieties is shown below:

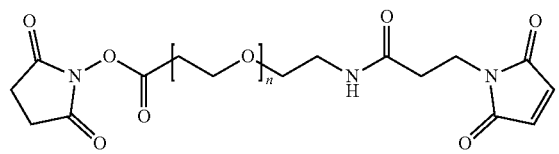

Compound III

Compound III comprises a maleimide group as a cell-reactive functional group and an NHS ester moiety that reacts readily with an amino group (e.g., an N-terminal amino group or an amino group of an amino acid side chain).

An embodiment of compound III in which n=2 can be used to generate the following cell-reactive compstatin analog using the compstatin analog of SEQ ID NO: 37:

```
                                        (SEQ ID NO: 40)
Maleimide-(CH2)2-C(=O)-NH-CH2CH2OCH2CH2OCH2CH2C (=O)-Ile-Cys*-Val-(1Me)Trp-Gln-Asp-Trp-Gly-Ala- His-Arg-Cys*-Thr-NH2
```

It will be appreciated that in the compound of SEQ ID NO: 40 a —C(=O) moiety is attached to the N-terminal amino acid (Ile residue via a C—N bond, wherein the N is part of the amino acid and is not shown. In some embodiments a linker has the formula of Compound III wherein n≥1. Exemplary values for n in a $(CH_2$—$CH_2$—$O)_n$ moiety are provided herein.

In some embodiments, the alkyl chain that links the maleimide moiety to the rest of the molecule contains more or fewer methylene units, the oligo(ethylene glycol) moiety contains more or fewer ethylene glycol units, and/or there are more or fewer methylene units flanking either or both sides of the oligo(ethylene glycol) moiety, as compared with the compound of SEQ ID NO: 39 or SEQ ID NO: 40. Exemplary cell-reactive compstatin analogs illustrative of a few such variations are presented below (SEQ ID NOs: 41-46):

```
                                        (SEQ ID NO: 41)
Maleimide-(CH2)2-C(=O)-NH-CH2CH2OCH2CH2C(=O)-Ile- Cys*-Val-(1Me)Trp-Gln-Asp-Trp-Gly-Ala-His-Arg- Cys*-Thr-NH2

(SEQ ID NO: 42)
Maleimide-(CH2)3-C(=O)-NH-CH2CH2OCH2CH2OCH2C(=O)-

Ile-Cys*-Val-(1Me)Trp-Gln-Asp-Trp-Gly-Ala-His-

Arg-Cys*-Thr-NH2
```

(SEQ ID NO :43)
Maleimide-(CH$_2$)$_5$-C(=O)-NH-CH$_2$CH$_2$OCH$_2$CH$_2$OCH$_2$C(=O)-

Ile-Cys*-Val-(1Me)Trp-Gln-Asp-Trp-Gly-Ala-His-Arg-

Cys*-Thr-NH$_2$ (SEQ ID NO: 44)
Maleimide-(CH$_2$)$_4$-C(=O)-NH-CH$_2$CH$_2$OCH$_2$CH$_2$OCH$_2$CH$_2$C (=O)-Ile-Cys*-Val-(1Me)Trp-Gln-Asp-Trp-Gly-Ala- His-Arg-Cys*-Thr-NH$_2$ (SEQ ID NO: 45)
Maleimide-(CH$_2$)$_2$-C(=O)-NH-CH$_2$CH$_2$OCH$_2$CH$_2$OCH$_2$CH$_2$C (=O)-Ile-Cys*-Val-(1Me)Trp-Gln-Asp-Trp-Gly-Ala- His-Arg-Cys*-Thr-NH$_2$ (SEQ ID NO: 46)
Maleimide-(CH$_2$)$_5$-C(=O)-NH-CH$_2$CH$_2$OCH$_2$CH$_2$OCH$_2$C(=O)-

Ile-Cys*-Val-(1Me)Trp-Gln-Asp-Trp-Gly-Ala-His-

Arg-Cys*-Thr-NH$_2$

In some embodiments, SEQ ID NO: 37 is extended to comprise a Lys residue at the N- or C-terminus of the peptide, e.g., as exemplified below for a C-terminal linkage:

(SEQ ID NO: 47)
Ac-Ile-Cys*-Val-(1Me)Trp-Gln-Asp-Trp-Gly-Ala-

His-Arg-Cys*-Thr-Lys-NH$_2$.

In some embodiments, a Lys residue is attached to the N- or C-terminus of SEQ ID NO: 37 via a peptide linker, e.g., as exemplified below for a C-terminal linkage:

(SEQ ID NO: 48)
Ac-Ile-Cys*-Val-(1Me)Trp-Gln-Asp-Trp-Gly-Ala-His-

Arg-Cys*-Thr-(Gly)$_5$-Lys-NH$_2$.

In some embodiments, a linker comprising a primary or secondary amine is added to the N- or C-terminus of a compstatin analog. In some embodiments, the linker comprises an alkyl chain and/or an oligo(ethylene glycol) moiety. For example, NH$_2$(CH$_2$CH$_2$O)nCH$_2$C(=O)OH (e.g., 8-amino-3,6-dioxaoctanoic acid (AEEAc) or 11-amino-3,6,9-trioxaundecanoic acid) or an NHS ester thereof (e.g., an NHS ester of 8-amino-3,6-dioxaoctanoic acid or 11-amino-3,6,9-trioxaundecanoic acid), can be used. In some embodiments, the resulting compound is as follows (wherein the portion contributed by the linker is shown in bold):

(SEQ ID NO: 49)
NH$_2$(CH$_2$)$_5$C(=O)-Ile-Cys-Val-(1Me)Trp-Gln-Asp-Trp-

Gly-Ala-His-Arg-Cys-Thr-NH$_2$ (SEQ ID NO: 50)
NH$_2$(CH$_2$CH$_2$O)$_2$CH$_2$C(=O)-Ile-Cys-Val-(1Me)Trp-Gln-

Asp-Trp-Gly-Ala-His-Arg-Cys-Thr-NH$_2$

In some embodiments, a Lys residue is attached to the N- or C-terminus of SEQ ID NO: 37 via a linker comprising a non-peptide portion. For example, the linker can comprise an alkyl chain, oligo(ethylene glycol) chain, and/or cyclic ring system. In some embodiments, 8-AEEAc or an NHS ester thereof is used, resulting (in the case of attachment of Lys at the C-terminus) in the following compound (wherein the portion contributed by 8-AEEAc is shown in bold):

(SEQ ID NO: 51)
Ac-Ile-Cys*-Val-(1Me)Trp-Gln-Asp-Trp-Gly-Ala-His-

Arg-Cys*-Thr-NH-CH$_2$CH$_2$OCH$_2$CH$_2$OCH$_2$-C(=O)-Lys-NH$_2$

It will be appreciated that in SEQ ID NOs: 49 and 50, a —C(=O) moiety is attached to the adjacent Ile residue via a C—N bond, wherein the N is part of the amino acid and is not shown. Similarly, in SEQ ID NO: 51, a —C(=O) moiety is attached to the adjacent Lys residue via a C—N bond, wherein the N is part of the amino acid and is not shown. It will also be appreciated that that in SEQ ID NO: 51 the NH moiety is attached to the immediately N-terminal amino acid (Thr), via a C—N bond, wherein the C is the carbonyl carbon of the amino acid and is not shown.

The compounds of SEQ ID NOs: 47-51 can readily be modified at the primary amine group to produce a cell-reactive compstatin analog. For example, the compounds of SEQ ID NOs: 47-51 (or other compounds comprising a primary or secondary amine and a compstatin analog moiety) can be reacted with 6-maleimidocaproic acid N-succinimidyl ester to produce the following cell-reactive compstatin analogs:

(SEQ ID NO: 52)
Ac-Ile-Cys*-Val-(1Me)Trp-Gln-Asp-Trp-Gly-Ala-His-

Arg-Cys*-Thr-Lys-(C(=O)-(CH$_2$)$_5$-Mal)-NH$_2$.

(SEQ ID NO: 53)
Ac-Ile-Cys*-Val-(1Me)Trp-Gln-Asp-Trp-Gly-Ala-His-

Arg-Cys*-Thr-(Gly)$_5$-Lys-—(C(=O)-(CH$_2$)$_5$-Mal)-NH$_2$.

(SEQ ID NO: 54)
Mal-(CH$_2$)$_5$-(C(=O)-NH(CH$_2$)$_5$CH$_2$C(=O)-Ile-Cys-Val-
(1Me)

Trp-Gln-Asp-Trp-Gly-Ala-His-Arg-Cys-Thr-NH$_2$ (SEQ ID NO: 55)
Mal-(CH$_2$)$_5$-(C(=O)NH(CH$_2$CH$_2$O)$_2$CH$_2$C(=O)-Ile-Cys-Val- (1Me)Trp-Gln-Asp-Trp-Gly-Ala-His-Arg-Cys-Thr-NH$_2$ (SEQ ID NO: 56)
Ac-Ile-Cys*-Val-(1Me)Trp-Gln-Asp-Trp-Gly-Ala-His-

Arg-Cys*-Thr-NH-CH$_2$CH$_2$OCH$_2$CH$_2$OCH$_2$-C(=O)-Lys- (C(=O)-(CH$_2$)$_5$-Mal)-NH$_2$

In another embodiment, a cell-reactive compstatin analog is represented as:

(SEQ ID NO: 57)
Ac-Ile-Cys*-Val-(1Me)Trp-Gln-Asp-Trp-Gly-Ala-His-

Arg-Cys*-Thr-Lys-C(=O)-CH$_2$(OCH$_2$CH2)$_2$NH(C(=O)-
(CH$_2$)$_5$-

Mal)-NH$_2$.

The invention provides variants of SEQ ID NOs: 38-57 in which -Ile-Cys*-Val-(1Me)Trp-Gln-Asp-Trp-Gly-Ala-His-Arg-Cys*-Thr- (SEQ ID NO: 37) is replaced by an amino acid sequence comprising the amino acid sequence of any other compstatin analog, e.g., of any of SEQ ID NOs 3-27 or 29-36, 37, 70, 71, 72, 73, or 74 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Other bifunctional cross-linkers comprising a maleimide as a cell-reactive moiety and an NHS ester as an amine-reactive moiety of use in various embodiments of the invention include, e.g., succinimidyl 4-(p-maleimidophenyl) butyrate (SMPB); succinimidyl 4-(N-maleimidomethyl)-cyclohexane-1-carboxylate (SMCC); N-γ-maleimidobutyryl-oxysuccinimide ester (GMBS). Addition of a sulfonate to the NHS ring results in water-soluble analogs such as sulfo-succinimidyl(4-iodoacetyl)-aminobenzoate (sulfo-SIAB), sulfo-succinimidyl 4-(N-maleimidomethyl)-cyclohexane-1-carboxylate (sulfo-SMCC), sulfo-succinimidyl 4-(p-maleimidophenyl)butyrate (sulfo-SMPB), sulfo-N-γ-maleimidobutyryl-oxysuccinimide ester (sulfo-GMBS) etc., which can avoid the need for an organic solvent. In some embodiments, a long chain version of any of the foregoing, comprising a spacer arm between the NHS ester moiety and the remainder of the molecule, is used. The spacer can comprise, e.g., an alkyl chain. An example is succinimidyl-4-[N-Maleimidomethyl]cyclohexane-1-carboxy-[6-amido-caproate].

In some embodiments, a bifunctional linker comprising an NHS ester (as an amine-reactive moiety) and an iodoacetyl group (reactive with sulfhydryl groups) is used. Such linkers include, e.g., A-succinimidyl(4-iodoacetyl)-aminobenzoate (SLAB); succinimidyl 6-[(iodoacetyl)-amino] hexanoate (SIAX); succinimidyl 6-[6-(((iodoacetyl)amino)-hexanoyl) amino]hexanoate (SIAXX); succinimidyl 4-((iodoacetyl)amino)methyl)-cyclohexane-1-carboxylate (SIAC); succinimidyl 6-((((4-(iodoacetyl)amino)methyl-cyclohexane-1-carbonyl)amino)hexanoate (SIACX);

In some embodiments, a bifunctional linker comprising an NHS ester (as an amine-reactive moiety) and a pyridy disulfide group (as a cell-reactive moiety reactive with sulfhydryl groups) is used. Examples include A-succinimidyl 3-(2-pyridyldithio)propionate (SPDP); succinimidyloxycarbonyl-α-methyl-α-(2-pyridyldithio)toluene (SMPT) and versions comprising a sulfonate on the NHS ring and/or a spacer comprising an alkyl chain between the NHS ester moiety and the rest of the molecule (e.g., succinimidyl 6-(3-[2-pyridyldithio]-propionamido)hexanoate) (LC-SPDP). Variations of such linkers that include additional or different moieties could be used. For example, a longer or shorter alkyl chain could be used in a spacer, or an oligo (ethylene glycol) moiety instead of an alkyl chain.

In general, a cell-reactive compstatin analog can be synthesized using a variety of approaches. Cell-reactive compounds that comprise a cell-reactive functional group and a linker can often be purchased as preformed building blocks. For example, 6-malemeidocaproic acid and 6-maleimidocaproic acid N-hydroxysuccinimide ester can be purchased from various suppliers. Alternately, such compounds can be synthesized using methods known in the art. See, e.g., Keller O, Rudinger J. Helv Chim Acta. 58(2):531-41, 1975 and Hashida S, et al., J Appl Biochem., 6(1-2):56-63, 1984. See also, Hermanson, G. supra, and references therein, for discussion of methods and reagents of use for synthesizing conjugates. In general, the invention encompasses any method of producing a compound comprising a compstatin analog moiety and a cell-reactive functional group, and the resulting compounds.

In some embodiments, an amino acid having a linker attached to a side chain is used in the synthesis of a linear peptide. The linear peptide can be synthesized using standard methods for peptide synthesis known in the art, e.g., standard solid-phase peptide synthesis. The linear peptide is then cyclized (e.g., by oxidation of the Cys residues to form an intramolecular disulfide). The cyclic compound may then be reacted with a linker comprising a cell-reactive functional group. In other embodiments, a moiety comprising a cell-reactive functional group is reacted with a linear compound prior to cyclization thereof. In general, reactive functional groups can be appropriately protected to avoid undesired reaction with each other during synthesis of a cell-reactive compstatin analog. The cell-reactive functional group, any of the amino acid side chains, and/or either or both termini of the peptide may be protected during the reaction and subsequently deprotected. For example, SH groups of Cys residues and/or SH-reactive moieties such as maleimides can be protected until after cyclization to avoid reaction between them. The reaction conditions are selected based at least in part on the requirements of the particular reactive functional group(s) to achieve reasonable yield in a reasonable time period. Temperature, pH, and the concentration of the reagents can be adjusted to achieve the desired extent or rate of reaction. See, e.g., Hermanson, supra. The desired product can be purified, e.g., to remove unreacted compound comprising the cell-reactive functional group, unreacted compstatin analog, linker(s), products other than the desired cell-reactive compstatin analog that may have been generated in the reaction, other substances present in the reaction mixture, etc. Compositions and methods for making the cell-reactive compstatin analogs, and intermediates in the synthesis, are aspects of the invention.

Figure 11:
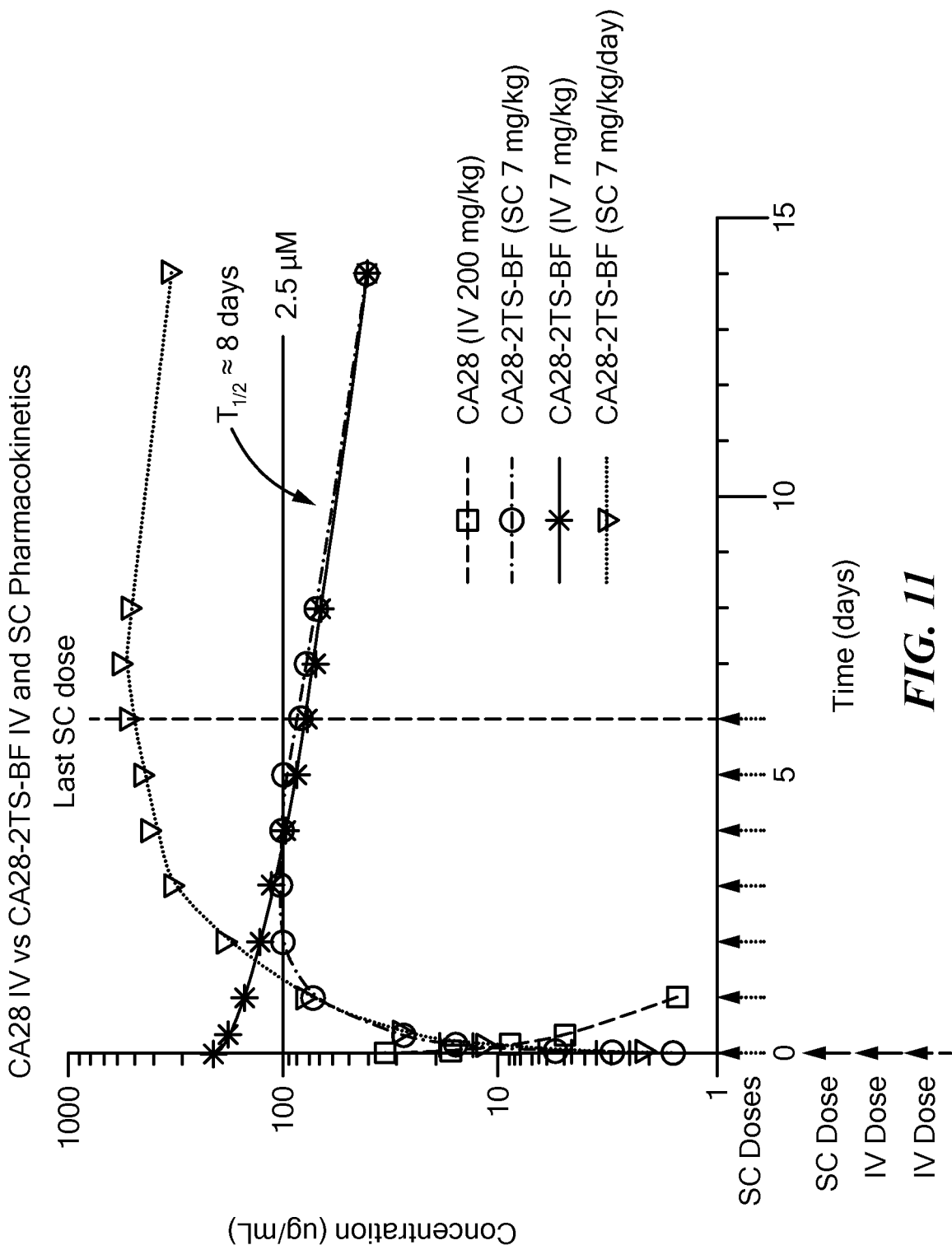
FIG. 11 is a plot that shows the plasma concentration versus time of CA28 and long-acting compstatin analog CA28-2TS-BF in Cynomolgus monkeys following a single intravenous injection of CA28 at 200 mg/kg (squares, red), a single intravenous injection of CA28-2TS-BF at 7 mg/kg (asterisks, purple), subcutaneous injection of CA28-2TS-BF at 7 mg/kg once only (circles, blue) or subcutaneous injection of CA28-2TS-BF at 7 mg/kg once daily for 7 consecutive days (inverted triangles, green). The vehicle in each case was 5% dextrose in water.

In some aspects of the invention, linker(s) described above are used in the production of compstatin analogs comprising a moiety such as a polyethylene glycol (PEG) chain or other polymer(s) that, e.g., stabilize the compound, increase its lifetime in the body, increase its solubility, decrease its immunogenicity, and/or increase its resistance to degradation. Without limiting the invention in any way, such a moiety may be referred to herein as a "clearance reducing moiety" (CRM), and a compstatin analog comprising such a moiety may be referred to as a "long-acting compstatin analog" (LACA). In some embodiments, a long-acting compstatin analog has an average plasma half-life of at least 1 day, e.g., 1-3 days, 3-7 days, 7-14 days, or 14-28 days, when administered IV at a dose of 10 mg/kg to humans or to non-human primates, or a dose of about 1-3 mg/kg, 3-5 mg/kg, 5-10 mg/kg, e.g., 7 mg/kg. In some embodiments, a long-acting compstatin analog has an average plasma half-life of at least 1 day, e.g., 1-3 days, 3-7 days, 7-14 days, or 14-28 days, when administered subcutaneously at, e.g., a dose of about 1-3 mg/kg, 3-5 mg/kg, 5-10 mg/kg, e.g., 7 mg/kg to humans or to non-human primates. In some embodiments, a long-acting compstatin analog has an average plasma half-life (e.g., a terminal half-life) of between about 4-10, 5-9, 5-8, 6-9, 7-9, or 8-9 days, e.g., about 4, 4.5, 5, 5.5, 6, 6.5, 7, 7.5, 8, 8.5, 9, 9.5 or 10 days when administered intravenously at, e.g., a dose of about 1-3 mg/kg, 3-5 mg/kg, or 5-10 mg/kg, e.g., 7 mg/kg to humans or to non-human primates. In some embodiments, a long-acting compstatin analog has an average plasma half-life (e.g., a terminal half-life) of between about 4-10, 5-9, 5-8, 6-9, 7-9, or 8-9 days, e.g., about 4, 4.5, 5.5.5, 6, 6.5, 7, 7.5, 8, 8.5, 9, 9.5 or 10 days, when administered subcutaneously at, e.g., a dose of about 1-3 mg/kg, 3-5 mg/kg, 5-10 mg/kg, e.g., 7 mg/kg to humans or to non-human primates. In certain embodiments a long-acting compstatin analog is characterized in that it is extensively absorbed from the site of administration during the time period following subcutaneous injection and provides, e.g., at or after about 1-2 days following administration, a blood level comparable to that which would be achieved had the same amount of compound been administered intravenously instead. In some embodiments, the blood level at or after about 2, 3, 4, 5, 6, 7, 8, or more days following administration of a subcutaneous dose is within about 5%, 10%, 15%, 20%, or 25% of the blood level which would be achieved had the same amount of compound been administered intravenously instead. See, e.g., FIG. 11, showing pharmacokinetics of an intravenously and subcutaneously administered dose of an exemplary compound described herein after about 1-2 days following administration. In some embodiments, average plasma half-life of a long-acting compstatin analog following administration IV at a dose of 10 mg/kg to humans or to non-human primates is increased by at least a factor of 2, e.g., by a factor of 2-5, 5-10, 10-50, or 50-100-fold or 100-150-fold or 150-200 fold as compared with that of a corresponding compstatin analog having the same amino acid sequence (and, if applicable, one or more blocking moiet(ies)) but not comprising the CRM. It will be understood that in various embodiments such an increase in half-life may be observed following administration via other routes such as subcutaneous administration and/or using other doses, e.g., other doses described herein, e.g., 20 mg/kg.

As noted above, in some embodiments a compstatin analog of any of SEQ ID NOs: 3-36, 37, 70, 71, 72, 73, or 74 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring, which facilitate conjugation with a reactive functional group to attach a CRM to the compstatin analog. It will be understood that a corresponding compstatin analog not comprising the CRM may also lack one or more such amino acids which are present in the long-acting compstatin analog to which it corresponds. Thus, a corresponding compstatin analog comprising any of SEQ ID NOs: 3-36, 37, 70, 71, 72, 73, or 74 and lacking a CRM will be understood to "have the same amino acid sequence" as SEQ ID NO: 3-36, 37, 70, 71, 72, 73, or 74, respectively. For example, a corresponding compstatin analog comprising the amino acid sequence of SEQ ID NO: 14, 21, 28, 29, 32, 33, 34, or 36 and lacking a CRM will be understood to "have the same amino acid sequence" as SEQ ID NO: 14, 21, 28, 29, 32, 33, 34, or 36, respectively.

In some embodiments, a plasma half-life is a terminal half-life after administration of a single IV dose. In some embodiments, a plasma half-life is a terminal half-life after steady state has been reached following administration of multiple IV doses. In some embodiments, a long-acting compstatin analog achieves a Cmax in plasma at least 5-fold as great as that of a corresponding compstatin analog not comprising the CRM, e.g., between 5- and 50-fold as great, following administration of a single IV dose to a primate, or following administration of multiple IV doses. In some embodiments, a long-acting compstatin analog achieves a Cmax in plasma between 10- and 20-fold as great as that of a corresponding compstatin analog not comprising the CRM following administration of a single IV dose to a primate, or following administration of multiple IV doses.

In some embodiments a primate is human. In some embodiments a primate is a non-human primate, e.g., a monkey, such as a Cynomolgus monkey or Rhesus monkey.

In some embodiments, renal clearance of a long-acting compstatin analog during the first 24 hours following administration IV at a dose of 10 mg/kg or 20 mg/kg to humans or to non-human primates is reduced by at least a factor of 2, e.g., by a factor of 2-5, 5-10, 10-50, or 50-100-fold or 100-150-fold or 150-200 fold as compared with renal clearance of a corresponding compstatin analog. It will be understood that in various embodiments such a reduction in renal clearance may be observed following administration via other routes such as subcutaneous administration and/or using other doses, e.g., other doses described herein, e.g., 20 mg/kg.

The concentration of compstatin analog can be measured in blood and/or urine samples using, e.g., UV, HPLC, mass spectrometry (MS) or antibody to the CRM, or combinations of such methods, such as LC/MS or LC/MS/MS. Pharmacokinetic parameters such as half-life and clearance can be determined using methods known to those of ordinary skill in the art. Pharmacokinetic analysis can be performed, e.g., with WinNonlin software v 5.2 (Pharsight Corporation, St. Louis, Mo.) or other suitable programs.

In certain embodiments a CRM is stable in physiological conditions for at least 24 hours or more. In certain embodiments a CRM is stable in mammalian, e.g., primate, e.g., human or non-human primate (e.g., monkey) blood, plasma, or serum for at least 24 hours. In various embodiments at least 50%, 60%, 70%, 80%, 90%, 95%, 96%, 97%, 98%, 99%, or more, of the CRM molecules remains intact upon incubation in physiological conditions for 24 hours, 48 hours, 72 hours, 96 hours, 120 hours, 144 hours, 168 hours, or more. In various embodiments at least 50%, 60%, 70%, 80%, 90%, 95%, 96%, 97%, 98%, 99%, or more, of the CRM molecules remains intact upon incubation in blood, plasma, or serum at 37 degrees C. for 48 hours, 72 hours, 96 hours, 120 hours, 144 hours, 168 hours, or more. Incubation may be performed using a CRM at a concentration of between 1 microgram/ml to about 100 mg/ml in various embodiments. Samples may be analyzed at various time points. Size or intactness may be assessed using, e.g., chromatography (e.g., HPLC), mass spectrometry, Western blot, or any other suitable method. Such stability characteristics may be conferred on a moiety conjugated to the CRM. In various embodiments, a long-acting compstatin analog comprising a CRM may have any of the afore-mentioned stability characteristics. In some aspects intact with regard to a long-acting compstatin analog means that the compstatin analog moiety remains conjugated to the CRM and the CRM size remains about the same as at the start of incubation or administration.

In some embodiments, a long-acting compstatin analog has a molar activity of at least about 10%, 20%, 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a CRM. In some embodiments wherein a long-acting compstatin analog comprises multiple compstatin analog moieties, the molar activity of the long-acting compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

In some embodiments, a polyethylene glycol (PEG) comprises a $(CH_2CH_2O)_n$ moiety having a molecular weight of at least 500 daltons.

In some embodiments, a linker described above comprises an $(CH_2CH_2O)_n$ moiety having an average molecular weight of between about 500; 1,000; 1,500; 2,000; 5,000; 10,000; 20,000; 30,000; 40,000; 50,000; 60,000; 70,000; 80,000; 90,000; and 100,000 daltons.

In some embodiments the average molecular weight of a PEG is at least 20,000 daltons, up to about 100,000; 120,000; 140,000; 160,000; 180,000; or 200,000 daltons. "Average molecular weight" refers to the number average molecular weight. In some embodiments, the polydispersity D of a $(CH_2CH_2O)n$ moiety is between 1.0005 and 1.50, e.g., between 1.005 and 1.10, 1.15, 1.20, 1.25, 1.30, 1.40, or 1.50, or any value between 1.0005 and 1.50.

In some embodiments, a $(CH_2CH_2O)n$ moiety is monodisperse and the polydispersity of a $(CH_2CH_2O)n$ moiety is 1.0. Such monodisperse $(CH_2CH_2O)n$ moieties are known in the art and are commercially available from Quanta BioDesign (Powell, Ohio), and include, by way of nonlimiting example, monodisperse moieties where n is 2, 4, 6, 8, 12, 16, 20, or 24.

In some embodiments, a compound comprises multiple $(CH_2CH_2O)_n$ moieties wherein the total molecular weight of said $(CH_2CH_2O)n$ moieties is between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)n$ moieties is at least 20,000 daltons, up to about 100,000; 120,000; 140,000; 160,000; 180,000; or 200,000 daltons. In some embodiments, the compound comprises multiple $(CH_2CH_2O)_n$ moieties having defined lengths, e.g., n=4, 6, 8, 10, 12, 14, 16, 18, 20, 22, 24, 26, 28, or 30 or more. In some embodiments, the compound comprises a sufficient number of $(CH_2CH_2O)n$ moieties having defined lengths to result in a total molecular weight of said $(CH_2CH_2O)_n$ moieties of between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments n is between about 30 and about 3000.

In some embodiments a compstatin analog moiety is attached at each end of a linear PEG. A bifunctional PEG having a reactive functional group at each end of the chain may be used, e.g., as described above. In some embodiments the reactive functional groups are identical while in some embodiments different reactive functional groups are present at each end.

In some embodiments, multiple $(CH_2CH_2O)_n$ moieties are provided as a branched structure. The branches may be attached to a linear polymer backbone (e.g., as a comb-shaped structure) or may emanate from one or more central core groups, e.g., as a star structure. In some embodiments, a branched molecule has 3 to 10 $(CH_2CH_2O)_n$ chains. In some embodiments, a branched molecule has 4 to 8 $(CH_2CH_2O)n$ chains. In some embodiments, a branched molecule has 10, 9, 8, 7, 6, 5, 4, or 3 $(CH_2CH_2O)_n$ chains. In some embodiments, a star-shaped molecule has 10-100, 10-50, 10-30, or 10-20 $(CH_2CH_2O)_n$ chains emanating from a central core group. In some embodiments a long-acting compstatin analog thus may comprise, e.g., 3-10 compstatin analog moieties, e.g., 4-8 compstatin analog moieties, each attached to a $(CH_2CH_2O)_n$ chain via a functional group at the end of the chain. In some embodiments a long-acting compstatin analog may comprise, e.g., 10-100 compstatin analog moieties, each attached to a $(CH_2CH_2O)_n$ chain via a functional group at the end of the chain. In some embodiments, branches (sometimes referred to as "arms") of a branched or star-shaped PEG contain about the same number of $(CH_2CH_2O)$ moieties. In some embodiments, at least some of the branch lengths may differ. It will be understood that in some embodiments one or more $(CH_2CH_2O)_n$ chains does not have a compstatin analog moiety attached thereto. In some embodiments at least about 30%, 40%, 50%, 60%, 70%, 80%, 90%, 95%, or 100% of the chains has a compstatin analog moiety attached thereto.

In general and compounds depicted herein, a polyethylene glycol moiety is drawn with the oxygen atom on the right side of the repeating unit or the left side of the repeating unit. In cases where only one orientation is drawn, the present invention encompasses both orientations (i.e., $(CH_2CH_2O)_n$ and $(OCH_2CH_2)_n$) of polyethylene glycol moieties for a given compound or genus, or in cases where a compound or genus contains multiple polyethylene glycol moieties, all combinations of orientations are encompasses by the present disclosure.

Formulas of some exemplary monofunctional PEGs comprising a reactive functional group are illustrated below. For illustrative purposes, formulas in which the reactive functional group(s) comprise an NHS ester are depicted, but other reactive functional groups could be used, e.g., as described above. In some embodiments, the $(CH_2CH_2O)_n$ are depicted as terminating at the left end with a methoxy group ($OCH_3$) but it will be understood that the chains depicted below and elsewhere herein may terminate with a different OR moiety (e.g., an aliphatic group, an alkyl group, a lower alkyl group, or any other suitable PEG end group) or an OH group. It will also be appreciated that moieties other than those depicted may connect the $(CH_2CH_2O)_n$ moieties with the NHS group in various embodiments.

In some embodiments, a monofunctional PEG is of formula A:

Formula A

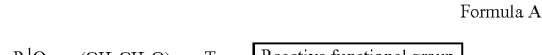

wherein "Reactive functional group" and n are as defined above and described in classes and subclasses herein;

$R^1$ is hydrogen, aliphatic, or any suitable end group; and

T is a covalent bond or a $C_{1-12}$ straight or branched, hydrocarbon chain wherein one or more carbon units of T are optionally and independently replaced by —O—, —S—, —N($R^x$)—, —C(O)—, —C(O)O—, —OC(O)—, —N($R^x$)C(O)—, —C(O)N($R^x$)—, —S(O)—, —S(O)$_2$—, —N($R^x$)SO$_2$—, or —SO$_2$N($R^x$)—; and each $R^x$ is independently hydrogen or $C_{1-6}$ aliphatic.

Exemplary monofunctional PEGs of formula A include:

Formula I

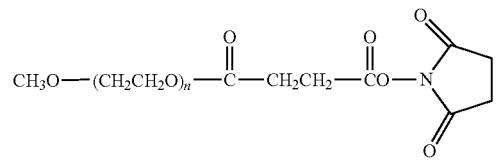

In Formula I, the moiety comprising the reactive functional group has the general structure —CO—$(CH_2)_m$—COO—NHS, where m=2. In some embodiments, a mono functional PEGs has the structure of Formula I, where m is between 1 and 10, e.g., between 1 and 5. For example, in some embodiments m is 3, as shown below:

Formula Ia

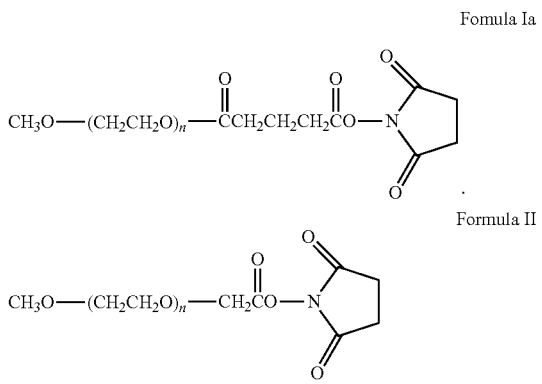

Formula II

In Formula II, the moiety comprising the reactive functional group has the general structure —$(CH_2)_m$—COO—NHS, where m=1. In some embodiments a monofunctional PEG has the structure of Formula II, where m is between 1 and 10 (e.g., wherein m is 5 as shown in Formula III below), or wherein m is 0 (as shown below in Formula IIIa).

Formula III

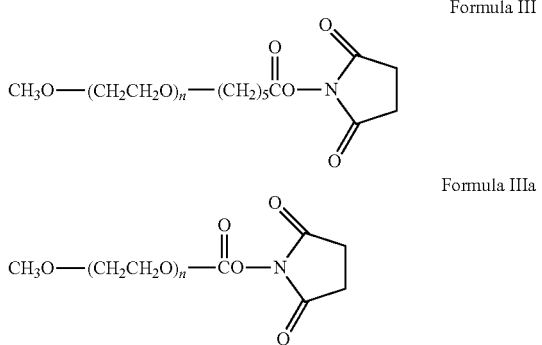

Formula IIIa

In some embodiments a bifunctional linear PEG comprises a moiety comprising a reactive functional group at each of its ends. The reactive functional groups may be the same (homobifunctional) or different (heterobifunctional). In some embodiments the structure of a bifunctional PEG may be symmetric, wherein the same moiety is used to connect the reactive functional group to oxygen atoms at each end of the —$(CH_2CH_2O)_n$ chain. In some embodiments different moieties are used to connect the two reactive functional groups to the PEG portion of the molecule. The structures of exemplary bifunctional PEGs are depicted below. For illustrative purposes, formulas in which the reactive functional group(s) comprise an NHS ester are depicted, but other reactive functional groups could be used.

In some embodiments, a bifunctional linear PEG is of formula B:

Formula B

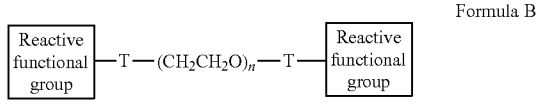

wherein each T and "Reactive functional group" is independently as defined above and described in classes and subclasses herein, and n is as defined above and described in classes and subclasses herein.

Exemplary bifunctional PEGs of formula B include:

Formula IV

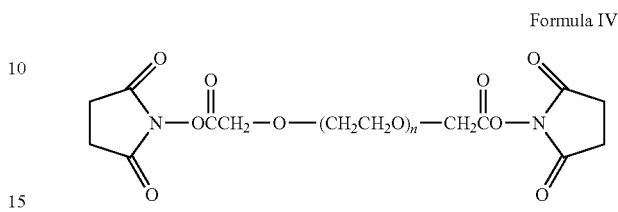

In Formula IV, the moiety comprising the reactive functional group has the general structure —$(CH_2)_m$—COO—NHS, where m=1. In some embodiments, a bifunctional PEG has the structure of Formula IV, where m is between 1 and 10, e.g., between 1 and 5. In certain embodiments m is 0, e.g., embodiments the moiety comprising the reactive functional group has the general structure —COO—NHS. For example, in some embodiments a bifunctional PEG has the structure of Formula IVa, as shown below:

Formula IVa

Formula V

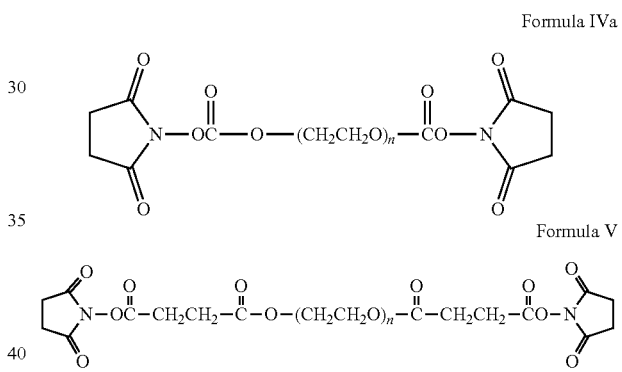

In Formula V, the moiety comprising the reactive functional group has the general structure —CO—$(CH_2)_m$—COO—NHS, where m=2. In some embodiments, a bifunctional PEGs has the structure of Formula V, where m is between 1 and 10, e.g., between 1 and 5. In certain embodiments, for example, m is 2, as shown below:

Formula Va

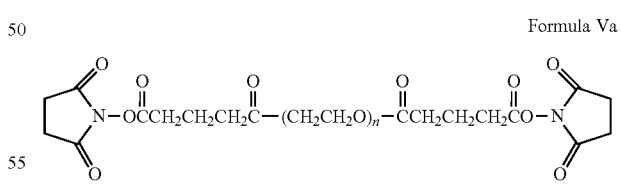

In some embodiments, the present invention provides a compstatin analog conjugated to a polymer. In certain embodiments, the present invention provides compstatin analog conjugates of PEG-containing compounds and genera depicted herein. In some embodiments, a functional group (for example, an amine, hydroxyl, or thiol group) on a compstatin analog is reacted with a PEG-containing compound having a "reactive functional group" as described herein, to generate such conjugates. By way of example, Formulae III and IV, respectively, can form compstatin analog conjugates having the structure:

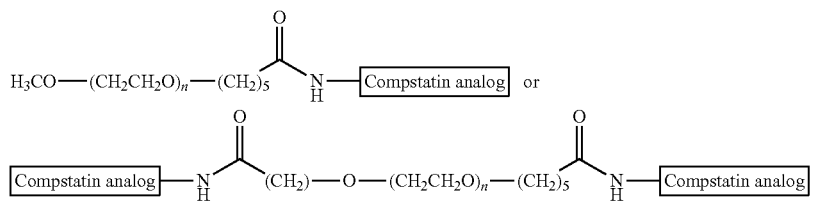

wherein,

represents the attachment point of an amine group on a compstatin analog. In certain embodiments, an amine group is a lysine side chain group.

It will be appreciated that corresponding conjugates can be formed with any of the PEG-containing compounds and genera depicted herein, depending on the choice of reactive functional group and/or compstatin functional group. For example, Formulae IVa and Va, respectively, can form compstatin analog conjugates having the following structures

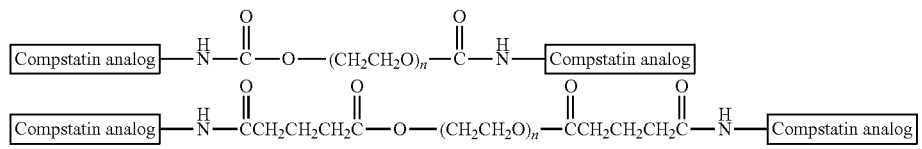

In certain embodiments, the PEG component of such conjugates has an average molecular weight of between about 20 kD-100 kD, about 20 kD-90 kD, about 20 kD-80 kD, about 20 kD-70 kD, about 20 kD-60 kD, about 20 kD-50 kD, about 30 kD-80 kD, about 30 kD-70 kD, about 30 kD-60 kD, about 30 kD-50 kD, about 30 kD-45 kD, about 35 kD-50 kD, about 35 kD-45 kD, about 36 kD-44 kD, about 37 kD-43 kD, about 38 kD-42 kD, or about 39 kD-41 kD. In certain embodiments, the PEG component of such conjugates has an average molecular weight of about 40 kD.

The term "bifunctional" or "bifunctionalized" is sometimes used herein to refer to a compound comprising two compstatin analog moieties linked to a CRM. Such compounds may be designated with the letter "BF". In some embodiments a bifunctionalized compound is symmetrical. In some embodiments the linkages between the CRM and each of the compstatin analog moieties of a bifunctionalized compound are the same. In some embodiments, each linkage between a CRM and a compstatin analog of a bifunctionalized compound comprises a carbamate. In some embodiments, each linkage between a CRM and a compstatin analog of a bifunctionalized compound comprises a carbamate and does not comprise an ester. In some embodiments, each compstatin analog of a bifunctionalized compound is directly linked to a CRM via a carbamate. In some embodiments, each compstatin analog of a bifunctionalized compound is directly linked to a CRM via a carbamate, and the bifunctionalized compound has the structure:

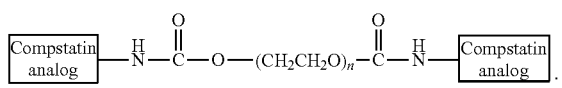

In some embodiments of formulae and embodiments described herein,

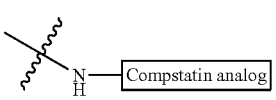

represents point of attachment of a lysine side chain group m a compstatin analog having the structure:

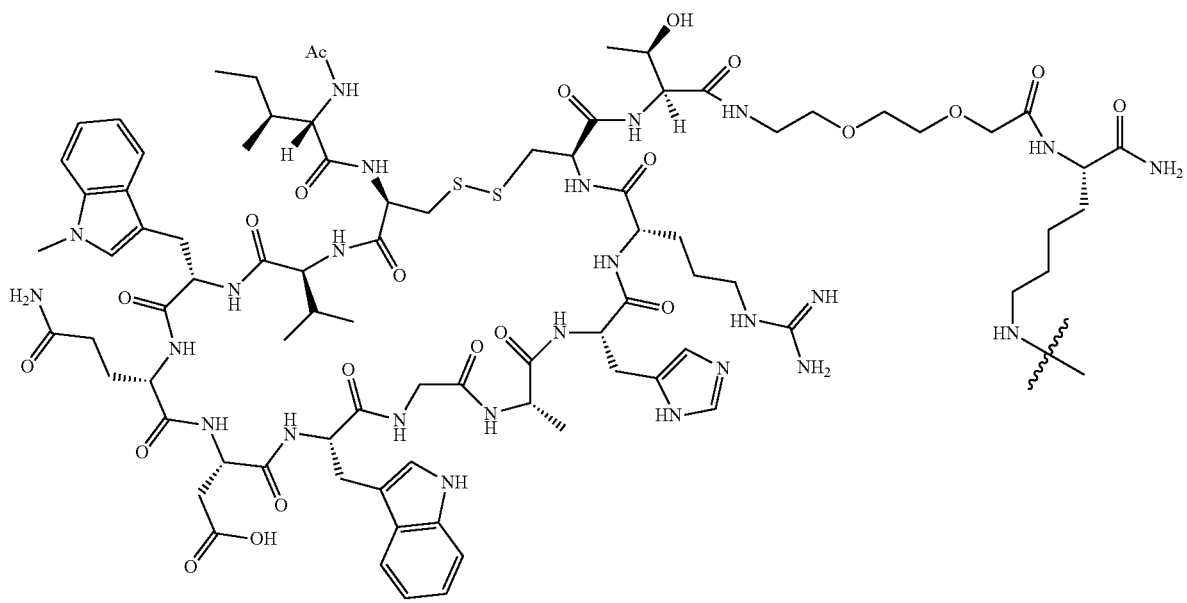 [SMILES: *NCCCC[C@H](NC(=O)COCCOCCNC(=O)[C@@H](NC(=O)[C@@H]1CSSC[C@H](NC(=O)[C@@H](NC(C)=O)[C@@H](C)CC)C(=O)N[C@@H](C(C)C)C(=O)N[C@@H](Cc2cn(C)c3ccccc23)C(=O)N[C@@H](CCC(N)=O)C(=O)N[C@@H](CC(=O)O)C(=O)N[C@@H](Cc2c[nH]c3ccccc23)C(=O)NCC(=O)N[C@@H](C)C(=O)N[C@@H](Cc2cnc[nH]2)C(=O)N[C@@H](CCCNC(=N)N)C(=O)N1)[C@@H](C)O)C(N)=O]

wherein the symbol " ⌇ " denotes the point of attachment of a chemical moiety to the remainder of a molecule or chemical formula.

In some embodiments, a branched, comb, or star-shaped PEG comprises a moiety comprising a reactive functional group at the end of each of multiple $-(CH_2CH_2O)_n$ chains. The reactive functional groups may be the same or there may be at least two different groups. In some embodiments, a branched, comb, or star-shaped PEG is of the following formulae:

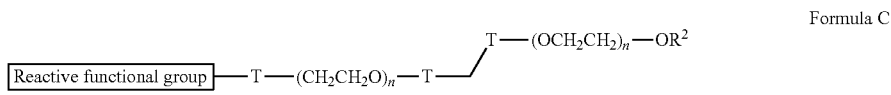

Formula C

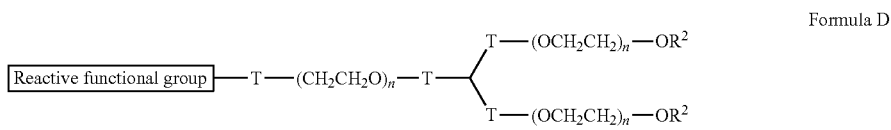

Formula D

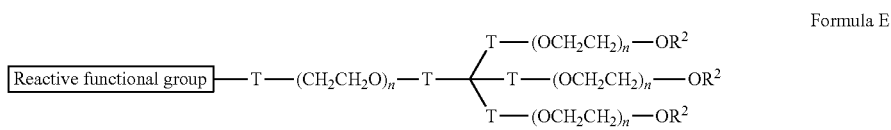

Formula E

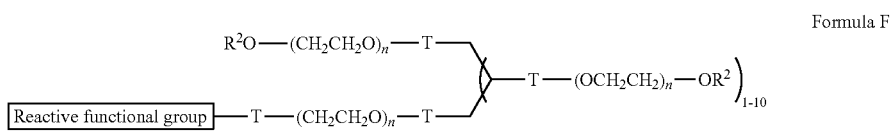

Formula F

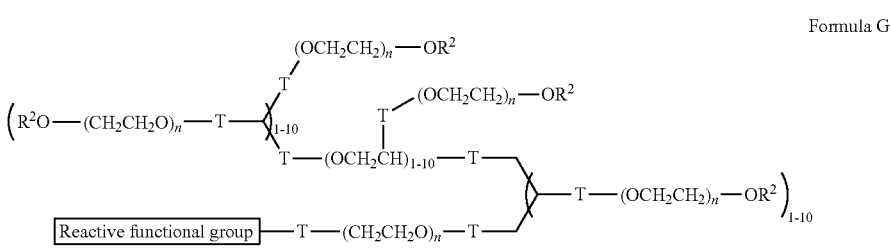

Formula G

Formula H

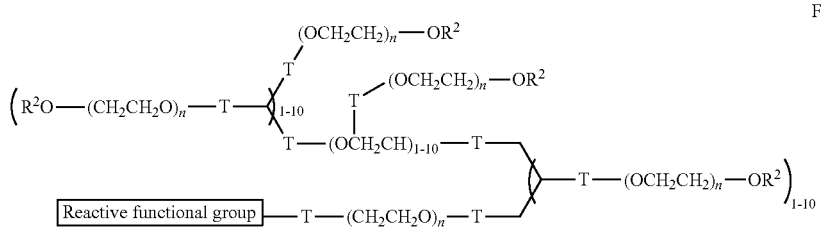

wherein each R² is independently a "Reactive functional group" or R¹, and each T, n, and "Reactive functional group" is independently as defined above and described in classes and subclasses herein. The structure of exemplary branched PEGs (having 8 arms, or branches) comprising NHS moieties as reactive functional groups is depicted below:

Formula VI

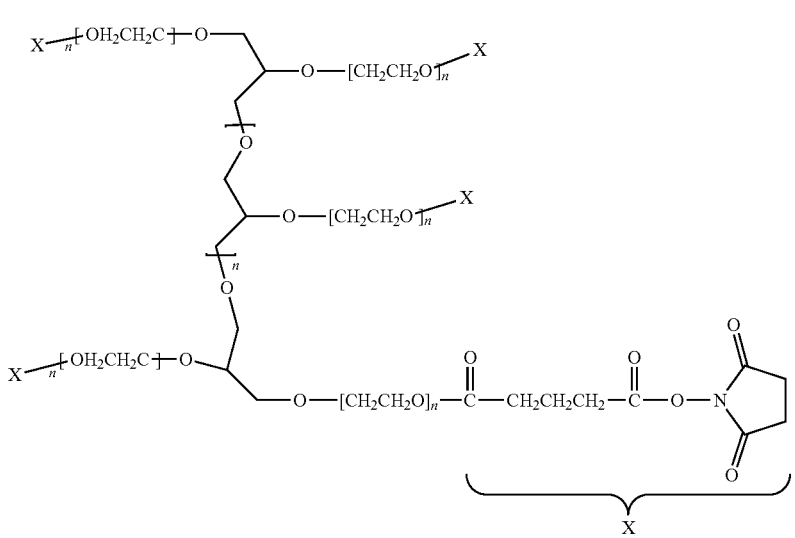

Formula VII

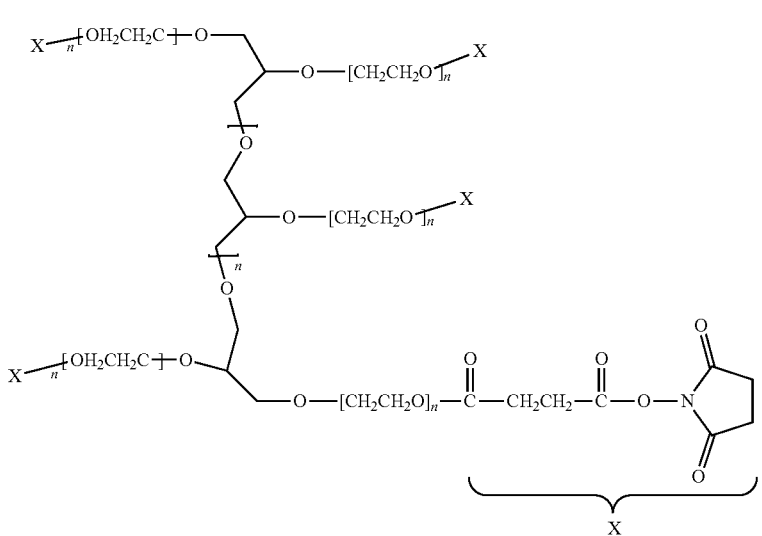

The structure of exemplary branched PEGs (having 4 arms, or branches) comprising NHS moieties as reactive functional groups is depicted below:

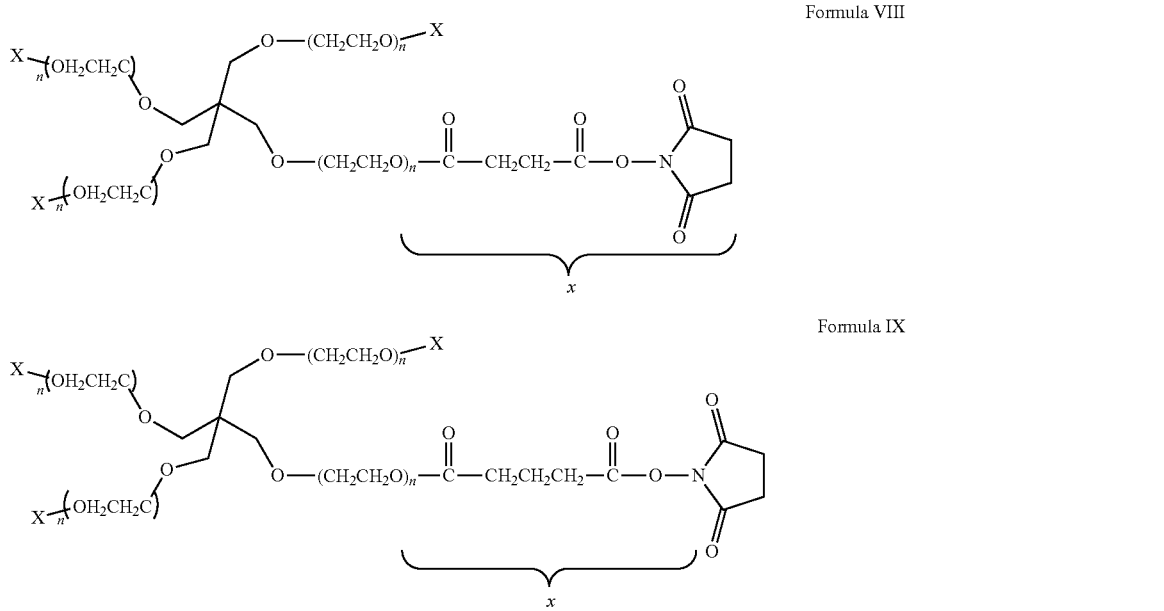

Formula VIII

Formula IX

The number of branches emanating from the backbone may be varied. For example, the number 4 in the above formulae VI and VII may be changed to any other integer between 0 and 10 in various embodiments. In certain embodiments, one or more branches does not contain a reactive function group and the branch terminates with a —CH$_2$CH$_2$OH or —CH$_2$CH$_2$OR group, as described above.

In some embodiments a branched PEG has the structure of Formula VII, VIII, or IX (or variants thereof having different numbers of branches) with the proviso that x is In some embodiments a branched PEG has the structure of Formula VII, VIII, or IX (or variants thereof having different numbers of branches) with the proviso that x is

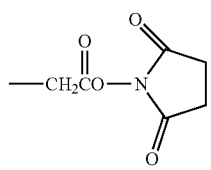

Of course the methylene (CH2) group in the above x moiety may instead comprise a longer alkyl chain (CH$_2$)$_m$, where m is up to 2, 3, 4, 5, 6, 8, 10, 20, or 30, or may comprise one or more other moieties described herein.

In some embodiments, exemplary branched PEGs having NHS or maleimide reactive groups are depicted below:

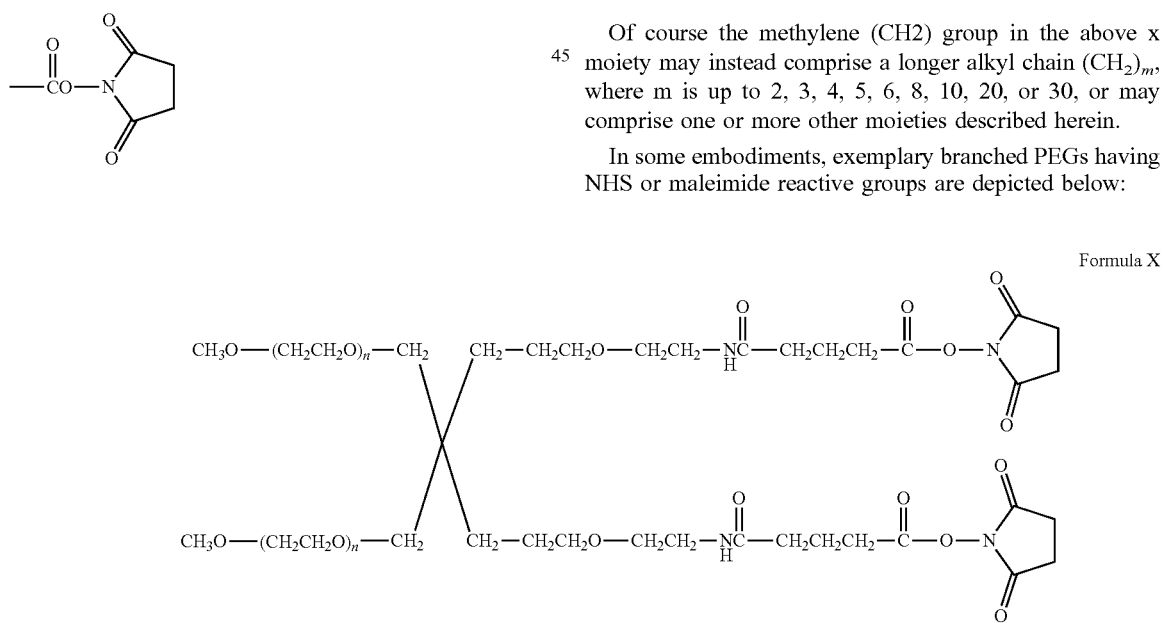

Formula X

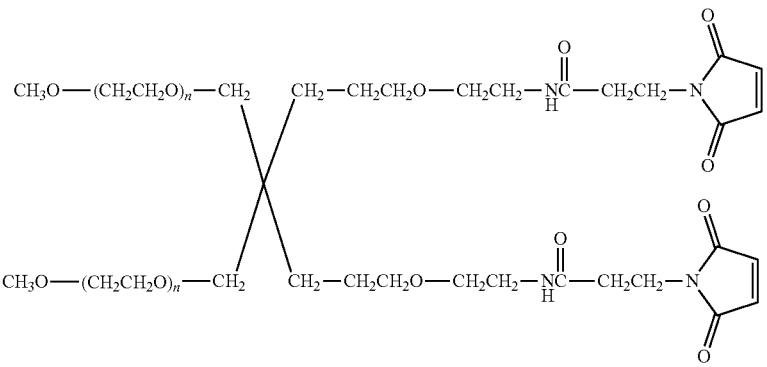

Formula XI

In some embodiments, a variant of Formula X or XI are used, wherein 3 or each of the 4 branches comprise a reactive functional group.

Still other examples of PEGs may be represented as follows:

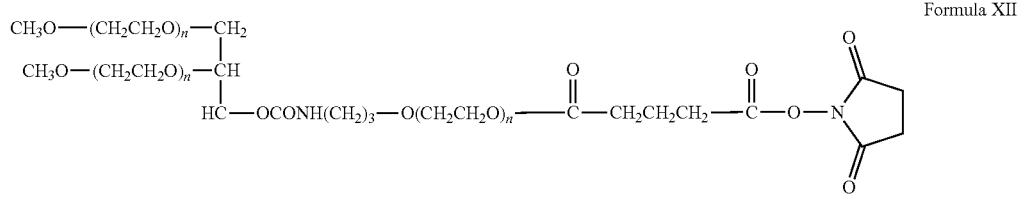

Formula XII

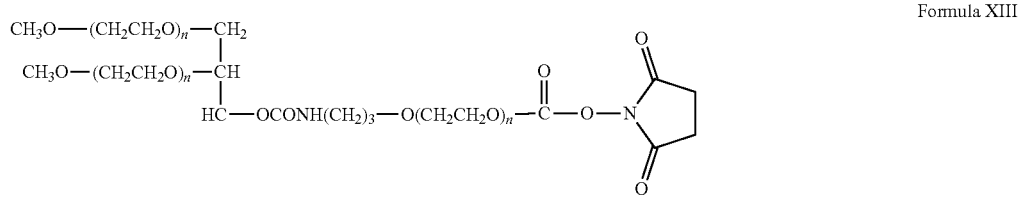

Formula XIII

As noted above, it will be appreciated that, as described herein, in various embodiments any of a variety of moieties may be incorporated between the peptide component and $(CH_2CH_2O)_n$—R moiety of a long-acting compstatin analog, such as an linear alkyl, ester, amide, aromatic ring (e.g., a substituted or unsubstituted phenyl), a substituted or unsubstituted cycloalkyl structure, or combinations thereof. In some embodiments such moiet(ies) may render the compound more susceptible to hydrolysis, which may release the peptide portion of the CRM. In some embodiments, such release may enhance the in vivo tissue penetration and/or activity of the compound. In some embodiments hydrolysis is general (e.g., acid-base) hydrolysis. In some embodiments hydrolysis is enzyme-catalyzed, e.g., esterase-catalyzed. Of course both types of hydrolysis may occur. Examples of PEGs comprising one or more such moieties and an NHS ester as a reactive functional group are as follows:

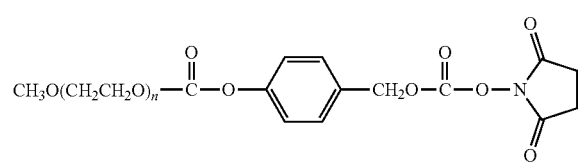

Formula XIV

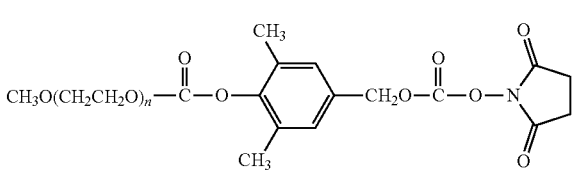

Formula XV

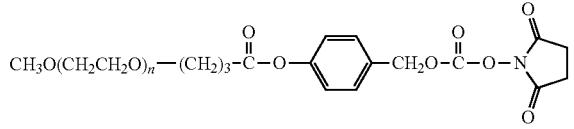

Formula XVI

In some embodiments a branched (multi-arm) PEG or star-shaped PEG comprises a pentaerythritol core, hexaglycerin core, or tripentaerythritol core. It will be understood that the branches may not all emanate from a single point in certain embodiments.

Mono functional, bifunctional, branched, and other PEGs comprising one or more reactive functional groups may, in some embodiments, be obtained from, e.g., NOF America Corp. White Plains, N.Y. or BOC Sciences 45-16 Ramsey Road Shirley, N.Y. 11967, USA, among others, or may be prepared using methods known in the art.

In some embodiments, a linkage between a CRM and a compstatin analog comprises a carbamate. In some embodiments, a compstatin analog is directly linked to a CRM via a carbamate. In some embodiments, a linkage between a CRM and a compstatin analog does not comprise an ester. In some embodiments, a linkage between a CRM and a compstatin analog comprises a carbamate and does not comprise an ester. In some embodiments, a linkage between a CRM and a compstatin analog comprises a carbamate and does not comprise a bond that is more susceptible to hydrolysis in aqueous medium than a carbamate. In some embodiments the CRM comprises or consists of a PEG moiety.

In some embodiments, a linkage between a CRM and a compstatin analog comprises an amide. In some embodiments, a compstatin analog is directly linked to a CRM via an amide. In some embodiments, a linkage between a CRM and a compstatin analog comprises an amide and does not comprise an ester. In some embodiments, a linkage between a CRM and a compstatin analog comprises an amide and does not comprise a bond that is more susceptible to hydrolysis in aqueous medium than an amide. In some embodiments the CRM comprises or consists of a PEG moiety.

In some embodiments, one or more compstatin analogs of a multifunctionalized compound (e.g., a bifunctionalized, trifunctionalized, or more extensively functionalized compound) is linked to a CRM by a linkage comprising a carbamate. In some embodiments, one or more compstatin analogs of a multifunctionalized compound (e.g., a bifunctionalized, trifunctionalized, or more extensively functionalized compound) is linked to a CRM by a linkage that does not comprise an ester. In some embodiments, one or more compstatin analogs of a multifunctionalized compound (e.g., a bifunctionalized, trifunctionalized, or more extensively functionalized compound) is linked to a CRM by a linkage that comprises a carbamate and does not comprise an ester. In some embodiments, one or more compstatin analogs of a multifunctionalized compound (e.g., a bifunctionalized, trifunctionalized, or more extensively functionalized compound) is linked to a CRM by a linkage that comprises a carbamate and does not comprise a bond that is more susceptible to hydrolysis in aqueous medium than a carbamate. In some embodiments, each compstatin analog of a multifunctionalized compound (e.g., a bifunctionalized, trifunctionalized, or more extensively functionalized compound) is directly linked to a CRM via a carbamate.

In some embodiments the CRM comprises or consists of a PEG moiety. In some embodiments, one or more compstatin analogs of a multifunctionalized compound (e.g., a bifunctionalized, trifunctionalized, or more extensively functionalized compound) is linked to a CRM by a linkage comprising an amide. In some embodiments, one or more compstatin analogs of a multifunctionalized compound (e.g., a bifunctionalized, trifunctionalized, or more extensively functionalized compound) is linked to a CRM by a linkage that comprises an amide and does not comprise an ester. In some embodiments, one or more compstatin analogs of a multifunctionalized compound (e.g., a bifunctionalized, trifunctionalized, or more extensively functionalized compound) is linked to a CRM by a linkage that comprises an amide and does not comprise a bond that is more susceptible to hydrolysis in aqueous medium than an amide. In some embodiments, each compstatin analog of a multifunctionalized compound (e.g., a bifunctionalized, trifunctionalized, or more extensively functionalized compound) is directly linked to a CRM via an amide. In some embodiments the CRM comprises or consists of a PEG moiety.

In some embodiments, the present invention provides a compstatin analog conjugated with a polymer, wherein the polymer is other than PEG. In some embodiments, a polymer is a polyoxazoline (POZ). Exemplary mono- and poly-functionalized polyoxazoline derivatives for direct conjugation, or for conjugation via a linker, are depicted below:

$$Z\text{-}T\text{-}[N(COR^x)CH_2CH_2]_n\text{-}T\text{-}R^1;$$

$$R^1\text{—}\{[N(CO\text{-}T\text{-}Z)CH_2CH_2]_m\text{—}[N(COR^x)CH_2CH_2]_n\}^a\text{-}T\text{-}R^1;$$

$$R^1\text{—}\{[N(CO\text{-}T\text{-}Z^1)CH_2CH_2]_p\text{—}[N(COR^x)CH_2CH_2]_n\text{—}[N(CO\text{-}T\text{-}Z^2)CH_2CH_2]_m\}^a\text{-}T\text{-}R^1;$$

$$R^1\text{—}\{[N(CO\text{-}T\text{-}Z^1)CH_2CH_2]_p\text{—}[N(COR^x)CH_2CH_2]_n\text{—}[N(CO\text{-}T\text{-}Z^2)CH_2CH_2]_m\}^a\text{-}T\text{-}Z;$$

$$R^1\text{—}[N(COR^x)CH_2CH_2]_n\text{-}T\text{-}B(\text{—}R^1)(\text{-}T\text{-}Z)\text{-}T\text{-}[N(COR^x)CH_2CH_2]_m\text{—}R^1;$$

wherein:
each of Z, $Z^1$ and $Z^2$ is independently a reactive functional group as defined above and described in classes and subclasses herein;
each of T, $R^x$, and $R^1$ is independently as defined above and described in classes and subclasses herein;
each of m, n, and p is independently an integer 0-1000, with the limitation that the sum of m, n, and p for each formula is not 0;
a is "ran," which indicates a random copolymer, or "block," which indicates a block copolymer;
B is a branching moiety that is linked with or without a linker to the other parts of the polymer.

Other examples of functionalized polyoxazoline derivatives for conjugation are extensively described in the art, including but not limited to those described in PCT Patent Application Publication Nos. WO/2010/006282, WO/2009/089542, WO/2009/043027 and WO/2008/106186, the entirety of each of which is hereby incorporated by reference.

Exemplary compstatin analog conjugates with polyoxazoline polymers are depicted below:

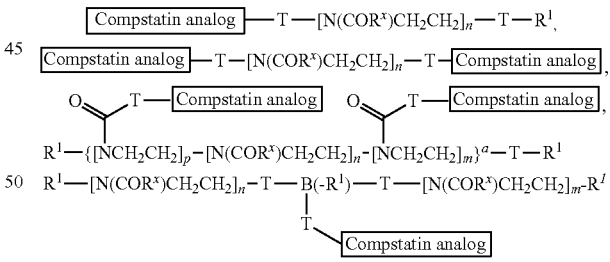

wherein each variable is independently as defined above and described in classes and subclasses herein.

In some embodiments, the present invention provides a compstatin analog conjugated with a polymer, wherein the compstatin analog is connected to the polymer via one or more linkers. In some embodiments, a polymer is selected from PEG-containing compounds and genera described above and in classes and subclasses herein. In some embodiments, the present invention provides compstatin analog conjugates of PEG-containing compounds and genera depicted herein, wherein the compstatin analog is connected to the PEG-containing moieties via one or more linkers. Mono- and poly-functional PEGs that comprise one or more reactive functional groups for conjugation are defined above and described in classes and subclasses herein, including but not limited to those of formula A, I, Ia, II, III, IIIa, B, IV, IVa, V, Va, C, D, E, F, G, H, VI, VII, VIII, IX, X, XI, XII, XIII, XIV, XV, or XVI.

Suitable linkers for connecting a compstatin analog and a polymer moiety such as PEG or polyoxazoline are extensively described above and in classes and subclasses herein. In some embodiments, a linker has multiple functional groups, wherein one functional group is connected to a compstatin analog and another is connected to a polymer moiety. In some embodiments, a linker is a bifunctional compound. In some embodiments, a linker has the structure of $NH_2(CH_2CH2O)nCH_2C(=O)OH$, wherein n is 1 to 1000. In some embodiments, a linker is 8-amino-3,6-dioxaoctanoic acid (AEEAc). In some embodiments, a linker is activated for conjugation with a polymer moiety or a functional group of a compstatin analog. For example, in some embodiments, the carboxyl group of AEEAc is activated before conjugation with the amine group of the side chain of a lysine group.

In some embodiments, a suitable functional group (for example, an amine, hydroxyl, thiol, or carboxylic acid group) on a compstatin analog is used for conjugation with a polymer moiety, either directly or via a linker. In some embodiments, a compstatin analog is conjugated through an amine group to a PEG moiety via a linker. In some embodiments, an amine group is the α-amino group of an amino acid residue. In some embodiments, an amine group is the amine group of the lysine side chain. In some embodiments, a compstatin analog is conjugated to a PEG moiety through the amino group of a lysine side chain (ε-amino group) via a linker having the structure of $NH_2(CH_2CH_2O)nCH_2C(=O)OH$, wherein n is 1 to 1000. In some embodiments, a compstatin analog is conjugated to the PEG moiety through the amino group of a lysine side chain via an AEEAc linker. In some embodiments, the $NH_2(CH_2CH_2O)nCH_2C(=O)OH$ linker introduces a $-NH(CH_2CH_2O)nCH_2C(=O)-$ moiety on a compstatin lysine side chain after conjugation. In some embodiments, the AEEAc linker introduces a $-NH(CH_2CH_2O)_2CH_2C(=O)-$ moiety on a compstatin lysine side chain after conjugation.

In some embodiments, a compstatin analog is conjugated to a polymer moiety via a linker, wherein the linker comprises an AEEAc moiety and an amino acid residue. In some embodiments, a compstatin analog is conjugated to a polymer moiety via a linker, wherein the linker comprises an AEEAc moiety and a lysine residue. In some embodiments, a polymer is PEG. In some embodiments, the C-terminus of a compstatin analog is connected to the amino group of AEEAc, and the C-terminus of AEEAc is connected to a lysine residue. In some embodiments, the C-terminus of a compstatin analog is connected to the amino group of AEEAc, and the C-terminus of AEEAc is connected to the α-amino group of a lysine residue. In some embodiments, the C-terminus of a compstatin analog is connected to the amino group of AEEAc, the C-terminus of AEEAc is connected to the α-amino group of the lysine residue, and a polymer moiety, such as a PEG moiety, is conjugated through the ε-amino group of said lysine residue. In some embodiments, the C-terminus of the lysine residue is modified. In some embodiments, the C-terminus of the lysine residue is modified by amidation. In some embodiments, the N-terminus of a compstatin analog is modified. In some embodiments, the N-terminus of a compstatin analog is acetylated.

Exemplary conjugates comprising an AEEAc linker and a polymer are depicted below, wherein

represents the attachment point of an amine group on a compstatin analog,

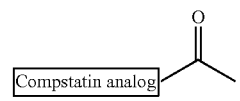

represents a compstatin analog attaching through its C-terminus, and wherein each of the other variables is independently as defined above and described in classes and subclasses herewith. In some embodiments, an amine group is the amino group of a lysine side chain.

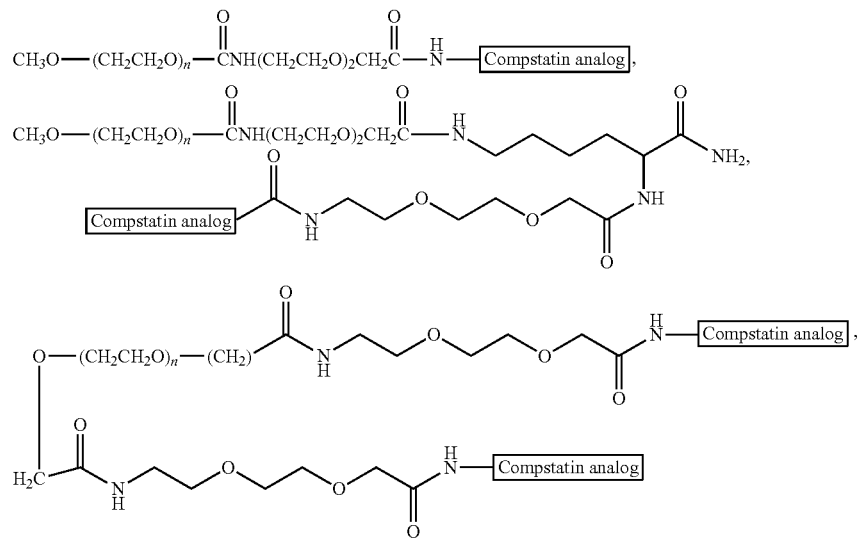

-continued
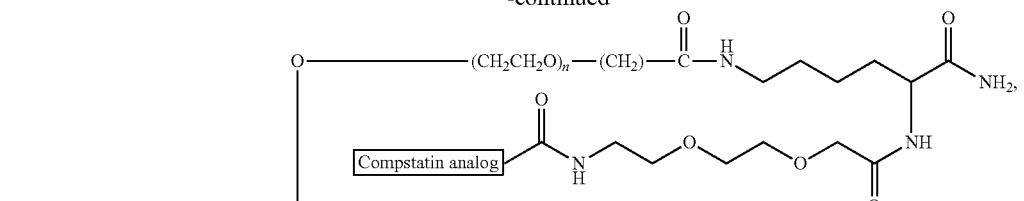
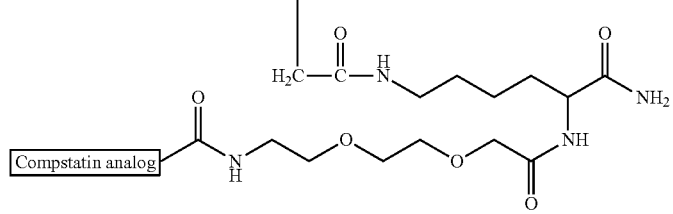
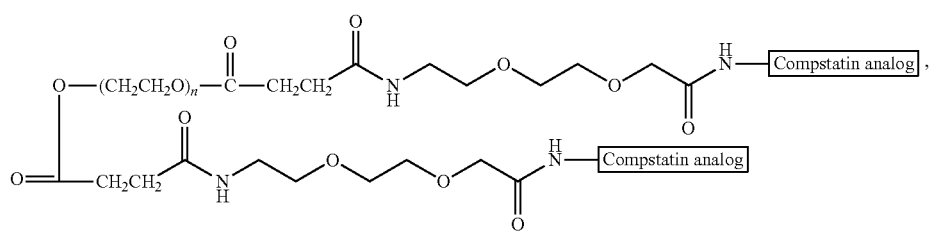
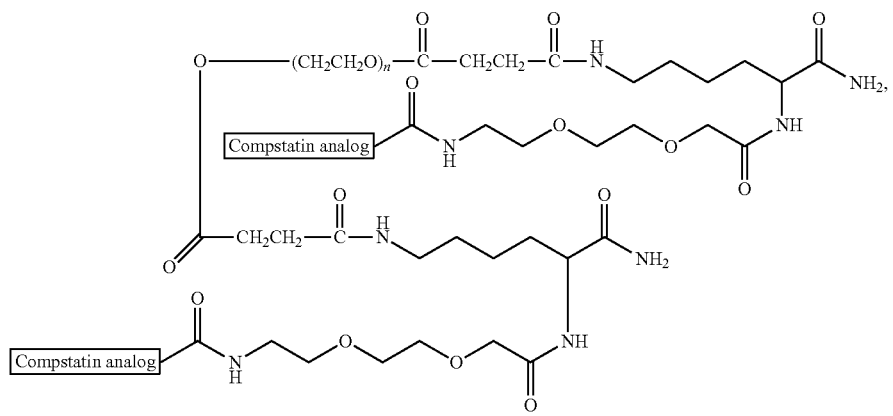
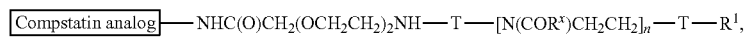
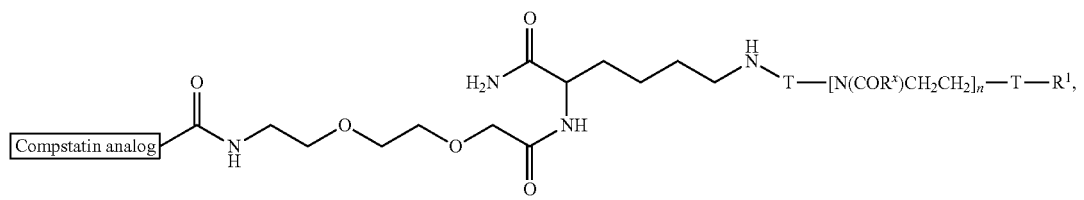
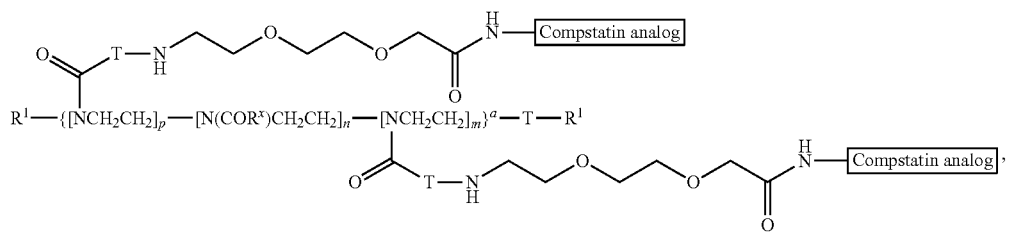

-continued
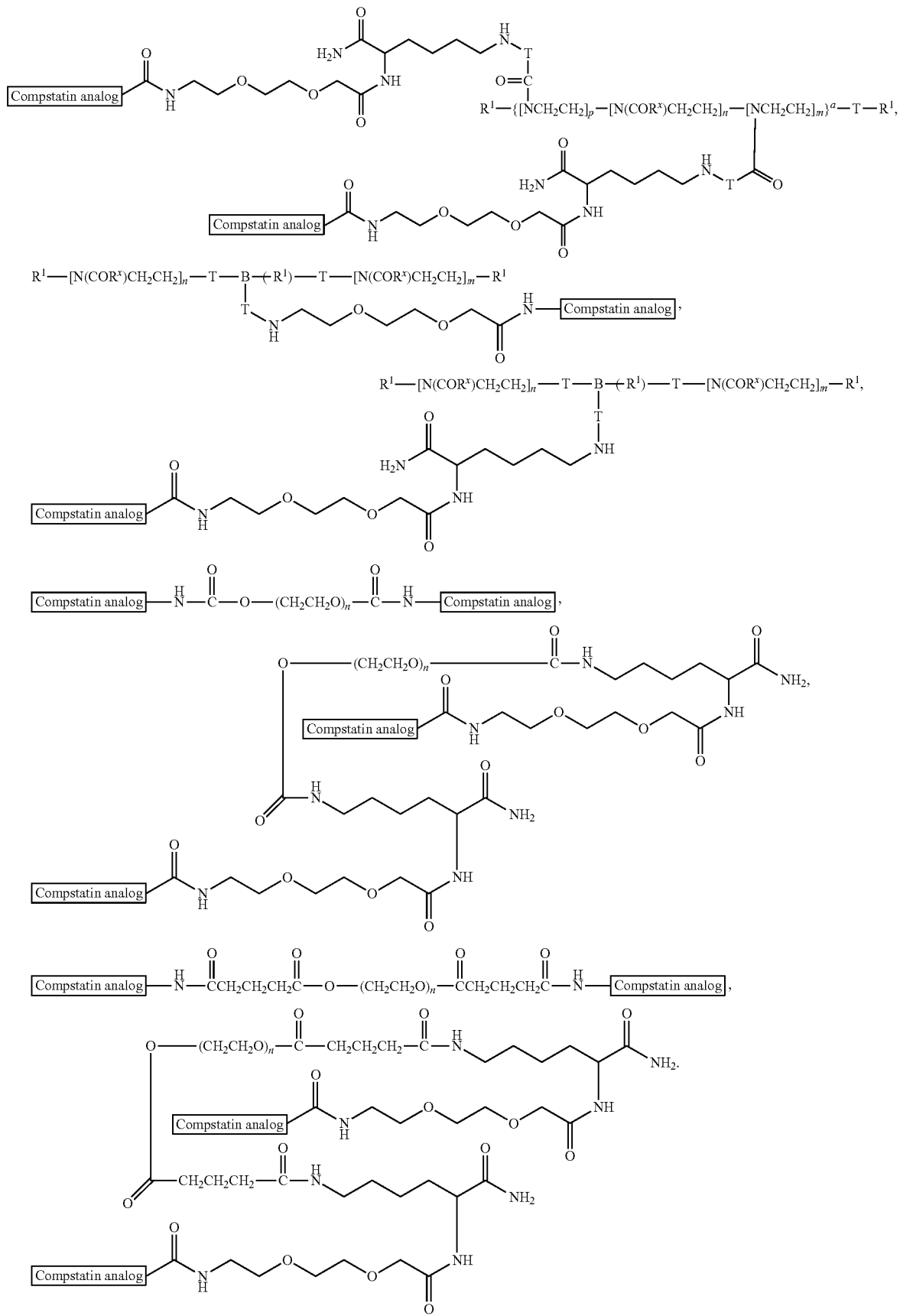

In certain embodiments a compstatin analog may be represented as M-AEEAc-Lys-B2, wherein B2 is a blocking moiety, e.g., $NH_2$, M represents any of SEQ ID NOs: 3-36, 37, 70, 71, 72, 73, or 74, with the proviso that the C-terminal amino acid of any of SEQ ID NOs: 3-36, 37, 70, 71, 72, 73, or 74 is linked via a peptide bond to AEEAc-Lys-$B_2$. The NHS moiety of a monofunctional or multifunctional (e.g., bifunctional) PEG reacts with the free amine of the lysine side chain to generate a monofunctionalized (one compstatin analog moiety) or multifunctionalized (multiple compstatin analog moieties) long-acting compstatin analog. In various embodiments any amino acid comprising a side chain that comprises a reactive functional group may be used instead of Lys (or in addition to Lys). A monofunctional or multifunctional PEG comprising a suitable reactive functional group may be reacted with such side chain in a manner analogous to the reaction of NHS-ester activated PEGs with Lys.

With regard to any of the above formulae and structures, it is to be understood that embodiments in which the compstatin analog component comprises any compstatin analog described herein, e.g., any compstatin analog of SEQ ID NOs; 3-36, 37, 70, 71, 72, 73, 74, are expressly disclosed. For example, and without limitation, a compstatin analog may comprise the amino acid sequence of SEQ ID NO: 28. An exemplary long-acting compstatin analog in which the compstatin analog component comprises the amino acid sequence of SEQ ID NO: 28 is depicted in FIG. 10(C). It will be understood that the PEG moiety may have a variety of different molecular weights or average molecular weights in various embodiments, as described herein. For example, individual PEG chains within a preparation may vary in molecular weight and/or different preparations may have different average molecular weights and/or polydispersity, as described herein. In certain embodiments, the PEG moiety in the compound of FIG. 10(C) has an average molecular weight of between about 20 kD-100 kD, about 20 kD-90 kD, about 20 kD-80 kD, about 20 kD-70 kD, about 20 kD-60 kD, about 20 kD-50 kD, about 30 kD-80 kD, about 30 kD-70 kD, about 30 kD-60 kD, about 30 kD-50 kD, about 30 kD-45 kD, about 35 kD-50 kD, about 35 kD-45 kD, about 36 kD-44 kD, about 37 kD-43 kD, about 38 kD-42 kD, or about 39 kD-41 kD. In some embodiments the PEG moiety in the compound of FIG. 10(C) has an average molecular weight between about 30 kD and about 50 kD, e.g., between about 35 kD and about 45 kD, between about 37.5 kD and about 42.5 kD. In certain embodiments in which the PEG moiety has an average molecular weight of about 40 kD, e.g., 37.5 kD-42.5 kD, 38 kD, 39 kD, 40 kD, 41 kD, 42 kD, the compound is sometimes referred to herein as CA28-2TS-BF. In certain embodiments a compound comprising a CRM, e.g., a PEG moiety, that has an average molecular weight of about 40 kD, e.g., 37.5 kD-42.5 kD, 38 kD, 39 kD, 40 kD, 41 kD, 42 kD, the compound has a terminal half-life of at least about 5 days, e.g., about 5-10 days, e.g., about 5, 6, 7, 8, 9 days, when administered IV or subcutaneously to non-human primates or humans, e.g., at a dose of about 1-3 mg/kg, 3-5 mg/kg, or 5-10 mg/kg.

In some aspects, the present invention relates to use of click chemistry in connection with compstatin analogs. "Click chemistry" is well known in the art and is useful in some aspects of the present invention. Click chemistry embodies, in certain embodiments, versatile cycloaddition reactions between azides and alkynes that enable a number of useful applications. Methods of carrying out click chemistry are known in the art, and are described by Kolb, H. C.; Sharpless, K. B., Drug Disc. Today, 2003, 1128-1137; Moses, J. E.; Moorhouse, A. D.; *Chem. Soc. Rev.*, 2007, 1249-1262; the entire contents of each are hereby incorporated by reference. Click chemistry is a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques and synthetic methods permit the introduction of azides and alkyne-bearing non-canonical amino acids into peptides, proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukheiji, M.; Chin, J. W.; Anderson, C.; Schultz, P. G. *J. Am. Chem. Soc.* 2003, 125, 11782-11783.

As used herein, the term "click chemistry group" is sometimes used to refer\to a reactive functional group capable of participating in a click chemistry reaction with an appropriate second reactive functional group, which second reactive functional group is also a click chemistry group. The first and second click chemistry groups, or entities (e.g., molecules) comprising such groups, may be referred to as complementary. First and second entities, e.g., molecules, that comprise complementary click chemistry groups may be referred to as click chemistry partners. An entity or molecule comprising a click chemistry group may be referred to as "click-functionalized". A bond formed by reaction of complementary click chemistry partners may be referred to as a "click chemistry bond".

In some embodiments, the present invention provides click-functionalized compstatin analogs for, e.g., conjugation to a complementary moiety on a partner molecule or biomolecule. In some embodiments, a complementary partner molecule or biomolecule is a polymer, peptide, protein, or a molecule that functions as a clearance-reducing moiety. In some embodiments, the "click-functionalized" moiety is an alkyne or an alkyne derivative which is capable of undergoing [3+2] cycloaddition reactions with complementary azide-bearing molecules and biomolecules. In another embodiment, the "click-functionalized" functionality is an azide or an azide derivative which is capable of undergoing [3+2]cycloaddition reactions with complementary alkyne-bearing molecules and biomolecules (i.e. click chemistry).

In some embodiments, a click-functionalized compstatin analog bears an azide group on any side chain group of the compstatin analog. In some embodiments, a click-functionalized compstatin analog bears an azide group on a lysine side chain group.

In some embodiments, a click-functionalized compstatin analog bears an alkyne group on any side chain group of the compstatin compstatin analog. In some embodiments, a click-functionalized compstatin analog bears an alkyne group on a lysine side chain group.

In some embodiments, the present invention provides compstatin conjugates comprising a compstatin analog, a molecule that functions as a clearance-reducing moiety, and a triazole linker. In some embodiments, a triazole linker is the result of click conjugation chemistry between a compstatin conjugate and a molecule that functions as a clearance-reducing moiety. In some embodiments the CRM may be any CRM disclosed herein. For example, the CRM may be a PEG, a polypeptide, or a POZ.

In some embodiments, the present invention provides compstatin conjugates comprising a compstatin analog, a PEG moiety, and a triazole linker. In some embodiments, a triazole linker is the result of click conjugation chemistry between a compstatin conjugate and a PEG moiety.

In some embodiments, the present invention provides compstatin conjugates comprising a compstatin analog, a polyoxazoline moiety, and a triazole linker. In some embodiments, a triazole linker is the result of click conjugation chemistry between a compstatin conjugate and a polyoxazoline moiety.

In some embodiments, click chemistry between a compstatin analog and another moiety is transition metal catalyzed. Copper-containing molecules which catalyze the "click" reaction include, but are not limited to, copper wire, copper bromide (CuBr), copper chloride (CuCl), copper sulfate (CuSO$_4$), copper sulfate pentahydrate (CuSO$_4$.5H$_2$O), copper acetate (Cu$_2$(AcO$_4$), copper iodide (CuI), [Cu(MeCN)$_4$](OTf), [Cu(MeCN)$_4$](PF$_6$), colloidal copper sources, and immobilized copper sources. In some embodiments other metals, such as ruthenium. Reducing agents as well as organic and inorganic metal-binding ligands can be used in conjunction with metal catalysts and include, but are not limited to, sodium ascorbate, tris(triazolyl)amine ligands, tris(carboxyethyl)phosphine (TCEP), sulfonated bathophenanthroline ligands, and benzimidazole-based ligands.

In some embodiments, compstatin analogs are conjugated to other moieties using metal free click chemistry (also known as copper free click chemistry) to give a metal free composition or conjugates. In contrast to standard click chemistry, also known as copper assisted click chemistry (CuACC), metal free click chemistry occurs between either a strained, cyclic alkyne or an alkyne precursor such as an oxanorbomadiene, and an azide group. As the name implies, no metal catalyst is necessary for the reaction to occur. Examples of such chemistries include reactions involving cyclooctyne derivatives (Codelli, et. al. *J. Am. Chem. Soc.*, 2008, I30, 11486-11493; Jewett, et. al. *J. Am. Chem. Soc.*, 2010, 132, 3688-3690; Ning, et. al. *Angew. Chem. Int. Ed.*, 2008, 47, 2253-2255), difluoro-oxanorbomene derivatives (van Berkel, et. al. *ChemBioChem*, 2007, 8, 1504-1508), or nitrile oxide derivatives (Lutz, et. al. Macromolecules, 2009, 42, 5411-5413). In certain embodiments a metal-free click chemistry reaction is a metal-free [3+2] cycloaddition reaction, Diels-Alder reaction, or thiol-alkene radical addition reaction. Exemplary click chemistry reactions and click chemistry groups are described in, e.g., Joerg Lahann, Click Chemistry for Biotechnology and Materials Science, 2009, John Wiley & Sons Ltd, ISBN 978-0-470-69970-6; Becer, Hoogenboom, and Schubert, Click Chemistry beyond Metal-Catalyzed Cycloaddition, Angewandte Chemie International Edition (2009) 48: 4900-4908. In certain embodiments a click chemistry group comprises a diarylcyclooctyne.

Certain examples of metal free click chemistry are shown in the scheme below.

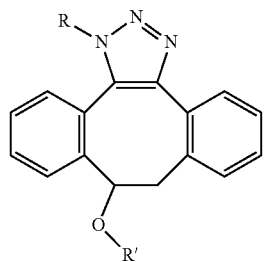

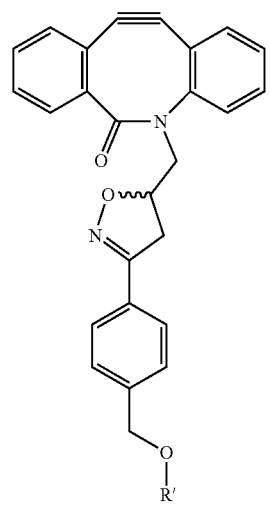

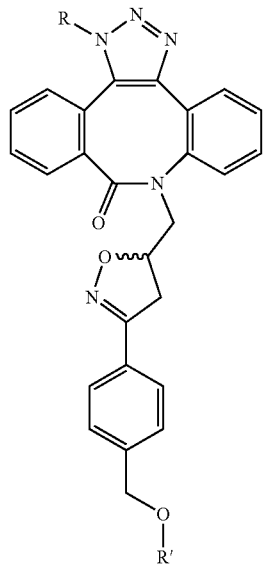

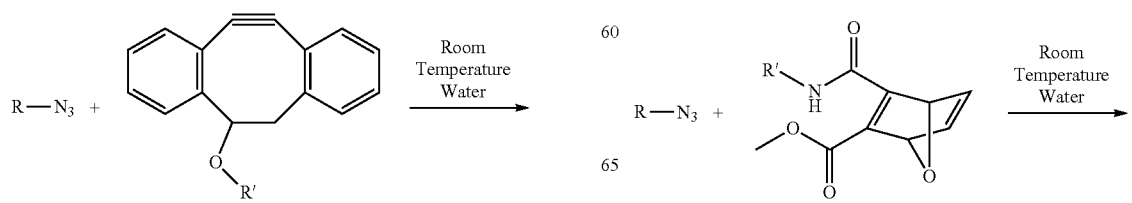

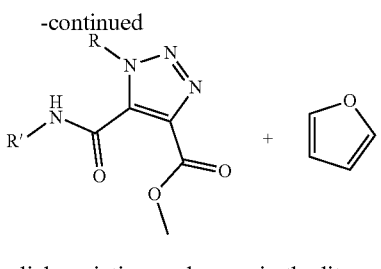

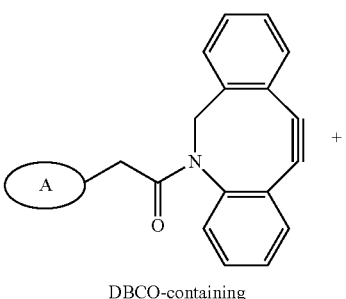

DBCO-containing
molecule A

Certain metal-free click moieties are known in the literature. Examples include 4-dibenzocyclooctynol (DIBO)

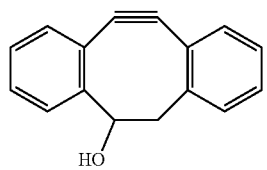 [SMILES: OC1Cc2ccccc2C#Cc2ccccc21]

(from Ning et. al; Angew Chem Int Ed, 2008, 47, 2253); difluorinated cyclooctynes (DIFO or DFO)

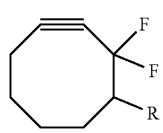

(from Codelli, et. al.; J. Am. Chem. Soc. 2008, 130, 11486-11493.); biarylazacyclooctynone (BARAC)

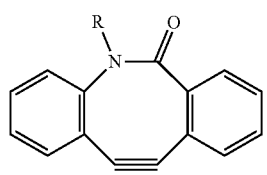

(from Jewett et. al.; J. Am. Chem. Soc. 2010, 132, 3688); or bicyclononyne (BCN)

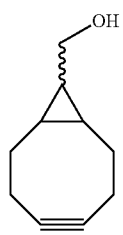

(From Dommerholt, et. al.; *Angew Chem Int Ed*, 2010, 49, 9422-9425) or dibenzylcyclooctyne (DBCO)

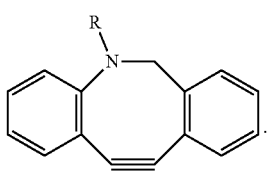

A reaction scheme involving reaction of DBCO and an azide is shown below:

Azide-containing
molecule B

Conjugate of A and B, cross-linked via a Triazole moiety

In the above scheme, in various embodiments, A may comprise or consist of a compstatin analog moiety and B may comprise or consist of a CRM, e.g., a polymer, such as a PEG or a POZ or a polypeptide, or B may comprise or consist of a compstatin analog moiety and A may comprise or consist of a CRM, e.g., a polymer, such as a PEG or a POZ or a polypeptide.

In some embodiments, the "metal free click-functionalized" moiety is an acetylene or an acetylene derivative which is capable of undergoing [3+2] cycloaddition reactions with complementary azide-bearing molecules and biomolecules without the use of a metal catalyst.

In some embodiments, the R and R' groups of the metal-free click chemistry reagents are a compstatin analog or any molecule described herein to which a compstatin analog may be conjugated. In some embodiments, such compstatin analogs bear a click-functionalized moiety on a lysine side chain. In some embodiments, such compstatin analogs are connected to a click-functionalized moiety via a linker. In some embodiments, such compstatin analogs are connected to a click-functionalized moiety via AEEAc.

In some embodiments, a click chemistry reagent comprises DBCO. Exemplary reagents and exemplary uses thereof are set forth below:

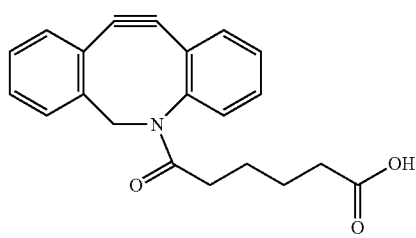 [SMILES: O=C(O)CCCCC(=O)N1Cc2ccccc2C#Cc2ccccc21]

DBCO-Acid. In some embodiments a DBCO-Acid may be used to react with an amine-containing moiety.

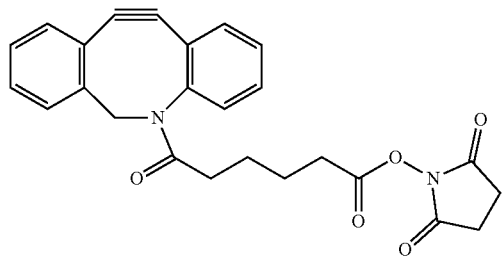 [SMILES: O=C(CCCCC(=O)N1Cc2ccccc2C#Cc2ccccc21)ON1C(=O)CCC1=O]

DBCO-NHS ester (above) or DBCO-sulfo-NHS ester (below) may be used to incorporate a DBCO functionality into an amine-containing molecule, such as a compstatin analog or a polypeptide comprising a lysine residue.

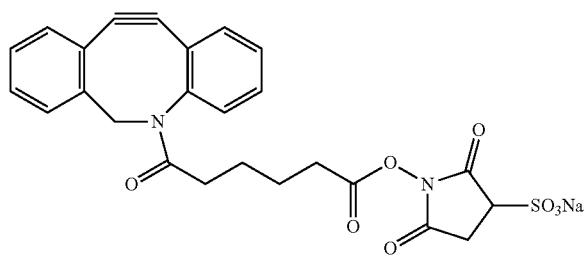

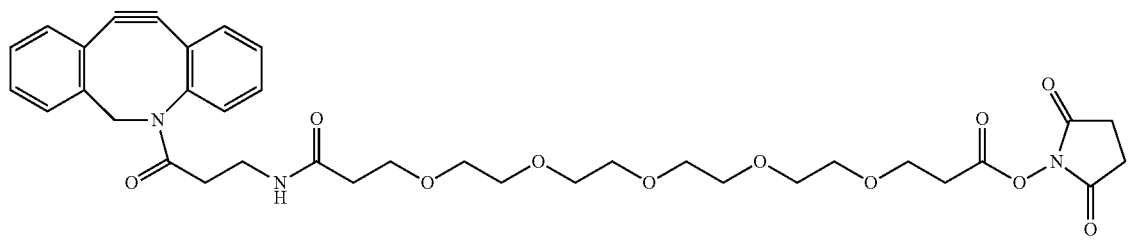

DBCO-PEG4-NHS ester. In some embodiments such reagent is useful for introducing a DBCO moiety by reaction with an available amine functionality. In some aspects, the presence of a PEG chain as a hydrophilic spacer may be useful to, e.g., increase solubility or provide flexibility.

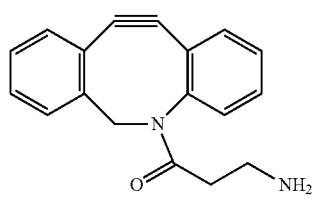 [SMILES: NCCC(=O)N1Cc2ccccc2C#Cc2ccccc21]

DBCO-Amine. In some embodiments a click chemistry reagent comprises a carbonyl/carboxyl reactive dibenzylcyclooctyne, which may react with acids, active esters and/or aldehydes.

In certain embodiments a click chemistry reaction involves a cyclooctyne depicted below:

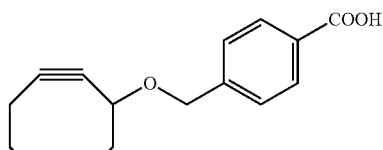
OCT

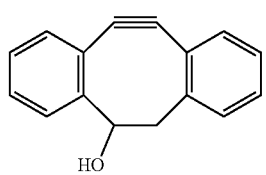
DIBO

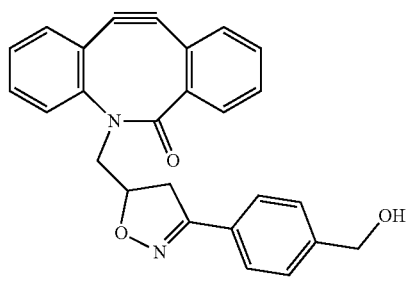
BARAC

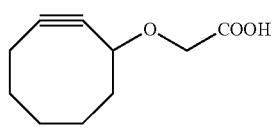
ALO

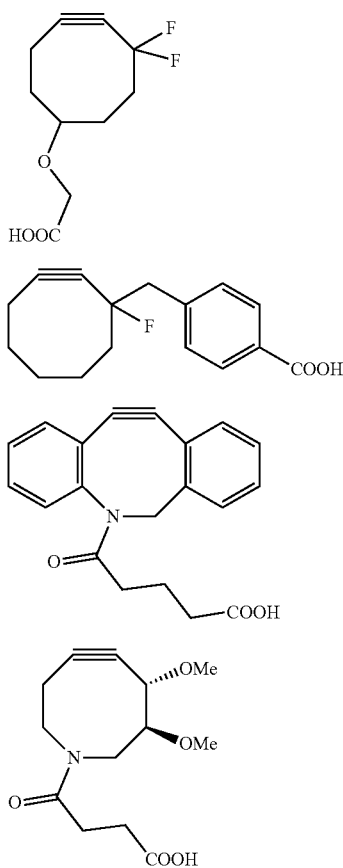

DIFO

MOFO

DIBAC

DIMAC

In certain embodiments click chemistry reactions comprise reactions between nitrones and cyclooctynes (see, e.g., Ning, Xinghai; Temming, Rinske P.; Dommerholt, Jan; Guo, Jun; Ania, Daniel B.; Debets, Marjoke F.; Wolfert, Margreet A.; Boons, Geert-Jan et al. (2010). "Protein Modification by Strain-Promoted Alkyne-Nitrone Cycloaddition". Angewandte Chemie International Edition 49 (17): 3065), oxime/hydrazone formation from aldehydes and ketones, tetrazine ligations (see, e.g., Blackman, Melissa L.; Royzen, Maksim; Fox, Joseph M. (2008). "The Tetrazine Ligation: Fast Bioconjugation based on Inverse-electron-demand Diels-Alder Reactivity". Journal of the American Chemical Society 130 (41): 13518-9), tetrazole ligations, the isonitrile-based click reaction (see, e.g., Stackmann, Henning; Neves, André A.; Stairs, Shaun; Brindle, Kevin M.; Leeper, Finian J. (2011). "Exploring isonitrile-based click chemistry for ligation with biomolecules". Organic & Biomolecular Chemistry 9 (21): 7303), and the quadricyclane ligation (see, e.g., Sletten, Ellen M.; Bertozzi, Carolyn R. (2011). "A Bioorthogonal Quadricyclane Ligation". Journal of the American Chemical Society 133 (44): 17570-3). In certain embodiments a click chemistry reaction is a Staudinger ligation (phosphine-azide).

Any compstatin analog may be modified to incorporate a click chemistry group in various embodiments. For example, a compstatin analog comprising the sequence of any of SEQ ID NOs: 3-36, 37, 70, 71, 72, 73, or 74 may be so modified. In some embodiments any such sequence further comprises a lysine residue or an AEEAc-Lys moiety, e.g., at the C-terminus. In some embodiments a click chemistry group is incorporated after peptide synthesis. For example, a Lys side chain may be reacted with azido acetic acid in order to introduce an azide moiety as a click chemistry group. In some embodiments a click chemistry group is incorporated after cyclization and, in some embodiments, after addition of a blocking moiety at the N- and/or C-terminus. In some embodiments a click chemistry group is incorporated during peptide synthesis. For example, an amino acid comprising a side chain that comprises a click chemistry group may be used in the synthesis of a compstatin analog. A variety of such amino acids are commercially available from a number of sources, e.g., AAPPTec (Louisville, Ky.), Jena Bioscience GmBH (Jena, Germany). In some aspects, methods of making a click chemistry functionalized compstatin analog are provided herein.

In some embodiments compositions comprising a compstatin analog and a click chemistry reagent are provided. The click chemistry reagent may be any molecule capable of reacting with an amino acid side chain or terminus of a compound comprising a compstatin analog so as to install a click chemistry group, e.g., any click chemistry group known in the art. In some aspects, the composition may be incubated under suitable conditions (which may include providing a suitable catalyst, light (e.g., UV)) to functionalize the compstatin analog with a click chemistry functionality. In some embodiments, the invention provides compstatin analogs that comprise any click chemistry group including, but not limited to, those described herein. In some embodiments methods of making a long-acting compstatin analog are provided. In some embodiments the methods comprise mixing a compstatin analog comprising a first click chemistry group with a CRM comprising a complementary click chemistry group under conditions suitable for a click chemistry reaction to occur. Additional steps may comprise purifying the resulting conjugate. In some embodiments purifying comprises removing at least some unreacted components, e.g., with an appropriate scavenger.

In some embodiments a click chemistry reaction is used to join two or more CRMs, at least two of which have a compstatin analog moiety attached thereto. The compstatin analog moieties may be the same or different in various embodiments. The compstatin analog moieties may or may not be attached to the CRM via a click chemistry reaction. For example, in some embodiments a first heterobifunctional PEG comprising a first click chemistry group at a first terminus and an NHS ester at a second terminus is coupled to a compstatin analog moiety via the NHS ester. In a separate reaction, a second heterobifunctional PEG comprising a second click chemistry group at a first terminus and an NHS ester at a second terminus is coupled to a compstatin analog moiety via the NHS ester. The resulting two compounds are then reacted via a click chemistry reaction to form a larger molecule comprising two compstatin analog moieties. PEG is mentioned as an example of a CRM but it should be understood that this approach may be used with any CRM. For example, in some embodiments it may be used with a CRM comprising a polypeptide, e.g., HSA or a portion thereof, or an albumin or albumin-binding peptide, or an antibody or portion thereof. In some embodiments this approach may be used with a POZ.

Compstatin analogs comprising a click chemistry group have a variety of uses. In some embodiments a compstatin analog comprising a first click chemistry group is reacted with any entity that comprises a complementary click chemistry group. The entity comprising the complementary click chemistry group may comprise, for example, a label (e.g., a flurophore, fluorescent protein, radioisotope, etc.), an affinity reagent, an antibody, a targeting moiety, a metal, a particle, etc. In some embodiments a click chemistry group is used to attach a compstatin analog moiety to a surface, wherein the surface comprises or is functionalized to comprise a complementary click chemistry group. In some embodiments a surface is for a sensor, e.g., a surface or sensor for capture/detection of C3. In some embodiments a surface forms part of a medical device, tubing, membrane, reservoir, implant, or other material that may come in contact with blood (e.g., extracorporeally) or be temporarily or indefinitely implanted into the body of a subject (e.g., a prosthetic device or drug delivery device). In some embodiments a surface is functionalized with compstatin analog to reduce complement activation thereon. In some embodiments a device or tubing is used for circulating blood, e.g., for dialysis, during surgery, etc. In some embodiments a device is a hemodialyzer or an extracorporeal circulatory support unit. Such compstatin analog functionalized devices and methods of making thereof are provided herein.

In some embodiments of the invention, a compstatin analog comprises both a cell-reactive functional group and a CRM. In some aspects, the invention provides variants of the molecules of any of the afore-mentioned cell-reactive compstatin analogs wherein a cell-reactive functional group or moiety is replaced by a $(CH_2CH_2O)_n$ moiety (e.g., any of the PEGs described herein) or other polymer (e.g., a POZ, a polypeptide) having a molecular weight of at least 500 daltons, e.g., at least 1,500 daltons up to about 100,000 daltons (e.g., an average molecular weight of about 20,000; 30,000; 40,000; 50,000; 60,000; 70,000; 80,000; 90,000; or 100,000 daltons). In some embodiments the average molecular weight of the compound or $(CH_2CH_2O)_n$ moieties (or other polymer, e.g., a POZ or polypeptide) is at least 20,000 daltons, up to about 100,000; 120,000; 140,000; 160,000; 180,000; or 200,000 daltons. It will thus be understood that the teachings herein regarding cell-reactive compstatin analogs, e.g., the compstatin analog moieties used and the linkages by which a compstatin analog moiety is attached to a cell-reactive moiety, can apply to long-acting compstatin analogs, and long-acting compstatin analog can have any of the structures denoted by A-L-M, as described above, wherein A comprises a clearance reducing moiety (e.g., any of the clearance reducing moieties described herein), and furthermore wherein there may be one, two, or more (e.g., 3, 4, 5, 6, 7, 8) compstatin analog moieties M attached to A via linking portions denoted as L (or $L^{P1}$, $L^{P2}$, or $L^{P3}$) herein). Compstatin analog moieties may comprise a peptide whose sequence comprises any of SEQ ID NOs: 3-36, 37, 70, 71, 72, 73, or 74, or variants thereof (e.g., any variant described herein), optionally extended by one or more amino acids at the N-terminus, C-terminus, or both wherein at least one of the amino acids has a side chain that comprises a reactive functional group such as a primary or secondary amine (e.g., a Lys), a sulfhydryl group, a carboxyl group (which may be present as a carboxylate group), a guanidino group, a phenol group, an indole ring, a thioether, or an imidazole ring, which facilitates conjugation of a moiety comprising a CRM to the compstatin analog (it being understood that after conjugation, such reactive functional group will have reacted to form a bond). It will further be understood that where a compstatin analog moiety comprising any of SEQ ID NOs: 3-36, 37, 70, 71, 72, 73, or 74, or variants thereof, is extended by one or more amino acids at the N-terminus, C-terminus, or both wherein at least one of the amino acids has a side chain that comprises a reactive functional group, such one or more amino acid extension may be separated from the cyclic portion of the compstatin analog moiety by a rigid or flexible spacer moiety comprising, for example, a substituted or unsubstituted, saturated or unsaturated alkyl chain, oligo(ethylene glycol) chain, and/or any of the other moieties denoted by L (or $L^{P1}$, $L^{P2}$, or $L^{P3}$) herein.

Exemplary long-acting compstatin analogs are set forth below, wherein n is sufficient to provide an average molecular weight of between about 500; 1,000; 1,500; 2,000; 5,000; 10,000; 20,000; 30,000; 40,000; 50,000; 60,000; 70,000; 80,000; 90,000; and 100,000 daltons. In some embodiments n is sufficient to provide an average molecular weight of between about 20,000 daltons, up to about 100,000; 120,000; 140,000; 160,000; 180,000; or 200,000 daltons.

(SEQ ID NO: 58)
$(CH_2CH_2O)_nC(=O)$-Ile-Cys-Val-(1Me)Trp-Gln-Asp-Trp-

Gly-Ala-His-Arg-Cys-Thr-$NH_2$)

(SEQ ID NO: 59)
Ac-Ile-Cys*-Val-(1Me)Trp-Gln-Asp-Trp-Gly-Ala-His-

Arg-Cys*-Thr-NH—$CH_2CH_2OCH_2CH_2OCH_2$—$C(=O)$-Lys- $C(=O)$—$(CH_2CH_2O)$n-$NH_2$ (SEQ ID NO: 60)
Ac-Ile-Cys*-Val-(1Me)Trp-Gln-Asp-Trp-Gly-Ala-His-

Arg-Cys*-Thr-Lys-$C(=O)$—$(CH_2CH_2O)$n-$NH_2$.

(SEQ ID NO: 61)
Ac-Ile-Cys*-Val-(1Me)Trp-Gln-Asp-Trp-Gly-Ala-His-

Arg-Cys*-Thr-(Gly)$_5$-Lys-$C(=O)$—$(CH_2CH_2O)$n-$NH_2$ (SEQ ID NO: 62)
Ac-$(CH_2CH_2O)$nC$(=O)$Lys-(Gly)$_5$-Ile-Cys*-Val-(1Me)

Trp-Gln-Asp-Trp-Gly-Ala-His-Arg-Cys*-Thr-$NH_2$)

(SEQ ID NO: 63)
Ac-$(CH_2CH_2O)$nC$(=O)$Lys-Ile-Cys*-Val-(1Me)Trp-Gln-

Asp-Trp-Gly-Ala-His-Arg-Cys*-Thr-$NH_2$)

In SEQ ID NO: 58, the $(CH_2CH_2O)$n is coupled via an amide bond to the N-terminal amino acid. In SEQ ID NOs: 59-63, the $(CH_2CH_2O)$n moiety is coupled via an amide bond to a Lys side chain; thus it will be understood that the $NH_2$ at the C-terminus in SEQ ID NOs: 59, 60, and 61, represents amidation of the C-terminus of the peptide, and it will be understood that in SEQ ID NOs: 62 and 63, the Ac at the N-terminus represents acetylation of the N-terminus of the peptide, as described above. It will also be appreciated by those of ordinary skill in the art that a free end of a $(CH_2CH_2O)_n$ moiety typically terminates with an (OR) where the underlined O represents the O atom in the terminal $(CH_2CH_2O)$ group. (OR) is often a moiety such as a hydroxyl (OH) or methoxy (—OCH$_3$) group though other groups (e.g., other alkoxy groups) could be used. Thus SEQ ID NO: 59, for example, may be represented as Ac-Ile-Cys*-Val-(1Me)Trp-Gln-Asp-Trp-Gly-Ala-His-Arg-Cys*-Thr-NH—$CH_2CH_2OCH_2CH_2OCH_2$—C(=O)-Lys-(C(=O)—$(CH_2CH_2O)_n$—R)—NH2 (SEQ ID NO: 64) wherein R is, e.g., either H or CH$_3$ in the case of a linear PEG. In the case of a bifunctional, branched or star-shaped PEG, R represents the remainder of the molecule. Further, it will be understood that the moiety comprising the reactive functional group may vary, as described herein (e.g., according to any of the formulas described herein). For example, long-acting compstatin analogs comprising the same peptide sequence as SEQ ID NO: 64, in which the moiety comprising the reactive functional group comprises an ester and/or alkyl chain may be represented as follows (SEQ ID NO: 65)
Ac-Ile-Cys*-Val-(1Me)Trp-Gln-Asp-Trp-Gly-Ala-His- Arg-Cys*-Thr-NH—CH$_2$CH$_2$OCH$_2$CH$_2$OCH$_2$—C(=O)-Lys- (C(=O)—(CH$_2$)$_m$—(CH$_2$CH$_2$O)$_n$-R)-NH$_2$;

(SEQ ID NO: 66)
Ac-Ile-Cys*-Val-(1Me)Trp-Gln-Asp-Trp-Gly-Ala-His-

Arg-Cys*-Thr-NH—CH$_2$CH$_2$OCH$_2$CH$_2$OCH$_2$—C(=O)-Lys- (C(=O)—(CH$_2$)$_m$—C(=O)—(CH$_2$CH$_2$O)$_n$-R)-NH$_2$ (SEQ ID NO: 67)
Ac-Ile-Cys*-Val-(1Me)Trp-Gln-Asp-Trp-Gly-Ala-His-

Arg-Cys*-Thr-NH—CH$_2$CH$_2$OCH$_2$CH$_2$OCH$_2$—C(=O)-Lys- (C(=O)—(CH$_2$)$_m$—C(=O)—(CH$_2$)j(CH$_2$CH$_2$O)$_n$-R)-NH$_2$

In SEQ ID NOs: 65-67 m may range from 1 up to about 2, 3, 4, 5, 6, 7, 8, 10, 15, 20, or 30 in various embodiments, In SEQ ID NOs: 67 j may range from 1 up to about 2, 3, 4, 5, 6, 7, 8, 10, 15, 20, or 30 in various embodiments.

It will also be appreciated that, as described herein, in various embodiments other moieties may be incorporated between the Lys-(C(=O)— and (CH$_2$CH$_2$O)$_n$—R, such as an amide, aromatic ring (e.g., a substituted or unsubstituted phenyl), or a substituted or unsubstituted cycloalkyl structure.

The invention provides variants of SEQ ID NOs: 58-67 in which -Ile-Cys*-Val-(1Me)Trp-Gln-Asp-Trp-Gly-Ala-His-Arg-Cys*-Thr- (SEQ ID NO: 37) is replaced by an amino acid sequence comprising the amino acid sequence of any other compstatin analog, e.g., of any of SEQ ID NOs 3-27 or 29-36, 37, 70, 71, 72, 73, or 74 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Any compstatin analog, e.g., any compound comprising any of SEQ ID NOs: 3-37, 70, 71, 72, 73, or 74 may, in various embodiments, can be attached via or near its N-terminal or C-terminal end (e.g., via a side chain of an amino acid at or near its N-terminal or C-terminal amino acid) directly or indirectly to any moiety comprising a reactive functional group, e.g., any compound of Formulae I-XVI or Formulae A-H.

In some embodiments the CRM comprises a polypeptide that occurs in human serum, or a fragment thereof or a substantially similar variant of the polypeptide or fragment thereof. In some embodiments the polypeptide, fragment, or variant has a molecular weight of between 5 kD and 150 kD, e.g., at least 5, 10, 20, 30, 40, 50, 60, 70, 80, 90, 100 kd, or more, e.g., between 100 and 120, or 120 and 150 kD. In some embodiments, producing a long-acting compstatin analog comprises reacting a compstatin analog comprising a reactive functional group with one or more amino acid side chains of the polypeptide, wherein the side chain comprises a compatible functional group. In some embodiments, producing a long-acting compstatin analog comprises reacting a compstatin analog comprising a reactive functional group with the N-terminal amine and/or C-terminal carboxyl group of the polypeptide. In some embodiments, producing a long-acting compstatin analog comprises reacting a compstatin analog comprising an amine-reactive functional group with amino acids having a side chain comprising a primary amine (e.g., lysine) and/or with the N-terminal amine of the polypeptide. In some embodiments, producing a long-acting compstatin analog comprises reacting a compstatin analog comprising a carboxyl-reactive functional group with the C-terminal carboxyl group of the polypeptide. In some embodiments a compstatin analog moiety is attached at each terminus of the polypeptide and, optionally, to the side chain of one or more internal amino acids. In some embodiments, producing a long-acting compstatin analog comprises reacting a compstatin analog comprising a sulfhydryl-reactive functional group with one or more sulfhydryl groups of the polypeptide.

In some embodiments, at least one reactive functional group is introduced into the polypeptide. For example, in some embodiments at least one side chain of the polypeptide is modified to convert a first reactive functional group to a different reactive functional group prior to reaction with the compstatin analog. In some embodiments a thiol is introduced. Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amines can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides. A polypeptide comprising one or more thiols may be reacted with a compstatin analog comprising a maleimide group, such as Ac-Ile-Cys*-Val-Trp(l-Me)-Gln-Asp-Trp-Gly-Ala-His-Arg-Cys*-Thr-AEEAc-Lys-(C(=O)—(CH$_2$)$_5$-Mal)-NH$_2$ (SEQ ID NO: 68) to generate a long-acting compstatin analog.

In some embodiments the polypeptide is recombinantly produced. In some embodiments the polypeptide is at least in part recombinantly produced (e.g., in bacteria or in eukaryotic host cells such as fungal, insect, plant, or vertebrate) and/or at least in part produced using chemical synthesis. In some embodiments the polypeptide is purified. For example, in some embodiments the polypeptide is purified from a host cell lysate or from culture medium into which it has been secreted by host cells. In some embodiments the polypeptide is glycosylated. In some embodiments the polypeptide is non-glycosylated. In some embodiments the polypeptide is human serum albumin (HSA). In some embodiments a substantially similar variant of the polypeptide is sufficiently similar to the polypeptide of which it is a variant so as to not be recognized as foreign by a normal immune system of a subject, e.g., a human subject. In some embodiments alterations in the sequence of substantially similar variant as compared with the polypeptide of which it is a variant are selected so as to avoid generating MHC Class I epitopes. Various methods known in the art can be used to predict whether a sequence comprises an MHC Class I epitope.

In some embodiments, one or more amino acids in a polypeptide or linker or composition may be selected to be hydrophobic or hydrophilic or selected to confer increased hydrophilicity or, in some embodiments, increased hydrophobicity, on a compound that contains it. As known in the art, the terms "hydrophilic" and "hydrophobic" are used to refer to the degree of affinity that a substance has with water. In some aspects a hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be classified based on their hydrophobicity as well known in the art. Examples of "hydrophilic amino acids" are arginine, lysine, threonine, alanine, asparagine, glutamine, aspartate, glutamate, serine, and glycine. Examples of "hydrophobic amino acids" are tryptophan, tyrosine, phenylalanine, methionine, leucine, isoleucine, and valine. In certain embodiments an analog of a standard amino acid is used, wherein the analog has increased or decreased hydrophilic or hydrophobic character as compared with the amino acid of which it is an analog.

The invention further provides multimers, e.g., concatamers, comprising two or more (e.g., between 2 and 10) compstatin analogs comprising a CRM, wherein the average molecular weight of the resulting molecule (or the CRM components thereof) is between 20,000; 30,000; 40,000; 50,000; 60,000; 70,000; 80,000; 90,000; and 100,000 daltons. In some embodiments the average molecular weight of the resulting molecule (or the CRM components thereof) is at least 20,000 daltons, up to about 100,000; 120,000; 140,000; 160,000; 180,000; or 200,000 daltons. In some embodiments, the compstatin analogs comprising a CRM can be linked using any of the linking moieties described above. Compositions and methods for making long-acting compstatin analogs, and intermediates in the synthesis, are aspects of the invention.

In some embodiments the total molecular weight of a long-acting compstatin analog, including the compstatin analog moieties, is no greater than 50 kD. For example, in the case of a LACA comprising a 40 kD PEG, in some embodiments the molecular weight contributed by the remainder of the compound, including the compstatin analog moie(ties), may be no greater than 10 kD, e.g., 1.5 kD-5.0 kD or 5.0 kD-10 kD. In some embodiments the total molecular weight of a LACA, including the compstatin analog moieties, is between 45 kD and 50 kD. In some embodiments the total molecular weight of a LACA, including the compstatin analog moieties, is between 40 kD and 45 kD, between 15 kD and 40 kD, e.g., between 15 kD and 25 kD, between 25 kD and 35 kD, between 35 kD and 40 kD. Thus, wherever the present disclosure refers to a compstatin analog comprising a polymer or CRM having a particular molecular weight, or having a molecular weight within a particular range, in some embodiments the total molecular weight of the compstatin analog may be, e.g., between 1.5 kD and 5 kD greater than the molecular weight of the polymer or CRM, or in some embodiments between 5 kD and 10 kD greater than the molecular weight of the polymer. It will be understood that molecular weight of a compound, e.g., a compound comprising a polymer, can refer to the average molecular weight of molecules of such compound in a composition.

A wide variety of methods and assays useful for detection of polymers, e.g., PEGs, POZs, and/or polypeptides and/or useful for measurement of physical and/or structural properties of polymers, e.g., PEGs, POZs, and/or polypeptides are known in the art and may, if desired, be used to detect a compstatin analog, e.g., a cell-reactive, long-acting, targeted compstatin analog or a compstatin analog moiety. For example, methods and assays useful for determining properties such as aggregation, solubility, size, structure, melting properties, purity, presence of degradation products or contaminants, water content, hydrodynamic radius, etc., are available. Such methods include, e.g., analytical centrifugation, various types of chromatography such as liquid chromatography (e.g., HPLC-ion exchange, HPLC-size exclusion, HPLC-reverse phase), light scattering, capillary electrophoresis, circular dichroism, isothermal calorimetry, differential scanning calorimetry, fluorescence, infrared (IR), nuclear magnetic resonance (NMR), Raman spectroscopy, refractometry, UV/Visible spectroscopy, mass spectrometry, immunological methods, etc. It will be understood that methods may be combined. In some aspects, a cell-reactive, long-acting, or targeted compstatin analog (or composition comprising a cell-reactive, long-acting, or targeted compstatin analog) has one or more properties described herein, as assessed using any of the foregoing methods. In some aspects, methods useful to detect and/or quantify a long-acting compstatin analog are described herein.

VI. Targeted Compstatin Analogs

The invention provides and/or utilizes targeted compstatin analogs that comprise a targeting moiety and a compstatin analog moiety, wherein the targeting moiety binds non-covalently to a target molecule. In some aspects, the invention provides targeted compstatin analogs analogous to the cell-reactive compstatin analogs described in Section VI, wherein the compounds comprise a targeting moiety in addition to, or instead of, a cell-reactive moiety. The targeting moiety can comprise, e.g., an antibody, polypeptide, peptide, nucleic acid (e.g., an aptamer), carbohydrate, small molecule, or supramolecular complex, that specifically binds to the target molecule. In some embodiments, the affinity (as measured by the equilibrium dissociation constant, Kd) of targeting moiety for the target molecule (as measured by the equilibrium dissociation constant, Kd) is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions.

In those embodiments of the invention in which the targeting moiety is an antibody, the antibody may be any immunoglobulin or a derivative thereof, which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', F(ab').sub.2, scFv (single-chain variable) or other fragment that retains an antigen binding site, or a recombinantly produced scFv fragment, including recombinantly produced fragments. See, e.g., Allen, T., Nature Reviews Cancer, Vol. 2, 750-765, 2002, and references therein. Monovalent, bivalent or multivalent antibodies can be used. The antibody may be a chimeric antibody in which, for example, a variable domain of rodent origin is fused to a constant domain of human origin, thus retaining the specificity of the rodent antibody. In some embodiments, a human antibody or portion thereof is generated, for example, in rodents whose genome incorporates human immunoglobulin genes, using a display technology such as phage display, etc. In some embodiments, a humanized antibody is generated by grafting one or more complementarity determining region(s) from a non-human species (e.g., mouse) into a human antibody sequence. The antibody may be partially or completely humanized. See, e.g., Almagro J C, Fransson J. Humanization of antibodies. Front Biosci. 13:1619-33 (2008) for review of various methods of obtaining humanized antibodies that may be used to obtain a targeting moiety of use in the invention. An antibody may be polyclonal or monoclonal, though for purposes of the present invention monoclonal antibodies are generally preferred. In certain embodiments of the invention a F(ab')2 or F(ab') fragment is use while in other embodiments antibodies comprising an Fc domain are used. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture. Methods of generating antibody fragments, e.g., by digestion, disulfide reduction, or synthesis are known in the art.

In various embodiments of the invention a targeting moiety can be any molecule that specifically binds to a target molecule through a mechanism other than an antigen-antibody interaction. Such a targeting moiety is referred to as a "ligand". For example, in various embodiments of the invention a ligand can be a polypeptide, peptide, nucleic acid (e.g., DNA or RNA), carbohydrate, lipid or phospholipid, or small molecule. In some embodiments a small molecule is an organic compound, whether naturally-occurring or artificially created, that has relatively low molecular weight and is not a protein, polypeptide, nucleic acid, or lipid, typically with a molecular weight of less than about 1500 g/mol and typically having multiple carbon-carbon bonds. In general, an aptamer is an oligonucleotide (e.g., RNA or DNA, optionally comprising one or more modified nucleosides (e.g., bases or sugars other than the 5 standard bases (A, G, C, T, U) or sugars (ribose and deoxyribose) found most commonly in RNA and DNA), or modified internucleoside linkages (e.g., non-phosphodiester bonds) that, e.g., stabilize the molecule, e.g., by rendering it more resistant to degradation by nucleases) that binds to a particular protein. In some embodiments an oligonucleotide is up to about 100 nucleosides long, e.g., between 12 and 100 nucleosides long. Aptamers can be derived using an in vitro evolution process called SELEX, and methods for obtaining aptamers specific for a protein of interest are known in the art. See, e.g., Brody E N, Gold L. J Biotechnol. 2000 March; 74(1):5-13. In some embodiments, a peptide nucleic acid or locked nucleic acid is used.

In certain embodiments of the invention a targeting moiety comprises a peptide. In some embodiments a peptide that binds to a target molecule of interest is identified using a display technology such as phage display, ribosome display, yeast display, etc.

Small molecules can be used as ligands. Methods for identifying such ligands are known in the art. For example in vitro screening of small molecule libraries, including combinatorial libraries, and computer-based screening, e.g., to identify small organic compounds that bind to concave surfaces (pockets) of proteins, can identify small molecule ligands for numerous proteins of interest (Huang, Z., Pharm. & Ther. 86: 201-215, 2000).

In certain embodiments of the invention targeting moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In certain embodiments of the invention the targeting moiety is not an Fc portion of an immunoglobulin molecule. In some embodiments, a targeting moiety is part of a complex comprising one or more additional moieties to which it is covalently or noncovalently attached.

In various embodiments of the invention a target molecule can be any molecule produced by a cell (including any forms expressed on the cell surface or modified forms thereof resulting at least in part from extracellular modification). In some embodiments a target molecule is an extracellular substance present in or on a tissue. In some embodiments, a target molecule is characteristic of a particular diseased or physiological state or characteristic of one or more cell type(s) or tissue type(s). A target molecule is often a molecule at least partly present at the cell surface (e.g., a transmembrane or otherwise membrane-attached protein) so that at least a portion of the molecule is accessible to binding by an extracellular binding agent such as an antibody. A target molecule may, but need not be, cell type specific. For example, a cell type specific target molecule is often a protein, peptide, mRNA, lipid, or carbohydrate that is present at a higher level on or in a particular cell type or cell type(s) than on or in many other cell types. In some instances a cell type specific target molecule is present at detectable levels only on or in a particular cell type of interest. However, it will be appreciated that a useful cell type specific target molecule need not be absolutely specific for the cell type of interest in order to be considered cell type specific. In some embodiments, a cell type specific target molecule for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. In some embodiments, the cell type specific target molecule is present at levels at least 4-5 fold, between 5-10 fold, or more than 10-fold greater than its average expression in a reference population. In some embodiments, detection or measurement of a cell type specific target molecule allows one of ordinary skill in the art to distinguish a cell type or types of interest from cells of many, most, or all other types. In general, the presence and/or abundance of most target molecules may be determined using one or more standard techniques such as Northern blotting, in situ hybridization, RT-PCR, sequencing, immunological methods such as immunoblotting, immunodetection (e.g., by immunohistochemistry), or fluorescence detection following staining with fluorescently labeled antibodies (e.g., using FACS), oligonucleotide or cDNA microarray or membrane array, protein microarray analysis, mass spectrometry, etc.

In some embodiments, a target molecule is a channel, transporter, receptor, or other molecule at least in part exposed at the cell surface. In some embodiments a target molecule is an anion transporter or water channel (e.g., an aquaporin protein).

In some embodiments, the target molecule is a protein at least in part exposed at the surface of red blood cells, such as a glycophorin (e.g., glycophorin A, B, C, or D) or band 3.

In some embodiments, the target molecule is a protein at least in part exposed at the surface of endothelial cells. In some embodiments, the target molecule is present at the surface of normal, healthy vasculature. In some embodiments, the target molecule is present at the surface of activated endothelial cells. In some embodiments, the target molecule is present at the surface of activated endothelial cells but not at the surface of non-activated endothelial cells. In some embodiments a target molecule is a molecule whose expression or exposure is induced by a stimulus such as injury or inflammation. In some embodiments, a target molecule would be recognized as "non-self" by a recipient receiving a transplant containing cells that express the target molecule. In some embodiments, the target molecule is a carbohydrate xenoantigen to which antibodies are commonly found in human beings. In some embodiments the carbohydrate comprises a blood group antigen. In some embodiments the carbohydrate comprises a xenoantigen, e.g., an alpha-gal epitope (Galalpha1-3Galbeta1-(3) 4GlcNAc-R) (see, e.g., Macher B A and Galili U. The Galalpha1, 3Galbeta1, 4GlcNAc-R (alpha-Gal) epitope: a carbohydrate of unique evolution and clinical relevance. Biochim Biophys Acta. 1780(2):75-88 (2008).

In some embodiments of the invention, a compstatin analog comprises both a targeting moiety and a CRM.

In some embodiments, a targeted compstatin analog comprises multiple targeting moieties, which can be the same or different. Different targeting moieties may bind to the same target molecule or to different target molecules. The invention provides a targeted compstatin analog that is multivalent with respect to the targeting moiety, the compstatin analog, or both.

In general, the invention encompasses any method of producing a compound comprising a compstatin analog moiety and a targeting moiety, and the resulting compounds. In some embodiments, a targeted compstatin analog may be produced using methods generally similar to those described in Section VI, wherein a targeting moiety is used instead of, or in addition to, a cell-reactive moiety. In some embodiments, a targeted compstatin analog comprising a peptide as a targeting moiety is synthesized as a polypeptide chain comprising a compstatin analog moiety and a peptide targeting moiety. Optionally, the polypeptide chain comprises one or more spacer peptides between the compstatin analog moiety and the targeting moiety.

In some embodiments, a targeted compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a targeting moiety. In some embodiments wherein a targeted compstatin analog comprises multiple compstatin analog moieties, the molar activity of the targeted compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties. Compositions and methods for making targeted compstatin analogs, and intermediates in the synthesis, are aspects of the invention.

VII. Uses

Cell-reactive, long-acting, or targeted compstatin analogs have a wide variety of uses. Without limiting the invention in any way, certain uses of cell-reactive, long-acting, or targeted compstatin analogs, and related aspects of the invention, are described herein. In some embodiments, a cell-reactive, long-acting, or targeted compstatin analog is administered to a subject suffering from or at risk of complement-mediated damage to an organ, tissue, or cells. In some embodiments, a cell-reactive compstatin analog is contacted with an organ, tissue, or cells ex vivo and become covalently attached thereto. The organ, tissue, or cells are introduced into a subject and are protected from damage that would otherwise be caused by the recipient's complement system.

Compstatin analogs that do not bind covalently to cells can be used for purposes described herein. For example, a compstatin analog modified with a moiety that increases the lifetime of the compound in the body and/or a compstatin analog comprising a moiety that targets the compstatin analog to a cell type or location susceptible to complement activation can be used, and the invention encompasses such uses. In some embodiments, a long-acting compstatin analog is used. In some embodiments a compstatin analog comprising a targeting moiety is used. In some embodiments, a compstatin analog comprising both a moiety that extends the lifetime of the compound in the body and a targeting moiety is used. Where the discussion below refers to a cell-reactive compstatin analog, the invention provides analogous compositions and methods relating to targeted compstatin analogs and (at least in those aspects pertaining to administration of a compstatin analog to a subject) embodiments in which a compstatin analog that does not comprise a targeting moiety or a cell-reactive moiety, optionally a long-acting compstatin analog, is used instead of, or in addition to, a cell-reactive compstatin analog.

Certain uses of interest include: (1) protecting red blood cells (RBCs) from complement-mediated damage in individuals with disorders such as paroxysmal nocturnal hemoglobinuria or atypical hemolytic uremic syndrome or other disorders characterized by complement-mediated RBC lysis; (2) protecting transplanted organs, tissues, and cells from complement-mediated damage; (3) reducing ischemia/reperfusion (I/R) injury (e.g., in individuals suffering from trauma, vascular obstruction, myocardial infarction, or other situations in which I/R injury may occur); and (4) protecting various body structures (e.g., the retina) or membranes (e.g., synovial membrane) that may be exposed to complement components from complement mediated damage in any of a variety of different complement-mediated disorders. The beneficial effects of inhibiting complement activation at the surface of cells or other body structures are not limited to those resulting directly from protection of the cells or structures themselves against direct complement-mediated damage (e.g., preventing cell lysis). For example, inhibiting complement activation using a cell-reactive compstatin analog may reduce the generation of anaphylotoxins and resulting influx/activation of neutrophils and other pro-inflammatory events and/or reduce potentially damaging release of intracellular contents, thereby potentially having beneficial effects on remote organ systems or throughout the body.

A. Blood Cell Protection

In some embodiments of the invention, a cell-reactive compstatin analog, cell-targeted compstatin analog, and/or non-targeted compstatin analog (e.g., a long-acting non-targeted compstatin analog) is used to protect blood cells against complement-mediated damage. The blood cells may be any cellular component of the blood, e.g., red blood cells (RBCs), white blood cells (WBCs), and/or platelets. In some embodiments, a cell-targeted compstatin analog is targeted to a target molecule exposed at the cell surface of RBCs such as a glycophorin or band 3. A variety of disorders are associated with complement-mediated damage to blood cells. Such disorders can result, for example, from deficiencies or defects in one or more of an individual's cellular or soluble CRPs, e.g., due to (a) mutation(s) in the gene(s) encoding such proteins; (b) mutation(s) in genes required for production or proper function of one or more CRPs, and/or (c) presence of autoantibodies to one or more CRPs. Complement-mediated RBC lysis can result from the presence of autoantibodies against RBC antigens which may arise due to a diverse set of causes (often being idiopathic). Individuals having such mutation(s) in genes encoding CRPs and/or having antibodies against CRPs or against their own RBCs are at increased risk of disorders involving complement-mediated RBC damage. Individuals who have had one or more episodes characteristic of a disorder are at increased risk of a recurrence.

Paroxysmal nocturnal hemoglobinuria (PNH) is a relatively rare disorder comprising an acquired hemolytic anemia characterized by complement-mediated intravascular hemolysis, hemoglobinuria, bone marrow failure, and thrombophilia (propensity to develop blood clots). It affects an estimated 16 individuals per million worldwide, occurs in both sexes, and can arise at any age, frequently striking young adults (Bessler, M. & Hiken, J., Hematology Am Soc Hematol Educ Program, 104-110 (2008); Hillmen, P. Hematology Am Soc Hematol Educ Program, 116-123 (2008)). PNH is a chronic and debilitating disease punctuated by acute hemolytic episodes and results in significant morbidities and reduced life expectancy. In addition to anemia, many patients experience abdominal pain, dysphagia, erectile dysfunction, and pulmonary hypertension, and are at increased risk of renal failure and thromboembolic events.

PNH was first described as a distinct entity in the 1800s, but it was only in the 1950s, with discovery of the alternative pathway of complement activation, that the cause of hemolysis in PNH was firmly established (Parker C J. Paroxysmal nocturnal hemoglobinuria: an historical overview. Hematology Am Soc Hematol Educ Program. 93-103 (2008)). CD55 and CD59 are normally attached to the cell membrane via glycosyl phosphatidylinositol (GPI) anchors (glycolipid structures that anchor certain proteins to the plasma membrane). PNH arises as a consequence of nonmalignant clonal expansion of hematopoietic stem cell(s) that have acquired a somatic mutation in the PIGA gene, which encodes a protein involved in synthesis of GPI anchors (Takeda J, et al. Deficiency of the GPI anchor caused by a somatic mutation of the PIG-A gene in paroxysmal nocturnal hemoglobinuria. Cell. 73:703-711 (1993)). Progeny of such stem cells are deficient in GPI-anchored proteins, including CD55 and CD59. This defect renders these cells susceptible to complement-mediated RBC lysis. Flow cytometric analysis using antibodies to GPI-anchored proteins is often used for diagnosis. It detects deficiency of GPI-anchored proteins at the cell surface and allows determination of the degree of deficiency and the proportion of affected cells (Brodsky R A. Advances in the diagnosis and therapy of paroxysmal nocturnal hemoglobinuria. Blood Rev. 22(2):65-74 (2008). PNH type III RBCs are completely deficient in GPI-linked proteins and are highly sensitive to complement whereas PNH type II RBCs have a partial deficiency and are less sensitive. FLAER is a fluorescently labeled inactive variant of proaerolysin (a bacterial toxin that binds GPI anchors) and is increasingly used together with flow cytometry for diagnosis of PNH. Lack of binding of FLAER to granulocytes is sufficient for diagnosis of PNH. In some embodiments, a cell-reactive compstatin analog protects PNH RBCs from deposition of C3b.

In some embodiments, a cell-reactive, long-acting, or targeted compstatin analog is administered to a subject suffering from atypical hemolytic syndrome (aHUS). aHUS is a chronic disorder characterized by microangiopathic hemolytic anemia, thrombocytopenia, and acute renal failure and is caused by inappropriate complement activation, often due to mutations in genes encoding complement regulatory proteins (Warwicker, P., et al. Kidney Int 53, 836-844 (1998); Kavanagh, D. & Goodship, T. Pediatr Nephrol 25, 2431-2442 (2010). Mutations in the complement factor H (CFH) gene are the most common genetic abnormality in patients with aHUS, and 60-70% of these patients die or reach end stage renal failure within one year after disease onset (Kavanagh & Goodship, supra.) Mutations in factor I, factor B, C3, factor H-related proteins 1-5, and thrombomodulin have also been described. Other causes of aHUS include autoantibodies against complement regulatory proteins such as CFH.

In some embodiments, a cell-reactive, long-acting, or targeted compstatin analog is administered to a subject that has been identified as having a mutation in factor I, factor B, C3, factor H-related proteins 1-5, or thrombomodulin or has been identified as having antibodies against a complement regulatory protein, e.g., CFH, or against a convertase (e.g., C3Nef) or complement factor.

Complement-mediated hemolysis occurs in a diverse group of other conditions including autoimmune hemolytic anemias that involve antibodies that bind to RBCs and lead to complement-mediated hemolysis. For example, such hemolysis can occur in primary chronic cold agglutinin disease, warm autoimmune hemolytic anemia (wAIHA), and certain reactions to drugs and other foreign substances (Berentsen, S., et al., Hematology 12, 361-370 (2007); Rosse, W. F., Hillmen, P. & Schreiber, A. D. Hematology Am Soc Hematol Educ Program, 48-62 (2004)). In some embodiments of the invention a cell-reactive compstatin analog is administered to a subject suffering from or at risk of chronic cold agglutinin disease. In some embodiments of the invention a cell-reactive compstatin analog is administered to a subject suffering from or at risk of wAIHA. In another embodiment, a cell-reactive compstatin analog is used to treat a subject suffering from or at risk of the HELLP syndrome, which is defined by the existence of hemolysis, elevated liver enzymes, and low platelet count and is associated with mutations in complement regulatory protein(s) in at least some subjects (Fakhouri, F., et al., 112: 4542-4545 (2008)).

In other embodiments, cell-reactive compstatin analogs are used to protect RBCs or other cellular components of blood to be transfused into a subject. Certain examples of such uses are discussed further in below. As noted above, targeted and/or long-acting compstatin analogs can be used in the above methods for inhibiting complement-mediated hemolysis and/or RBC damage. In some embodiments, a long-acting compstatin analog comprising a (CH2CH2O) moiety is used to treat PNH or aHUS.

B. Transplantation

Transplantation is a therapeutic approach of increasing importance, providing a means to replace organs and tissues that have been damaged through trauma, disease, or other conditions. Kidneys, liver, lungs, pancreas, and heart are among the organs that can be successfully transplanted.

Tissues that are frequently transplanted include bones, cartilage, tendons, cornea, skin, heart valves, and blood vessels. Pancreatic islet or islet cell transplantation is a promising approach for treatment of diabetes, e.g., type I diabetes. For purposes of the invention, an organ, tissue, or cell (or population of cells) that is be transplanted, is being transplanted, or has been transplanted may be referred to as a "graft". For purposes hereof, a blood transfusion is considered a "graft".

Transplantation subjects the graft to a variety of damaging events and stimuli that can contribute to graft dysfunction and, potentially, failure. For example, ischemia-reperfusion (I/R) injury is a common and significant cause of morbidity and mortality in the case of many grafts (particularly solid organs) and can be a major determinant of likelihood of graft survival. Transplant rejection is one of the major risks associated with transplants between genetically different individuals and can lead to graft failure and a need to remove the graft from the recipient.

In some embodiments of the invention, a cell-reactive compstatin analog, cell-targeted compstatin analog, and/or a long-acting compstatin analog is used to protect a graft from complement-mediated damage. A cell-reactive compstatin analog reacts with cells of the graft, becomes covalently attached thereto, and inhibits complement activation. A cell-targeted compstatin analog binds to a target molecule in the graft (e.g., expressed by endothelial cells or other cells in the graft) and inhibits complement activation. A target molecule may be, e.g., is a molecule whose expression is induced or stimulated by a stimulus such as injury or inflammation, molecule that would be recognized as "nonself" by the recipient, a carbohydrate xenoantigen to which antibodies are commonly found in human beings such as a blood group antigen or a xenoantigen, e.g., a molecule comprising an alpha-gal epitope. In some embodiments, a reduction in complement activation can be demonstrated by a reduction in average C4d deposition in blood vessels of grafts that have been contacted with a compstatin analog, e.g., a cell-reactive compstatin analog, as compared with the average level of C4d deposition in grafts that have not been contacted with a compstatin analog (e.g., in subjects who are matched with respect to the grafts and other therapy that they receive).

A graft can be contacted with a cell-reactive, long-acting, or targeted compstatin analog prior to, during, and/or after being transplanted, in various embodiments of the invention. For example, prior to transplantation a graft removed from a donor can be contacted with a liquid comprising a cell-reactive, long-acting, or targeted compstatin analog. For example, the graft can be bathed in and/or perfused with the solution. In another embodiment, a cell-reactive, long-acting, or targeted compstatin analog is administered to a donor prior to removal of the graft. In some embodiments, a cell-reactive, long-acting, or targeted compstatin analog is administered to a recipient during and/or after the introduction of the graft. In some embodiments, a cell-reactive compstatin, long-acting, or targeted analog is delivered locally to the transplanted graft. In some embodiments a cell-reactive compstatin analog is administered systemically, e.g., intravenously.

The invention provides a composition comprising: (a) an isolated graft; and (b) a cell-reactive, long-acting, or targeted compstatin analog. In some embodiments the composition further comprises a liquid solution suitable for contacting (e.g., suitable for rinsing, washing, bathing, perfusing, maintaining, or storing) a graft (e.g., an organ) such as an isolated graft that has been removed from a donor and is awaiting transplantation to a recipient. In some embodiments the invention provides a composition comprising: (a) a liquid solution suitable for contacting a graft (e.g., an organ); and (b) a cell-reactive, long-acting, or targeted compstatin analog. The liquid solution can be any liquid solution that is physiologically acceptable to the graft (e.g., appropriate osmotic composition, non-cytotoxic) and medically acceptable in view of the subsequent introduction of the graft into the recipient (e.g., preferably sterile or at least reasonably free from microorganisms or other contaminants) and compatible with the cell-reactive compstatin analog (i.e., will not destroy the reactivity of the compstatin analog) or compatible with the long-acting or targeted compstatin analog. In some embodiments, a solution is any solution own in the art for any such purposes. In some embodiments, a liquid solution is Marshall's or Hyperosmolar Citrate (Soltran®, Baxter Healthcare), University of Wisconsin (UW) solution (ViaSpan™, Bristol Myers Squibb), Histidine Tryptophan Ketoglutarate (HTK) solution (Custodial®, Kohler Medical Limited), EuroCollins (Fresenius), and Celsior® (Sangstat Medical), Polysol, IGL-1, or AQIX® RS-1. Of course other solutions, e.g., containing equivalent or similar ingredients in the same or different concentrations could be used within the scope of physiologically acceptable compositions. In some embodiments a solution does not contain ingredient(s) with which the cell-reactive compstatin analog would be expected to significantly react, and any solution may be modified or designed to lack such ingredients. In some embodiments, the cell-reactive compstatin analog is present in the graft-compatible solution at a concentration of, e.g., between 0.01 mg/ml and 100 mg/ml or may be added to the solution to achieve such concentration.

In some embodiments, the invention provides a kit comprising: (a) a cell-reactive, long-acting, or targeted compstatin analog; and (b) a graft-compatible solution or solid (e.g., powder) components thereof. The cell-reactive, long-acting, or targeted compstatin analog may be provided in solid form (e.g., powder) or at least in part dissolved in a solution. In some embodiments the cell-reactive, long-acting, or targeted compstatin analog and/or graft-compatible solution are provided in predetermined amounts, so that when combined, a solution of appropriate concentration for contacting a graft with the cell-reactive, long-acting, or targeted compstatin analog is produced. In many embodiments the cell-reactive, long-acting, or targeted compstatin analog and graft-compatible solution or solid (e.g., powder) components thereof are in separate containers within the kit. In some embodiments the cell-reactive compstatin analog and components of a graft-compatible solution are both provided in solid (e.g., powder) form, either in separate containers or mixed. In some embodiments the kit comprises instructions for use, e.g., instructions for adding a cell-reactive, long-acting, or targeted compstatin analog to a graft-compatible solution and/or instructions for contacting a graft with a cell-reactive compstatin analog. Optionally the kit contains a label approved by a government agency responsible for regulating products used in transplantation, cell therapy, and/or blood transfusion.

The invention further provides a method of covalently attaching a compstatin analog to an isolated graft comprising contacting the isolated graft with a cell-reactive compstatin analog. The invention further provides an isolated graft having a compstatin analog covalently attached thereto. Typically the isolated graft has many molecules of compstatin analog attached thereto. In some embodiments, a graft is or comprises a solid organ such as a kidney, liver, lung, pancreas, or heart. In some embodiments, a graft is or comprises bone, cartilage, fascia, tendon, ligament, cornea, sclera, pericardium, skin, heart valve, blood vessel, amniotic membrane, or dura mater. In some embodiments, a graft comprises multiple organs such as a heart-lung or pancreas-kidney graft. In some embodiments, a graft comprises less than a complete organ or tissue. For example, a graft may contain a portion of an organ or tissue, e.g., a liver lobe, section of blood vessel, skin flap, or heart valve. In some embodiments, a graft comprises a preparation comprising isolated cells or tissue fragments that have been isolated from their tissue of origin but retain at least some tissue architecture, e.g., pancreatic islets. In some embodiments, a preparation comprises isolated cells that are not attached to each other via connective tissue, e.g., hematopoietic stem cells or progenitor cells derived from peripheral and/or cord blood, or whole blood or any cell-containing blood product such as red blood cells (RBCs) or platelets. In some embodiments a graft is obtained from a deceased donor (e.g., a "donation after brain death" (DBD) donor or "donation after cardiac death" donor). In some embodiments, depending on the particular type of graft, a graft is obtained from a living donor. For example, kidneys, liver sections, blood cells, are among the types of grafts that can often be obtained from a living donor without undue risk to the donor and consistent with sound medical practice.

In some embodiments, a graft is a xenograft (i.e., the donor and recipient are of different species). In some embodiments a graft is an autograft (i.e., a graft from one part of the body to another part of the body in the same individual). In some embodiments, a graft is an isograft (i.e., the donor and recipient are genetically identical). In most embodiments, the graft is an allograft (i.e., the donor and recipient are genetically non-identical members of the same species). In the case of an allograft, the donor and recipient may or may not be genetically related (e.g., family members). Typically, the donor and recipient have compatible blood groups (at least ABO compatibility and optionally Rh, Kell and/or other blood cell antigen compatibility). The recipient's blood may have been screened for alloantibodies to the graft and/or the recipient and donor since the presence of such antibodies can lead to hyperacute rejection (i.e., rejection beginning almost immediately, e.g., within several minutes after the graft comes into contact with the recipient's blood). A complement-dependent cytotoxicity (CDC) assay can be used to screen a subject's serum for anti-HLA antibodies. The serum is incubated with a panel of lymphocytes of known HLA phenotype. If the serum contains antibodies against HLA molecules on the target cells, cell death due to complement-mediated lysis occurs. Using a selected panel of target cells allows one to assign specificity to the detected antibody. Other techniques useful for determining the presence or absence anti-HLA antibodies and, optionally, determining their HLA specificity, include ELISA assays, flow cytometry assays, microbead array technology (e.g., Luminex technology). The methodology for performing these assays is well known, and a variety of kits for performing them are commercially available.

In some embodiments a cell-reactive, long-acting, or targeted compstatin analog inhibits complement-mediated rejection. For example, in some embodiments a cell-reactive, long-acting, or targeted compstatin analog inhibits hyperacute rejection. Hyperacute rejection is caused at least in part by antibody-mediated activation of the recipient's complement system via the classical pathway and resulting MAC deposition on the graft. It typically results from the presence in the recipient of pre-existing antibodies that react with the graft. While it is desirable to attempt to avoid hyperacute rejection by appropriate matching prior to transplantation, it may not always possible to do so due, e.g., to time and/or resource constraints. Furthermore, some recipients (e.g., multiply transfused individuals, individuals who have previously received transplants, women who have had multiple pregnancies) may already have so many pre-formed antibodies, potentially including antibodies to antigens that are not typically tested for, that it can be difficult or perhaps almost impossible to obtain with confidence a compatible graft in a timely manner. Such individuals are at increased risk of hyperacute rejection.

In some embodiments, a cell-reactive, long-acting, or targeted compstatin analog inhibits acute rejection or graft failure. As used herein, "acute rejection" refers to rejection occurring between at least 24 hours, typically at least several days to a week, after a transplant, up to 6 months after the transplant. Acute antibody-mediated rejection (AMR) often involves an acute rise in donor-specific alloantibody (DSA) in the first few weeks after transplantation. Without wishing to be bound by any theory, it is possible that pre-existing plasma cells and/or the conversion of memory B cells to new plasma cells play a role in the increased DSA production. Such antibodies can result in complement-mediated damage to the graft, which can be inhibited by contacting the graft with a cell-reactive compstatin analog. Without wishing to be bound by any theory, inhibiting complement activation at the graft may reduce leukocyte (e.g., neutrophil) infiltration, another contributor to acute graft failure.

In some embodiments, a cell-reactive, long-acting, or targeted compstatin analog inhibits complement-mediated I/R injury to a graft. As discussed further below, I/R injury can occur upon reperfusion of tissue whose blood supply has been temporarily disrupted, as occurs in transplanted organs. Reducing I/R injury would reduce the likelihood of acute graft dysfunction or reduce its severity, and reduce the likelihood of acute graft failure.

In some embodiments, a cell-reactive, long-acting, or targeted compstatin analog inhibits chronic rejection and/or chronic graft failure. As used herein, "chronic rejection or graft failure" refers to rejection or failure occurring at least 6 months post-transplant, e.g., between 6 months and 1, 2, 3, 4, 5 years, or more post-transplant, often after months to years of good graft function. It is caused by a chronic inflammatory and immune response against the graft. For purposes hereof, chronic rejection can include chronic allograft vasculopathy, a term used to refer to fibrosis of the internal blood vessels of the transplanted tissue. As immunosuppressive regimens have reduced the incidence of acute rejection, chronic rejection is becoming more prominent as a cause of graft dysfunction and failure. There is increasing evidence that B-cell production of alloantibody is an important element in the genesis of chronic rejection and graft failure (Kwun J. and Knechtle S J, Transplantation, 88(8): 955-61 (2009). Earlier damage to the graft may be a contributing factor leading to chronic processes such as fibrosis that can ultimately lead to chronic rejection. Thus, inhibiting such earlier damage using a cell-reactive compstatin analog may delay and/or reduce the likelihood or severity of chronic graft rejection.

In some embodiments, a long-acting compstatin analog is administered to a graft recipient to inhibit graft rejection and/or graft failure.

C. Ischemia/Reperfusion Injury

Ischemia-reperfusion (I/R) injury is an important cause of tissue damage following trauma and in other conditions associated with temporary disruption of blood flow such as myocardial infarction, stroke, severe infection, vascular disease, aneurysm repair, cardiopulmonary bypass, and transplantation.

In the setting of trauma, systemic hypoxemia, hypotension, and local interruption of the blood supply resulting from contusions, compartment syndrome, and vascular injuries cause ischemia that damages metabolically active tissues. Restoration of the blood supply triggers an intense systemic inflammatory reaction that is often more harmful than the ischemia itself. Once the ischemic region is reperfused, factors that are produced and released locally enter the circulatory system and reach remote locations, sometimes causing significant damage to organs not affected by the original ischemic insult, such as the lungs and intestine, leading to single and multiple organ dysfunction. Complement activation occurs soon after reperfusion and is a key mediator of post-ischemic damage, both directly and through its chemoattractive and stimulatory effects on neutrophils. All three major complement pathways are activated and, acting cooperatively or independently, are involved in I/R related adverse events affecting numerous organ systems. In some embodiments of the invention, a cell-reactive, long-acting, or targeted compstatin analog is administered to a subject who has recently (e.g., within the preceding 2, 4, 8, 12, 24, or 48 hours) experienced trauma, e.g., trauma that puts the subject at risk of I/R injury, e.g., due to systemic hypoxemia, hypotension, and/or local interruption of the blood supply. In some embodiments the cell-reactive compstatin analog may be administered intravascularly, optionally into a blood vessel that supplies an injured body part or directly to the body part. In some embodiments, the subject suffers from spinal cord injury, traumatic brain injury, burn, and/or hemorrhagic shock.

In some embodiments, a cell-reactive, long-acting, or targeted compstatin analog is administered to a subject prior to, during, or after a surgical procedure, e.g., a surgical procedure that is expected to temporarily disrupt blood flow to a tissue, organ, or portion of the body. Examples of such procedures include cardiopulmonary bypass, angioplasty, heart valve repair/replacement, aneurysm repair, or other vascular surgeries. The cell-reactive compstatin analog may be administered prior to, after, and/or during an overlapping time period with the surgical procedure.

In some embodiments, a cell-reactive, long-acting, or targeted compstatin analog is administered to a subject who has suffered an MI, thromboembolic stroke, deep vein thrombosis, or pulmonary embolism. The cell-reactive compstatin analog may be administered in combination with a thrombolytic agent such as tissue plasminogen activator (tPA) (e.g., alteplase (Activase), reteplase (Retavase), tenecteplase (TNKase)), anistreplase (Eminase), streptokinase (Kabikinase, Streptase), or urokinase (Abbokinase). The cell-reactive, long-acting, or targeted compstatin analog may be administered prior to, after, and/or during an overlapping time period with the thrombolytic agent.

In some embodiments, a cell-reactive, long-acting, or targeted compstatin analog is administered to a subject to treat I/R injury.

D. Other Complement-Mediated Disorders

In some embodiments, a cell-reactive, long-acting, or targeted compstatin analog is introduced into the eye for treatment of an eye disorder such as age-related macular degeneration (AMD), diabetic retinopathy, glaucoma, or uveitis. For example, a cell-reactive, long-acting, or targeted compstatin analog may be introduced into the vitreous cavity (e.g., by intravitreal injection), for treatment of a subject suffering from or at risk of AMD. In some embodiments the AMD is neovascular (wet) AMD. In some embodiments the AMD is dry AMD. As will be appreciated by those of ordinary skill in the art, dry AMD encompasses geographic atrophy (GA), intermediate AMD, and early AMD. In some embodiments, a subject with GA is treated in order to slow or halt progression of the disease. For example, in some embodiments, treatment of a subject with GA reduces the rate of retinal cell death. A reduction in the rate of retinal cell death may be evidenced by a reduction in the rate of GA lesion growth in patients treated with a LACA as compared with control (e.g., patients given a sham injection). In some embodiments, a subject has intermediate AMD. In some embodiments, a subject has early AMD. In some embodiments, a subject with intermediate or early AMD is treated in order to slow or halt progression of the disease. For example, in some embodiments, treatment of a subject with intermediate AMD may slow or prevent progression to an advanced form of AMD (neovascular AMD or GA). In some embodiments, treatment of a subject with early AMD may slow or prevent progression to intermediate AMD. In some embodiments an eye has both GA and neovascular AMD. In some embodiments an eye has GA but not wet AMD. In some embodiments a cell-reactive, long-acting, or targeted compstatin analog is administered by intravitreal injection to treat glaucoma, uveitis (e.g., posterior uveitis), or diabetic retinopathy. In some embodiments a cell-reactive, long-acting, or targeted compstatin analog is introduced into the anterior chamber, e.g., to treat anterior uveitis.

In some embodiments a cell-reactive, long-acting, or targeted compstatin analog is used to treat a subject suffering from or at risk of an autoimmune disease, e.g., an autoimmune disease mediated at least in part by antibodies against one or more self antigens.

Cell-reactive, long-acting, or targeted compstatin analogs may be introduced into the synovial cavity, e.g., in a subject suffering from arthritis (e.g., rheumatoid arthritis). Of course they may be administered systemically in addition or In some embodiments, a cell-reactive, long-acting, or targeted compstatin analog is used to treat a subject suffering from or at risk of an intracerebral hemorrhage.

In some embodiments a cell-reactive, long-acting, or targeted compstatin analog is used to treat a subject suffering from or at risk of myasthenia gravis.

In some embodiments a cell-reactive, long-acting, or targeted compstatin analog is used to treat a subject suffering from or at risk of neuromyelitis optica (NMO), In some embodiments a cell-reactive, long-acting, or targeted compstatin analog is used to treat a subject suffering from or at risk of membranoproliferative glomerulonephritis (MPGN), e.g., MPGN type I, MPGN type II, or MPGH type III.

In some embodiments a cell-reactive, long-acting, or targeted compstatin analog is used to treat a subject suffering from or at risk of a neurodegenerative disease. In some embodiments a cell-reactive, long-acting, or targeted compstatin analog is used to treat a subject suffering from neuropathic pain or at risk of developing neuropathic pain. In some embodiments a cell-reactive, long-acting, or targeted compstatin analog is used to treat a subject suffering from or at risk of rhinosinusitis or nasal polyposis. In some embodiments a cell-reactive, long-acting, or targeted compstatin analog is used to treat a subject suffering from or at risk of cancer. In some embodiments a cell-reactive, long-acting, or targeted compstatin analog is used to treat a subject suffering from or at risk of sepsis. In some embodiments a cell-reactive, long-acting, or targeted compstatin analog is used to treat a subject suffering from or at risk of adult respiratory distress syndrome.

In some embodiments a cell-reactive, long-acting, or targeted compstatin analog is used to treat a subject suffering from or at risk of anaphylaxis or infusion reaction. For example, in some embodiments a subject may be pretreated prior to, during, or after receiving a drug or a vehicle that may cause anaphylaxis or infusion reaction. In some embodiments a subject at risk of or suffering from anaphylaxis from a food (e.g., peanut, shellfish, or other food allergens), insect sting (e.g., bee, wasp), is treated with a cell-reactive, long-acting, or targeted compstatin analog.

The cell-reactive long-acting, or targeted compstatin analog may be administered locally or systemically, in various embodiments of the invention.

In some embodiments, a cell-reactive, long-acting, or targeted compstatin analog is used to treat a respiratory disease, e.g., asthma or chronic obstructive pulmonary disease (COPD) or idiopathic pulmonary fibrosis. The cell-reactive, long-acting, or targeted compstatin analog may, for example, be administered to the respiratory tract by inhalation, e.g., as a dry powder or via nebulization, or may be administered by injection, e.g., intravenously, intramuscularly, or subcutaneously, in various embodiments. In some embodiments, a cell-reactive, long-acting, or targeted compstatin analog is used to treat severe asthma, e.g., asthma that is not sufficiently controlled by bronchodilators and/or inhaled corticosteroids.

In some aspects, methods of treating a complement-mediated disorder, e.g., a chronic complement-mediated disorder, are provided, the methods comprising administering a long-acting complement inhibitor to a subject in need of treatment for the disorder. The long-acting compstatin analog may be any long-acting compstatin analog described herein, in various embodiments. In some aspects, methods of treating a Th17-associated disorder are provided, the methods comprising administering a long-acting complement inhibitor to a subject in need of treatment for the disorder.

In some aspects, a "chronic disorder" is a disorder that persists for at least 3 months and/or is accepted in the art as being a chronic disorder. In many embodiments, a chronic disorder persists for at least 6 months, e.g., at least 1 year, or more, e.g., indefinitely. One of ordinary skill in the art will appreciate that at least some manifestations of various chronic disorders may be intermittent and/or may wax and wane in severity over time. A chronic disorder may be progressive, e.g., having a tendency to become more severe or affect larger areas over time. A number of chronic complement-mediated disorders are discussed herein. A chronic complement-mediated disorder may be any chronic disorder in which complement activation (e.g., excessive or inappropriate complement activation) is involved, e.g., as a contributing and/or at least partially causative factor. For convenience, disorders are sometimes grouped by reference to an organ or system that is often particularly affected in subjects suffering from the disorder. It will be appreciated that a number of disorders can affect multiple organs or systems, and such classification(s) are in no way limiting. Furthermore, a number of manifestations (e.g., symptoms) may occur in subjects suffering from any of a number of different disorders. Non-limiting information regarding disorders of interest herein may be found, e.g., in standard textbooks of internal medicine such as Cecil Textbook of Medicine (e.g., 23rd edition), Harrison's Principles of Internal Medicine (e.g., 17th edition), and/or standard textbooks focusing on particular areas of medicine, particular body systems or organs, and/or particular disorders.

In some embodiments, a chronic complement-mediated disorder is a Th2-associated disorder. As used herein, a Th2-associated disorder is a disorder characterized by an excessive number and/or excessive or inappropriate activity of CD4+ helper T cells of the Th2 subtype ("Th2 cells") in the body or a portion thereof, e.g., in at least one tissue, organ, or structure. For example, there may be a predominance of Th2 cells relative to CD4+ helper T cells of the Th1 subtype ("Th1 cells") e.g., in at least one tissue, organ, or structure affected by a disorder. As known in the art, Th2 cells typically secrete characteristic cytokines such as interleukin-4 (IL-4), interleukin-5 (IL-5), and interleukin-13 (IL-13), while Th1 cells typically secrete interferon-γ (IFN-γ) and tumor necrosis factor β (TNF β). In some embodiments, a Th2-associated disorder is characterized by excessive production and/or amount of IL-4, IL-5, and/or IL-13, e.g., relative to IFN-γ and/or TNF β e.g., in at least some at least one tissue, organ, or structure In some embodiments, a chronic complement-mediated disorder is a Th17-associated disorder. In some aspects, as described in further detail in PCT/US2012/043845, filed Jun. 22, 2012, entitled "Methods of Treating Chronic Disorders with Complement Inhibitors", complement activation and Th17 cells participate in a cycle that involves dendritic cells and antibodies and that contributes to maintenance of a pathologic immunologic microenvironment underlying a range of disorders. Without wishing to be bound by any theory, the pathologic immunologic microenvironment, once established, is self-sustaining and contributes to cell and tissue injury. In some aspects, long-acting compstatin analogs are of use to treat Th17-associated disorders.

As used herein, a Th17-associated disorder is a disorder characterized by an excessive number and/or excessive or inappropriate activity of CD4+ helper T cells of the Th17 subtype ("Th17 cells") in the body or a portion thereof, e.g., in at least one tissue, organ, or structure. For example, there may be a predominance of Th17 cells relative to Th1 and/or Th2 cells, e.g., in at least one tissue, organ, or structure affected by a disorder. In some embodiments a predominance of Th17 cells is a relative predominance, e.g., the ratio of Th17 cells to Th1 cells and/or the ratio of Th17 cells to Th2 cells, is increased relative to normal values. In some embodiments the ratio of Th17 cells to T regulatory cells ($CD4^+CD25^+$ regulatory T cells, also termed "Treg cells"), is increased relative to normal values. Formation of Th17 cells and/or activation of Th17 cells is promoted by various cytokines, e.g., interleukin 6 (IL-6), interleukin 21 (IL-21), interleukin 23 (IL-23), and/or interleukin 1β (IL-1β). Formation of Th17 cells encompasses differentiation of precursor T cells, e.g., naïve CD4+ T cells, towards a Th17 phenotype and their maturation into functional Th17 cells. In some embodiments, formation of Th17 cells encompasses any aspect of development, proliferation (expansion), survival, and/or maturation of Th17 cells. In some embodiments, a Th17-associated disorder is characterized by excessive production and/or amount of IL-6, IL-21, IL-23, and/or IL-1β. Th17 cells typically secrete characteristic cytokines such as interleukin-17A (IL-17A), interleukin-17F (IL-17F), interleukin-21 (IL-21), and interleukin-22 (IL-22). In some embodiments, a Th17-associated disorder is characterized by excessive production and/or amount of a Th17 effector cytokine, e.g., IL-17A, IL-17F, IL-21, and/or IL-22. In some embodiments excessive production or amount of a cytokine is detectable in the blood. In some embodiments excessive production or amount of a cytokine is detectable locally, e.g., in at least one tissue, organ or structure. In some embodiments a Th17-associated disorder is associated with a decreased number of Tregs and/or decreased amount of a Treg-associated cytokine. In some embodiments a Th17 disorder is any chronic inflammatory disease, which term encompasses a range of ailments characterized by self-perpetuating immune insults to a variety of tissues and that seem to be dissociated from the initial insult that caused the ailment (which may be unknown). In some embodiments a Th17-associated disorder is any autoimmune disease. Many if not most "chronic inflammatory diseases" may in fact be auto-immune diseases. Examples of Th17-associated disorders include inflammatory skin diseases such as psoriasis and atopic dermatitis; systemic scleroderma and sclerosis; inflammatory bowel disease (IBD) (such as Crohn's disease and ulcerative colitis); Behcet's Disease; dermatomyositis; polymyositis; multiple sclerosis (MS); dermatitis; meningitis; encephalitis; uveitis; osteoarthritis; lupus nephritis; rheumatoid arthritis (RA), Sjogren's syndrome, multiple sclerosis, vasculitis; central nervous system (CNS) inflammatory disorders, chronic hepatitis; chronic pancreatitis, glomerulonephritis; sarcoidosis; thyroiditis, pathologic immune responses to tissue/organ transplantation (e.g., transplant rejection); COPD, asthma, bronchiolitis, hypersensitivity pneumonitis, idiopathic pulmonary fibrosis (IPF), periodontitis, and gingivitis. In some embodiments a Th17 disease is a classically known auto-immmune disease such as Type I diabetes or psoriasis. In some embodiments a Th17-associated disorder is age-related macular degeneration.

In some embodiments, a chronic complement-mediated disorder is an IgE-associated disorder. As used herein, an "IgE-associated disorder" is a disorder characterized by excessive and/or inappropriate production and/or amount of IgE, excessive or inappropriate activity of IgE producing cells (e.g., IgE producing B cells or plasma cells), and/or excessive and/or inappropriate activity of IgE responsive cells such as eosinophils or mast cells. In some embodiments, an IgE-associated disorder is characterized by elevated levels of total IgE and/or in some embodiments, allergen-specific IgE, in the plasma of a subject and/or locally.

In some embodiments, a chronic complement-mediated disorder is characterized by the presence of autoantibodies and/or immune complexes in the body, which may activate complement via, e.g., the classical pathway. Autoantibodies may, for example, bind to self antigens, e.g., on cells or tissues in the body. In some embodiments, autoantibodies bind to antigens in blood vessels, skin, nerves, muscle, connective tissue, heart, kidney, thyroid, etc. In some embodiments, a subject has neuromyelitis optica and produces an autoantibody (e.g., an IgG autoantibody) to aquaporin 4. In some embodiments, a subject has pemphigoid and produces an autoantibody (e.g., an IgG or IgE autoantibody) to a structural component of the hemidesmosome (e.g., transmembrane collagen XVII (BP180 or BPAG2) and/or plakin family protein BP230 (BPAG1). In some embodiments, a subject has a polyneuropathy, e.g., a chronic polyneuropathy such as multifocal motor neuropathy or an acute polyneuropathy and produces an anti-ganglioside autoantibody that binds to gangliosides present in nerve cell membranes. In some embodiments, a chronic complement-mediated disorder is not characterized by autoantibodies and/or immune complexes.

In some embodiments, a chronic complement-mediated disorder is a respiratory disorder. In some embodiments, a chronic respiratory disorder is asthma or chronic obstructive pulmonary disease (COPD). In some embodiments, a chronic respiratory disorder is pulmonary fibrosis (e.g., idiopathic pulmonary fibrosis), radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans. In some embodiments, the invention provides a method of treating a subject in need of treatment for a chronic respiratory disorder, e.g., asthma, COPD, pulmonary fibrosis, radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans, the method comprising administering a long-acting complement inhibitor to a subject in need of treatment for the disorder.

In some embodiments, a chronic complement-mediated disorder is allergic rhinitis, rhinosinusitis, or nasal polyposis. In some embodiments, the invention provides a method of treating a subject in need of treatment for allergic rhinitis, rhinosinusitis, or nasal polyposis, the method comprising administering a long-acting complement inhibitor to a subject in need of treatment for the disorder.

In some embodiments, a chronic complement-mediated disorder is a disorder that affects the musculoskeletal system. Examples of such disorders include inflammatory joint conditions (e.g., arthritis such as rheumatoid arthritis or psoriatic arthritis, juvenile chronic arthritis, spondyloarthropathies Reiter's syndrome, gout). In some embodiments, a musculoskeletal system disorder results in symptoms such as pain, stiffness and/or limitation of motion of the affected body part(s). Inflammatory myopathies include dermatomyositis, polymyositis, and various others are disorders of chronic muscle inflammation of unknown etiology that result in muscle weakness. In some embodiments, a chronic complement-mediated disorder is myasthenia gravis. In some embodiments, the invention provides a method of treating any of the foregoing disorders affecting the musculoskeletal system, the method comprising administering a long-acting complement inhibitor to a subject in need of treatment for the disorder.

In some embodiments, a chronic complement-mediated disorder is a disorder that affects the integumentary system. Examples of such disorders include, e.g., atopic dermatitis, psoriasis, pemphigoid, pemphigus, systemic lupus erythematosus, dermatomyositis, scleroderma, sclerodermatomyositis, Sjögren syndrome, and chronic urticaria. In some aspects, the invention provides a method of treating any of the foregoing disorders affecting the integumentary system, the method comprising administering a long-acting complement inhibitor to a subject in need of treatment for the disorder.

In some embodiments, a chronic complement-mediated disorder affects the nervous system, e.g., the central nervous system (CNS) and/or peripheral nervous system (PNS). Examples of such disorders include, e.g., multiple sclerosis, other chronic demyelinating diseases (e.g., neuromyelitis optica), acute or chronic neuropathies associated with autoantibodies against nerve components, such as anti-ganglioside antibodies (e.g., Guillain-Barre syndrome, multifocal motor neuropathy), amyotrophic lateral sclerosis, chronic pain, stroke, allergic neuritis, Huntington's disease, Alzheimer's disease, and Parkinson's disease. In some embodiments, the invention provides a method of treating any of the foregoing disorders affecting the nervous system, the method comprising administering a complement inhibitor, e.g., a long-acting, targeted or cell-reactive compstatin analog, to a subject in need of treatment for the disorder.

In some embodiments, a chronic complement-mediated disorder affects the circulatory system. For example, in some embodiments the disorder is a vasculitis or other disorder associated with vessel inflammation, e.g., blood vessel and/or lymph vessel inflammation. In some embodiments, a vasculitis is polyarteritis *nodosa*, Wegener's granulomatosis, giant cell arteritis, Churg-Strauss syndrome, microscopic polyangiitis, Henoch-Schonlein purpura, Takayasu's arteritis, Kawasaki disease, or Behcet's disease. In some embodiments, a subject, e.g., a subject in need of treatment for vasculitis, is positive for antineutrophil cytoplasmic antibody (ANCA).

In some embodiments, a chronic complement-mediated disorder affects the gastrointestinal system. For example, the disorder may be inflammatory bowel disease, e.g., Crohn's disease or ulcerative colitis. In some embodiments, the invention provides a method of treating a chronic complement-mediated disorder that affects the gastrointestinal system, the method comprising administering a long-acting complement inhibitor to a subject in need of treatment for the disorder.

In some embodiments, a chronic complement-mediated disorder is a thyroiditis (e.g., Hashimoto's thyroiditis, Graves' disease, post-partum thyroiditis), myocarditis, hepatitis (e.g., hepatitis C), pancreatitis, glomerulonephritis (e.g., membranoproliferative glomerulonephritis or membranous glomerulonephritis), or panniculitis.

In some embodiments a chronic complement-mediated disorder affects the kidney. For example, the disorder may be glomerulonephritis (e.g., membranoproliferative glomerulonephritis or membranous glomerulonephritis). In some aspects, such disorders are characterized by deposition of complement fragments in the kidney, which may be present together with antibodies. For example, in some embodiments the disorder that affects the kidney is C3 glomerulopathy, which encompasses dense deposit disease (DDD) and C3 glomerulonephritis (C3G). Patients suffering from C3 glomerulopathy show staining for C3 fragments (e.g., iC3b, C3c, C3dg) in glomeruli, which may be detected using antibodies. Such patients may exhibit alternative complement pathway overactivation, e.g., due to the presence of autoantibodies that stabilize the C3 convertase, such as C3Nef or anti-factorB or anti-C3b. C3 glomerulopathy encompasses conditions in which a mutation in a gene encoding a complement component or complement-like protein is causally associated with the renal pathology. Examples include dense deposit disease with C3 mutation and C3 glomerulonephritis with mutations in CFH or CFH-related (CFHR) genes, e.g., CFHR1, CFHR3, and/or CFRH5. In some embodiments the disorder that affects the kidney is IgA nephropathy, which is characterized by mesangial deposits of IgA, C3 and/or C3 fragments, and, to a lesser extent, IgG and IgM. In some embodiments the subject may exhibit overactivation of the alternative and/or lectin pathway.

In some embodiments, the invention provides methods of treating a subject suffering from chronic pain, the methods comprising administering a long-acting complement inhibitor to a subject in need thereof. In some embodiments, a subject suffers from neuropathic pain. Neuropathic pain has been defined as pain initiated or caused by a primary lesion or dysfunction in the nervous system, in particular, pain arising as a direct consequence of a lesion or disease affecting the somatosensory system. For example, neuropathic pain may arise from lesions that involve the somatosensory pathways with damage to small fibres in peripheral nerves and/or to the spino-thalamocortical system in the CNS. In some embodiments, neuropathic pain arises from autoimmune disease (e.g., multiple sclerosis), metabolic disease (e.g., diabetes), infection (e.g., viral disease such as shingles or HIV), vascular disease (e.g., stroke), trauma (e.g., injury, surgery), or cancer. For example, neuropathic pain can be pain that persists after healing of an injury or after cessation of a stimulus of peripheral nerve endings or pain that arises due to damage to nerves. Exemplary conditions of or associated with neuropathic pain include painful diabetic neuropathy, post-herpetic neuralgia (e.g., pain persisting or recurring at the site of acute herpes zoster 3 or more months after the acute episode), trigeminal neuralgia, cancer related neuropathic pain, chemotherapy-associated neuropathic pain, HIV-related neuropathic pain (e.g., from HIV neuropathy), central/post-stroke neuropathic pain, neuropathy associated with back pain, e.g., low back pain (e.g., from radiculopathy such as spinal root compression, e.g., lumbar root compression, which compression may arise due to disc herniation), spinal stenosis, peripheral nerve injury pain, phantom limb pain, polyneuropathy, spinal cord injury related pain, myelopathy, and multiple sclerosis. In certain embodiments of the invention a complement inhibitor is administered according to an inventive dosing schedule to treat neuropathic pain in a subject with one or more of the afore-mentioned conditions.

In some embodiments, a chronic complement-mediated disorder is a chronic eye disorder. In some embodiments, the chronic eye disorder is characterized by macular degeneration, choroidal neovascularization (CNV), retinal neovascularization (RNV), ocular inflammation, or any combination of the foregoing. Macular degeneration, CNV, RNV, and/or ocular inflammation may be a defining and/or diagnostic feature of the disorder. Exemplary disorders that are characterized by one or more of these features include, but are not limited to, macular degeneration related conditions, diabetic retinopathy, retinopathy of prematurity, proliferative vitreoretinopathy, uveitis, keratitis, conjunctivitis, and scleritis. Macular degeneration related conditions include, e.g., age-related macular degeneration (AMD). In some embodiments, a subject is in need of treatment for wet AMD. In some embodiments, a subject is in need of treatment for dry AMD. In some embodiments, a subject is in need of treatment for geographic atrophy (GA). In some embodiments, a subject is in need of treatment for ocular inflammation. Ocular inflammation can affect a large number of eye structures such as the conjunctiva (conjunctivitis), cornea (keratitis), episclera, sclera (scleritis), uveal tract, retina, vasculature, and/or optic nerve. Evidence of ocular inflammation can include the presence of inflammation-associated cells such as white blood cells (e.g., neutrophils, macrophages) in the eye, the presence of endogenous inflammatory mediator(s), one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. In some embodiments, a subject is in need of treatment for geographic atrophy (GA). In some embodiments, the chronic eye disorder is an eye disorder characterized by optic nerve damage (e.g., optic nerve degeneration), such as glaucoma.

As noted above, in some embodiments the chronic respiratory disease is asthma. Information regarding risk factors, epidemiology, pathogenesis, diagnosis, current management of asthma, etc., may be found, e.g., in "Expert Panel Report 3: Guidelines for the Diagnosis and Management of Asthma". National Heart Lung and Blood Institute. 2007. http://www.nhlbi.nih.gov/guidelines/asthma/asthgdln.pdf. ("NHLBI Guidelines"; www.nhlbi.nih.gov/guidelines/asthma/asthgdln.htm), Global Initiative for Asthma, Global Strategy for Asthma Management and Prevention 2010 "GINA Report") and/or standard textbooks of internal medicine such as Cecil Textbook of Medicine (20th edition), Harrison's Principles of Internal Medicine (17th edition), and/or standard textbooks focusing on pulmonary medicine. Asthma is a chronic inflammatory disorder of the airways in which many cells and cellular elements play a role, such as, mast cells, eosinophils, T lymphocytes, macrophages, neutrophils, and epithelial cells Asthmatic individuals experience recurrent episodes associated with symptoms such as wheezing, breathlessness (also termed dyspnea or shortness of breath), chest tightness, and coughing. These episodes are usually associated with widespread but variable airflow obstruction that is often reversible, either spontaneously or with treatment. The inflammation also causes an associated increase in the existing bronchial hyperresponsiveness to a variety of stimuli. Airway hyperresponsiveness (an exaggerated bronchoconstrictor response to stimuli) is a typical feature of asthma. In general, airflow limitation results from bronchoconstriction and airway edema. Reversibility of airflow limitation may be incomplete in some patients with asthma. For example, airway remodeling can lead to fixed airway narrowing. Structural changes can include thickening of the sub-basement membrane, subepithelial fibrosis, airway smooth muscle hypertrophy and hyperplasia, blood vessel proliferation and dilation, and mucous gland hyperplasia, and hypersecretion.

Individuals with asthma may experience exacerbations, which are identified as events characterized by a change from the individual's previous status. Severe asthma exacerbations can be defined as events that require urgent action on the part of the individual and his/her physician to prevent a serious outcome, such as hospitalization or death from asthma. For example, a severe asthma exacerbation may require use of systemic corticosteroids (e.g., oral corticosteroids) in a subject whose asthma is usually well controlled without OCS or may require an increase in a stable maintenance dose. Moderate asthma exacerbations can be defined as events that are troublesome to the subject, and that prompt a need for a change in treatment, but that are not severe. These events are clinically identified by being outside the subject's usual range of day-to-day asthma variation.

Current medications for asthma are typically categorized into two general classes: long-term control medications ("controller medications") such as inhaled corticosteroids (ICS), oral corticosteroids (OCS), long-acting bronchodilators (LABAs), leukotriene modifiers (e.g., leukotriene receptor antagonists or leukotriene synthesis inhibitors, anti-IgE antibodies (omalizumab (Xolair®)), cromolyn and nedocromil, which are used to achieve and maintain control of persistent asthma and quick-relief medications such as short-acting bronchodilators (SABAs), which are used to treat acute symptoms and exacerbations. For purposes of the present invention, these treatments may be referred to as "conventional therapy". Treatment of exacerbations may also include increasing the dose and/or intensity of controller medication therapy. For example, a course of OCS can be used to regain asthma control. Current guidelines mandate daily administration of controller medication or, in many cases, administration of multiple doses of controller medication each day for subjects with persistent asthma (with the exception of Xolair, which is administered every 2 or 4 weeks).

Figure 3:
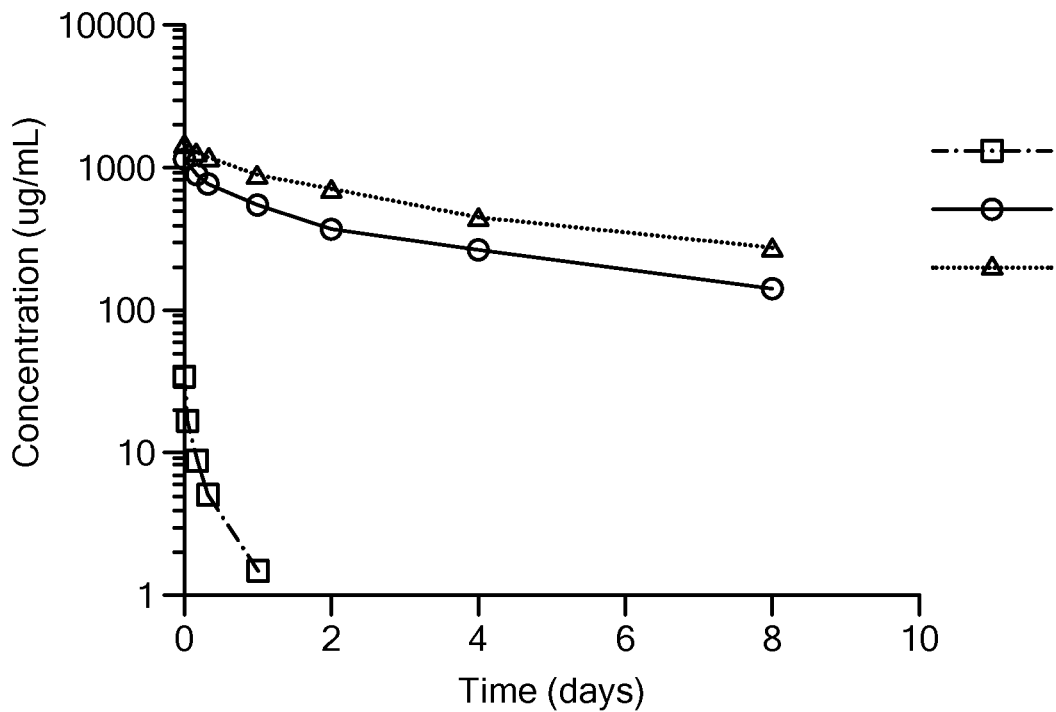
FIG. 3 is a plot that shows plasma concentrations versus time of CA28 and long-acting compstatin analogs CA28-2 and CA28-3 in Cynomolgus monkeys following a single intravenous injection. CA28 was administered at 200 mg/kg. CA28-2 and CA28-3 were each administered at 50 mg/kg. In calculating the doses for these experiments the administered CA28-2 and CA28-3 substance was assumed to consist 80% of active compound w/w based on dry weight. However, during the sample analysis, the standard curve assumed a 100% of active compound w/w based on dry weight, by an estimated 30%. Thus, the values for Cmax overestimate the actual Cmax. CA28 (squares, light gray), CA28-2 (triangles, black), CA28-3 (circles, dark gray).

A subject is generally considered to have persistent asthma if the subject suffers from symptoms on average more than twice a week and/or typically uses a quick relief medication (e.g., SABA) more than twice a week for symptom control. "Asthma severity" can be classified based on the intensity of treatment required to control the subject's asthma once relevant comorbidities have been treated and inhaler technique and adherence have been optimized (see, e.g., GINA Report; Taylor, D R, Eur Respir J 2008; 32:545-554). The description of treatment intensity can be based on the medications and doses recommended in the stepwise treatment algorithm found in guidelines such as NHLBI Guidelines 2007, GINA Report, and their predecessors and/or in standard medical textbooks. For example, asthma can be classified as intermittent, mild, moderate, or severe as indicated in Table X, where "treatment" refers to treatment sufficient to achieve subject's best level of asthma control. (It will be understood that the categories of mild, moderate, and severe asthma in general imply persistent rather than intermittent asthma). One of ordinary skill in the art will appreciate that Table X is exemplary, and that not all of these medications will be available in all healthcare systems, which may affect the assessment of asthma severity in some environments. It will also be appreciated that other emerging or new approaches may affect the classification of mild/moderate asthma. However, the same principle, of mild asthma being defined by the ability to achieve good control using very low-intensity treatment and severe asthma being defined by the requirement for high-intensity treatment, can still be applied. Asthma severity can also or alternately be classified based on intrinsic intensity of the disease in the absence of treatment (see, e.g., NHBLI Guidelines 2007). Assessment can be made on the basis of current spirometry and the patient's recall of symptoms over the previous 2-4 weeks. Parameters of current impairment and future risk may be assessed and included in a determination of the level of asthma severity. In some embodiments, asthma severity is defined as shown in FIG. 3.4(a), 3.4(b), 3.4(c) of the NHBLI Guidelines, for individuals 0-4, 5-11, or ≥12 years of age, respectively.

TABLE X

Treatment-based Asthma Classification

| Asthma Classification | Treatment |
|---|---|
| Intermittent | SABA as needed (typically no more than twice a week) |
| Mild | Low-dose ICS or other low-intensity treatment (e.g., LTRA, cromolyn, nedocromil, theophylline) |
| Moderate | Low to moderate dose ICS and LABA or other extra treatment |
| Severe | High-intensity treatment (high-dose ICS and LABA ± oral corticosteroids and/or other extra treatment) |

Figure 4:
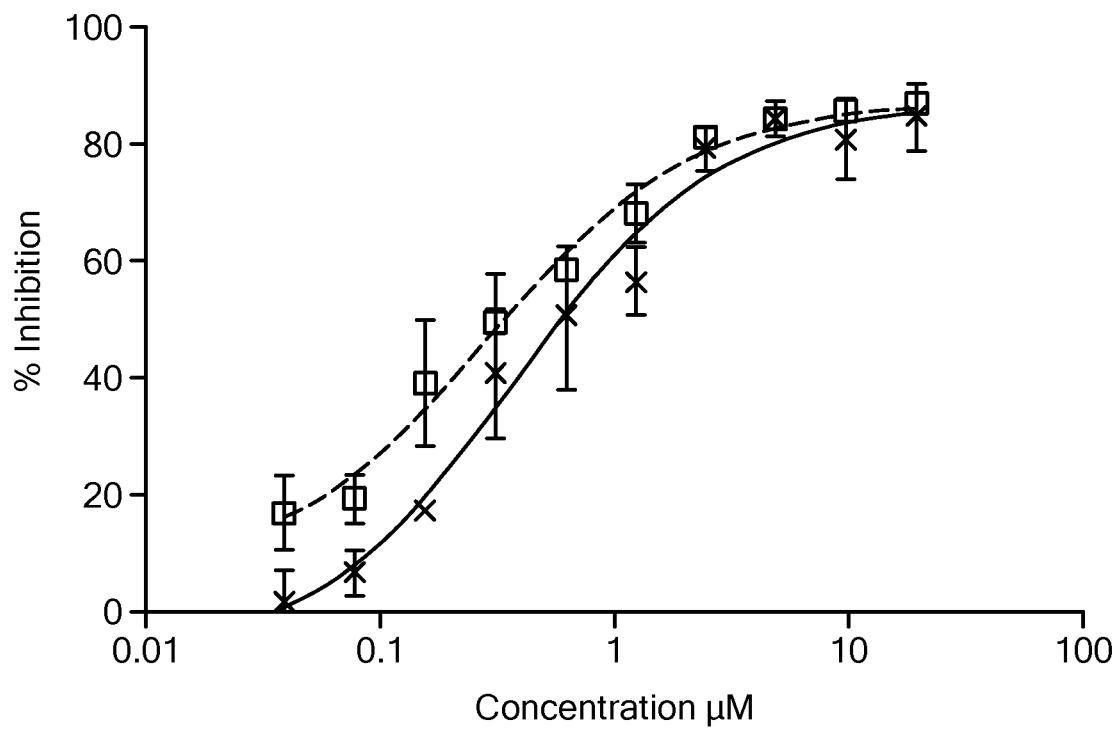
FIG. 4 is a plot that shows percent complement activation inhibiting activity of CA28 and long-acting compstatin analog CA28-4, as a function of compound concentration (μM). Inhibition of complement activation was tested in vitro using a classical complement inhibition assay. The plot shows values obtained by averaging the results of four sets of measurements for CA28-4. CA28 (squares, light gray), CA28-4 (crosses, black).

"Asthma control" refers to the extent to which the manifestations of asthma have been reduced or removed by treatment (whether pharmacological or non-pharmacological). Asthma control can be assessed based on factors such as symptom frequency, nighttime symptoms, objective measures of lung function such as spirometry parameters (e.g., % $FEV_1$ of predicted, $FEV_1$ variability, requirement for use of SABA for symptom control. Parameters of current impairment and future risk may be assessed and included in a determination of the level of asthma control. In some embodiments, asthma control is defined as shown in FIG. 4.3(a), 4.3(b), or 4.3(c) of NHBLI Guidelines, for individuals 0-4, 5-11, or ≥12 years of age, respectively.

In general, one of ordinary skill in the art can select an appropriate means of determining asthma severity level and/or degree of control, and any classification scheme considered reasonable by those of ordinary skill in the art can be used.

In some embodiments of the invention, a subject suffering from persistent asthma is treated with a complement inhibitor using an inventive dosing regimen. In some embodiments, the subject suffers from mild or moderate asthma. In some embodiments, the subject suffers from severe asthma. In some embodiments, a subject has asthma that is not well controlled using conventional therapy. In some embodiments, a subject has asthma that, when treated using conventional therapy, requires use of ICS in order to be well controlled. In some embodiments, a subject has asthma that fails to be well controlled despite use of ICS. In some embodiments, a subject has asthma that, if treated using conventional therapy, would require use of OCS in order to be well controlled. In some embodiments, a subject has asthma that fails to be well controlled despite use of high intensity conventional therapy that includes OCS. In some embodiments of the invention a long-acting complement inhibitor is administered as a controller medication or allow the subject to avoid using or reduce their dose of a conventional controller medication.

In some embodiments, the subject suffers from allergic asthma, which is the case for most asthmatic individuals. In some embodiments, an asthmatic subject is considered to have allergic asthma if a non-allergic trigger for the asthma (e.g., cold, exercise) is not known and/or is not identified in a standard diagnostic evaluation. In some embodiments, an asthmatic subject is considered to have allergic asthma if the subject (i) reproducibly develops asthma symptoms (or worsening of asthma symptoms) following exposure to an allergen or allergen(s) to which the subject is sensitive; (ii) exhibits IgE specific for an allergen or allergen(s) to which the subject is sensitive; (iii) exhibits a positive skin-prick test to an allergen or allergen(s) to which the subject is sensitive; and/or (iv) exhibits other symptom(s) of characteristic(s) consistent with atopy such as allergic rhinitis, eczema, or elevated total serum IgE. It will be appreciated that a specific allergic trigger may not be identified but may be suspected or inferred if the subject experiences worsening symptoms in particular environments, for example.

Allergen challenge by inhalation is a technique that is widely used in evaluating allergic airway disease. Inhalation of allergen leads to cross-linking of allergen-specific IgE bound to IgE receptors on, e.g., mast cells and basophils. Activation of secretory pathways ensues, resulting in release of mediators of bronchoconstriction and vascular permeability. Individuals with allergic asthma may develop various manifestations following allergen challenge, e.g., early asthmatic response (EAR), late asthmatic response (LAR), airway hyperreactivity (AHR), and airway eosinophilia, each of which can be detected and quantified as known in the art. For example, airway eosiphophilia may be detected as an increase in eosinophils in sputum and/or BAL fluid. The EAR, sometimes referred to as the immediate asthmatic response (IAR), is a response to allergen challenge by inhalation that becomes detectable shortly after the inhalation, typically within 10 minutes (min) of the inhalation, e.g., as a decrease in FEV). The EAR typically reaches a maximum within 30 min and resolves within 2-3 hours (h) post-challenge. For example, a subject may be considered to exhibit a "positive" EAR if his/her FEV) decreases by at least 15%, e.g., at least 20%, within this time window relative to baseline $FEV_1$ (where "baseline" in this context refers to conditions before the challenge, e.g., conditions equivalent to the subject's usual condition when not experiencing an asthma exacerbation and not exposed to allergic stimuli to which the subject is sensitive). The late asthmatic response (LAR) typically starts between 3 h and 8 h post-challenge and is characterized by cellular inflammation of the airway, increased bronchiovascular permeability, and mucus secretion. It is typically detected as a decrease in $FEV_1$, which may be greater in magnitude than that associated with the EAR and potentially more clinically important. For example, a subject may be considered to exhibit a "positive" LAR if his/her FEV) decreases by at least 15%, e.g., at least 20%, relative to baseline $FEV_1$ within the relevant time period as compared with baseline FEV). A delayed airway response (DAR) may occur beginning between about 26 and 32 h, reaching a maximum between about 32 and 48 h and resolving within about 56 h after the challenge (Pelikan, Z. Ann Allergy Asthma Immunol. 2010, 104(5):394-404).

In some embodiments, the chronic respiratory disorder is chronic obstructive pulmonary disease (COPD). COPD encompasses a spectrum of conditions characterized by airflow limitation that is not fully reversible even with therapy and is usually progressive. Symptoms of COPD include dyspnea (breathlessness), decreased exercise tolerance, cough, sputum production, wheezing, and chest tightness. Persons with COPD can experience episodes of acute (e.g., developing over course of less than a week and often over the course of 24 hours or less) worsening of symptoms (termed COPD exacerbations) that can vary in frequency and duration and are associated with significant morbidity. They may be triggered by events such as respiratory infection, exposure to noxious particles, or may have an unknown etiology. Smoking is the most commonly encountered risk factor for COPD, and other inhalational exposures can also contribute to development and progression of the disease. The role of genetic factors in COPD is an area of active research. A small percentage of COPD patients have a hereditary deficiency of alpha-1 antitrypsin, a major circulating inhibitor of serine proteases, and this deficiency can lead to a rapidly progressive form of the disease.

Characteristic pathophysiologic features of COPD include narrowing of and structural changes in the small airways and destruction of lung parenchyma (in particular around alveoli), most commonly due to chronic inflammation. The chronic airflow limitation observed in COPD typically involves a mixture of these factors, and their relative importance in contributing to airflow limitation and symptoms varies from person to person. The term "emphysema" refers to enlargement of the air spaces (alveoli) distal to the terminal bronchioles, with destruction of their walls. It should be noted that the term "emphysema" is often used clinically to refer to the medical condition associated with such pathological changes. Some individuals with COPD have chronic bronchitis, which is defined in clinical terms as a cough with sputum production on most days for 3 months of a year, for 2 consecutive years. Further information regarding risk factors, epidemiology, pathogenesis, diagnosis, and current management of COPD may be found, e.g., in "Global Strategy for the Diagnosis, Management, and Prevention of Chronic Obstructive Pulmonary Disease" (updated 2009) available on the Global Initiative on Chronic Obstructive Pulmonary Disease, Inc. (GOLD) website (www.goldcopd.org), also referred to herein as the "GOLD Report", the American Thoracic Society/European Respiratory Society Guidelines (2004) available on the ATS website at www.thoracic.org/clinical/copd-guidelines/resources/copddoc.pdf, referred to herein as "ATC/ERS COPD Guidelines" and standard textbooks of internal medicine such as Cecil Textbook of Medicine ($20^{th}$ edition), Harrison's Principles of Internal Medicine ($17^{th}$ edition), and/or standard textbooks focusing on pulmonary medicine.

In some embodiments methods disclosed herein inhibit (interfere with, disrupt) the DC-Th17-B-Ab-C-DC cycle discussed above. For example, administration of a complement inhibitor may break the cycle by which complement stimulates DC cells to promote the Th17 phenotype. As a result, the number and/or activity of Th17 cells diminishes, which in turn reduces the amount of Th17-mediated stimulation of B cells and polyclonal antibody production. In some embodiments, these effects result in "resetting" the immunological microenvironment to a more normal, less pathological state. As described in Example 1 of PCT/US2012/043845 (WO/2012/178083) and USSN 20140371133 (summarized briefly hereinbelow in Example 27) evidence supporting the capacity of complement inhibition to have a prolonged inhibitory effect on Th17-associated cytokine production has been obtained in an animal model of asthma.

In some embodiments, inhibiting the DC-Th17-B-Ab-C-DC cycle has a disease-modifying effect. Without wishing to be bound by any theory, rather than merely treating symptoms of a disorder, inhibiting the DC-Th17-B-Ab-C-DC cycle may interfere with fundamental pathologic mechanisms that may contribute to ongoing tissue damage even when symptoms are well controlled and/or that may contribute to exacerbations of the disease. In some embodiments, inhibiting the DC-Th17-B-Ab-C-DC cycle causes a chronic disorder to go into remission. In some embodiments, remission refers to a state of absence or substantial absence of disease activity in a subject with a chronic disorder, with the possibility of return of disease. In some embodiments remission may be sustained for a prolonged period of time (e.g., at least 6 months, e.g., 6-12 months, 12-24 months, or more) in the absence of continued therapy or with a reduced dose or increased dosing interval. In some aspects, inhibition of complement may change the immunological micro-environment of a tissue that is rich in Th17 cells and modify it into a micro-environment that is rich in regulatory T cells (Tregs). Doing so could allow the immune system to "reset" itself and go into a state of remission. In some embodiments, for example, remission may be sustained until occurrence of a triggering event. A triggering event may be, for example, an infection (which may result in production of polyclonal antibodies that react both with an infectious agent and a self protein), exposure to particular environmental conditions (e.g., high levels of air pollutants such as ozone or particulate matter or components of smoke such as cigarette smoke, allergens), etc. Genetic factors may play a role. For example, individuals having particular alleles of genes encoding complement components may have a higher baseline level of complement activity, a more reactive complement system and/or a lower baseline level of endogenous complement regulatory protein activity. In some embodiments an individual has a genotype associated with increased risk of AMD. For example, the subject may have a polymorphism in a gene encoding a complement protein or complement regulatory protein, e.g., CFH, C3, factor B, wherein the polymorphism is associated with an increased risk of AMD.

In some embodiments an immunologic microenvironment may become progressively more polarized towards a pathological state over time, e.g., in a subject who has not yet developed symptoms of a chronic disorder or in a subject who has developed the disorder and has been treated as described herein. Such a transition may occur stochastically (e.g., due at least in part to apparently random fluctuations in antibody levels and/or affinity) and/or as a result of accumulated "sub-threshold" trigger events that are not of sufficient intensity to trigger a symptomatic outbreak of a disorder.

In some embodiments it is contemplated that a relatively short course of a long-acting compstatin analog, e.g., between 1 week and 6 weeks, e.g., about 2-4 week, may provide a long-lasting benefit. In some embodiments a remission is achieved for a prolonged period of time, e.g., 1-3 months, 3-6 months, 6-12 months, 12-24 months, or more. In some embodiments a subject may be monitored and/or treated prophylactically before recurrence of symptoms. For example, a subject may be treated prior to or upon exposure to a triggering event. In some embodiments a subject may be monitored, e g., for an increase in a biomarker, e.g., a biomarker comprising an indicator of Th17 cells or Th17 cell activity, or complement activation, and may be treated upon increase in the level of such biomarker. See, e.g., PCT/US2012/043845 for further discussion.

VIII. Compositions and Administration

The invention provides and/or utilizes a variety of compositions comprising a cell-reactive, long-acting, or targeted compstatin analog. In various embodiments, a composition can have any feature or combination of features discussed herein so long as they are not mutually exclusive. The invention provides embodiments of such compositions, and methods of use thereof, in which the compstatin analog is any compstatin analog.

In some embodiments, a composition comprises a purified cell-reactive, long-acting, or targeted compstatin analog. Purification can be achieved using a variety of approaches that can be selected by one of ordinary skill in the art based to achieve a desired degree of purity with respect to various components present in the composition prior to purification. For example, filtration, high performance liquid chromatography, affinity chromatography, and/or other approaches and combinations thereof can be used. In some embodiments, the composition comprises at least 80%, 85%, 90%, 95%, 98%, 99%, or more cell-reactive, long-acting, or targeted compstatin analog as a percentage of the total compstatin analog by weight. In some embodiments, the composition comprises at least 80%, 85%, 90%, 95%, 98%, 99%, or more cell-reactive, long-acting, or targeted compstatin analog as a percentage of the total compstatin analog on a molar basis. In some embodiments, a composition consists or consists essentially of a cell-reactive, long-acting, or targeted compstatin analog.

In some embodiments, a composition comprising a cell-reactive compstatin analog and a compound comprising a cell-reactive functional group is characterized in that the ratio of the cell-reactive compstatin analog to the compound comprising the cell-reactive functional group on a molar basis is at least 10:1, 20:1, 50:1, 100:1, 500:1, 1,000:1, or more. In some embodiments the composition comprises at least 80%, 85%, 90%, 95%, 98%, 99%, or more cell-reactive compstatin analog as a percentage of the total compstatin analog by weight. In some embodiments the composition comprises at least 80%, 85%, 90%, 95%, 98%, 99%, or more cell-reactive compstatin analog as a percentage of the total compstatin analog on a molar basis. In some embodiments a composition comprises at least 80%, 85%, 90%, 95%, 98%, 99%, or more cell-reactive compstatin analog by weight. In some embodiments a composition comprises at least 80%, 85%, 90%, 95%, 98%, 99%, or more long-acting compstatin analog by weight. In some embodiments a composition comprises at least 80%, 85%, 90%, 95%, 98%, 99%, or more targeted compstatin analog by weight. In some embodiments a composition comprises at least 80%, 85%, 90%, 95%, 98%, 99%, or more targeted compstatin analog by weight. In some embodiments weight is dry weight.

In some aspects, the invention provides a pharmaceutical grade composition comprising a cell-reactive, long-acting, or targeted compstatin analog. The pharmaceutical grade composition can have any of the above-mentioned characteristics in terms of purity in various embodiments. The pharmaceutical grade composition is sufficiently free of endotoxin, heavy metals, and unidentified and/or uncharacterized substances so as to be acceptable, without further purification, as a pharmaceutical composition suitable for administration to a human subject or for the manufacture of a pharmaceutical composition to be administered to a human subject. In some embodiments, the pharmaceutical grade composition is sterile.

Suitable preparations, e.g., substantially pure preparations of a cell-reactive, long-acting, or targeted compstatin analog or other active agent, may be combined with pharmaceutically acceptable carriers or vehicles, etc., to produce an appropriate pharmaceutical composition. The term "pharmaceutically acceptable carrier or vehicle" refers to a non-toxic carrier or vehicle that does not destroy the pharmacological activity of the compound with which it is formulated. One of skill in the art will understand that a carrier or vehicle is "non-toxic" if it is compatible with administration to a subject in an amount appropriate to deliver the compound without causing undue toxicity. Pharmaceutically acceptable carriers or vehicles that may be used in the compositions of this invention include, but are not limited to, water, physiological saline, Ringer's solution, sodium acetate or potassium acetate solution, 5% dextrose, and the like. The composition may include other components as appropriate for the formulation desired, e.g., as discussed herein. Supplementary active compounds, e.g., compounds independently useful for treating a subject suffering from a complement-mediated disorder, can also be incorporated into the compositions. The invention provides such pharmaceutical compositions comprising a cell-reactive, long-acting, or targeted compstatin analog and, optionally, a second active agent useful for treating a subject suffering from a complement-mediated disorder.

In some embodiments, the invention provides a pharmaceutically acceptable composition suitable for administration to humans, packaged together with a label approved by a government agency responsible for regulating pharmaceutical agents, e.g., the U.S. Food & Drug Administration. In some embodiments, the invention provides a pharmaceutical kit or pack comprising: (a) a pharmaceutically acceptable cell-reactive, long-acting, or targeted compstatin analog in solid form; (b) a pharmaceutically acceptable carrier or vehicle. In some embodiments the solid form is a lyophilized form. In some embodiments the solid form is a powder form, e.g., a lyophilized powder. Optionally the kit or pack contains instructions for dissolving the cell-reactive, long-acting, or targeted compstatin analog in the carrier. In some embodiments a pharmaceutical kit or pack is provided. In some embodiments the pack or kit comprises sufficient amount of pharmaceutical composition for at least 1 dose, e.g., between 1 and 200 doses or any intervening number or subrange. In some embodiments a kit or pack comprises (i) a first container containing sufficient cell-reactive, long-acting, or targeted compstatin analog for one or more doses; (ii) a second container comprising a pharmaceutically acceptable carrier to be combined with the contents of the first vessel to produce a composition suitable for administration to a subject by, e.g., subcutaneous (abbreviated as SQ or SC) or intravitreal (IVT) injection. In some embodiments a pharmaceutical pack or kit comprises one or more needles and, optionally, one or more syringes. In some embodiments at least one prefilled syringe is provided (e.g., between 1 and 200 or any intervening number of subrange). In some embodiments one or more unit dosage forms or premeasured aliquots are provided. In some embodiments one or more pens or pen cartridges are provided. In some embodiments instructions for administration, which in some embodiments comprise instructions for self-administration, e.g., via subcutaneous injection, are provided.

A pharmaceutical composition can be administered to a subject by any suitable route of administration including, but not limited to, intravenous, intramuscular, subcutaneously, by inhalation, by nasal delivery, intrathecally, intracranially, intraarterially, orally, rectally, transdermally, intradermally, subdermally, etc. In some embodiments, a composition comprising a cell-reactive, long-acting, or targeted compstatin analog is administered intravenously. In some embodiments, a composition comprising a cell-reactive, long-acting, or targeted compstatin analog is administered intraarterially. The composition can be administered locally, either into the vascular system supplying an organ or tissue, or extra-vascularly in the vicinity of an organ or tissue. It will be understood that "administration" encompasses directly administering a compound or composition to a subject, instructing a third party to administer a compound or composition to a subject, prescribing or suggesting a compound or composition to a subject (e.g., for self-administration), self-administration, and, as appropriate, other means of making a compound or composition available to a subject.

Pharmaceutical compositions suitable for injectable use (e.g., intravenous administration) or by pump or catheter typically include sterile aqueous solutions (where water soluble) or dispersions and sterile powders for the extemporaneous preparation of sterile injectable solutions or dispersion. Sterile solutions can be prepared by incorporating the compound in the required amount in an appropriate solvent, optionally with one or a combination of ingredients such as buffers such as acetates, citrates, lactates or phosphates; agents for the adjustment of tonicity such as sodium chloride or dextrose; antibacterial agents such as benzyl alcohol or methyl parabens; antioxidants such as ascorbic acid, glutathione, or sodium bisulfite; chelating agents such as ethylenediaminetetraacetic acid; and other suitable ingredients etc., as desired, followed by filter-based sterilization. One of skill in the art will be aware of numerous physiologically acceptable compounds that may be included in a pharmaceutical composition. Other useful compounds include, for example, carbohydrates, such as glucose, sucrose, lactose; dextrans; amino acids such as glycine; polyols such as mannitol or sorbitol. These compounds may, for example, serve as bulking agents and/or stabilizers, e.g., in a powder and/or when part of the manufacture or storage process involves lyophilization. Surfactant(s) such as Tween-80, Pluronic-F108/F68, deoxycholic acid, phosphatidylcholine, etc., may be included in a composition, e.g., to increase solubility or to provide microemulsion to deliver hydrophobic drugs. pH can be adjusted with acids or bases, such as hydrochloric acid or sodium hydroxide, if desired. The parenteral preparation can be enclosed in ampoules, disposable syringes or infusion bags or single or multiple dose vials made of glass or plastic. Preferably solutions for injection are sterile and acceptably free of endotoxin.

Among other things, the present disclosure provides the particular insight that subcutaneous and/or intramuscular injection may be particularly desirable for administration of a compstatin analog as described herein (e.g., a LACA) in certain contexts. For example, in some embodiments, subcutaneous and/or intramuscular injection may be preferred (relative, for example to intravenous delivery) in particular for treatment of chronic disorders. Alternatively or additionally, subcutaneous and/or intramuscular injection may be particularly useful when, for example, it will be desirable and/or expected that patients self-administer a compstatin analog composition (for example, rather than requiring or relying on administration by a health care provider, particularly where such administration by a health care provider might require travel to an infusion center).

In some particular aspects, the present disclosure encompasses the insight that, in those embodiments in which drug is administered daily, it may be feasible to maintain a more constant blood level than with a longer dosing interval such as weekly or every 2 weeks. A more constant blood level may be desirable, particularly in certain embodiments (e.g., treatment of chronic disorder as described herein). The present disclosure appreciates that daily IV infusion on a long-term basis could be very inconvenient, particularly for a non-hospitalized patient.

The present disclosure particularly appreciates that, in certain embodiments, subcutaneous administration may be even more effective and/or desirable than intramuscular injection, particularly where self-administration is expected or desired.

In some embodiments a composition as described herein, and particularly a composition comprising a LACA, may be administered using a device that delivers a dose of a pharmaceutical composition by injection, in some embodiments in an at least partly automated fashion upon activation. Such a device is referred to in the art as a "pen" or "autoinjector", and these terms are used interchangeably herein. In general, a pen or autoinjector allows for injecting a dose of pharmaceutical composition contained in a cartridge, reservoir, or syringe through an automatically or manually inserted hypodermic needle(s) or through a high velocity jet. It may be designed for administration of a single dose or multiple doses.

In some particular embodiments such a pen or autoinjector is utilized for intramuscular and/or subcutaneous injection. In accordance with the present disclosure, a pen or other autoinjector may be particularly useful for embodiments that utilize subcutaneous injection. Pens are typically devices that contain (or can be loaded with) a medication in a self-contained cartridge or reservoir and to which a needle can be attached.

In some embodiments, as noted herein, the present disclosure provides the insight that SC and/or IM injection might be a particularly desirable mode of delivery for one or more LACA as described herein. For example, the present disclosure documents certain particularly desirable and/or effective dosing regimens involving administration of a LACA by injection (e.g., by SC injection); in some embodiments, such injection is achieved by use of a pen (e.g., that may have been pre-loaded with an appropriate dose or volume). Pens can be durable (and reusable) or disposable. A durable pen typically uses a replaceable cartridge, which is disposed of when empty, and a new one is inserted in the pen. A disposable pen typically comes pre-filled with a medication in a cartridge or reservoir. When the cartridge or reservoir is empty, the pen is discarded. The cartridge or reservoir may contain a single dose or multiple doses. To use a pen, a needle is attached to the pen and inserted into the skin. Typically, a button is pushed to administer a dose though in some embodiments other activation methods may be used. In some embodiments, an autoinjector may comprise a spring-loaded syringe, though one of ordinary skill in the art will appreciate that a variety of technologies are available to afford automatic administration. In some embodiments, by pressing a button or otherwise activating the device, the needle is automatically inserted, and the medication is delivered. In some embodiments, an autoinjector may be designed to insert the needle automatically and/or accurately to a desired depth in the subcutaneous tissue. A pen or autoinjector may comprise means such as a dial that allows a user to select or adjust a dose or injection depth.

In some embodiments a composition as described herein, and particularly a composition comprising a LACA, is administered using a device comprising a dual chamber syringe. Dry drug (e.g., lyophilized) is contained in one chamber. The second chamber contains a suitable pharmaceutically acceptable carrier. In order to use the device, the drug is first reconstituted by mixing the contents of the chambers. This can be accomplished in various ways. In some embodiments, pushing the plunger causes the contents of the chambers to mix, e.g., by transferring the carrier into the chamber containing the lyophilized drug.

Thus a variety of drug delivery devices comprising a composition as described herein (e.g., comprising an LACA) may be provided e.g., prefilled syringes, dual chamber syringes, durable and/or disposable pens, and cartridges suitable for use with a pen. Such devices may contain one or more doses (e.g., one or more of any of the dose amounts described herein).

In certain embodiments a LACA may be administered, e.g., subcutaneously, using a drug delivery device (sometimes referred to simply as a "delivery device") that comprises a pump to introduce a liquid composition comprising the LACA into the subject's body. As will be appreciated, a pump may be any device that moves fluids by mechanical action as opposed to a conventional manually actuated syringe characterized in that the individual administering the medication (e.g., a health care provider or a subject who self-administers the medication) must directly depress a plunger into a barrel containing medication in order to effect the injection. It will be appreciated that a pump may be powered electrically or mechanically, e.g., as described herein. In some aspects, a delivery device comprising a pump may allow for convenient administration of doses useful in an alternate day, thrice weekly, twice weekly, every third, fourth, fifth, or sixth day, or once weekly dosing regimen, e.g., as described below. Of course such delivery devices may also be used for administration according to other dosing regimens, e.g., regimens featuring more frequent administration, e.g., regimens featuring daily administration.

In certain embodiments, the delivery device is portable. A portable device, also referred to as an "ambulatory" device, is sufficiently light in weight and has appropriate dimensions so as to permit the subject to move about freely while the device is in use and does not require attachment to a pole or power outlet. In some embodiments a portable delivery device may be attached to a belt or shoulder strap or worn in a case that may be attached to a belt or shoulder strap, or may be placed in a pocket of a garment.

One of ordinary skill in the art appreciates that a pump may operate in any of a variety of ways and may utilize a variety of energy sources, e.g., disposable or rechargeable batteries, alternating current power supply (e.g., via a wall socket in a building), compressed gas, or energy stored in a compressed spring or in a stretched expandable resilient chamber. A device in which fluid is held in a stretchable balloon reservoir, and pressure from the elastic walls of the balloon reservoir drives fluid delivery may be referred to as an "elastomeric infusion pump".

In some embodiments, a delivery device comprises a pump and a syringe containing a liquid to be administered and removably associated with the device, and a driving unit, which may be electronically controlled by a controller, arranged to make the plunger of the syringe slide so as to cause infusion of the liquid directly or via flexible tubing through a piercing member such as a needle or cannula that is introduced into the subject's body under the skin. For example, in some embodiments a pump may comprise a motor that turns a screw that pushes the plunger on a syringe that contains the liquid. Pushing of the plunger causes liquid to be expelled from the syringe and introduced into the subject's body via an attached piercing member. Exemplary pumps are described in, e.g., U.S. Pat. Nos. 6,447,487; 6,592,551; 6,645,177; 8,187,228; US Patent Application Publication Nos. 20020123740, 20030229311, 20060184123, 20070100281, 20090123309, 20150038906. The Crono PID (NDC No.: 8423.2000.02), Crono S-PID30, and Crono S-PID 50 (NDC No.: 8423.2000.04) (Cane s.r.l. Medical Technology (Rivoli, Italy)), and the T34™ Ambulatory Syringe Pump and the T60™ Ambulatory Syringe Pump (CME Medical, Blackpool, UK) are exemplary portable syringe inlusion pumps that may be used in certain embodiments.

In some embodiments the pump may be electronically programmable or controlled. In some embodiments the pump is not electronically programmable or controlled.

In some embodiments a pump uses electricity as a source of power. In some embodiments a pump does not use electricity as a source of power. Such a pump may, for example, use a compressed spring or compressed gas as an energy source.

In some embodiments the pump is a constant-pressure pump that applies a constant pressure to depress the barrel of a syringe containing the liquid to be administered. An example of a constant-pressure pump is the Freedom60® infusion system (RMS Medical Products, Chester, N.Y.). In some embodiments a FreedomEdge® infusion system (RMS Medical Products) may be used, e.g., with a syringe capable of holding up to 20 ml or a syringe capable of holding up to 30 ml. Another example of a constant pressure device is the SCIg60 syringe pump (EMED Technologies, El Dorado Hills, Calif.). In some embodiments a valve may control the flow rate of the liquid. In some embodiments tubing connected to the syringe may control the flow rate of the liquid, e.g., as described in US Patent Application Nos. 20150374911 and/or 20160256625.

In some embodiments the liquid to be administered is contained in a pressurized chamber prior to administration. In some embodiments the liquid is contained in a resilient, expandable container portion such as a bladder or balloon prior to delivery. The expandable container portion may be made of or comprise an inner lining of compatible medical grade butyl, silicone or other material suitable for holding the liquid. The container portion expands upon filling with liquid (e.g., with a unit dose of the compound to be administered), so as to exert pressure on the liquid. One of ordinary skill in the art appreciates that the container portion may be filled in a variety of ways. In some embodiments filling of the expandable container portion may be accomplished manually, e.g., using a manually actuated syringe, or may be performed using a filling apparatus. After the device is attached to the subject's skin, a piercing member such as a needle or cannula, which may be spring loaded, may automatically or following additional activation, such as by pressing a button, emerge from the device's housing and pierce the skin. Subsequently, either automatically or following additional activation, such as by pressing a button, pressure forces the liquid out of the chamber or container and into the subject's body via the needle or cannula. Exemplary devices are described in US Patent Application Pub. Nos. 20130018326, and/or 20150217058.

In some embodiments the delivery device is an "on-body delivery device", which term refers to a delivery device comprising a chamber or other container portion for holding a liquid to be administered to a subject, wherein the device can deliver the liquid while attached directly to the subject's skin without the need for a separate support or external reservoir and, typically, permits the subject to be mobile during delivery. The chamber for holding the liquid may be contained in a housing. Typically, an on-body delivery device is affixed to the subject's skin using an adhesive. The device is affixed sufficiently strongly so that the device is self-supporting. The device may be provided with an adhesive layer, e.g., on the outer surface of the housing, for use to secure the device directly to the skin. The adhesive layer may surround the portion of the device from which a piercing member such as a needle or cannula projects so as to provide a seal around the penetrated skin. In some embodiments an on-body delivery device is available from Sensile Medical AG (Hagendorf, Switzerland). For example, devices known as Senselnfuse, SensePatch, or Senseflex, may be used. In some embodiments an on-body delivery device is available from Enable Injections, Inc. (Cincinnati, Ohio). In some embodiments the device that comprises a resilient, expandable container portion such as a bladder or balloon to expel the liquid is an on-body delivery device. In some embodiments the device, e.g., an on-body delivery device, is configured such that the piercing member, e.g., needle, is not visible to the user prior to or during use of the device. In some embodiments, the piercing member, e.g., needle, may retract when delivery of the liquid is complete or when the device is removed from the skin. It will be appreciated that a piercing member, e.g., a needle, for use with a delivery device described herein may have any suitable gauge or inner diameter, e.g., such gauge or inner diameters as described elsewhere herein.

In some embodiments, a delivery device comprises a housing into which a vial, cartridge, or syringe containing a liquid (e.g., a liquid comprising a LACA) may be inserted. The liquid is administered upon activation of the device. In some embodiments the liquid is transferred to a chamber of the device prior to administration. In some embodiments a delivery device is reusable, e.g., it can be re-filled or supplied with a new vial, cartridge, or syringe following administration of the contents.

Those skilled in the art, reading the present disclosure, will appreciate that, in accordance with standard practice in the field, a container containing a particular volume, as described herein my include an additional volume sufficient to permit the designated particular volume (e.g., unit dose) to be withdrawn from the container for administration.

In some embodiments a delivery device is a single use device, i.e., the device is designed to be used to administer a single dose or for use in a single administration session. For example, a device may be designed to be affixed to the skin of a subject, activated to administer a dose, removed, and then recycled or discarded rather than used to administer one or more additional doses.

In some embodiments a delivery device that allows delivery of a liquid into two or more sites may be used. In some embodiments the number of sites is between 1 and 5. In some embodiments the number of sites is greater than 5, e.g., between 6 and 10. Delivery to the two or more sites may be simultaneous or sequential. The device may comprise a pair of syringes, each arranged to be connected to one of the sites and coupled to a body that houses a driving system of the device. Exemplary devices are described in WO2011154928 and US Patent Application Publication No. 20120143133. In some embodiments a multi-needle infusion set may be used. In some embodiments a multi-needle infusion set comprises a flexible tube that communicates at one end with a chamber (which term is used interchangeably with "reservoir") containing the liquid (e.g., a syringe) while the other end bifurcates into multiple tubes each having a needle at the end. The Neria™ multi infusion sets (Unomedical A/S, Osted, Denmark) are exemplary multi-needle infusion sets.

In some embodiments a delivery device may collect data regarding use of the device. Such data may comprise, for example, the date and time at which the device was used, delivery parameters such as the volume administered, the duration of administration, whether any problems occurred during administration, etc. The data may be stored on a computer-readable medium physically associated with the device and/or may be transmitted to a remote location, e.g., a remote server, where it may be stored, analyzed, or further transmitted for storage or analysis. The device may comprise one or more processors, sensors, software programs, and appropriate connectivity that allow data to be exchanged between the device and other products and systems. Data may be transferred via radio-frequency identification (RFID), bar-code/QR-code scanning, cellular, Bluetooth low energy (BTLE), physical wire, or a combination thereof. The data may be transmitted over any suitable network, e.g., the Internet. The data may be analyzed and/or stored in the Cloud. In some embodiments the device comprises an active or passive RFID tag or chip, hereinafter referred to as an "RFID tag". The RFID tag may contain data that identifies the device. The RFID tag may be an active tag or chip that signals usage-related information such as activation of the device and/or completion of an administration of a dose. In some embodiments data acquired from a particular device may be made available to one or more entities or individuals, such as health care providers or caregivers of the subject. Such entities or individuals may additionally or alternately be automatically notified of the occurrence or non-occurrence of specified events. For example, if a dose is not administered on a day on which such administration is to take place according to the dosing schedule, or if the device is deployed on a day when administration is not supposed to take place according to the dosing schedule, one or more health care providers or caregivers of the subject may be notified. Once notified, an entity or individual may take appropriate action, such as contacting the subject. In some embodiments a monitoring system automatically attempts to contact the subject, e.g., by phone or text message, if a dose is not administered as scheduled.

In some embodiments a delivery system may comprise a delivery device and a remote control device. The remote control device may, for example, allow programming of the delivery device and/or may be used to activate the delivery device to start delivery of the fluid or to cause the delivery device to cease delivery of the fluid.

In some embodiments, the present disclosure contemplates providing to a subject (e.g., by mail or arranged pickup or other regular mode of delivery) a set of devices as described herein that together provide a supply of active agent (e.g., LACA) sufficient to last for a predetermined period of time (e.g., one week, two weeks, three weeks, four weeks, etc.). In some embodiments, such a set is sent to the patient's residence on a regular basis (e.g., every week, two weeks, three weeks, four weeks, etc.) with a timing selected such that the patient does not run out. In some embodiments, a composition (e.g., a LACA) may be contained in a container (e.g., a vial) or in any of the herein-mentioned drug delivery devices or packs. In some embodiments the supply is sufficient to last for between 4 and 12 weeks, between 12 and 26 weeks, or more.

In some embodiments the composition is either lyophilized or kept refrigerated or frozen until shortly before administration, at which time it is reconstituted (if lyophilized) or thawed (if frozen). The composition may be brought to room temperature prior to administration.

In certain embodiments a composition may be administered using a patch system (e.g., for subcutaneous or transdermal administration). In some embodiments the patch may comprise or be attached to a reservoir that may contain, e.g., up to about 10 ml of solution, allowing the administration of 10 ml of solution to a patient in a single administration. In some embodiments the reservoir may contain more than 10 ml, e.g., between 10 ml and 20 ml, between 20 ml and 30 ml, between 30 ml and 50 ml, or more.

In some embodiments a composition comprising a compstatin analog described herein, e.g., a cell-reactive compstatin analog, LACA, or targeted compstatin analog, and a pharmaceutically acceptable carrier has a pH of between 6.5 and 7.5, e.g., between 6.8 and 7.2, e.g., 7.0. In the course of performing stability tests, it was observed that a lower pH results in increased stability of certain LACAs relative to neutral pH. Accordingly, in some embodiments a composition comprising a LACA and a pharmaceutically acceptable carrier has a pH of between 6.0 and 6.5, between 5.5 and 6.0, or between 5.0 and 5.5. In certain embodiments a yet lower pH, e.g., between 4.5 and 5.0 may be used. In some embodiments the composition further comprises one or more pharmaceutically acceptable buffer substances appropriate to maintain the pH within a selected range (e.g., any of the afore-mentioned ranges). Suitable buffer substances are described herein (e.g., acetates, citrates, lactates or phosphates). In some embodiments the composition additionally or alternately comprises a salt, e.g., any of the pharmaceutically acceptable salts described herein. In certain particular embodiments, the composition comprises a phosphate.

It is noted that, for purposes of conciseness, certain aspects and embodiments described in the present disclosure, e.g., relating to dosing regimens, doses, methods of administration, devices of use for administration, and/or methods of treatment, are described with reference to long-acting compstatin analogs. However, it should be understood that analogous embodiments in which the compstatin analog is not a LACA are provided. The compstatin analog may, for example, be a cell-reactive or targeted compstatin analog that does not comprise a clearance reducing moiety.

Generally, dispersions are prepared by incorporating the active compound into a sterile vehicle which contains a basic dispersion medium and appropriate other ingredients from those enumerated above. In the case of sterile powders for the preparation of sterile injectable solutions, methods of preparation can include vacuum drying and freeze-drying which yields a powder of the active ingredient plus any additional desired ingredient, e.g., from a previously sterile-filtered solution thereof.

Oral administration may be used in certain embodiments. Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. A liquid composition can also be administered orally. Formulations for oral delivery may incorporate agents to improve stability within the gastrointestinal tract and/or to enhance absorption.

For administration by inhalation, a compstatin analog may be delivered in the form of an aerosol spray from a pressured container or dispenser which contains a suitable propellant, e.g., a gas such as carbon dioxide. A metered dose inhaler or nebulizer may be used. The aerosol may comprise liquid particles or dry aerosol (e.g., dry powders, large porous particles, etc.). Suitable aqueous vehicles useful in various embodiments include water or saline, in some embodiments, optionally including an alcohol. In certain embodiments the composition comprises glycerol in water, e.g., about 2% glycerol in water. In some embodiments the composition comprises a surfactant suitable for introduction into the lung. Other excipients suitable for pulmonary administration can additionally or alternately be used.

A variety of different devices are available for administration by inhalation (which is referred to interchangeably as "inhaled administration", "respiratory administration" or "pulmonary administration"). Nebulizers are devices that transform solutions or suspensions of medications into aerosols that are suitable for deposition in the lower airway. Nebulizer types include jet nebulizers, ultrasonic wave nebulizers, and vibrating mesh nebulizers. A partial list of available vibrating mesh nebulizers includes eFlow (Pari), i-Neb (Respironics), MicroAir (Omron), IHSO Nebulizer (Berner), and Aeroneb® (Aerogen). A Respimat.®Soft Mist.™ Inhaler (Boeringer Ingelheim) may be used. A metered dose inhaler (MDI) is a handheld aerosol device that uses a propellant to deliver the therapeutic agent. MDIs include a pressurized metal canister that contains pharmacological agent in suspension or solution, propellant, surfactant (typically), and metering valve. Chloroflourocarbons (CFCs) had been widely used as propellants but have been largely replaced by hydrofluorocarbons (HFCs, also known as hydrofluoroalkanes (HFA)) such as HFC-134a and HFC-227ea. Carbon dioxide and nitrogen are other alternatives. A dry powder inhaler (DPI) is a breath-actuated device that delivers the drug in the form of particles contained in a capsule or blister that is punctured prior to use and typically does not employ a propellant. Examples of DPIs currently used to deliver medications for treating asthma and/or COPD include, e.g., Diskus, Aerolizer, HandiHaler, Twisthaler, Flexhaler. Such devices may be used to deliver a compstatin analog in various embodiments. Other exemplary DPI devices that may be used in various embodiments include 3M Conix™, TAIFUN® (AKELA Pharma), AcuBreathe™ (Respirics), and devices that incorporate Taper Dry Powder Inhalation technology such as the API-5000 in which the active pharmaceutical ingredient (API) is stored on a microstructured carrier tape.

Inhalation accessory devices (IADs) generally fall into 2 categories: spacers and holding chambers. Spacers and holding chambers extend the mouthpiece of the inhaler and direct the mist of medication toward the mouth, reducing medication lost into the air. Using a spacer with an MDI can help reduce the amount of drug that sticks to the back of the throat, improving direction and deposition of medication delivered by MDIs. Valved holding chambers (VHCs) allow for a fine cloud of medication to stay in the spacer until the patient breathes it in through a one-way valve, drawing the dose of medicine into the lungs. Examples include Aerochamber and Optichamber.

Particulate compositions may be characterized on the basis of various parameters such as the fine particle fraction (FPF), the emitted dose, the average particle density, and the mass median aerodynamic diameter (MMAD). Suitable methods are known in the art, some of which are described in U.S. Pat. Nos. 6,942,868 and 7,048,908 and U.S. Publication Nos. 20020146373, 20030012742, and 20040092470. In certain embodiments aerosol particles are between approximately 0.5 μm-10 μm (MMAD), e.g., about 5 μm for respiratory delivery, though smaller or larger particles could also be used. In certain embodiments particles having a mass mean aerodynamic diameter of between 1 μm and 25 μm, e.g., between 1 μm and 10 μm, are used.

A dry particle composition containing particles smaller than about 1 mm in diameter is also referred to herein as a dry powder. A "dry" composition has a relatively low liquid content, so that the particles are readily dispersible, e.g., in a dry powder inhalation device to form an aerosol or spray. A "powder" consists largely or essentially entirely of finely dispersed solid particles that are relatively free flowing and capable of being readily dispersed in an inhalation device and subsequently inhaled by a subject, preferably so that a significant fraction of the particles can reach a desired portion of the respiratory tract. In certain embodiments large porous particles having mean geometric diameters ranging between 3 and 15 μm and tap density between 0.04 and 0.6 $g/cm^3$ are used. See, e.g., U.S. Pat. No. 7,048,908; Edwards, D. et al, Science 276:1868-1871, 1997; and Vanbever, R., et al., Pharmaceutical Res. 16:1735-1742, 1999).

In some aspects, described herein are various doses, dosing regimens, compositions, and methods useful for treating patients by inhaled administration of a compstatin analog. The compstatin analog may be any of the compstatin analogs described herein. The compstatin analog may comprise any of the peptides described in Section III hereof. For example, the compstatin analog may comprise or consist of any of SEQ ID Nos: 3-36, as described herein and/or may comprise any of the modifications relative to compstatin described herein. In particular embodiments the compstatin analog comprises or consists of a peptide whose sequence is listed in Table 1, e.g., SEQ ID NO: 14, 21, 28, 29, 32, 33, 34, or 36. In particular embodiments the compstatin analog does not comprise a clearance reducing moiety, cell-reactive moiety, or targeting moiety. In some embodiments the compstatin analog has a molecular weight of between 1.5 kD and 2.0 kD, or between 2.0 kD and 2.5 kD. In some embodiments the compstatin analog has between 11 and 25 amino acids, e.g., exactly 13, 14, 15, 16, 17, or 18 amino acids.

In some embodiments the total daily dose for administration of a compstatin analog by inhalation (referred to interchangeably herein with "pulmonary administration" or "respiratory administration") is at least 5 mg/day, e.g., at least 10 mg/day, at least 15 mg/day, at least 20 mg/day, at least 25 mg/day, or at least 30 mg/day. In certain embodiments the daily dose is between 5 mg/day-20 mg/day, e.g., 10 mg/day or 15 mg/day. In certain embodiments the daily dose is between 20 mg/day-60 mg/day. In certain particular embodiments the dose is 10 mg/day, 15 mg/day, 20 mg/day, 25 mg/day, 30 mg/day, 35 mg/day, 40 mg/day, 45 mg/day, 50 mg/day, 55 mg/day, or 60 mg/day. As described in the Examples, in a Phase 1 clinical trial of a compstatin analog administered by inhalation to healthy subjects, possible evidence of pharmacological activity was observed at doses of 30 mg/day or 60 mg/day.

In certain embodiments the daily dose is between 60 mg/day-150 mg/day, e.g., 60, 70, 80, 90, 100, 110, 120, 130, 140, or 150 mg/day. In certain embodiments the daily dose is between 150 mg/day-350 mg/day, e.g., 150, 160, 170, 180 190, 200, 210, 220, 230, 240, 250, 260, 270, 280, 290, 300, 310, 320, 330, 340, or 350 mg/day. In certain embodiments the daily dose may be administered during a single administration. In certain embodiments the daily dose may be administered as two or more doses during the course of a day (e.g., in the morning and evening).

For topical application, a compstatin analog may be formulated in a suitable ointment containing the active component suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated as a suitable lotion or cream containing a compstatin analog suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

Systemic administration can also be by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished, e.g., through the use of nasal sprays or suppositories. For transdermal administration, the active compounds are typically formulated into ointments, salves, gels, or creams as generally known in the art.

The compounds can also be prepared in the form of suppositories (e.g., with conventional suppository bases such as cocoa butter and other glycerides) or retention enemas for rectal delivery.

In certain embodiments of the invention, a compstatin analog or other active compound is prepared with carriers that will protect the compound against rapid elimination from the body, such as a controlled release formulation, including implants and microencapsulated delivery systems. For example, a compstatin analog may be incorporated into or encapsulated in a microparticle or nanoparticle formulation. Biodegradable, biocompatible polymers can be used, such as ethylene vinyl acetate, polyanhydrides, polyglycolic acid, collagen, polyorthoesters, polyethers, polylactic acid, PLGA, etc. Liposomes or other lipid-based particles can be used as pharmaceutically acceptable carriers. These can be prepared according to methods known to those skilled in the art, for example, as described in U.S. Pat. No. 4,522,811 and/or other references listed herein. Depot formulations containing a compstatin analog may be used. The compstatin analog is released from the depot over time, e.g., so as to provide a therapeutic concentration for longer than if the compound was administered intravenously. In some aspects, a CRM confers depot properties on a compstatin analog. One of ordinary skill in the art will appreciate that the materials and methods selected for preparation of a controlled release formulation, implant, etc., should be such as to retain activity of the compound.

It will be appreciated that the compstatin analog and/or additional active agent(s) can be provided as a pharmaceutically acceptable salt. Pharmaceutically acceptable salts include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Also, pharmaceutically-acceptable salts can be prepared as alkaline metal or alkaline earth salts, such as sodium, potassium or calcium salts, if appropriate depending on the identity of the active agent.

It will be understood that the pharmaceutically acceptable carriers, compounds, and preparation methods mentioned herein are exemplary and non-limiting. See, e.g., Remington: The Science and Practice of Pharmacy. 21st Edition. Philadelphia, Pa. Lippincott Williams & Wilkins, 2005, for additional discussion of pharmaceutically acceptable compounds and methods of preparing pharmaceutical compositions of various types.

A pharmaceutical composition can be administered in an amount effective to achieve a desired beneficial effect. In some embodiments, an effective amount is sufficient to provide one or more of the following benefits: (i) reduction in at least one symptom or sign of a complement-mediated disorder; (ii) increased quality of life; (iii) reduced hospitalization; (iv) reduced mortality. One of ordinary skill in the art will appreciate that the particular beneficial effect will depend at least in part on various factors, such as the particular disorder being treated. One of ordinary skill in the art will be aware of the symptoms and signs that may occur in subjects with complement-mediated disorders. Examples of symptoms and signs of various complement-mediated disorders are provided herein. For example, in some embodiments, e.g., wherein a subject suffers from PNH or aHUS, a beneficial effect is a reduction in complement-mediated red blood cell lysis. In some aspects, a beneficial effect is statistically significant and/or therapeutically meaningful within the judgement of one or ordinary skill in the art.

In certain embodiments of the invention a pharmaceutical composition comprising a cell-reactive, long-acting, or targeted compstatin analog is administered parenterally. In some embodiments, the composition is administered intravenously. In some embodiments, the composition is administered by intravenous injection. In some embodiments the composition is administered as an IV bolus or an IV infusion. In some embodiments the composition is administered as an IV drip. In some embodiments the composition is administered as an IV bolus followed by an IV infusion or IV drip. In some embodiments an IV infusion is administered over about 1, 2, 3, 4, 5, 15, 20, 30, 60, or 120 minutes. In some embodiments an IV drip is administered over more than about 60 minutes, e.g., over about 1, 2, 3, or more hours.

In some embodiments, a total amount of between about 0.1 mg/kg/day and about 2,000 mg/kg/day of compstatin analog is administered, e.g., between about 1 mg/kg/day and about 1,000 mg/kg/day, e.g., between about 5 mg/kg/day and about 500 mg/kg/day. In some embodiments, a total amount of between about 10 mg/kg/day and about 100 mg/kg/day of compstatin analog is administered, e.g., between about 10 mg/kg/day and about 50 mg/kg/day e.g., between about 10 mg/kg/day and about 20 mg/kg/day. In some embodiments, between about 0.5 mg/kg/day to about 10 mg/kg/day of compstatin analog is administered. In some embodiments, between about 1 mg/kg/day to about 5 mg/kg/day of compstatin analog is administered. In some embodiments, between about 1 mg/kg/day to about 3 mg/kg/day of compstatin analog is administered. In some embodiments, between about 3 mg/kg/day to about 5 mg/kg/day of compstatin analog is administered. In some embodiments, between about 5 mg/kg/day to about 7.5 mg/kg/day of compstatin analog is administered. In some embodiments, between about 7.5 mg/kg/day to about 10 mg/kg/day of compstatin analog is administered. It will be appreciated that a variety of different dosing regimens could be used to administer a desired total daily amount. For example, a desired amount of compstatin analog could be administered in a single administration or in multiple administrations, e.g., during a 24 hour period. For example, a subject could receive two or more doses within a 24 hour period, which doses could be administered over the same length of time or over different lengths of time.

In some embodiments, a cell-reactive, long-acting, or targeted compstatin analog is administered at time intervals greater than 24 hours. For example, doses could be administered on average every other day, every 3-4 days, weekly, every other week, etc., in various embodiments. In some embodiments, covalently attached, long-acting, or targeted compstatin analogs protect cells, tissues, organs, for a period of weeks or months without need for retreatment. For example, subjects may be maintained with retreatment at intervals of between 1-2 weeks, 2-4 weeks, 4-6 weeks, 6-8 weeks, or even longer. In some embodiments subcutaneous administration is used to administer at least some doses. For example, administration of approximately 0.1-5 mg/kg/day, e.g., about 0.5-2 mg/kg/day is contemplated in some embodiments, e.g., in a volume of about 0.25 ml-2 mL, e.g., a volume of about 1 ml. In some embodiments the concentration is about 50 mg/ml to about 300 mg/ml, e.g., about 50 mg/ml-about 100 mg/ml or about 100 mg/ml-about 200 mg/ml.

In some embodiments administration is daily. In some embodiments administration is 1 or 2 times per day. As described further in the Examples, daily subcutaneous administration of an exemplary long-acting compstatin analog readily achieved blood levels well above 5 micromolar. In some embodiments, intramuscular administration is used to deliver similar amounts of compound.

In some embodiments a long-acting compstatin analog is administered using a therapeutically effective amount to a subject, wherein such administration results in blood concentrations of the compound that achieve a level above at least 1 µM, at least 2 µM, at least 2.5 µM, at least 3 µM, at least 4 µM, at least 5 µM, at least 6 µM, at least 7 µM, at least 8 µM, at least 9 µM, at least 10 µM, at least 11 µM, at least 12 µM, or at least 13 µM, at least 14 µM, at least 15 µM, at least 16 µM, at least 18 µM, or at least about 20 µM, or at least about 25 µM or within any range between 4 µM and about 15 µM or about 20 µM or about 25 µM. In some embodiments such level is maintained for at least about 24 hours, or at least about 48 hours, or at least about 72 hours, or at least about 96 hours, or at least about 120 hours, or at least about 144 hours following a single IV injection or following daily subcutaneous injections for about 5-7 days. Sustained levels may be achieved for longer, e.g., up to about 10 days, 12 days, 14 days, or more.

In some embodiments a subject is treated so as to maintain a steady state level of about 1.0 µM, about 2.0 µM, about 2.5 µM, about 3.0 µM, about 3.5 µM, about 4.0 µM, about 4.5 µM, about 5.0 µM, about 5.5 µM, about 6.0 µM, about 6.5 µM, about 7.0 µM, about 7.5 µM, about 8.0 µM, about 8.5 µM, about 9.0 µM, about 9.5 µM, or about 10 µM. In some embodiments a steady state level has a value between about 1.0 µM and about 10.0 µM, e.g., between about 2.0 µM and about 5.0 µM, between about 2.5 µM and about 5.0 µM, between about 5.0 µM and about 7.5 µM, or between about 7.5 µM, and about 10 µM, or any intervening value within any of the afore-mentioned ranges. In some embodiments a concentration is sufficient to substantially inhibit lysis of red blood cells of PNH patients exposed to human serum in vitro, e.g., using a modified Ham's assay using human serum (see, e.g., Example 8). In some embodiments a concentration is sufficient to reduce by at least 50%, 60%, 70%, 80%, 90%, or more, lysis of red blood cells of PNH patients exposed to human serum in vitro, e.g., using a modified Ham's assay using human serum (see, e.g., Example 8). In some embodiments a Ham's assay may be performed using human serum adjusted to a magnesium level at about 0.005 mol/L and a pH lowered to about 6.2 to activate complement. Examples 18 and 19 present data confirming the ability of compstatin analogs described herein to inhibit lysis of RBCs from PNH patients.

In some aspects compstatin analogs, e.g., long-acting compstatin analogs, may protect red blood cells of PNH patients from accumulating significant amounts of C3 and/or products of C3 activation on their surface. For example, PNH red blood cells that are protected from complement-mediated lysis by compstatin analogs, e.g., long-acting compstatin analogs, may also be protected from accumulating significant amounts of C3 and/or products of C3 activation on their surface. As known in the art, eculizumab (Soliris®, Alexion Pharmaceuticals. Inc.), is a humanized anti-C5 monoclonal antibody that is approved for treatment of PNH and aHUS in a number of countries (see, e.g., Dmytrijuk A, FDA report: eculizumab (Soliris) for the treatment of patients with paroxysmal nocturnal hemoglobinuria. Oncologist. 2008 September; 13(9):993-1000. doi: 10.1634/theoncologist.2008-0086. Epub 2008 Sep. 10; Westra D., A new era in the diagnosis and treatment of atypical haemolytic uraemic syndrome. Neth J Med. 2012 April; 70(3):121-9). It has been reported that when PNH RBCs are exposed to eculizumab they may exhibit accumulation of significant amounts of C3 and/or products of C3 activation on their surface, which may contribute to the clearance and/or extravascular hemolysis of these cells (e.g., in the spleen) and may thus at least in part account for persistent hematologic abnormalities, e.g., persistent anemia, observed in some PNH patients despite treatment with eculizumab. Without wishing to be bound by any theory, this may occur due to inhibition of formation of the MAC by eculizumab, which protects cells from MAC-mediated lysis but does not inhibit C3 activation or deposition of C3 and/or products of C3 activation and leaves PNH cells vulnerable to surface C3 activation and deposition of C3 and/or products of C3 activation due to their lack of GPI-anchored complement inhibiting proteins. Without wishing to be bound by any theory, the ability of compstatin analogs described herein to inhibit C3 activation and thereby inhibit the production of C3 activation products may afford a significant advantage. In some embodiments a subject who has been or is being treated with eculizumab and continues to exhibit evidence of hemolysis, e.g., clinically significant hemolysis, such as causing anemia and/or requiring transfusion is treated with a compstatin analog described herein. In some embodiments a compstatin analog is used at a concentration sufficient such that the level of C3 and/or C3 activation products on PNH RBCs exposed to the compstatin analog (in vitro (e.g., in a Ham's assay) or in vivo) is within the range exhibited by normal RBCs from healthy subjects. In some embodiments the level of C3 and/or C3 activation products on PNH RBCs exposed to the compstatin analog (in vitro (e.g., in a Ham's assay) or in vivo) is within about 1.2, 1.5, 2.0, 2.5, 3.0, 3.5, 4.0, 4.5, or 5.0 of the average level or upper limit of normal. In some embodiments the level of C3 and/or C3 activation products on PNH RBCs exposed to a compstatin analog (in vitro (e.g., in a Ham's assay) or in vivo) is less than the level of C3 and/or C3 activation products on PNH RBCs exposed to Soliris at a concentration that provides equivalent protection against complement-mediated lysis. In some embodiments the level of C3 and/or C3 activation products on PNH RBCs exposed to a compstatin analog (in vitro or in vivo) is no more than about 5%, 10%, 15%, 20%, 25%, 30%, 40%, or 50% of the level of C3 and/or C3 activation products on PNH RBCs exposed to eculizumab at a concentration that provides equivalent protection against complement-mediated lysis. In some embodiments the level of C3 and/or C3 activation products on PNH RBCs exposed to the compstatin analog (in vitro or in vivo) is within about 1.2, 1.5, 2.0, 2.5, 3.0, 3.5, 4.0, 4.5, or 5.0 of the average level or upper limit of a normal range. In some embodiments the PNH cells comprise or consist of Type II PNH cells, Type III PNH cells, or a mixture thereof. In some embodiments the RBCs are at least 50%, 60%, 70%, 75%, 80%, 85%, 90%, 95%, or more Type III and/or Type II RBCs. In some embodiments the cells may comprise some Type I cells. In some embodiments RBCs may be classified as Type I, II, or III based on the level of a GPI-anchored protein such as CD59 on their surface, which may be measured using flow cytometry, immunofluorescence, or ELISA, e.g., using an antibody (e.g., a monoclonal antibody) or other binding agent that binds to said GPI-anchored protein. In some aspects inhibition of deposition of C3 and/or products of C3 activation on cells or surfaces may be used as an indicator of efficacy of a compstatin analog in other complement-mediated diseases such as aHUS, other complement-mediated hemolytic diseases, or other complement-mediated diseases. For example, in some embodiments a compstatin analog inhibits such deposition on endothelial cells in a subject with aHUS. In some embodiments the level of C3 and/or C3 activation product(s) may be measured using flow cytometry, immunofluorescence, or ELISA, e.g., using an antibody (e.g., a monoclonal antibody) or other binding agent that binds to C3 and/or to one or more C3 activation product(s). In some embodiments a C3 activation product is C3b, C3c, or C3d. In some embodiments a binding agent binds to C3d. In some embodiments a binding agent binds to C3d and at least one other C3 activation product. In some embodiments PNH patient RBCs contacted with a compstatin analog in vitro (e.g., in a Ham's assay) are protected from activated complement such that the relative proportion (percentages) of Type I, Type II, and Type III cells or the relative proportion or percentages of Type III and Type I, Type II and Type I, or Type III and Type II, are approximately the same as in a control assay in which inactivated complement (e.g., heat inactivated complement) is used. In some embodiments PNH patient RBCs contacted with a compstatin analog in vitro (e.g., in a Ham's assay) are protected from activated complement such that the relative proportion or percentages of Type I, Type II, and Type III cells or the relative proportion or percentages of Type III and Type I, Type II and Type I, or Type III and Type II, are within 5% of the proportions or percentages obtained in a control assay in which inactivated complement (e.g., heat inactivated complement) is used. In some embodiments complement may be inactivated by heat inactivation, which may be performed by heating complement components or serum or plasma containing complement components to 56 degrees C. or higher.

In some embodiments measurements of LDH (an enzyme that is abundant in red blood cells and can function as a marker for hemolysis), one or more hematologic parameters such as hematocrit, hemoglobin, and/or reticulocyte measurements may additionally or alternately be used in determining the amount of lysis. In some embodiments one or more such methods may be used to determine the amount of lysis of RBCs, e.g., RBCs that are susceptible to complement-mediated lysis, e.g., PNH patient cells, aHUS patient cells, cells from subjects with other complement-mediated hematologic disorders, cells exposed to abnormally high levels of complement activation. In some aspects, the disclosure provides a method comprising contacting one or more cells in vitro or in vivo with a compstatin analog described herein and measuring the effect of the compstatin analog on one or more indicators of complement-mediated cell damage and/or cell surface complement activation or deposition. In some embodiments contacting the one or more cells for a sufficient time at a sufficient concentration results in a reduction of an abnormally high value or an increase in an abnormally low value to within a normal range or to within 5%, 10%, 15%, 20%, or 25% of the lower or upper limit of a normal range.

In some aspects, the disclosure provides a method of selecting or modifying a dosing regimen or one or more components of a dosing regimen for a patient with a complement-mediated hemolytic disease such as PNH. The one or more components of a dosing regimen may comprise a dose, dosing interval, route of administration (e.g., IV or subcutaneous), or combination thereof. A dose may be a loading dose, maintenance dose, or both. In some embodiments, one or more blood samples may be obtained from a patient and a dosing regimen or component thereof for a compstatin analog, e.g., a long-acting compstatin analog, may be selected or modified to achieve a desired level of protection of the patient's RBCs from lysis and/or from accumulation of C3 and/or C3 activation product(s) in vitro. In some embodiments one or more doses of a compstatin analog, e.g., a long-acting compstatin analog, may be administered to a patient, and one or more blood samples may be subsequently obtained from a patient and assessed for level of C3 and/or C3 activation product(s) on their surface. In some embodiments a dosing regimen or component thereof, e.g., a dose, dosing interval, or route of administration, may be selected or modified to achieve a desired level of protection of the patient's RBCs from lysis and/or from accumulation of C3 and/or C3 activation products in vitro or in vivo. In some embodiments a dosing regimen or component thereof, e.g., dose, dosing interval, or route of administration, may be selected or modified to achieve a desired level of protection of the patient's RBCs from extravascular clearance and/or extravascular lysis in vivo. A desired level may be, e.g., a level that is accepted in the art as providing a clinically meaningful benefit, a level that provides a clinically meaningful benefit to a particular patient, a level that is within the normal range, a level selected by a medical practitioner, or any other selected level. A normal range for a parameter may be known in the art and/or may be a reference range established by a laboratory, e.g., a clinical laboratory, wherein the value of the relevant parameter as measured in at least 95%, 96%, 97%, 98%, or 99% of the general population or at least 95%, 96%, 97%, 98%, or 99% of healthy individuals (which may optionally be matched for one or more demographic variables such as gender, age, etc.) or biological specimens obtained therefrom (such as blood samples) would fall within the reference range. A reference range may be established using a sample population representative of the general population or representative of healthy individuals.

In some embodiments a long-acting compstatin analog comprising a CRM is designed to confer a slower rate of systemic absorption after subcutaneous or intramuscular administration to a subject as compared with a compstatin analog not comprising a CRM. In some embodiments particular CRM properties, e.g., length, are selected to confer a desired rate of systemic absorption after subcutaneous or intramuscular administration as compared with at least some other CRMs. In some embodiments, the Cmax is reduced in comparison to a comparable dose of a compstatin analog not linked to a CRM, which may thereby contribute to keeping the plasma concentration within a desired window, e.g., the therapeutic window, for the compound. In some embodiments a long-acting compstatin analog composition is characterized in that a dose, when administered subcutaneously, appears fully absorbed within about 1, 2, 3, 4, 6, 8, 12, 15, 30, 45, 60, 90, or 120 hours following administration based on visual observation at the injection site.

It will be understood that there may be an initial treatment phase during which treatment is more frequent and/or in which higher doses are administered. For example, in a subject with PNH or aHUS, it may require several doses to achieve protection of a substantial fraction of the subject's RBCs. After that, lower doses and/or less frequent dosing could be used, e.g., to protect newly formed RBCs and/or to replenish protection of existing RBCs. Of course similar approaches may be followed for treatment of any disease where appropriate. In some embodiments treatment is started using IV administration and then switched to an alternate route, e.g., subcutaneous, intramuscular, transdermal, or intradermal, for maintenance therapy. Depending on the disease, treatment may continue at intervals for, e.g., months, years, or indefinitely. For example, in some embodiments, a subject may be treated using a dosing regimen described herein, e.g., an alternate day, thrice weekly, every third day, twice weekly, or weekly dosing regimen for a period of at least 6 weeks, at least 13 weeks, at least 26 weeks, at least 52 weeks, or more. In some embodiments the subject may be treated for 1-2 years, 2-5 years, e.g., 5 to 10 years, or more. In some embodiments the disorder is a chronic disorder, which may be a lifelong disorder, and the subject is treated for as long as he or she continues to suffer from the disorder, e.g., for the remainder of the subject's life. Appropriate doses and dosing regimen depend at least in part upon the potency and half-life of the compstatin analog (or other active agent), and may optionally be tailored to the particular recipient, for example, through administration of increasing doses until a preselected desired response is achieved, such as a desired degree of complement inhibition and/or cell protection. If desired, the specific dose level for any particular subject may be selected based at least in part upon a variety of factors including the activity of the specific compound employed, the particular condition being treated, the age, body weight, general health, route of administration, the rate of excretion, any drug combination, and/or the degree of complement protein expression or activity measured in one or more samples obtained from the subject.

In some aspects, described herein are methods in which a patient is switched from treatment with a complement inhibitor that does not comprise a compstatin analog to treatment with a compstatin analog, e.g., a long-acting compstatin analog (LACA), cell-reactive, or targeted compstatin analog. For purposes of conciseness, such methods are described with reference to a LACA but may alternately be employed for switching a patient to treatment with a cell-reactive or targeted compstatin analog. In some embodiments a patient to whom a compstatin analog, e.g., a LACA, is administered is under treatment with a different complement inhibitor that does not comprise a compstatin analog at the time therapy with a compstatin analog, e.g., a LACA, is started. In embodiments in which a patient to whom a compstatin analog is administered is under treatment with a different complement inhibitor that does not comprise a compstatin analog at the time therapy with a compstatin analog is started, the patient's complement system (e.g., as measured with a suitable assay such as an ex vivo serum-induced hemolysis assay using the patient's serum) may already be inhibited at the time therapy with a LACA is started. In some embodiments the different complement inhibitor is a C5 inhibitor (i.e., an agent that inhibits activation and/or activity of C5, typically by binding to C5). In some embodiments the C5 inhibitor is an anti-C5 antibody such as eculizumab, an anti-C5 siRNA such as ALN-CC5 (Alnylam Pharmaceuticals), an anti-C5 polypeptide such as Coversin (Volution Immuno Pharmaceuticals, Ltd.), or an anti-C5 small molecule. In some embodiments the different complement inhibitor may be a C3 inhibitor. In some embodiments, treatment with the different complement inhibitor, e.g., C5 inhibitor, is stopped and the patient is switched to treatment with the LACA. It would be understood that the switch to treatment with a LACA is desirably performed in such a way that the patient does not experience a clinically significant decrease in complement system inhibition during the transition to treatment with a LACA as sole complement inhibitor therapy.

For example, in the case of a patient with a complement-mediated hemolytic anemia such as PNH, the patient does not experience a clinically significant increase in hemolysis, e.g., as measured by LDH level and/or ex vivo serum hemolytic activity when treatment with the different complement inhibitor is stopped. In some embodiments the patient is monitored and the transition is managed such that the patient does not experience a measured increase of more than 10% in LDH level or a measured increase of more than 10% in hemolytic activity. In some embodiments the transition to treatment with a LACA as sole complement inhibitor therapy is performed in such a way as to maintain at least an 80% inhibition of ex vivo serum hemolytic activity during the transition period. "Transition period" refers to the time period starting on the day of the first dose of a LACA and ending 4 times X days after the last dose of the different complement inhibitor, where "X" represents the dosing interval at which the different complement inhibitor was being administered to the patient prior to the first dose of the LACA, e.g., the recommended dosing interval of the different complement inhibitor when used at the recommended dose. "Recommended dose" for a medication refers to the dose specified in the prescribing information for that medication on the label approved by the US FDA or, if the medication is not approved by the FDA, the dose specified in the prescribing information for a medication on the label approved by the government agency responsible for approval of medications in the particular jurisdiction in which the medication is used. "Recommended dosing interval" for a medication refers to the dosing interval specified for that medication in the prescribing information and/or on the label approved by the US FDA or, if the medication is not approved by the FDA, the dosing interval specified in the prescribing information and/or on the label approved by the government agency responsible for approval of medications in the particular jurisdiction in which the medication is used. It will be understood that a medication may have two or more distinct recommended dosing regimens. Such dosing regimens may be appropriate for different indications, appropriate for patients having different characteristics, or simply alternate therapeutically effective combinations of dose, dosing interval, and administration route. Where a medication has two or more recommended dosing regimens, it will be understood that the term "recommended dosing interval" refers to the recommended dosing interval for the particular dose being administered by the particular administration route being used.

In some embodiments a LACA is first administered to a patient who has received at least one dose of a different complement inhibitor within a time period no greater than 1.5 times the recommended dosing interval of the different complement inhibitor, e.g., within a time period no greater than the recommended dosing interval of the different complement inhibitor, e.g., within a time period no greater than half the recommended dosing interval of the different complement inhibitor. In some embodiments the patient has received at least one dose of the different complement inhibitor within the 2 weeks preceding the patient's first dose of a LACA. In some embodiments the patient has received at least one dose of the different complement inhibitor within 1 week preceding the patient's first dose of a LACA. In some embodiments the patient has received a dose of the different complement inhibitor less than a week before the patient's first dose of a LACA. In some embodiments the patient received a dose of the different complement inhibitor on day of the patient's first dose of a LACA. In some embodiments the patient is treated with an effective amount of different complement inhibitor and an effective amount of a LACA so as to maintain therapeutically effective blood levels of both the different complement inhibitor and the LACA for a time period. Such a period of co-treatment may last for, e.g., between 1 week and 2 weeks, between 2 weeks and 4 weeks, between 4 weeks and 6 weeks, between 6 weeks and 8 weeks, between 8 weeks and 12 weeks, between 12 weeks and 26 weeks. In some embodiments the period of co-treatment may be 1, 2, 3, 4, 5, or 6 months. In some embodiments the co-treatment period is the period of time from the first dose of the LACA to the last dose of the different complement inhibitor. The different complement inhibitor may be administered at the usual maintenance dose that the patient had been receiving prior to initiation of treatment with the LACA. In some embodiments, the different complement inhibitor is administered at a dose that is reduced over time (tapered) until eventually treatment with the different complement inhibitor is stopped. For example, in some embodiments the dose of the different complement inhibitor may be reduced to about 67% of the maintenance dose, then about 33% of the maintenance dose for the last dose. In some embodiments the dose of the different complement inhibitor may be reduced to about 75% of the maintenance dose, then about 50% of the maintenance dose, then about 25% of the maintenance dose for the last dose. In some embodiments the total period during which the patient is treated with both a LACA and a different complement inhibitor (i.e., the time from the first dose of the LACA to the last dose of the first complement inhibitor) is between 2 weeks and 26 weeks. In some embodiments the different complement inhibitor is not tapered. Instead, in some embodiments, e.g., after the LACA has reached a therapeutically effective blood level, the blood level of the different complement inhibitor is allowed to decline as it is metabolized or otherwise removed from the body. In some embodiments a patient ex vivo serum-induced hemolysis by the patient's serum is monitored during the transition and/or thereafter. In some embodiments, if ex vivo serum-induced hemolysis by the patient's serum is not reduced by at least 80%, e.g., at least 90%, when measured during the transition from treatment with the different complement inhibitor to treatment with the LACA as the sole complement inhibitor, the dose of the LACA may be increased. In some embodiments reduction in opsonization of a PNH patient's red blood cells by C3 fragments such as C3d serves as an indicator that the patient is receiving a therapeutically effective amount of a LACA. In some embodiments treatment with both the different complement inhibitor, e.g., C5 inhibitor, and LACA is continued for at least 6 months e.g., between 6 and 12 months, between 12 and 24 months, or more (e.g., indefinitely). In some embodiments the different complement inhibitor and/or the LACA is administered at a lower dose than would be used if it were being used as the sole complement inhibitor therapy for the patient. It should be noted that analogous methods can be used to switch a patient from treatment with a LACA to treatment with a different complement inhibitor, if desired, or to switch a patient from treatment with a first LACA to treatment with a different LACA.

In some aspects, a subject suffering from any of the complement-mediated disorders described herein who is treated using a long-acting, targeted, or cell-reactive compstatin analog, is refractory to one or more alternate therapies (i.e., therapies that do not comprise a long-acting, targeted, or cell-reactive compstatin analog) or exhibits a suboptimal response to such alternate therapy. In some embodiments the alternate therapy comprises a corticosteroid. In some embodiments the alternate therapy comprises an anti-B cell antibody such as rituximab. In some embodiments the alternate therapy comprises a complement inhibitor that is a C5 inhibitor, a factor D inhibitor, or a C1 inhibitor. In some embodiments the alternate therapy comprises an antibody that is a C5 inhibitor, a factor D inhibitor, or a C1 inhibitor.

In some aspects, described herein are certain doses, dosing regimens, compositions, and methods useful for administering a long-acting compstatin analog (LACA) to a subject. In some aspects, certain doses, dosing regimens, compositions, and methods described herein have been used in clinical trials involving subcutaneous or intravitreal administration of a LACA comprising a linear PEG having a molecular weight of 40 kD and two compstatin analog moieties (one linked to each end of the linear PEG) to healthy human subjects or to patients with PNH or involving intravitreal administration of this same LACA to patients with AMD (see Examples). Accordingly, in some aspects, doses, dosing regimens, compositions, and/or methods described herein may be used to administer a LACA comprising a linear PEG having a molecular weight of about 40 kD and two compstatin analog moieties to a subject (e.g., a patient having a complement-mediated disorder). In some embodiments, the two compstatin analog moieties are linked to the ends of a linear PEG (i.e., one compstatin analog moiety is linked to each end of the PEG). In some embodiments, each compstatin analog moiety is linked via its C-terminal end to the linear PEG. In some embodiments, the LACA may be CA28-2GS-BF or CA28-2TS-BF.

As described herein, a compstatin analog moiety may comprise a spacer separating an amino acid having a side chain comprising a reactive functional group, e.g., a primary or secondary amine, sulfhydryl, or sulfhydryl-reactive group (or an amino acid sequence comprising such an amino acid) from the portion of a compstatin analog moiety comprising a cyclic portion or such a linking portion may be absent. Where present, such a spacer moiety may comprise a substituted or unsubstituted, saturated or unsaturated alkyl chain, oligo(ethylene glycol) chain, and/or any of the other moieties denoted by L (or $L^{P1}$, $L^{P2}$, or $L^{P3}$) herein. Where two or more compstatin analog moieties comprising spacer moieties are present in a compound, the spacer moieties may be the same or different in various embodiments. Doses, dosing regimens, compositions, and/or methods may be used to administer long-acting compstatin analogs comprising compstatin analog moieties comprising any such spacer moieties.

As also described herein, compstatin analog moieties may be linked to a PEG (or other polymer) via any of a wide variety of different linkages in various embodiments. In certain embodiments a (one or more) compstatin analog moiet(ies) may be linked to a CRM via a moiety comprising an unsaturated alkyl moiety, a moiety comprising a non-aromatic cyclic ring system, an aromatic moiety, an ether moiety, an amide moiety, an ester moiety, a carbonyl moiety, an imine moiety, a thioether moiety, an amino acid residue, and/or any of the moieties denoted as L (or $L^{P1}$, $L^{P2}$, or $L^{P3}$) above. For example as described herein, in particular embodiments a (one or more) compstatin analog moiet(ies) may be linked to a CRM via a carbamate linkage, an ester linkage, an amide linkage, or a combination of two or more such linkages. Where two or more compstatin analog moieties are present in a compound, the linkages to the polymer may be the same or different in various embodiments. Doses, dosing regimens, compositions, and/or methods may be used to administer long-acting compstatin analogs comprising compstatin analog moieties linked to a CRM via any such moieties.

In some embodiments doses, dosing regimens, compositions, and/or methods described herein may be used to administer a LACA that differs in one or more ways from the LACA used in the clinical trials described herein. For example, such a LACA may comprise: (i) a different polymer as a CRM (e.g., a POZ, a polypeptide, a branched PEG), (ii) a polymer having a molecular weight that is lower or higher than 40 kD as a CRM; (iii) a different number of compstatin analog moiet(ies) (e.g., 1, 3, 4, or more compstatin analog moiet(ies), instead of 2 compstatin analog moieties), (iv) one or more compstatin analog moiet(ies) comprising a sequence that differs from SEQ ID NO: 28 in place of SEQ ID NO: 28 (e.g., any of the other compstatin analog moieties described herein); (v) a (one or more) compstatin analog moiet(ies) extended with a different amino acid residue (or amino acid sequence comprising such amino acid residue) having a side chain comprising a primary or secondary amine instead of lysine or comprising a different reactive functional group such as a sulfhydryl or sulfhydryl-reactive group; (vi) a (one or more) compstatin analog moiet(ies) linked to a CRM via the N-terminal end of the compstatin analog moiety rather than via the C-terminal end; (vii) different blocking moiet(ies) at the free end of one or more compstatin analog moiet(ies); (viii) any combination of two or more of (i), (ii), (iii), (iv), (v), (vi), (vii), and (vii).

As mentioned above, in some aspects, doses, dosing regimens, compositions, and/or methods described herein may be used to administer a LACA comprising a polymer (e.g., a PEG) having a molecular weight of about 40 kD as a CRM, e.g., a polymer having a molecular weight of 36 kD-44 kD, 37 kD-43 kD, 38 kD-42 kD, or 39 kD-41 kD. However, in some embodiments doses, dosing regimens, compositions, and/or methods may be used to administer a LACA comprising a polymer whose molecular weight is within a broader range. In some embodiments of particular interest the molecular weight of the polymer is no greater than 45 kD. In some embodiments the polymer has a molecular weight of 10 kD-45 kD. In some embodiments the polymer has a molecular weight of 20 kD-45 kD. In some embodiments the polymer has a molecular weight of 30 kD-40 kD. In some embodiments the polymer has a molecular weight of 30 kD-45 kD. In some embodiments the polymer has a molecular weight of 35 kD-45 kD. In some embodiments the polymer has a molecular weight that is greater than 45 kD, e.g., up to 50 kD. It will be understood that molecular weights of a polymer can refer to the average molecular weight of polymer molecules in a composition as discussed herein.

In some embodiments the compositions comprise 5% dextrose as a pharmaceutically acceptable carrier. However, any pharmaceutically acceptable carrier may be used.

Doses, dosing regimens, compositions, and/or methods described herein can be used to treat any of the complement-mediated mentioned herein, in various embodiments. Without limitation, such disorders include, e.g., PNH, NMO, myasthenia gravis, aHUS, COPD, idiopathic pulmonary fibrosis, organ rejection after transplantation (e.g., acute or chronic rejection), pemphigoid, and AMD. In some embodiments the complement-mediated disorder is a chronic complement-mediated disorder, e.g., any of the chronic complement-mediated disorders mentioned herein. In some embodiments the complement-mediated disorder is a Th17-associated disorder, e.g., any of the Th17-associated disorders mentioned herein.

In some aspects, described herein are various doses, dosing regimens, compositions, and methods useful for treating patients by subcutaneous administration of a LACA. In experiments with a LACA comprising a 40 kD PEG moiety it was found that viscosity rather than solubility is the main factor that limits the concentration of a composition comprising the LACA that can be administered by subcutaneous or IVT injection in a manner that is acceptable to physicians and patients in terms of the time and pressure required to deliver a given volume of the composition through a needle of a given inner diameter or gauge number. Gauge number describes the outer diameter of a hollow needle, with a higher gauge number indicating a smaller outer diameter. Generally, needles having a higher gauge number may be preferred by patients and physicians as they may be associated with (or may be perceived to be associated with) less pain and/or tissue damage as compared with needles having a lower gauge number. Inner diameter depends on both outer diameter and wall thickness. For standard needles, the higher the gauge number, the smaller the inner diameter (e.g., a 27 gauge needle has a larger inner diameter than a 29 gauge needle, which in turn has a larger inner diameter than a 30 gauge needle).

In some embodiments a composition, e.g., a pharmaceutical composition, comprising a LACA has a concentration of 150 mg/ml. It was found that a 150 mg/ml solution of a LACA comprising a 40 kD PEG can readily be delivered using a 27 gauge needle. Accordingly, in some embodiments a 27 gauge needle is used to administer a dose of a LACA comprising a PEG having a molecular weight of about 40 kD at a concentration of up to 150 mg/ml, e.g., 75 mg/ml-90 mg/ml, 85 mg/ml-95 mg/ml, 90 mg/ml-100 mg/ml, 95 mg/ml-105 mg/ml 100 mg/ml-110 mg/ml, 105 mg/ml-115 mg/ml, 110 mg/ml-120 mg/ml, 115 mg/ml-125 mg/ml, 120 mg/ml-130 mg/ml, 125 mg/ml-135 mg/ml, 130 mg/ml-140 mg/ml, 135 mg/ml-145 mg/ml, 140 mg/ml-150 mg/ml, e.g., 100 mg/ml, 125 mg/ml, or 150 mg/ml. In some embodiments a composition comprising a LACA comprising a PEG having a molecular weight of about 40 kD has a concentration of up to 150 mg/ml, e.g., 75 mg/ml-90 mg/ml, 85 mg/ml-95 mg/ml, 90 mg/ml-100 mg/ml, 95 mg/ml-105 mg/ml 100 mg/ml-110 mg/ml, 105 mg/ml-115 mg/ml, 110 mg/ml-120 mg/ml, 115 mg/ml-125 mg/ml, 120 mg/ml-130 mg/ml, 125 mg/ml-135 mg/ml, 130 mg/ml-140 mg/ml, 135 mg/ml-145 mg/ml, 140 mg/ml-150 mg/ml, e.g., 100 mg/ml, 125 mg/ml, or 150 mg/ml. In some embodiments a composition comprising a LACA comprising a 40 kD PEG has a concentration of 150 mg/ml-180 mg/ml. In some embodiments a composition comprising a LACA comprising a PEG having a molecular weight of about 40 kD has a concentration of 180 mg/ml-200 mg/ml. In some embodiments a 27 gauge needle is used to administer a composition comprising a LACA comprising a PEG having a molecular weight of about 40 kD at a concentration of 150 mg/ml-160 mg/ml, 160 mg/ml-170 mg/ml, 170 mg/ml-180 mg/ml, 180 mg/ml-190 mg/ml, or 190 mg/ml-200 mg/ml. Of course a needle with a lower gauge number (e.g., 25, 26 gauge) may alternately be used instead of a needle with a gauge number of 27 gauge (or higher).

The present disclosure encompasses the finding that a 200 mg/ml solution of a LACA comprising a 40 kD PEG can readily be delivered using a 25 gauge needle. In some embodiments a 25 gauge needle or a 26 gauge needle is used to administer a composition comprising a LACA comprising a 40 kD PEG at a concentration of 200 mg/ml, or more. In some embodiments a 25 gauge needle or a 26 gauge needle is used to administer a composition comprising a LACA at a concentration of 200 mg/ml-225 mg/ml or 225 mg/ml-250 mg/ml.

In some aspects, the present disclosure teaches particular utility of certain thin-walled needles for administration of a LACA in accordance with the present invention. For example, in some embodiments a thin wall needle is used for subcutaneous, intramuscular, or intraocular (e.g., intravitreal) injection of a LACA. Thin wall needles have identical outer diameters to standard needles but larger inner diameters for a given gauge. For example, a thin wall needle may have an internal diameter size that is the same as that of a standard needle of a gauge one to two numbers lower (e.g., a 29 gauge thin wall needle may have an internal diameter that is the same as that of a 27 gauge or 28 gauge standard needle but an outer diameter that is the same as that of a standard 29 gauge needle). An increase in internal diameter can result in a considerable increase in fluid flow for a given pressure and/or a considerable reduction in pressure needed to maintain a given flow. Lower pressure means that less injection force is needed to administer a composition of a given viscosity. In general, low injection force facilitates administration and is therefore typically a desirable feature. In some embodiments a thin wall needle has a given internal diameter that is uniform along the length of the needle. In some embodiments a thin wall needle has an internal diameter that varies along the length of the needle. For example, the diameter may be the same as that of a standard 29 gauge needle at one end of the needle and progress to the diameter of a standard 27 gauge needle at the other end. In some embodiments a microtapered needle may be used. In some embodiments a needle with a scalpel-like tip may be used. The length of the needle may vary. In some embodiments a short needle such as a 5 mm or 6 mm needle may be used. In some embodiments a needle having a length between 6 mm and 8 mm, or between 8 mm and 12 mm may be used. Suitable needles and syringes are available commercially, e.g., from Becton Dickinson and Company (BD), Terumo Corp., etc.

In some embodiments a composition having a given viscosity and/or concentration may be administered using a thin wall needle having a gauge that is one or two numbers higher than the gauge size that is preferably used when a standard needle is used to administer a composition of the same viscosity and/or concentration at a selected flow rate and/or with a selected injection force. For example, in some embodiments a composition that is preferably administered using a 25 gauge standard needle in order to attain a desired flow rate and/or injection force can be administered with such a flow rate and/or injection force using a 26 or 27 gauge thin wall needle. In some embodiments a composition that is preferably administered using a 27 gauge standard needle in order to attain a desired flow rate and/or injection force can be administered with such a flow rate and/or injection force using a 28 or 29 gauge thin wall needle. In some embodiments a composition that is preferably administered using a 29 gauge standard needle in order to attain a desired flow rate and/or injection force can be administered with such a flow rate and/or injection force using a 30 or 31 gauge thin wall needle. In some embodiments a 29 gauge thin wall needle is used to administer a composition comprising a LACA comprising a polymer (e.g., a PEG) having a molecular weight of about 40 kD at a concentration of 150 mg/ml-160 mg/ml, 160 mg/ml-170 mg/ml, 170 mg/ml-180 mg/ml, 180 mg/ml-190 mg/ml, or 190 mg/ml-200 mg/ml. Of course a thin wall needle with a lower gauge number (e.g., 27, 28 gauge) may alternately be used instead of a thin wall needle with a gauge number of 29 gauge (or higher).

In some aspects, a suitable volume for an individual SC injection may be up to 2 milliliters (ml)-3 ml. Thus, for example, in some embodiments, a volume greater than 1.0 ml may be administered by SC injection, e.g., 1.1, 1.2, 1.3, 1.4, 1.5, 1.6, 1.7, 1.8, 1.9, or 2.0 ml. In some embodiments, a volume greater than 2.0 ml may be administered by SC injection, e.g., 2.1, 2.2, 2.3, 2.4, or 2.5 ml. In some embodiments, a volume greater than 2.5 ml may be administered by SC injection, e.g., 2.6, 2.7, 2.8, 2.9, or 3.0 ml. In some embodiments a volume of 1 ml or less per injection is used, e.g., 0.5, 0.6, 0.7, 0.8, 0.9, or 1.0 ml. In some embodiments the total daily volume administered to a patient is between 1.0 and 2.5 ml, e.g., 1.0, 1.1, 1.2, 1.3, 1.4, 1.5, 1.6, 1.7, 1.8, 1.9, 2.0, 2.1, 2.2, 2.3, 2.4, or 2.5 ml. In some embodiments the total daily volume administered to a patient is between 2.5 and 3.0 ml, e.g., 2.5, 2.6, 2.7, 2.8, 2.9, or 3.0 ml. In some embodiments in which two SC injections are administered, a volume of up to 5 ml may be administered. In some embodiments a volume of 1.0-2.5 ml is administered as a single daily injection. In some embodiments a volume of 1.0-2.5 ml is administered as two separate injections. In some embodiments a volume of 2.5-3.0 ml is administered as two separate injections. The volumes administered in the two separate injections may the same or different, so long as together they provide a total volume sufficient to administer a desired amount of LACA. In some embodiments the two separate injections may be administered up to 12 hours apart. However, in some embodiments the two separate injections are administered within up to 5, 10, 15, 20, 30, or 60 minutes of each other.

In some aspects, one or more fixed doses may be used for different patients whose weight and/or body surface area may vary over relatively wide ranges. In some embodiments, 2, 3, or more different fixed doses may be provided, wherein different doses may, for example be more suitable for individuals whose weight and/or body surface area lie within different ranges.

In some embodiments, a fixed dose may be used to administer an amount of compstatin analog (e.g., LACA) that would achieve a desired level of complement inhibition (e.g., as measured in a sample of plasma) in at least 25%, at least 50%, at least 75%, at least 90%, or at least 95%, or more, of healthy subjects and/or in at least 25%, at least 50%, at least 75%, at least 90%, or at least 95%, or more, of patients in need of treatment for a particular disorder mentioned herein. In some embodiments, a fixed dose may be used to administer an amount that would achieve a desired level of efficacy (e.g., as measured using an appropriate endpoint) in at least 25%, at least 50%, at least 75%, or at least 90% of patients in need of treatment for a particular disorder mentioned herein. In some aspects, a dose described herein may be particularly useful for subcutaneous (SC) administration. However, in certain embodiments doses described herein may be administered to a subject using other parenteral routes of administration instead of or in addition to the subcutaneous route, such as intravenous, transdermal, or intramuscular. Thus, where the description refers to subcutaneous administration of a particular dose, the disclosure provides embodiments in which such dose is administered by a different route of administration (e.g., intravenous, transdermal, or intramuscular).

In some embodiments the total daily dose for parenteral administration, e.g., subcutaneous administration, of a LACA comprising two compstatin analog moieties and a PEG having a molecular weight of about 40 kD is at least 30 mg/day, e.g., at least 45 mg/day, e.g., at least 90 mg/day, e.g., at least 150 mg/day, e.g., at least 180 mg/day. In certain embodiments the daily dose is between 90 mg/day-180 mg/day. In certain embodiments the daily dose is between 180 mg/day-270 mg/day. In some embodiments the dose is, e.g., 180 mg/day-230 mg/day. In some embodiments the dose is at least 190 mg/day, e.g., 190 mg/day-240 mg/day. In some embodiments the dose is at least 200 mg/day, e.g., 200 mg/day-250 mg/day. In some embodiments the dose is at least 210 mg/day, e.g., 210 mg/day-260 mg/day. In some embodiments the dose is at least 220 mg/day, e.g., 220 mg/day-270 mg/day. In some embodiments the dose is at least 230 mg/day, e.g., 230 mg/day-280 mg/day. In certain particular embodiments the dose is 180 mg/day, 190 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, or 270 mg/day. In some embodiments a dose of 180 mg/day-270 mg/day is administered in a single daily injection in a volume of 1.5 ml-2.0 ml. In some embodiments a dose of 180 mg/day-270 mg/day is administered in a single daily injection in a volume of up to 2.0-2.5 ml. In some embodiments a dose of 180 mg/day-270 mg/day is administered in two daily injections, each having a volume of less than 2.0 ml, e.g., between 1.0 ml and 1.9 ml. For example, in a particular embodiment a daily dose of 270 mg/day is administered in a single injection in a volume of 1.5 ml. In another particular embodiment a daily dose of 270 mg/day is administered in a single injection in a volume of 1.8 ml. In another particular embodiment a daily dose of 270 mg/day is administered in two daily injections in a volume of 0.9 ml each. In some particular embodiments a daily dose of 270 mg/day is administered in two daily injections in a volume of 0.9 ml-1.2 ml each, e.g., 1.0 ml, 1.05 ml, 1.1 ml, 1.15 ml, or 1.2 ml. In some particular embodiments a daily dose of 270 mg/day is administered in two daily injections in a volume of 1.2 ml-1.5 ml each, e.g., 1.2 ml, 1.25 ml, 1.35 ml, 1.40 ml, 1.45 ml, or 1.5 ml. In some particular embodiments a daily dose of 270 mg/day is administered in two daily injections in a volume of 1.5 ml-1.9 ml each, e.g., 1.55 ml, 1.6 ml, 1.65 ml, 1.7 ml, 1.75 ml, 1.8 ml, 1.85 ml, or 1.90 ml.

In some embodiments the total daily dose for parenteral administration, e.g., subcutaneous administration, of a LACA comprising two compstatin analog moieties and a PEG having a molecular weight of about 40 kD is between 270 mg/day-360 mg/day. In some embodiments the dose is 270 mg/day-300 mg/day. In some embodiments the dose is 300 mg/day-330 mg/day. In some embodiments the dose is 330 mg/day-360 mg/day. In certain particular embodiments the dose is 295 mg/day, 300 mg/day, 305 mg/day, 310 mg/day, 315 mg/day, 320 mg/day, 325 mg/day, 330 mg/day, 335 mg/day, 340 mg/day, 345 mg/day, 350 mg/day, 355 mg/day, or 360 mg/day. In some embodiments a dose of 270 mg/day-360 mg/day is administered in a single daily injection in a volume of 1.5 ml-2.0 ml or in a single daily injection in a volume of up to 2.0-2.5 ml. In some embodiments a dose of 270 mg/day-360 mg/day (e.g., any of the afore-mentioned doses) is administered in two daily injections, each having a volume of less than 2.0 ml, e.g., between 1.0 ml and 1.9 ml, e.g., 1.0 ml, 1.05 ml, 1.10 ml, 1.15 ml, 1.20 ml, 1.25 ml, 1.30 ml, 1.35 ml, 1.40 ml, 1.45 ml, 1.50 ml, 1.55 ml, 1.60 ml, 1.65 ml, 1.70 ml, 1.75 ml, 1.80 ml, 1.85 ml, 1.90 ml.

In some embodiments the total daily dose for SC administration of a LACA comprising two compstatin analog moieties and a PEG having a molecular weight of about 40 kD is at least 360 mg/day, e.g., 360 mg/day-540 mg/day. In some embodiment the total daily dose is more than 360 mg/day, e.g., up to about 540 mg/day. For example, the total daily dose may be 370 mg/day, 380 mg/day, 390 mg/day, 400 mg/day, 410 mg/day, 420 mg/day, 430 mg/day, 440 mg/day, 450 mg/day, 460 mg/day, 470 mg/day, 480 mg/day, 490 mg/day, 500 mg/day, 510 mg/day, 520 mg/day, 530 mg/day, or 540 mg/day. In some embodiments a dose of 360 mg/day-540 mg/day is administered in a single daily injection, e.g., in a volume of about 2.0-2.5 ml or 2.5 ml-3.0 ml. In some embodiments a dose of 360 mg/day up to about 540 mg/day is administered in two daily injections, each having a volume of less than 2.0 ml, e.g., between 1.0 ml and 1.9 ml.

It will be understood that the doses and volumes described herein for subcutaneous administration (or other parenteral administration route) may be administered using a free-standing needle and syringe, pen device, autoinjector, or other means known to those of skill in the art. In some embodiments a syringe pump may be used. In some embodiments an on-body drug delivery device may be used.

In some aspects, described herein are methods that comprise administering a long-acting compstatin analog subcutaneously at intervals of 2 days or more to a subject. As described herein and in PCT/US2016/56144, subcutaneous (SC) administration of 180 mg or more per day of a compound comprising a PEG having a molecular weight of about 40 kD and two compstatin analog moieties, referred to herein as LACA-40, resulted in pharmacologically relevant levels of complement inhibition in a clinical trial in healthy subjects (e.g., as described in Example 20). Furthermore, in clinical trials in subjects with PNH, subcutaneous administration of 180 mg or more per day of LACA-40 resulted in relevant changes in blood biomarkers (e.g., as described in Examples 21 and 22). Daily SC administration of LACA-40 has been well tolerated at doses of up to 360 mg (the highest dose administered in multiple dose clinical trials as of the filing date of the present application). In some aspects, the present disclosure provides the insight, based at least in part on data acquired in these clinical trials and pharmacokinetic modeling, that a LACA comprising a PEG having a molecular weight of about 40 kD and two compstatin analog moieties has a suitable profile for administration according to dosing regimens in which doses are administered subcutaneously no more often than once every two days, e.g., every other day, three times a week (sometimes referred to as "thrice weekly"), every third day, twice a week (sometimes referred to as "twice weekly"), every fourth day, every fifth day, every sixth day, or once a week (sometimes referred to as "once weekly" or "weekly"). In some aspects, such dosing regimens may provide increased convenience for patients as compared, e.g., to regimens in which a LACA is administered daily. In some aspects, such dosing regimens may provide a similar or greater average (mean) plasma concentration of LACA-40 at steady state as does daily subcutaneous (SC) administration at a lower dose (e.g., between 180 mg and 270 mg daily) and/or a similar or greater minimum (trough) plasma concentration of LACA-40 at steady state as does daily SC administration at a lower dose (e.g., between 180 mg and 270 mg daily), yet avoid excessive fluctuations in plasma concentration that may potentially result in a peak (maximum) plasma concentration that might be undesirably high and/or a trough (minimum) plasma concentration that might be undesirably low and might have an adverse impact on efficacy. Without wishing to be bound by any theory, this may in part be a consequence of LACA-40 having a relatively slow rate of absorption into the vascular compartment following subcutaneous administration.

A thrice weekly dosing schedule is a dosing schedule in which a compound, e.g., a LACA, e.g., LACA-40, is administered on three days of the week, with two of these administration days being followed by a day on which the compound is not administered, and the other administration day being followed by two days on which the compound is not administered. For purposes of describing a dosing schedule, the days of the week may be numbered Day 1 to Day 7. It will be appreciated that any day of the week may be considered "Day 1". Exemplary dosing schedules for thrice weekly administration entail administering a dose on Day 1, Day 3, and Day 5 each week or on Day 1, Day 4 and Day 6 each week. For example, assuming that Monday is considered Day 1, an exemplary thrice weekly dosing schedule entails administering a dose on Monday, Wednesday, and Friday. A variety of different doses of a LACA, e.g., LACA-40, may be administered according to a thrice weekly dosing schedule. In some embodiments, a dose of at least 375 mg, e.g., between 375 mg and 585 mg, is administered subcutaneously thrice weekly. In some embodiments, a dose of at least 585 mg, e.g., between 585 mg and 885 mg is administered thrice weekly. In some embodiments, a dose of between 585 mg and 630 mg is administered thrice weekly. In some embodiments, a dose of at least 630 mg, e.g., between 630 mg and 675 mg, is administered subcutaneously thrice weekly. In some embodiments, a dose of at least 675 mg, e.g., between 675 mg and 795 mg, is administered thrice weekly. For example, the dose may be between 675 mg and 715 mg, between 715 mg and 755 mg, or between 755 mg and 795 mg. In some embodiments, a dose of at least 795 mg, e.g., between 795 mg and 885 mg is administered thrice weekly. In some embodiments, a dose of at least 840 mg, e.g., between 840 mg and 885 mg, or between 885 and 930 mg, is administered thrice weekly. It is also within the scope of the present disclosure to administer doses of at least 930 mg thrice weekly, e.g., doses between 930 mg and 975 mg, between 975 mg and 1030 mg, between 1030 and 1075 mg, between 1075 mg and 1150 mg, between 1150 mg and 1240 mg, between 1240 mg and 1330 mg, between 1330 mg and 1420 mg, between 1420 mg and 1510 mg, between 1510 mg and 1600 mg, or between 1600 mg and 1690 mg.

An "every other day" dosing schedule, also referred to as an "alternate day" or "every two day" dosing schedule, is a dosing schedule in which a compound, e.g., a LACA, e.g., LACA-40, is administered once a day on alternate days but not on the intervening days. For example, a compound may be administered on Days 1, 3, 5, and 7 of a given week, and then on Days 2, 4, and 6 of the following week, in a pattern that repeats each 2 week period. In some embodiments, any of the doses described herein in regard to thrice weekly dosing schedules may be administered according to an alternate day dosing schedule. In some embodiments, any of the doses described above in regard to thrice weekly dosing may be modified for alternate day dosing by reducing the dose by between 10% and 15%.

A twice weekly dosing schedule is a dosing schedule in which a compound, e.g., a LACA, e.g., LACA-40, is administered on two days of the week, with one of these administration days being followed by two days on which the compound is not administered, and the other administration day being followed by three days on which the compound is not administered. Such a dosing schedule may entail administering a dose on Day 1 and Day 4 or on Day 1 and Day 5. For example, assuming that Monday is considered "Day 1", an exemplary twice weekly dosing schedule entails administering a dose on Monday and Thursday. A variety of different doses may be administered according to a twice weekly dosing schedule. In some embodiments, a dose of at least 585 mg, e.g., between 585 mg and 900 mg, is administered subcutaneously twice weekly. For example, the dose may be between 585 mg and 630 mg, between 630 mg and 675 mg, between 675 mg and 720 mg, between 720 mg and 765 mg, between 765 mg and 810 mg, between 810 mg and 855 mg, or between 855 mg and 900 mg. In some embodiments, a dose of at least 900 mg, e.g., between 900 mg and 945 mg, is administered subcutaneously twice weekly. In certain embodiments of particular interest, a dose of at least 945 mg, e.g., between 945 mg and 990 mg, is administered subcutaneously twice weekly. In certain embodiments of particular interest, a dose of at least 990 mg, e.g., between 990 mg and 1350 mg, e.g., between 990 mg and 1215 mg or between 1215 mg and 1305 mg or between 1305 mg and 1350 mg, is administered subcutaneously twice weekly. For example, the dose may be between 990 mg and 1035 mg, between 1035 mg and 1080 mg, between 1080 mg and 1125 mg, between 1125 mg and 1170 mg, or between 1170 mg and 1215 mg. In some embodiments, a dose of at least 1215 mg, e.g., between 1215 mg and 1260 mg, is administered subcutaneously twice weekly. In some embodiments, a dose of between 1215 mg and 1395 mg is administered subcutaneously twice weekly. In some embodiments, a dose of at least 1260 mg, e.g., between 1260 mg and 1305 mg, or between 1305 mg and 1350 mg, is administered subcutaneously twice weekly. It is also within the scope of the present disclosure to administer doses of at least 1350 mg twice weekly. For example, in certain embodiments the dose is between 1350 mg and 1395 mg, between 1395 mg and 1440 mg, between 1440 mg and 1485, between 1485 mg and 1530 mg, between 1530 mg and 1575 mg, between 1575 mg and 1620 mg, between 1620 mg and 1665 mg, between 1665 mg and 1710 mg, between 1710 mg and 1755 mg, between 1755 mg and 1800 mg, between 1800 mg and 1925 mg, between 1925 mg and 1970 mg, between 1970 mg and 2015 mg, between 2015 mg and 2060 mg, between 2060 mg and 2105 mg, between 2105 mg and 2150 mg, between 2150 mg and 2195 mg, between 2195 mg and 2240 mg, between 2240 mg and 2285 mg, between 2285 mg and 2330 mg, between 2330 mg and 2375 mg, between 2375 mg and 2420 mg, between 2420 mg and 2465 mg, or between 2465 mg and 2510 mg.

An "every third day" dosing schedule is a dosing schedule in which a compound, e.g., a LACA, e.g., LACA-40, is administered once on every third day but not on the intervening days. For example, a compound may be administered on Days 1, 4, and 7 of a given week, and then on Days 2 and 5 of the following week, in a pattern that repeats each 2 week period. In some embodiments, any of the doses described herein in regard to twice weekly dosing schedules may be administered according to an every third day dosing schedule. In some embodiments, any of the doses described above in regard to twice weekly dosing may be modified for every third day dosing by reducing the dose by between 10% and 20% or between 20% and 30%.

An "every fourth day" dosing schedule is a dosing schedule in which a compound, e.g., a LACA, e.g., LACA-40, is administered on every fourth day but is not administered on the intervening days. For example, assuming the days are numbered consecutively starting on Day 1, the compound may be administered on Days 1, 5, 9, 13, 17, 21, 25, 29, etc. In some embodiments, an every fourth day dosing schedule may utilize any of the doses described herein in regard to twice weekly dosing schedules. In some embodiments, any of the doses described above in regard to twice weekly dosing may be modified for every fourth day dosing by increasing the dose by between 10% and 20% or between 20% and 30%.

An "every fifth day" dosing schedule is a dosing schedule in which a compound, e.g., a LACA, e.g., LACA-40, is administered on every fifth day but is not administered on the intervening days. For example, assuming the days are numbered consecutively starting on Day 1, the compound may be administered on Days 1, 6, 11, 16, 21, 26, 31, etc. In some embodiments, an every fifth day dosing schedule may utilize any of the doses described herein in regard to twice weekly dosing schedules. In some embodiments, any of the doses described herein in regard to twice weekly dosing may be modified for every fourth day dosing by increasing the dose by between 20% and 30%. In some embodiments, any of the doses described herein in regard to twice weekly dosing may be modified for every fourth day dosing by increasing the dose by between 30% and 40%.

An "every sixth day" dosing schedule is a dosing schedule in which a compound, e.g., a LACA, e.g., LACA-40, is administered on every fifth day but is not administered on the intervening days. For example, assuming the days are numbered consecutively starting on Day 1, the compound may be administered on Days 1, 7, 13, 19, 25, 31, etc. In some embodiments, an every sixth day dosing schedule may utilize any of the doses described herein in regard to weekly dosing schedules. In some embodiments, any of the doses described herein in regard to weekly dosing may be modified for every sixth day dosing by decreasing the dose by between 10% and 15%. In some embodiments, any of the doses described herein in regard to weekly dosing may be modified for every sixth day dosing by decreasing the dose by between 15% and 20%.

A once weekly dosing schedule is a dosing schedule in which a compound, e.g., a LACA, e.g., LACA-40, is administered on one day of each week, followed by six days on which the compound is not administered, i.e., the dosing interval is 7 days. For example, a dose may be administered every Monday. Of course any day of the week may be selected as the day on which a dose is to be administered. A variety of different doses may be administered according to a weekly dosing schedule. In some embodiments, a dose of at least 1080 mg, e.g., between 1080 mg and 5040 mg, is administered subcutaneously weekly. In some embodiments the dose is between 1080 mg and 1440 mg. In some embodiments the dose is between 1440 mg and 1800 mg. In some embodiments the dose is between 1800 mg and 2160 mg. In some embodiments of particular interest the dose is at least 2160 mg. For example, in some embodiments the dose is between 2160 mg and 2520 mg. Without wishing to be bound by any theory, a dose of 2160 mg administered subcutaneously weekly is predicted to provide exposure to the LACA that is at least as great as that provided by a 270 mg dose administered subcutaneously daily, while a dose of 2520 mg administered subcutaneously weekly is predicted to provide exposure that is greater than that provided by a 270 mg dose administered subcutaneously daily. In some embodiments the dose is between 2520 mg and 2880 mg. In some embodiments the dose is between 2880 mg and 3240 mg. Without wishing to be bound by any theory, a dose of 2880 mg administered subcutaneously weekly is predicted to provide exposure to the LACA that is at least as great as that provided by a 360 mg dose administered subcutaneously daily, while a dose of 3240 mg administered subcutaneously weekly is predicted to provide exposure that is greater than that provided by a 360 mg dose administered subcutaneously daily. In some embodiments the dose is between 3240 mg and 3600 mg. It is also within the scope of the present disclosure to administer doses of at least 3600 mg once weekly, e.g., doses between 3600 mg and 3960 mg, between 3960 mg and 4320 mg, between 4320 mg and 4680 mg, between 4680 mg and 5040 mg.

In some embodiments, an alternate day, thrice weekly, every third day, twice weekly, every fourth day, every fifth day, every sixth day, or weekly dosing regimen provides a trough plasma concentration of a LACA, e.g., LACA-40, at steady state that is at least 300 µg/ml, e.g., between 300 µg/ml and 325 µg/ml, between 325 µg/ml and 350 µg/ml, between 350 µg/ml and 375 µg/ml between 375 µg/ml and 400 µg/ml, or between 400 µg/ml and 425 µg/ml. In some embodiments, an alternate day, thrice weekly, every third day, twice weekly, every fourth day, every fifth day, every sixth day, or weekly dosing regimen provides a trough plasma concentration of a LACA, e.g., LACA-40, at steady state that is at least 425 µg/ml, e.g., between 425 µg/ml and 450 µg/ml, between 450 µg/ml and 475 µg/ml, between 475 µg/ml and 500 µg/ml, between 500 µg/ml and 525 µg/ml, between 525 µg/ml and 550 µg/ml, or between 550 µg/ml and 575 µg/ml. In some embodiments, an alternate day, thrice weekly, every third day, twice weekly, every fourth day, every fifth day, every sixth day, or weekly dosing regimen provides a trough plasma concentration of a LACA, e.g., LACA-40, at steady state that is at least 575 µg/ml, e.g., between 575 µg/ml and 600 µg/ml, between 600 µg/ml and 625 µg/ml. In some embodiments an alternate day, thrice weekly, every third day, twice weekly, every fourth day, every fifth day, every sixth day, or weekly dosing regimen provides a trough plasma concentration at steady state that is at least 625 µg/ml, e.g., between 625 µg/ml and 650 µg/ml, between 650 µg/ml and 675 µg/ml. In some embodiments, any of the afore-mentioned values may be measured in an individual subject, who may be a healthy subject or may suffer from a complement-mediated disorder. In some embodiments, a value may be a median or mean value as measured in a group of two or more subjects, who may be healthy subjects or may suffer from a complement-mediated disorder.

In some embodiments the ratio of the maximum plasma concentration to the trough plasma concentration (i.e., maximum plasma concentration divided by trough plasma concentration), sometimes referred to as the peak/trough ratio, at steady state, provided by an alternate day, thrice weekly, every third day, twice weekly, every fourth day, every fifth day, every sixth day, or weekly dosing regimen is no more than 1.5. For example, the peak/trough ratio may be between 1.05 and 1.1, between 1.1 and 1.2, between 1.2 and 1.3, between 1.3 and 1.4, or between 1.4 and 1.5. In some embodiments, any of the afore-mentioned ratios may be measured in an individual subject, who may be a healthy subject or may suffer from a complement-mediated disorder. In some embodiments, a value may be a median or mean value as measured in a group of two or more subjects, who may be healthy subjects or may suffer from a complement-mediated disorder.

In some embodiments a LACA, e.g., LACA-40, may be administered at a concentration of between 25 mg/ml and 50 mg/ml, e.g., when administered according to an alternate day, thrice weekly, twice weekly, every third, fourth, fifth, or sixth day, or once weekly dosing regimen. In some embodiments such administration is performed using a pump, e.g., a syringe pump. In some embodiments such administration is performed using an on-body delivery device. In some embodiments a LACA, e.g., LACA-40, may be administered at a concentration of between 50 mg/ml and 75 mg/ml, e.g., when administered according to an alternate day, thrice weekly, twice weekly, every third, fourth, fifth, or sixth day, or once weekly dosing regimen. In some embodiments such administration is performed using a pump, e.g., a syringe pump. In some embodiments such administration is performed using an on-body delivery device. In some embodiments a LACA, e.g., LACA-40, may be administered at a concentration of between 75 mg/ml and 100 mg/ml, e.g., when administered according to an alternate day, thrice weekly, twice weekly, every third, fourth, fifth, or sixth day, or once weekly dosing regimen. In some embodiments such administration is performed using a pump, e.g., a syringe pump. In some embodiments such administration is performed using an on-body delivery device. In some embodiments a LACA, e.g., LACA-40, may be administered at a concentration of between 100 mg/ml and 150 mg/ml, e.g., when administered according to an alternate day, thrice weekly, twice weekly, every third, fourth, fifth, or sixth day, or once weekly dosing regimen. In some embodiments such administration is performed using a pump, e.g., a syringe pump. In some embodiments such administration is performed using an on-body delivery device. Thus, in various embodiments, a LACA, e.g., LACA-40, may be administered according to any of the dosing regimens described herein, e.g., subcutaneously at intervals of 2 days or more, e.g., according to an alternate day, thrice weekly, every third day, twice weekly, every fourth day, every fifth day, every sixth day, or weekly dosing regimen, using any suitable delivery device, e.g., from any of the device suppliers described herein.

The concentration of the LACA composition and the volume administered may be selected to provide a desired dose for weekly, twice weekly, or thrice weekly administration (or for alternate day, every third day, every fourth day, every fifth day, every sixth day administration), e.g., any of the doses described herein. In some embodiments the LACA, e.g., LACA-40, is administered in a volume of between 2 ml and 50 ml, e.g., between 5 ml and 10 ml, between 10 ml and 15 ml, between 15 ml and 20 ml, between 20 ml and 25 ml, between 25 ml and 30 ml, between 30 ml and 35 ml, between 35 ml and 40 ml, between 40 ml and 45 ml, or between 45 ml and 50 ml. It should be understood that such volumes may be used for administration according to other dosing schedules described herein, e.g., for more frequent administration, e.g., daily administration, in certain embodiments. For example, in some embodiments a dose of 270 mg is administered daily SC in a volume of 10 ml at 27 mg/ml or in a volume of 5 ml at 54 mg/ml. In some embodiments a dose of 360 mg is administered daily SC in a volume of 10 ml at 36 mg/ml or in a volume of 5 ml at 72 mg/ml. Typically the volume is not greater than 50 ml, although in certain embodiments a larger volume may be used, e.g., up to 100 ml, or more, particularly if doses greater than about 5000 mg are administered.

It will be understood that a subject treated according to any of the dosing regimens described herein (e.g., dosing regimens featuring daily, every other day, thrice weekly, every third day, twice weekly, every fourth day, every fifth day, every sixth day, or weekly administration) may suffer from any of the complement-mediated disorders described herein. For example, in some embodiments the subject suffers from a complement-mediated hemolytic anemia such as PNH or a hemolytic anemia that involves antibodies that bind to RBCs, leading to complement-mediated lysis, such as warm antibody autoimmune hemolytic anemia or cold agglutinin disease. In some embodiments the subject suffers from myasthenia gravis. In some embodiments the subject suffers from neuromyelitis optica. In some embodiments the subject suffers from a complement-mediated disorder that affects the kidney, such as C3 glomerulopathy or IgA nephropathy.

In some aspects, a unit dose of a LACA, e.g., LACA-40, may contain any of the amounts described herein as useful for a daily, alternate day, thrice weekly, twice weekly, every third, fourth, fifth, or sixth day, or once weekly dosing regimen. In some embodiments the unit dose is more than 540 mg, e.g., at least 541 mg, e.g., at least 545 mg. The unit dose may contain an amount within any of the ranges described herein, or any particular value within said range. In some embodiments, described herein is a container, cartridge, syringe, or drug delivery device comprising such a unit dose.

In some embodiments, treatment with compstatin analog, e.g., a LACA, by subcutaneous administration or other parenteral administration route, e.g., according to any of the dosing regimens and/or using any of the doses or administration devices described herein may be continued for any period of time, e.g., indefinitely. In some embodiments, a patient may be treated with a short course of treatment (e.g., for up to 1 week, 2 weeks, or up to 1, 2, 3, 4, 5, 6 months). In some embodiments, such a short course of treatment may be sufficient to modify the course of a disorder (e.g., PNH, AIHA, NMO, myasthenia gravis, COPD, asthma, idiopathic pulmonary fibrosis, vasculitis, pemphigoid, nephropathy), such that a prolonged remission (e.g., as evidenced by absence of flare-ups or exacerbations) is sustained with intermittent treatment, i.e., the LACA is allowed to wash out of the body between treatment courses. In some embodiments a subject may be treated with a short course once or twice a year, every two years, etc. In some embodiments, a short course of treatment may modify the course of a disorder (e.g., PNH, AIHA, NMO, myasthenia gravis, COPD, asthma, idiopathic pulmonary fibrosis, vasculitis, pemphigoid, nephropathy), such that a prolonged remission or cure is achieved without further treatment. Without wishing to be bound by any theory, a short course of treatment with a compstatin analog, e.g., a LACA, may be sufficient to disrupt a cycle that perpetuates an immune response against cells or tissues (e.g., components thereof such as proteins or lipids) that are a target of immune system attack in a complement-mediated disorder. In some embodiments, for example, a short course of treatment with a LACA may be sufficient to disrupt a cycle that perpetuates an immune response against cells or tissues in the bone marrow (e.g., hematopoietic stem cells) (e.g., in a patient with PNH), nervous system (e.g., nerve cells, glial cells) (e.g., in a patient with NMO or myasthenia gravis), circulatory system (e.g., endothelial cells, red blood cells) (e.g., in a patient with a vasculitis), respiratory system (e.g., in a patient with COPD, asthma, or idiopathic pulmonary fibrosis), integumentary system (e.g., in a patient with pemphigoid).

In some aspects, described herein are various doses, dosing regimens, compositions and methods of use for treating a patient in need of treatment for a complement-mediated eye disorder that affects the posterior segment of the eye, e.g., the retina, by intravitreal (IVT) administration of a LACA. In some embodiments, the eye disorder is AMD, e.g., advanced AMD (geographic atrophy (GA) or neovascular AMD), diabetic retinopathy, glaucoma, or uveitis.

In some embodiments a dose for intravitreal injection of a LACA comprising two compstatin analog moieties and a PEG having a molecular weight of about 40 kD is 5 mg-20 mg. In some embodiments the dose is 10 mg. In some embodiments the dose is 10 mg, 11 mg, 12 mg, 13 mg, 14 mg, 15 mg, 16 mg, 17 mg, 18 mg, 19 mg, or 20 mg. In certain particular embodiments the dose is 15 mg. In some embodiments, any of the afore-mentioned doses is administered by intravitreal injection in a volume of between 90 and 110 microliters, e.g., in a volume of 100 microliters. In some embodiments, any of the afore-mentioned doses is administered by intravitreal injection) using a 27, 28, 29, or 30 gauge needle. In a Phase 1b clinical trial, it was found that doses of up to 20 mg (i.e., 5 mg, 10 mg, and 20 mg) in a volume of 100 microliters administered by intravitreal injection using a 29 gauge needle were well tolerated by patients with AMD. In certain embodiments a combination of dose and needle gauge that allows administration by IVT injection in 10 seconds or less is selected. In certain embodiments a combination of dose and needle that allows administration of the dose by IVT injection in 5-6 seconds, or less, is used. It was found that a dose of 15 mg in a volume of 100 microliters (150 mg/ml) results in a composition that has a favorable viscosity for administration by intravitreal injection in 5-6 seconds or less via a thin wall 27 gauge needle.

In certain embodiments a dose of a composition comprising a LACA is administered by IVT injection in a volume greater than 100 microliters. For example, a volume of 100-110 microliters, 110-125 microliters, or 125-150 microliters may be used. Such larger volumes may permit administration of a higher dose as compared with a 100 microliter injection volume, without an increase in time required to deliver the dose and/or without requiring use of a lower gauge (wider diameter) needle. Such increase in total dose may be proportional to the increased volume. For example, an increase in dose volume of 50% would allow an increase of 50% in amount of LACA administered without an increase in time required to deliver the dose and/or without requiring use of a lower gauge needle.

In some embodiments a dose of a composition comprising a LACA is administered by ocular administration (e.g., IVT injection) once a month, every 6 weeks, or every 2 months (i.e., every other month). In some embodiments a dose of a composition comprising a LACA is administered by IVT injection every 3 months, every 4 months, every 5 months, or every 6 months, or less frequently, e.g., every 9 months, every year). Thus in some embodiments a patient may receive between 1 and 6 injections per year, typically at approximately equal intervals. In some embodiments a patient is initially treated with monthly injections (e.g., for the first 3-6 months or the first 6-12 months), followed by less frequent administration (e.g., every 2, 3, 4, 5, or 6 months, or less frequently, e.g., every 9 months, every year).

In some embodiments, treatment with a LACA by IVT injection according to any of the afore-mentioned dosing regimens may be continued indefinitely. In some embodiments, a patient may be treated with a short course of treatment (e.g., 1, 2, 3, 4, 5, or 6 IVT injections). In some embodiments, a short course of treatment may be sufficient to halt or substantially halt progression of a disorder (e.g., AMD, e.g., GA or early or intermediate AMD), such that further treatment is not needed. For example, a short course of treatment with a LACA may be sufficient to disrupt a cycle that perpetuates an immune response against the retina or retinal pigment epithelium.

In some embodiments a LACA is administered using a syringe with one or more design features that reduce friction and/or required injection force, such as a relatively short barrel and/or relatively large plunger size.

In experiments performed using LACAs comprising PEGs of different molecular weights, it was determined that a solution of LACA comprising a lower molecular weight PEG (e.g., 10 kD-30 kD) has reduced viscosity as compared to a LACA comprising a 40 kD PEG at the same concentration in mg/ml. Lower viscosity can facilitate use of a higher gauge number needle (e.g., 29 gauge rather than 27 gauge). In some embodiments a LACA comprising a polymer, e.g., a PEG, having a molecular weight below 40 kD may be administered using a needle with a smaller inner diameter and/or higher gauge number than a LACA comprising a polymer, e.g., a PEG, having a molecular weight of 40 kD or more. In some embodiments a LACA comprising a polymer, e.g., a PEG, having a molecular weight below 40 kD may be administered at a concentration between 80 mg/ml and 150 mg/ml, e.g., about 100 mg/ml or about 125 mg/ml. In some embodiments a LACA comprising a polymer, e.g., a PEG, having a molecular weight below 40 kD may be administered at a concentration between 150 mg/ml and 250 mg/ml. In some embodiments a LACA comprising a polymer, e.g., a PEG, having a molecular weight below 40 kD (e.g., 10 kD-35 kD) may be administered at a higher concentration than 250 mg/ml, e.g., up to 300 mg/ml, 300 mg/ml-400 mg/ml, 400 mg/ml-500 mg/ml, or more.

In some embodiments, a LACA comprising a CRM (e.g., a PEG, POZ, polypeptide, or other polymer) having a molecular weight below about 40 kD (e.g., 10 kD-35 kD) and a specified number of compstatin analog moieties (e.g., 1, 2, 3, 4) may be administered at about the same dose in terms of moles as any of the amounts described above in regard to a LACA comprising a CRM having a molecular weight of about 40 kD, resulting in a lower dose by weight yet containing about the same number of compstatin analog moieties. Administering a lower total amount of compound per dose (by weight) may permit a reduced dosing volume. A reduced dosing volume may allow a reduced number of injections (e.g., a single daily injection instead of two daily injections in some embodiments) and/or may afford a reduced injection time (length of time to administer an individual dose). A lower total dose (by weight) may permit use of a lower concentration (by weight) of compound in a given volume, resulting in reduced viscosity, allowing use of a needle with a smaller inner diameter and/or shorter injection time. In some embodiments, a LACA comprising a CRM (e.g., a PEG, POZ, polypeptide, or other polymer) having a molecular weight below about 40 kD (e.g., 10 kD-30 kD) and a specified number of compstatin analog moieties (e.g., 1, 2, 3, 4) may be administered at a higher molar dose than a LACA comprising a CRM having a molecular weight of about 40 kD, resulting in administration of a greater number of compstatin analog moieties per dose. In some embodiments the molar dose may be up to 1.2, 1.5, 2.0, 2.5, 3.0, 3.5, 4.0, 4.5, or 5-fold greater depending, e.g., on the molecular weight of the CRM.

In some embodiments, a LACA comprising a CRM (e.g., a PEG, POZ, polypeptide, or other polymer) having a molecular weight below about 40 kD (e.g., 10 kD-35 kD) and a specified number of compstatin analog moieties (e.g., 1, 2, 3, 4) may be administered at a lower dose (by weight) per unit time (e.g., lower daily dose, lower weekly dose, lower monthly dose, etc.), about the same dose per unit time, or a higher dose per unit time than a dose described above in regard to a LACA comprising a CRM having a molecular weight of about 40 kD. In some embodiments, it is contemplated that a dose (by weight), of a LACA comprising a CRM having a molecular weight below about 40 kD (e.g., 10 kD-30 kD) may be lower or higher by a factor of up to about 3 (e.g., about 1.1, 1.2, 1.5, 2.0, 2.5, 3.0) relative to a daily dose of a LACA comprising a 40 kD CRM.

The invention encompasses administration of a compstatin analog in combination with additional therapy. Such additional therapy may include administration of any agent(s) used in the art or potentially useful for treating a subject suffering from the disease. For example, in some embodiments a LACA, cell-reactive, or targeted compstatin analog is administered in combination with a C5 inhibitor (e.g., eculizumab or any of the other C5 inhibitors mentioned herein or known in the art) to a patient, e.g., a patient with PNH or any of the other complement-mediated disorders mentioned herein. In some embodiments a LACA, cell-reactive, or targeted compstatin analog is administered in combination with an anti-vascular endothelial growth factor (VEGF) agent to a subject with wet AMD. Anti-VEGF agents include antibodies that bind to VEGF such as ranibizumab (Lucentis) and bevacizumab (Avastin), polypeptides comprising a soluble portion of VEGF receptor such as aflibercept (Eylea, also known as VEGF-Trap).

When two or more therapies (e.g., compounds or compositions) are used or administered "in combination" with each other, they may be given at the same time, within overlapping time periods, or sequentially (e.g., separated by up to 2 weeks in time, or more, e.g., separated by up to about 4, 6, 8, or 12 weeks in time), in various embodiments of the invention. They may be administered via the same route or different routes. In some embodiments, the compounds or compositions are administered within 48 hours of each other. In some embodiments, a compstatin analog can be given prior to or after administration of the additional compound(s), e.g., sufficiently close in time that the compstatin analog and additional compound(s) are present at useful levels within the body at least once. In some embodiments, the compounds or compositions are administered sufficiently close together in time such that no more than 90% of the earlier administered composition has been metabolized to inactive metabolites or eliminated, e.g., excreted, from the body, at the time the second compound or composition is administered.

In some embodiments, a composition that includes both the cell-reactive compstatin analog, or long-acting or targeted compstatin analog and additional compound(s) is administered.

In some embodiments a subject who is treated or is to be treated with a compstatin analog using, e.g., inhaled administration or parenteral administration via, e.g., subcutaneous, intramuscular, or intravenous injection, is vaccinated against one or more pathogens. For example, the subject may receive a vaccine against *Neisseria meningitidis, Haemophilus influenzae* and/or *Streptococcus pneumoniae*. In some embodiments a subject is vaccinated against all three of these microorganisms. In some embodiments, a subject may receive the vaccine at least 1, 2, 3, 4, 5, or 6 weeks prior to the first dose of a compstatin analog. The subject may receive one or more additional vaccine doses if appropriate.

In some embodiments a subject who is treated or is to be treated with a compstatin analog using, e.g., inhaled administration or parenteral administration via, e.g., subcutaneous, intramuscular, or intravenous injection, may receive an antibiotic expected to be effective in preventing or limiting infection by one or more pathogens, e.g., *Neisseria meningitidis, Haemophilus influenzae* and/or *Streptococcus pneumoniae*. In some embodiments the subject may receive an antibiotic prophylactically. Prophylactic administration may begin before the subject receives the first dose of a compstatin analog, or at any time thereafter. Those of ordinary skill in the art are aware of suitable antibiotics. For example, a

EXEMPLIFICATION

Example 1

Development of PEGylated Compstatin Analogs that Retain Substantial Complement Inhibiting Activity A compstatin analog having the amino acid sequence of the compstatin analog of SEQ ID NO: 28, but incorporating an AEEAc-Lys moiety located C-terminal to the Thr residue of SEQ ID NO: 28 for purposes of subsequent conjugation of an NHS ester activated PEG to the amino group of the Lys side chain was synthesized. The compound was synthesized using standard methods. Briefly, amino acids (including AEEAc) were obtained as Fmoc-protected amino acids, in which the α-amino group of each amino acid was protected with Fmoc. Side chain functional groups were also blocked with various appropriate protective groups. Synthesis was accomplished following the solid phase methodology described by Merrifield (J. Amer. Chem. Soc. 85, 2149 (1963)). Chain assembly was performed on solid phase, at the conclusion of which the N-terminus was acetylated; the peptide was then cleaved from the solid phase and simultaneously deprotected via acidolysis using TFA and amidated. The linear peptide was then oxidized and purified. The resulting compstatin analog is represented as follows Ac-Ile-Cys*-Val-(1Me)Trp-Gln-Asp-Trp-Gly-Ala-His-Arg-Cys*-Thr-AEEAc-Lys-NH2 (SEQ ID NO: 51), abbreviated as CA28-AEEAc-Lys. Note that for purposes of brevity, the N-terminal acetyl group and C-terminal amino groups are omitted in this abbreviation. Monofunctional, linear NHS-ester activated PEGs with molecular weights of 30 kD and 40 kD (NOF America Corp. White Plains, N.Y., Cat. No. SUNBRIGHT® ME-300GS and Cat. No. SUNBRIGHT® ME-400GS), respectively, were coupled to the lysine side chain of CA28-AEEAc-Lys, resulting in long-acting compstatin analogs represented as follows: CA28-AEEAc-Lys-(PEG30k) and CA28-AEEAc-Lys-(PEG40k), and purified. Note that the term after the term "PEG" and preceding the letter "k" represents the molecular weight of the PEG moiety in kilodaltons, and the "k" is an abbreviation for kD). CA28-AEEAc-Lys-(PEG30k) is also referred to as CA28-1. CA28-AEEAc-Lys-(PEG40k) is also referred to as CA28-2.

Inhibitory activity of the synthesized compounds was assessed by measuring the effect of the compounds on complement activation via the classical pathway using a standard complement inhibition assay. The protocol measures C3b deposition in an ELISA format. C3b deposition monitored using this method is generated through complement activated by the classical pathway. Briefly, 96-well plates are coated with BSA. Human plasma, chicken ovalbumin (OVA), polyclonal anti-OVA antibodies and compound being tested (referred to as "drug") are added and incubated, followed by addition of Anti-human C3 HRP-conjugated antibody. After an additional incubation, substrate is added and signal detected. Details of the protocol are as follows:

Protocol for Classical Complement Inhibition Assay
Materials:
  Ninety-six well plate (polystyrene plate, Thermo Scientific, 9205)
  Chicken OVA (Sigma A5503-5G)
  Rabbit anti-chicken OVA (Abcam ab1221)
  Blocking buffer (Startingblock buffer, Thermo Scientific 37538)
  Veronal Buffer (5× concentration, Lonza 12-624E)
  Human plasma (collected with Lepirudin at 50 ug/ml final concentration)
  Goat anti-human C3 HRP-conjugated Ab (MP Biomedicals, 55237)
  Tween-20 Wash Buffer (0.05% Tween 20-PBS buffer)
  TMB (Peroxidase substrate, BD 555214)—1:1 mixture of BD 51-2607KC and 51-2606KC.
  1M $H_2SO_4$
Protocol:
1. Add 100 ul/well of 1% chicken OVA (in PBS)
2. Incubate overnight @4° C. or room temperature for 1-2 hr.
3. Remove by shaking and tapping the plate.
4. Block by adding 200 ul of blocking buffer
5. Incubate for 1 h at room temp
6. Remove by shaking and tapping the plate
7. Add 100 ul of 1:1000 dilution of Polyclonal anti-chicken OVA in blocking buffer
8. Incubate for 1 h at room temp
9. Wash twice with wash buffer
10. Add 50 ul $VB^{++}$ to wells #2 to 12
11. Add 100 ul of starting drug dilution (2× in $VB^{++}$) to well 1.
12. Serially dilute (1:2) the drug from wells 1 to 10 as follow
   a. Take 50 ul of solution from the originating well
   b. Add this to the next well
   c. Mix by pipetting several times
   d. Repeat up to well #10
Note: from well #10 remove 50 ul and discard.
13. Add 50 ul of 2× plasma (1:37.5 dilution of original plasma) dilution to wells 1 to 11
14. Incubate for 1 h
15. Wash with wash buffer
16. Add 100 ul of 1/1000 dilution of anti-C3-HRP Ab in blocking buffer
17. Incubate for 1 h
18. Wash with wash buffer
19. Add 100 ul of TMB to all wells
20. Incubate for 5-10 min in dark
21. Add 50 ul 1M $H_2SO_4$
22. Read the plate at 450 nm $VB^{++}$
Formula:

| | |
|---|---|
| Barbital | 5 mM |
| NaCl | 72.5 mM |
| $MgCl_2$ | 0.5 mM |
| $CaCl_2$ | 0.15 mM |
| PH | 7.4 |

Stock Solutions:

| Veronal Buffer (5X) | | | |
|---|---|---|---|
| | Prod # | MW | For 500 ml |
| 9 mM Sodium Barbitone | Sigma B0500 | 206.17 | 927 mg |
| 15.5 mM diethylbarbituric acid | Sigma B0375 | 184.19 | 1.42 grams |

| | Prod # | MW | For 50 ml |
|---|---|---|---|
| | Mg—Cl2 (200X) | | |
| 100 mM $MgCl_2$—$6H_2O$ | Sigma M0250 | 203.30 | 1.00 gram |
| | $CaCl_2$ (500x) | | |
| 75 mM $CaCl_2$ | Sigma C7902 | 147.01 | 551.28 mg |

To Prepare 50 ml of Working Buffer:
  Weight 210 mg NaCl
  Add 10 ml of 5× VB
  Add 100 ul of $CaCl_2$ (500×)
  Add 250 ul MgCl (200×)
  Adjust volume to 50 ml with $H_2O$
  Adjust pH to 7.4

Data was analyzed using GraphPad Prism5 software. Data sets from each experiment were normalized to percent activation compared to the 100% activation control corresponding to the well to which no compound is added. Drug concentration values (X values) were transformed to their logarithms, and percent activation (Pa) (Y values) was transformed to percent inhibition (Pi) using the following formula Pi=100−Pa (Yi=100−Ya). The percent inhibition was plotted against the drug concentration and the resulting data set was fit to a sigmoidal-dose response function [Y=Bottom+(Top−Bottom)/(1+10 ((Log EC−X)))]. $IC_{50}$ values were obtained from the fit parameters.

Results are presented in FIG. 1, and the $IC_{50}$ values are shown in Table 2 (in Example 2). As indicated, CA28-1 and CA28-2 displayed about 30% of the activity of CA28 on a molar basis.

Example 2

Figure 2:
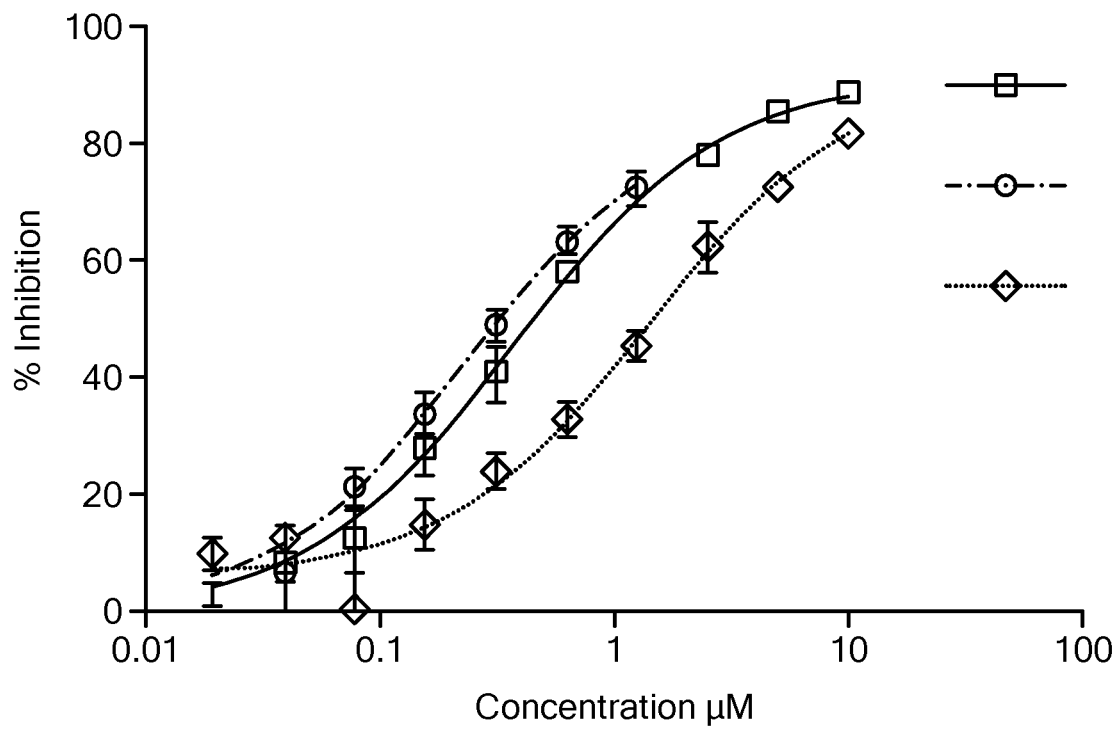
FIG. 2 is a plot that shows percent complement activation inhibiting activity of CA28 and long-acting compstatin analogs CA28-2 and CA28-3, as a function of compound concentration (μM). CA28 (squares, light gray), CA28-2 (diamonds, black), CA28-3 (circles, dark gray). CA28-3 is a compound that contains multiple peptide moieties. Although the activity per peptide moiety is less than the activity of an individual CA28 molecule, the total activity of CA28-3 exceeds the activity of CA28 on a molar basis.

Development of Long-Acting Compstatin Analogs that Demonstrate Increased Molar Activity Eight-arm NHS-ester activated PEG with molecular weight of 40 kD (NOF America Corp. White Plains, N.Y., Cat. No. SUNBRIGHT® HGEO-400GS; chemical formula: hexaglycerol octa(succinimidyloxyglutaryl) polyoxyethylene) was coupled to the lysine side chain of CA28-AEEAc-Lys, resulting in long-acting compstatin analogs represented as follows: $(CA28-AEEAc)_8$-PEG40k, also referred to as CA28-3. Complement inhibiting activity of CA28-3 was tested using the assay described in Example 1. Results are plotted in FIG. 1 and IC50 value is listed in Table 2, both as a function of CA28 concentration. The concentration of CA28 was calculated using the extinction coefficient of CA28 at 283 nm (10208.14 L·mol-1·cm-1). Based on other analysis (UV absorption vs. mass of material, and elemental CHN % analysis) it was concluded that there are 7.5 CA28 moieties per molecule of CA28-3. Thus, the activity of CA28-3 on a molar basis is 7.5-fold higher than shown in FIG. 1 and Table 2. Thus, the IC50 value in Table 2 is 7.5-fold higher than the actual IC50 of CA28-3 on a molar basis. The IC50 of CA28-3 on a molar basis is calculated as about 0.26 (lower than that of the parent compound CA28). FIG. 2 shows percent complement activation inhibiting activity of CA28 and long-acting compstatin analogs CA28-2 and CA28-3, as a function of CA28-3 concentration (μM), i.e., the activity of CA28-3 has been corrected to account for the fact that the compound contains 7.5 CA28 moieties. On a molar basis, the complement inhibiting activity of CA28-3 exceeds that of CA28.

TABLE 2

|  | CA28 | CA28-1 | CA28-2 | CA28-3 |
|---|---|---|---|---|
| IC50 | 0.3909 | 1.264 | 1.288 | 1.927 |

The solubility of CA28-1, CD28-2, and CA28-3 in water with or without a variety of buffer substances and/or excipients was observed to exceed that of the parent compound CA28.

Example 3

Long-Acting Compstatin Analogs that Demonstrate Dramatically Increased Plasma Half-Life and Cmax This Example describes determination of pharmacokinetic parameters of long-acting compstatin analogs CA28-2 and CA28-3 following administration to Cynomolgus monkeys.

Dosing and Sample Collection

CA28-2 and CA28-3 were administered at time 0 via intravenous injection into female Cynomolgus monkeys (three per group, 2-5 yrs old, 2.9-3.5 kg). Compounds were administered at 50 mg/kg in 5% dextrose in water at a concentration of 25 mg/ml. Blood specimens (~1 mL each) were collected from the femoral vein at the following timepoints: Pre-dose, 5 min, 15 min, 30 min, 1 hour (h), 4 h, 8 h, 24 h, 48 h, 96 h (4 days), and 192 h (8 days) post dose. Specimens were collected via direct venipuncture and placed into a red top serum tube containing no anticoagulant, and kept at room temperature for at least 30 minutes. Blood samples were centrifuged at a temperature of 4° C. at 3000×g for 5 minutes. Samples were maintained chilled throughout processing. Serum samples were collected after centrifugation and placed into sample tubes. Samples were stored in a freezer set to maintain −60° C. to −80° C. All animals showed normal activity throughout the study. No compound-related abnormalities were noted in the animals throughout the study.

Sample Analysis. Plasma samples obtained as described above were analyzed by LC/MS/MS using the following methods to determine the concentration of compound: 50 μL of sample was mixed with internal standard (CA28-AEEAc-Arg) and then 100 μL of 1 M $NH_4OAc$, pH 3.5 with HO Ac was added and mixed. Then 250 μL of acetonitrile was added and mixed. The sample was centrifuged and supernatant poured into another tube and dried. The sample was reconstituted and injected onto the LC/MS/MS system. Mobile phase A was 5 mM $NH_4OAc$ with 0.1% FA and Mobile Phase B was 90:10 (ACN:50 mM $NH_4OAc$) with 0.1% FA. The LC column was the Intrada WP-RP 2×150 mm, 3μ. Quantitation was on an Applied Biosystems API-4000 triple quadrupole mass spectrometer operated in positive ion mode. In-source collision induced dissociation (CID) was used to fragment the compound in the mass spectrometer source and the m/z 144 ion was mass selected in Q1, fragmented, and the m/z 77 ion mass selected in Q3 and detected. Data was processed using Analyst 1.4.2 software.

Results. The serum concentrations in micrograms/ml of CA28-2 and CA28-3 at each time point are presented in Table 3 below. Data for each of 3 monkeys that received the indicated compound are shown. Average values and standard deviations are readily calculated. There was notable consistency between animals. CA28 are historical data obtained in a previous study in which CA28 was administered intravenously to Cynomolgus monkeys. In that study, CA28 was detected in samples using HPLC.

TABLE 3

| | Serum Concentration in ug/mL | | | | | | |
|---|---|---|---|---|---|---|---|
| Time (days) | CA28-3(8-arm 40 k PEG) (50 mg/kg) | | | CA28 (200 mg/kg) | CA28-2 (linear 40 k PEG) (50 mg/kg) | | |
| 0.0035 | 1600 | 1330 | 1300 | | 1460 | 1660 | 1610 |
| 0.01 | 1600 | 1220 | 1480 | | 1360 | 1430 | 1530 |
| 0.02 | 1510 | 1170 | 1270 | 34 | 1310 | 1510 | 1500 |
| 0.042 | 1270 | 1030 | 1220 | 17 | 1290 | 1340 | 1540 |
| 0.167 | 926 | 893 | 934 | 9 | 1200 | 1210 | 1390 |
| 0.333 | 797 | 714 | 792 | 5 | | 1190 | 1180 |
| 1 | 621 | 479 | 558 | 1.5 | 927 | 853 | 881 |
| 2 | 384 | 355 | 360 | | 612 | 733 | 760 |
| 4 | 280 | 252 | 262 | | 461 | 458 | 424 |
| 8 | 151 | 136 | 136 | | 268 | 282 | 293 |

Results for each compound were averaged and are plotted in FIG. 3. A remarkable increase in half-life and Cmax was observed for both CA28-2 and CA28-3 compared to CA28. The terminal half-lives of both CA28-2 and CA28-3 were around 4-4.5 days. Based on these data, it is expected that intravenous administration at approximately 1-2 week dosing intervals will provide sustained levels of compound and effectively inhibit complement activation in human subjects, though shorter or longer dosing intervals may be used.

Example 4

Long-Acting Compstatin Analog Comprising HSA as a Clearance Reducing Moiety

Figure 5:
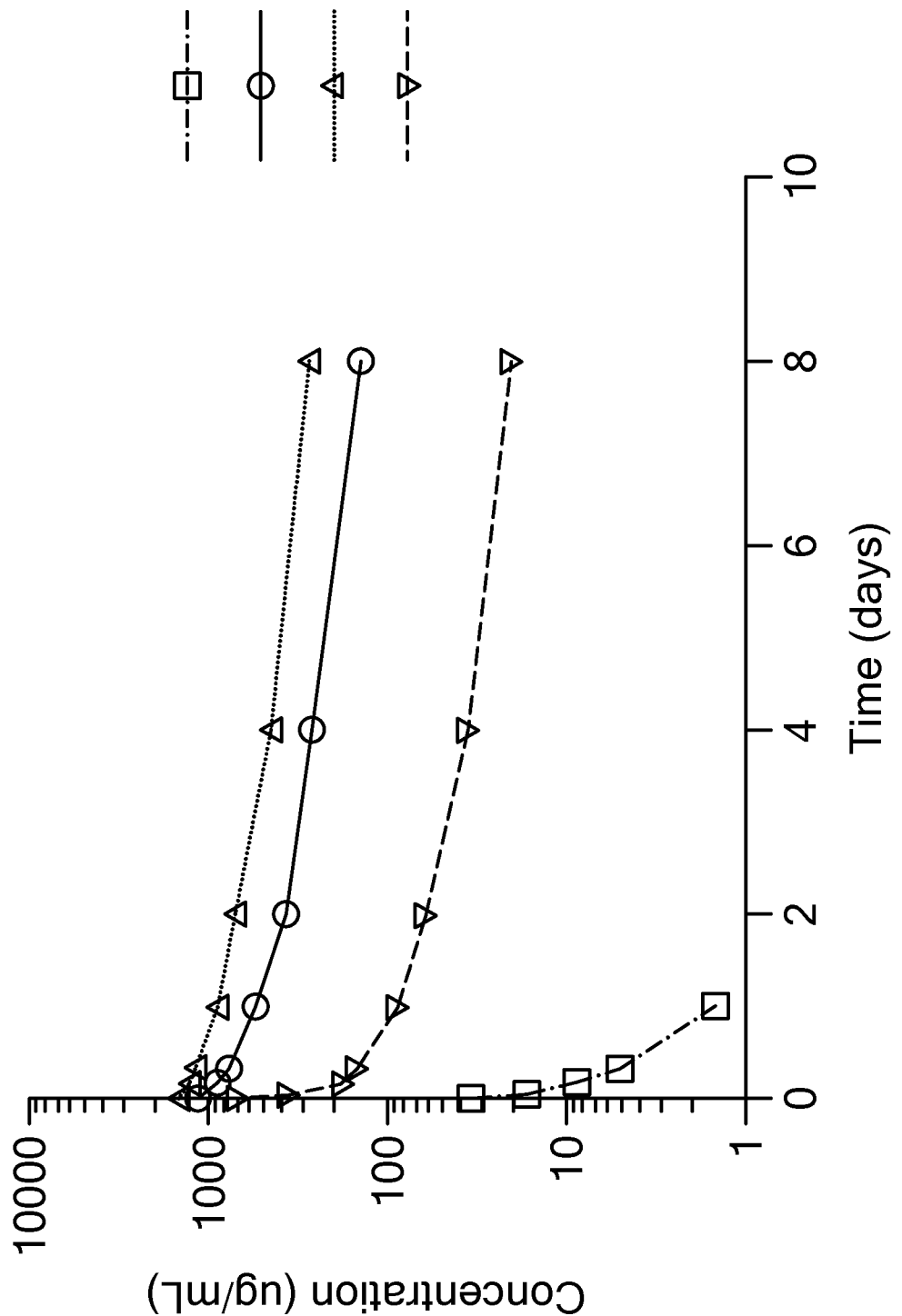
FIG. 5 is a plot that shows concentrations versus time of CA28 and long-acting compstatin analogs CA28-2, CA28-3, and CA28-4 in Cynomolgus monkeys following a single intravenous injection. CA28 was administered at 200 mg/kg. CA28-2, CA28-3, and CA28-4 were each administered at 50 mg/kg. In calculating the doses for these experiments the administered CA28-2 and CA28-3 substance was assumed to consist 80% of active compound w/w based on dry weight. However, during the sample analysis, the standard curve assumed a 100% of active compound w/w based on dry weight. Thus, the values for Cmax overestimate the Cmax that would be achieved if these compounds had been administered at the indicated doses on a dry mass basis, by an estimated 30%. CA28 (squares, light gray), CA28-2 (triangles, black), CA28-3 (circles, dark gray), CA28-4 (inverted triangles, black).

Side chain lysines of human serum albumin (HSA) were converted to thiols using 2-iminothiolane and reacted with a compstatin analog comprising a maleimide as a reactive functional group: Ac-Ile-Cys*-Val-Trp(l-Me)-Gln-Asp-Trp-Gly-Ala-His-Arg-Cys*-Thr-AEEAc-Lys-(C(=O)—(CH$_2$)$_5$-Mal)-NH$_2$ (SEQ ID NO: 68). The resulting long-acting compstatin analog (CA28-4) was tested in vitro for complement inhibiting activity (FIG. 4) as described in Example 1 and in vivo for pharmacokinetic properties as described in Example 3. Pharmacokinetic parameters of CA28-4 following administration to Cynomolgus monkeys were determined as described in preceding example. Results are shown in FIG. 5 (along with results for CA28, CA28-1, CA28-2, and CA28-3). PK data for CA28-4 are presented in Table 4.

TABLE 4

| Time (hr) | Serum Concentration in ug/mL | | |
|---|---|---|---|
| 0.0035 | 1790.0 | 1445.00 | 1395.00 |
| 0.0100 | 1195.0 | 915.50 | 885.00 |
| 0.0200 | 900.0 | 504.50 | 553.50 |
| 0.0420 | 449.0 | 267.50 | 295.00 |
| 0.1670 | 194.0 | 164.00 | 158.50 |
| 0.3330 | 150.0 | 163.00 | 119.50 |
| 1.0000 | 97.2 | 86.00 | 78.05 |
| 2.0000 | 73.3 | 51.55 | 57.40 |
| 4.0000 | 43.1 | 29.20 | 34.15 |
| 8.0000 | 24.1 | 16.25 | 20.00 |

Example 5

Synthesis and Activity of PEG-Based Compstatin Analogs Using Different NHS-Activated PEGs A compstatin analog having the amino acid sequence of the compstatin analog of SEQ ID NO: 28, but incorporating an AEEAc-Lys moiety located C-terminal to the Thr residue of SEQ ID NO: 28 for purposes of subsequent conjugation of an NHS ester activated PEG to the amino group of the Lys side chain was synthesized as described in Example 1. The resulting compstatin analog is represented as follows Ac-Ile-Cys*-Val-(1Me)Trp-Gln-Asp-Trp-Gly-Ala-His-Arg-Cys*-Thr-AEEAc-Lys-NH$_2$ (SEQ ID NO: 51), abbreviated as CA28-AEEAc-Lys. Monofunctional, linear monomethoxy-NHS-activated ester/carbonate PEGs with molecular weights of 40 kD and differing in terms of the NHS carboxylate attachment chemistry (NOF America Corp. White Plains, N.Y., Cat. Nos. SUNBRIGHT® ME-400CS, SUNBRIGHT® ME-400GS, SUNBRIGHT® ME-400HS, SUNBRIGHT® ME-400TS) were coupled to the lysine side chain of CA28-AEEAc-Lys via an amide bond. (The Lys reside is Lys 15 since the AEEAc linker contains an amino acid residue.) All compounds were acetylated on the N-terminus, amidated on the C-terminus, and cyclized via a disulfide bond between Cys2 and Cys12. (The acetylation, amidation, and cyclization were performed prior to coupling to the PEG.) The compounds were prepared as trifluoroacetate salts and were purified. The compounds are represented as shown in the following table (Table 5). The letters CS, GS, HS, and TS represent the different linker moieties between the PEG moiety and the NHS moiety as indicated in further detail in Table 5. It will be understood that various names and abbreviations for each compound may be used interchangeably. Note that CA28-2 (see Example 1) is the same as CA28-2GS.

TABLE 5

PEG-Based Compstatin Analogs Containing One Compstatin Analog Moiety

| Compound Abbreviation and ID | Compound Name*,† | Activated PEG |
|---|---|---|
| CA28-2CS | CA28-AEEAc-LysCS = CA28-AEEAc-Lys(mPEG40K-succinyl) | PEG40K: Methoxy-PEG-CO(CH$_2$)$_2$COO-NHS (NOF Sunbright 400CS) Chemical Name: α-Succinimidyloxysuccinyl-ω-methoxy, polyoxyethylene CAS#: 78274-32-5 |
| CA28-2GS (also referred to as CA28-2) | CA28-AEEAc-LysGS CA28-AEEAc-Lys(mPEG40K-pentanedioyl) | PEG40K: Methoxy-PEG-CO(CH$_2$)$_3$COO-NHS (NOF Sunbright 400GS) Chemical Name: α-Succinimidyloxyglutaryl-ω-methoxy, polyoxyethylene CAS#: 111575-54-3 |
| CA28-2HS | CA28-AEEAc-LysHS CA28-AEEAc-Lys(mPEG40K-hexanoyl) | PEG40K: Methoxy-PEG-(CH$_2$)$_5$COO-NHS (NOF Sunbright 400HS) Chemical Name: Poly(oxy-1,2-ethanediyl), α-methyl-ω-{2-[(2,5-dioxo-1-pyrrolidinyl)oxy]-6-oxohexyloxy}- |

TABLE 5-continued

PEG-Based Compstatin Analogs Containing One Compstatin Analog Moiety

| Compound Abbreviation and ID | Compound Name*,† | Activated PEG |
|---|---|---|
| CA28-2TS | CA28-AEEAc-LysTS CA28-AEEAc-Lys(mPEG40K-carbonyl) | PEG40K: Methoxy-PEG-COO-NHS (NOF Sunbright 400TS) Chemical Name: α-Succinimidyl carbonyl-ω-methoxy, polyoxyethylene CAS# 135649-01-3 |

Figure 6:
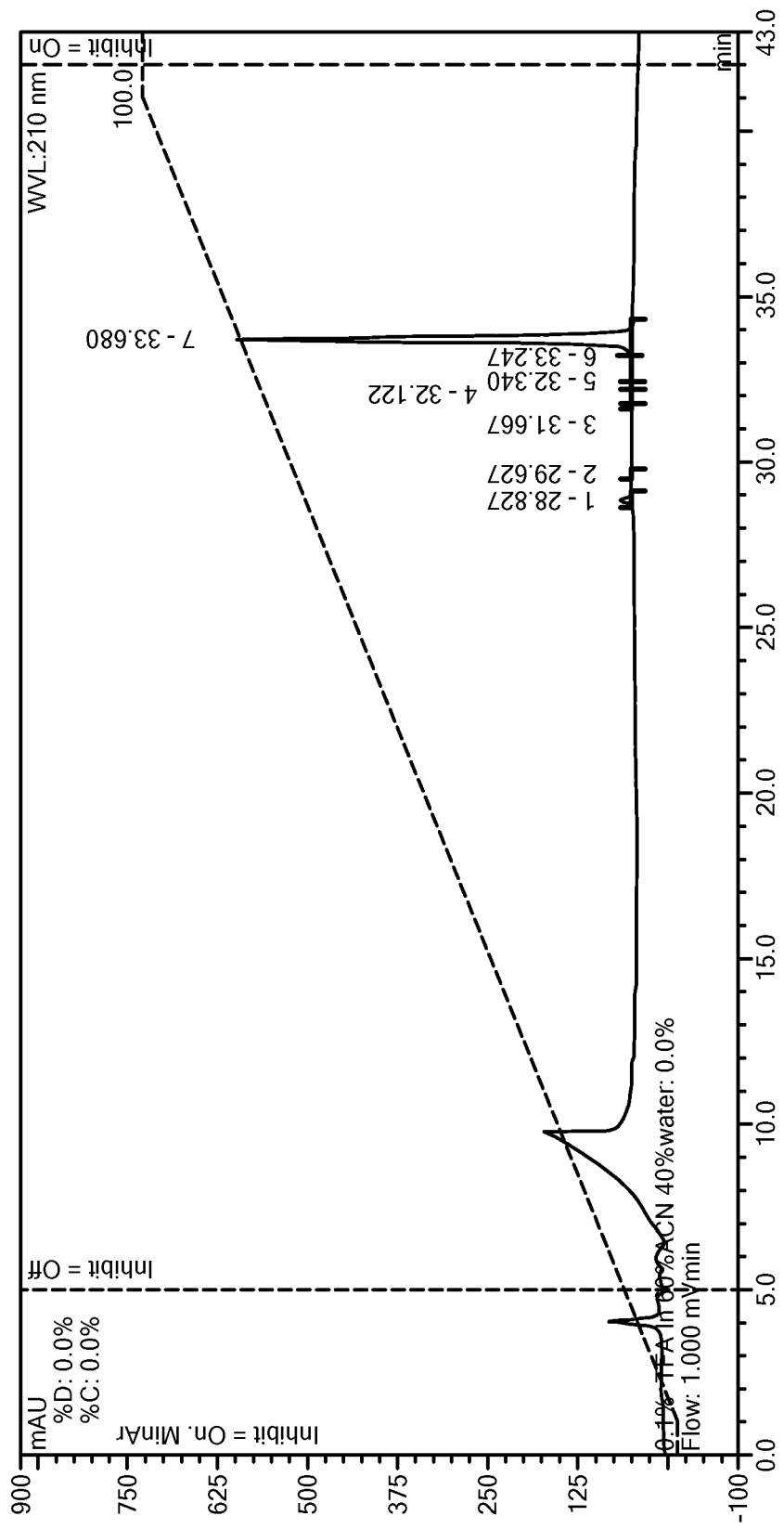
FIG. 6 is a representative chromatogram showing ultraviolet (UV) detection of a PEG-based long-acting compstatin analog using reverse phase HPLC. The peak with a retention time (RT) of 33.68 minutes represents the PEGylated compstatin analog and had a relative area of 96%.

*AEEAc = 8 = Amino-3,6-dioxa-octanoyl
†Compounds were prepared as trifluoroacetate salts but other counterions could be used Compounds were analyzed by reverse phase HPLC. FIG. 6 shows a representative chromatogram for one of the compounds. A VariTide RPC column was used. Eluent A was 0.1% TFA in water; Eluent B was 0.1% TFA in 50% CAN/40% water. Flow rate was 1.000 ml/min with a gradient of 0% B to 100% B over 40 minutes. The peak with a retention time of 33.68 minutes represents the PEGylated compound and has a relative area of 96.50%.

Figure 7:
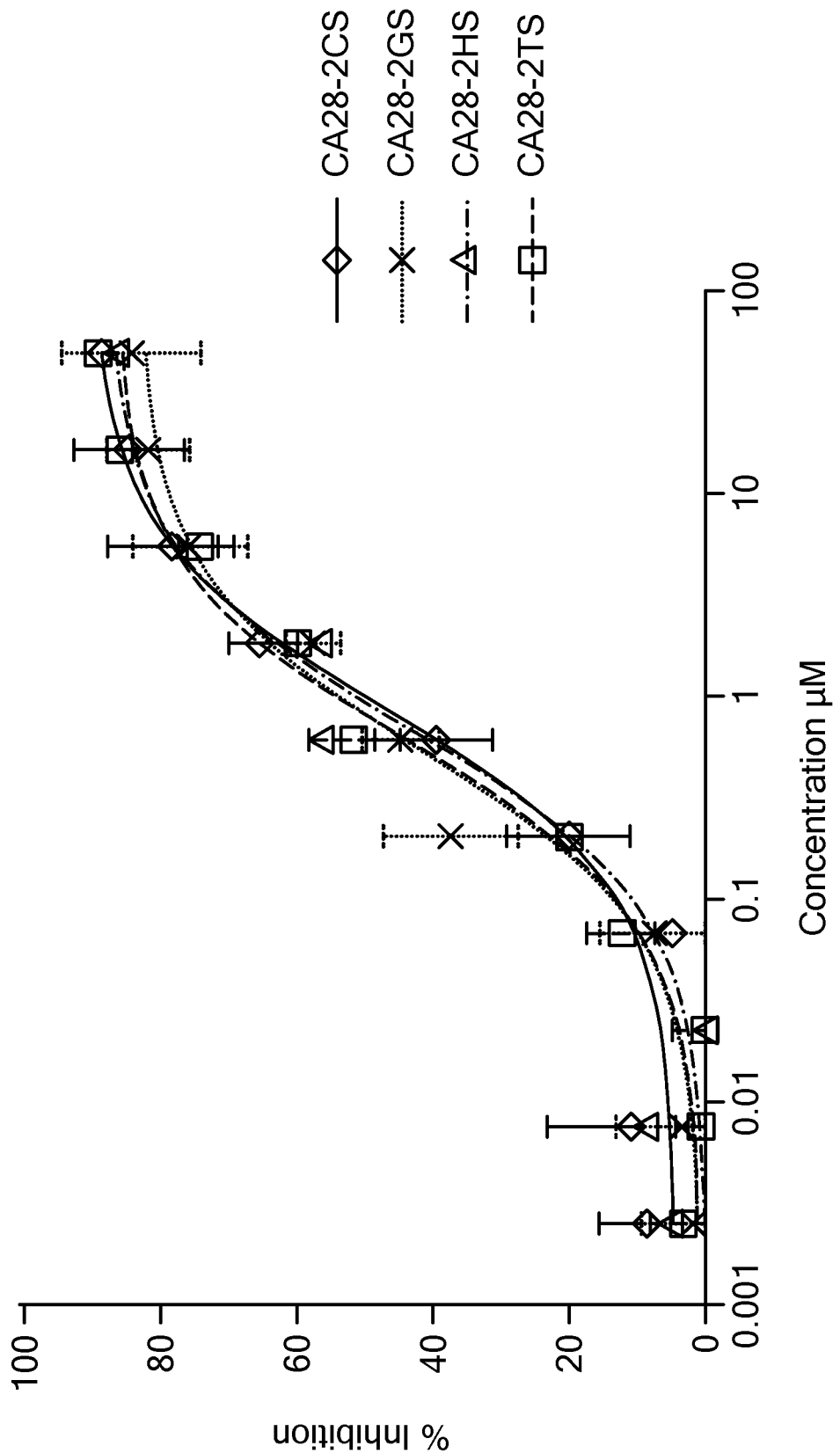
FIG. 7 is a plot that shows percent complement activation inhibiting activity of CA28 and long-acting compstatin analogs CA28-2CS, CA28-2GS, CA28-2HS, and CA28-2TS as a function of compound concentration (μM). CA28-2CS (diamonds, red); CA28-2GS (crosses, blue); CA28-2HS (triangles, green); CA28-2TS (squares, black).

Inhibitory activity of the compounds was assessed by measuring the effect of the compounds on complement activation via the classical pathway using a standard complement inhibition assay as described in Example 1. Results are plotted in FIG. 7. These results represent a combination of two separate experiments. The compounds showed notably similar complement inhibiting activity.

Example 6

Synthesis and Activity of Bifunctionalized PEG-Based Compstatin Analogs

Bifunctional, linear monomethoxy-NHS-activated ester/carbonate PEGs with molecular weights of 40 kD and differing in terms of the NHS carboxylate attachment chemistry were obtained from NOF America Corp. (White Plains, N.Y.). The activated PEGs were coupled to the lysine side chain of CA28-AEEAc-Lys via an amide bond such that two CA28-AEEAc-Lys moieties were coupled to each PEG chain. All compounds were acetylated on the N-terminus and amidated on the C-terminus of the CA28-AEEAc-Lys moieties, and cyclized via a disulfide bond between Cys2 and Cys12. (The acetylation, amidation, and cyclization were performed prior to coupling to the PEG.) The compounds were prepared as acetate salts and were purified. The compounds are represented as shown in the following table (Table 6).

TABLE 6

Bifunctionalized PEG-Based Compstatin Analogs

| Compound Abbreviation and ID | Compound Name*,† | Activated PEG |
|---|---|---|
| CA28-2CS-BF | CA28-AEEAc-LysCS = CA28-AEEAc-Lys(mPEG40K-succinyl) | PEG40K: NHS-OCO(CH$_2$)$_2$COO-PEG-CO(CH$_2$)$_2$COO-NHS Chemical Name: α-Succinimidyloxysuccinyl-ω-succinimidyloxysuccinyloxy, polyoxyethylene CAS#: 85419-94-9 |
| CA28-2GS-BF | CA28-AEEAc-LysGS CA28-AEEAc-Lys(mPEG40K-pentanedioyl) | PEG40K: NHS-OCO(CH$_2$)$_3$COO-PEG-CO(CH$_2$)$_3$COO-NHS Chemical Name: α-Succinimidyloxyglutaryl-ω-succinimidyloxyglutaryloxy-, polyoxyethylene CAS#: 154467-38-6 |
| CA28-2HS-BF | CA28-AEEAc-LysHS CA28-AEEAc-Lys(mPEG40K-hexanoyl) | PEG40K: NHS-OCO(CH$_2$)$_5$O-PEG-(CH$_2$)$_5$COO-NHS Chemical Name: α-[6-[(2,5-dioxo-1-pyrrolidinyl)oxy]-6-oxohexyl]-ω-[6-[(2,5-dioxo-1-pyrrolidinyl)oxy]-6-oxohexyloxy]-, polyoxyethylene |
| CA28-2TS-BF | CA28-AEEAc-LysTS CA28-AEEAc-Lys(mPEG40K-carbonyl) | PEG40K: NHS-OCO-PEG-COO-NHS Chemical Name: α-Succinimidyl carbonyl-ω-Succinimidyl carbonyl, polyoxyethylene |

Figure 8:
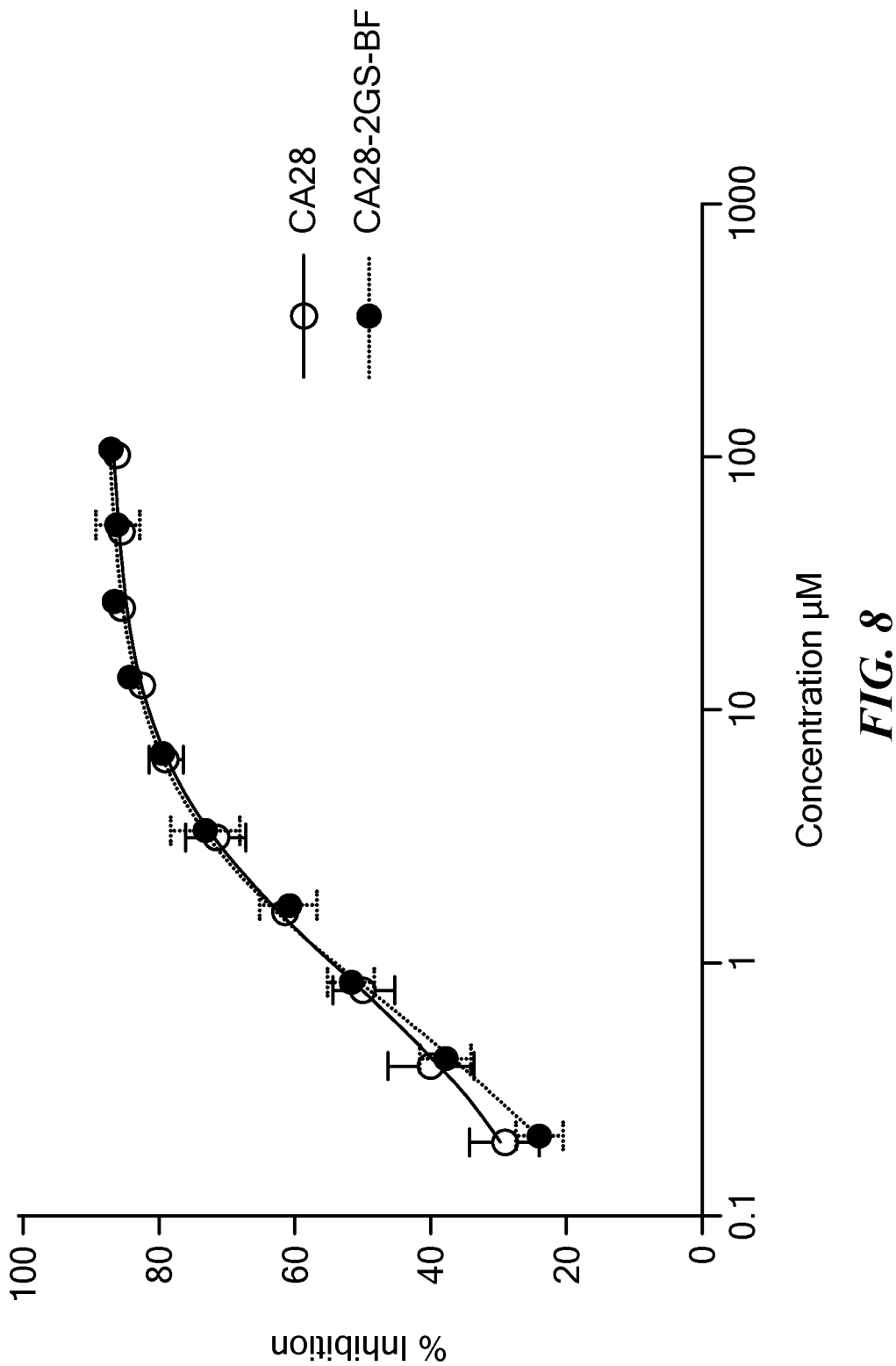
FIG. 8 is a plot that shows percent complement activation inhibiting activity of CA28 and bifunctionalized long-acting compstatin analog, CA28-2GS-BF, as a function of compound concentration (micromoles). CA28 (open circles, blue); CA28-2G-SBF (filled circles, red)

*AEEAc = 8 = Amino-3,6-dioxa-octanoyl
†Compounds were prepared as acetate salts but other counterions could be used Inhibitory activity of CA28-2GS-BF was assessed by measuring the effect of the compound on complement activation via the classical pathway using a standard complement inhibition assay as described in Example 1 and analyzed as described in Example 1. Results are plotted in FIG. 8. As described above, CA28-2GS-BF contains two compstatin analog moieties per molecule. Although the activity per compstatin analog moiety of CA28-2GS-BF is less than the activity of an individual CA28 molecule, the activity of the two compounds on a molar basis is virtually identical over a broad range of concentrations.

Example 7

Subcutaneous Administration of Bifunctionalized PEG-Based Compstatin Analog

This Example describes determination of pharmacokinetic parameters of long-acting compstatin analog CA28-2GS-BF following administration to Cynomolgus monkeys either via a single intravenous (IV) injection or with repeated (once daily) subcutaneous administration for seven days.

Dosing and Sample Collection CA28-2GS was administered at time 0 via intravenous injection or via repeat subcutaneous injection (daily, for seven days) into male Cynomolgus monkeys. Six non-naïve male Cynomolgus monkeys, age 1-5 years, ranging in weight from 4.6 to 5.3 kilograms, were used in this study (three per group). The animals were healthy at the start of the trial seven days. The study was not blinded. Animals were supplied with water ad libitum and a commercial diet twice daily prior to initiation of the study. Food was supplied to the animals per facility SOP prior to the study. Animals were not fasted. Animals were dosed via intravenous and subcutaneous administration at time 0 on the appropriate day. A size 22 gauge needle was used for the subcutaneous administration. The compound was administered at 50 mg/kg in 5% dextrose in water at a concentration of 25 mg/ml. Blood specimens (~1 mL each) were collected from the femoral vein at the following timepoints: Day 1: Pre-dose, 5 min, 15 min, 30 min, 1 hour (h), 4 h, 8 h. Days 2-9:0 min. Day 16: Final sample based on Day 1 dosing. Each blood sample (~1.0 mL) was collected from the monkey's femoral or saphenous vein via direct venipuncture and placed into a red top serum tube containing no anticoagulant, and kept at room temperature for at least 30 minutes. Blood samples were centrifuged at a temperature of 4° C. at 3000×g for 5 minutes. Samples were maintained chilled throughout processing. Serum samples were collected after centrifugation and placed into sample tubes. Samples were stored in a freezer set to maintain −60° C. to −80° C. Serum samples and leftover dosing solutions were shipped frozen on dry ice for analysis.

The site of each subcutaneous administration was observed to see how fast the injection volume was absorbed and also to see if the formulation left behind a lump or fully went away. The dose sites were observed at each collection timepoint and in the afternoon of days 2-7. All doses were absorbed during the duration of the study. Based on the observations it is estimated that doses were absorbed within fifteen minutes after administration. All animals showed normal activity throughout the study. No compound-related abnormalities were noted in the animals throughout the study.

Sample Analysis. Plasma samples obtained as described above were analyzed by LC/MS/MS leveraging CID (collision induced degradation) similarly to the method described in Example 3.

Figure 9:
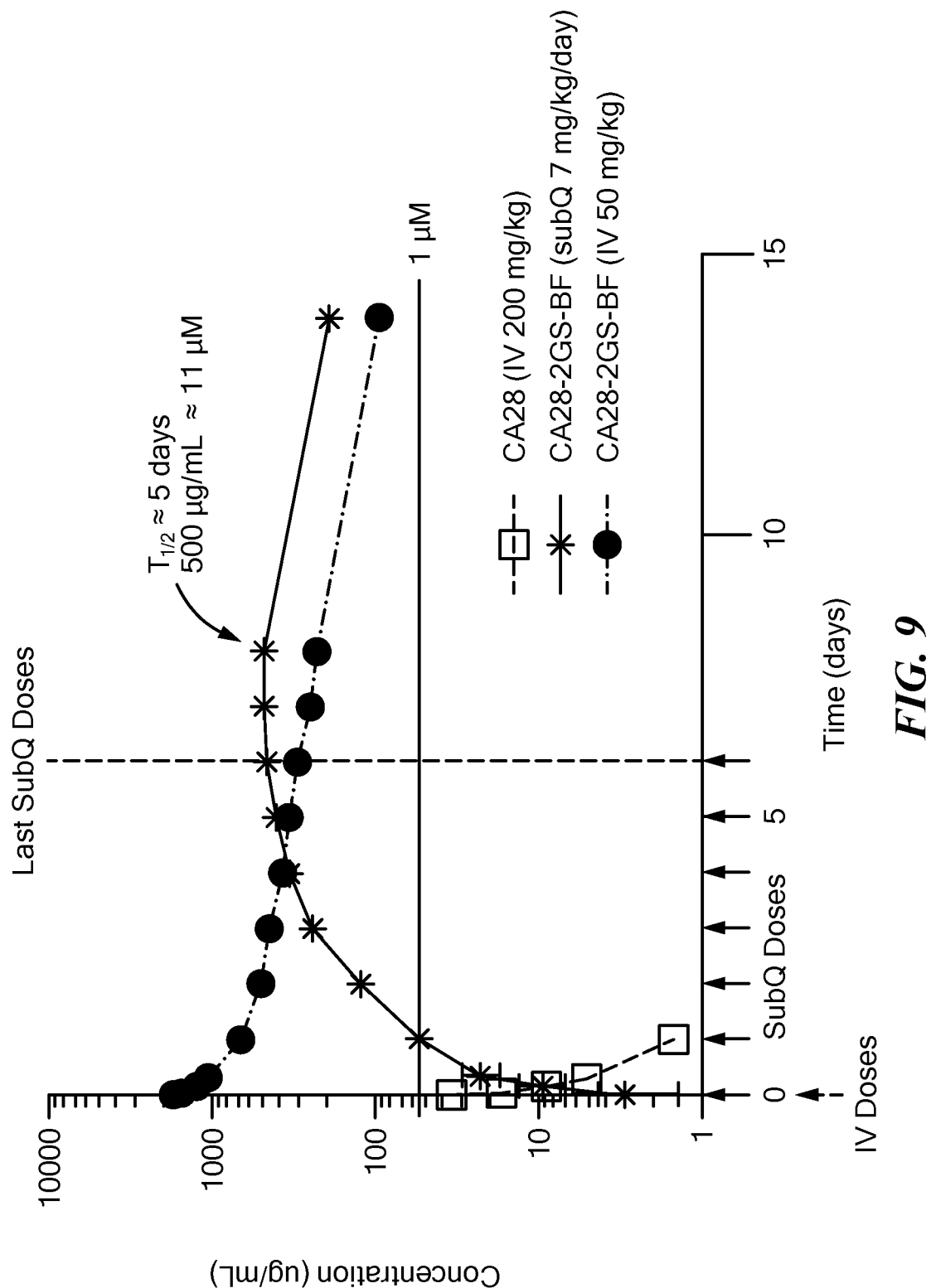
FIG. 9 is a plot that shows the plasma concentration versus time of CA28 and long-acting compstatin analog CA28-2GS-BF in Cynomolgus monkeys following either a single intravenous injection (CA28 (squares, red) and CA28-2GS-BF (circles, purple) or when administered by subcutaneous injection once daily for 7 days (CA28-2GS-BF only, asterisks, blue). CA28-2GSBF was administered at 25 mg/ml. Dosing volume was 2 ml/kg for IV and 0.28 ml/kg/day for the subcutaneous administration. Data for CA28 was from a different experiment in which the compound was also in 5% dextrose and was formulated as 20 mg/ml with a 10 ml/kg dosing volume. The vehicle in each case was 5% dextrose in water.

Results. Serum concentration vs time for CA28-2GS-BF when administered IV or subcutaneously as described above are plotted in FIG. 9, The data points represent all PEGylated CA28 compound detected. CA28 data shown on FIG. 9 are historical data obtained in a previous study in which CA28 was administered intravenously to Cynomolgus monkeys. In that study, CA28 was detected in samples using HPLC.

A peak serum concentration of 500 μg/ml (11 μM) was achieved by subcutaneous administration of CA28-2GS-BF. The terminal half-life of CA28-2GS-BF was approximately 5 days when administered either IV or subcutaneously. Results are summarized in the tables below:

TABLE 7

Summary of Study Sample Concentrations for CA28-2GS-BF in Monkey Serum (IV @ 50 mg/kg on Day 0)

| Timepoint | CA28-2GS-BF Conc. (μg/mL) | | |
|---|---|---|---|
| | Animal 1 | Animal 2 | Animal 3 |
| 5 min | 1850 | 1550 | 2030 |
| 15 min | 1760 | 1440 | 2000 |
| 30 min | 1560 | 1380 | 1810 |
| 1 hr | 1650 | 1330 | 1710 |
| 4 hr | 1270 | 1000 | 1510 |
| 8 hr | 1050 | 913 | 1360 |
| Day 2 | 684 | 661 | 711 |
| Day 3 | 541 | 471 | 538 |
| Day 4 | 463 | 417 | 492 |
| Day 5 | 366 | 384 | 389 |
| Day 6 | 346 | 331 | 358 |
| Day 7 | 303 | 306 | 311 |
| Day 8 | 257 | 252 | 259 |
| Day 9 | 217 | 252 | 233 |
| Day 15 | 92.8 | 107 | 95.6 |

TABLE 8

Summary of Study Sample Concentrations for CA28-2GS-BF in Monkey Serum (SQ @ 7 mg/kg/day × 7 days)

| Timepoint | CA28-2GS-BF Conc. (μg/mL) | | |
|---|---|---|---|
| | Animal 1 | Animal 2 | Animal 3 |
| 5 min | 0 | 5.18 | 3.55 |
| 15 min | 0 | 5.57 | 3.47 |
| 30 min | 0 | 4.66 | 3.93 |
| 1 hr | 0 | 5.41 | 3.56 |
| 4 hr | 4.41 | 12.6 | 11.1 |
| 8 hr | 32.0 | 15.3 | 21.5 |
| Day 2 | 54.2 | 56.6 | 53.5 |
| Day 3 | 135 | 117 | 122 |
| Day 4 | 248 | 260 | 234 |
| Day 5 | 398 | 316 | 311 |
| Day 6 | 447 | 391 | 419 |
| Day 7 | 564 | 412 | 448 |
| Day 8 | 591 | 432 | 468 |
| Day 9 | 596 | 423 | 455 |
| Day 15 | 152 | 241 | 199 |

Example 8

Inhibition of Complement-Mediated Lysis of Red Blood Cells from Patients with PNH A modified Ham's test is performed to measure the ability of compstatin analogs to inhibit complement-mediated lysis of red blood cells from patients with PNH in vitro. Complement is activated by acidified serum with added magnesium to lyse the PNH red cells. The incubation is performed for 90 minutes. The read out is flow cytometry for PNH red cells using standard markers. Heat inactivated serum is used as a control (produces no hemolysis). Acidified serum in the absence of added complement inhibitor produces maximum lysis. The experiment is performed with serial two-fold dilutions of compstatin analogs CA28, CA28-2, CA28-2CS, CA28-2CS-BD, CA28-2GS, CA28-2GS-BF, CA28-2HS, CA28-2HS-BF, CA28-2TS, CA28-2GS-BF, and CA28-3.

The concentration of each compound required to fully block hemolysis in vitro is determined. Red blood cells are also stained for C3 fragment deposition using anti-C3 polyclonal antibodies that do not contain any bridge leading to agglutination (e.g., either Ab4214 or Ab14396, both commercially available FITC-conjugated Abeam, Cambridge, United Kingdom) in order to measure the ability of the compounds to inhibit deposition of C3 fragments on PNH red blood cells. Results are compared with those obtained with eculizumab using the same assays.

Example 9

Long-Acting Compstatin Analogs in Patients with PNH

A cohort of subjects diagnosed with PNH is divided into 4 groups. Subjects in Groups 1 and 2 are treated with intravenous administration of CA28-2 or CA28-3, respectively, at a dose of between 5 mg/kg and 20 mg/kg, at time intervals between 1 and 2 weeks. Optionally, treatment is started at more frequent time intervals and then reduced in frequency for maintenance therapy. Subjects in Group 3 are treated with eculizumab according to the recommended dosing regimen. Group 4 serves as a control (no complement inhibitor therapy). Intravascular hemolysis (based on LDH measurement and/or (5 1)Cr labeling of RBCs), reticulocytosis (an indicator of anemia), hematocrit, hemoglobin concentration in the blood, opsonization of red blood cells (deposition of products of C3 activation, such as C3b, on red blood cells, which may be detected using flow cytometry), PNH symptoms, transfusion requirements, thromboembolic events, haemolysis-associated nitric oxide depletion, measures of pulmonary hypertension, quality of life, and survival are monitored over time. Results are compared between groups and with historical data from control PNH patients obtained in clinical trials of eculizumab. An improvement in persistent anemia (e.g., as evidenced by reduced reticulocytosis, reduced evidence of hemolysis, increased hematocrit, increased hemoglobin), improved quality of life, reduced PNH symptoms, reduced transfusion requirements, reduced thromboembolic events, reduced haemolysis-associated nitric oxide depletion, reduced measures of pulmonary hypertension increased quality of life, and/or increased survival, in subjects receiving CA28-2 (Group 1) or CA28-3 (Group 2), as compared with subjects in Group 4 is indicative of efficacy.

Example 10

Long-Acting Compstatin Analogs in Patients with PNH

Example 9 is repeated with the modification that subjects are individuals with PNH who remain transfusion-dependent and/or continue to have a hemoglobin below a cutoff (such as 9.0 g/dL) despite treatment with eculizumab. Results are compared among groups.

Example 11

Long-Acting Compstatin Analogs in Patients with aHUS

A cohort of subjects diagnosed with aHUS is divided into 4 groups. Subjects in groups 1 and 2 are treated with intravenous administration of CA28-2 or CA28-3, respectively, at a dose of between 5 mg/kg and 20 mg/kg, at time intervals between 1 and 2 weeks. Optionally, treatment is started at more frequent time intervals and then reduced in frequency for maintenance therapy. Subjects in Group 3 are treated with eculizumab according to the recommended dosing regimen. Intravascular hemolysis (based on LDH measurement), opsonization of red blood cells (deposition of products of C3 activation, such as C3b, on red blood cells), aHUS symptoms, renal function, need for plasma exchange or dialysis, quality of life, and survival are monitored over time. Results are compared between groups and with historical data from control aHUS patients obtained in clinical trials of eculizumab. Reduced evidence of hemolysis, improved quality of life, reduced aHUS symptoms, reduced need for plasma exchange or dialysis, increased quality of life, and/or increased survival, in subjects receiving CA28-2 or CA28-3, as compared with subjects in group 4 are indicative of efficacy.

Example 12

Examples 8-11 are repeated using CA28-2GS-BF, CA28-2HS, CA28-2HS-BF, CA28-2TS, and CA28-2GS-TS-BF.

Example 14

Examples 9-12 are repeated using CA28-2GS-BF, CA28-2HS, CA28-2HS-BF, CA28-2TS, and CA28-2GS-TS-BF administered daily by subcutaneous injection.

Example 14

Examples 8-11 are repeated using additional long-acting compstatin analogs.

Example 15

Examples 8-11 are repeated using cell-reactive compstatin analogs.

Example 16

Complement Activation Inhibiting Activity of a Long-Acting Compstatin Analog

CA28 and CA28-AEEAc-Lys were synthesized as described above. CA28-2TS-BF was synthesized using a reactive bifunctional PEG of the TS type in terms of the NHS carboxylate attachment chemistry, which was linked to two molecules of CA28-AEEAc-Lys via the primary amine of the lysine side chain. The complement activation inhibitory activity of CA28 and CA28-2TS-BF was assessed by measuring the effect of the compounds on complement activation via the classical pathway and via the alternative pathways using standard complement inhibition assays. The protocol for the classical pathway activation assay is described in Example 1. The protocol for alternative pathway activation also measures C3b deposition in an ELISA format and is described below. C3b deposition monitored using this method is generated through complement activated by the alternative pathway by lipopolysaccharide (LPS). Briefly, 96-well plates are coated with LPS. Compound being tested (referred to as "drug") is added, followed by addition of plasma or serum as a source of complement, and incubated. This is followed by addition of anti-human C3 HRP-conjugated antibody. After an additional incubation, substrate is added and signal detected. Details of the protocol are as follows:

ELISA-Based Assay for Alternative Complement Pathway Activation

Materials:
  Ninety six-well ELISA plate (Corning 3590)
  LPS from *Salmonella typhosa*—Sigma L7136 (40 ug/ml in PBS)
  BSA 1% in PBS—Calbiochem #126626 1/30 dilution
  Veronal Buffer+10 mM $MgCl_2$+10 mM EGTA (VB-Mg EGTA)
  Human plasma (collected with Lepirudin at 5 ug/ml final concentration)
  Anti-human C3 HRP-conjugated Ab (Poli to C3-HRP Ab, Cappel 55237)
  Tween-20 Wash Buffer (0.05% in PBS)
  TMB (Peroxidase substrate)—1:1 mixture of BD 51-2607KC and 51-2606KC.
  3M $H_2SO_4$
  Micro-plate Reader Protocol:
1. Add 50 ul/well of LPS at 40 ug/ml (in PBS)
2. Incubate for 2 hours at room temp
3. Remove by shaking and tapping the plate.
4. Block by adding 200 ul of 1% BSA/PBS
5. Incubate for 1 h at room temp
6. Remove by shaking and tapping the plate
7. Add 50 ul VB-Mg EGTA to wells #2 to 12
8. Add 100 ul of starting drug dilution (2× in VB-Mg EGTA) to well 1.
9. Serially dilute (1:2) the drug from wells 1 to 10 as follow
   a. Take 50 ul of solution from the originating well
   b. Add this to the next well
   c. Mix by pipetting several times
   d. Repeat up to well #10
Note: from well #10 remove 50 ul and discard.
10. Add 50 ul of 2× plasma dilution to wells 1 to 11
11. Incubate for 1 h
12. Wash twice with wash buffer
13. Add 50 ul of 1/1000 dilution of C3-HRP Ab in 1% BSA/PBS
14. Incubate for 1 h
15. Add 100 ul of TMB to all wells
16. Incubate for 30 min
17. Add 50 ul 3M $H_2SO_4$
18. Read the plate at 450 nm Formula for VB Mg EGTA

| | |
|---|---|
| Barbital | 5 mM |
| NaCl | 72.5 mM |
| MgCl2 | 10 mM |
| EGTA | 10 mM |
| pH | 7.3-7.4 |

Stock Solutions:

| Veronal Buffer (5X) | | | |
|---|---|---|---|
| | Prod # | MW | For 500 ml |
| 9 mM Sodium Barbitone | Sigma B0500 | 206.17 | 927 mg |
| 15.5 mM diethylbarbituric acid | Sigma B0375 | 184.19 | 1.42 grams |

| Mg—Cl2 (10X) | | | |
|---|---|---|---|
| | Prod # | MW | For 50 ml |
| 100 mM $MgCl_2$—$6H_2O$ | Sigma M0250 | 203.30 | 1.00 gram |

| EGTA (10x) | | | |
|---|---|---|---|
| | Prod # | MW | For 25 ml |
| 100 mM EGTA | Sigma E8145 | 468.3 | 1.17 grams |

To Prepare 20 ml of Working Buffer:
  Weight 84 mg NaCl
  Add 4 ml of 5× VB
  Add 2 ml of EDTA 10×
  Add 2 ml MgCl 10×
  Adjust volume to 20 ml with $H_2O$
  Adjust pH to 7.4

Results

Figure 10A:
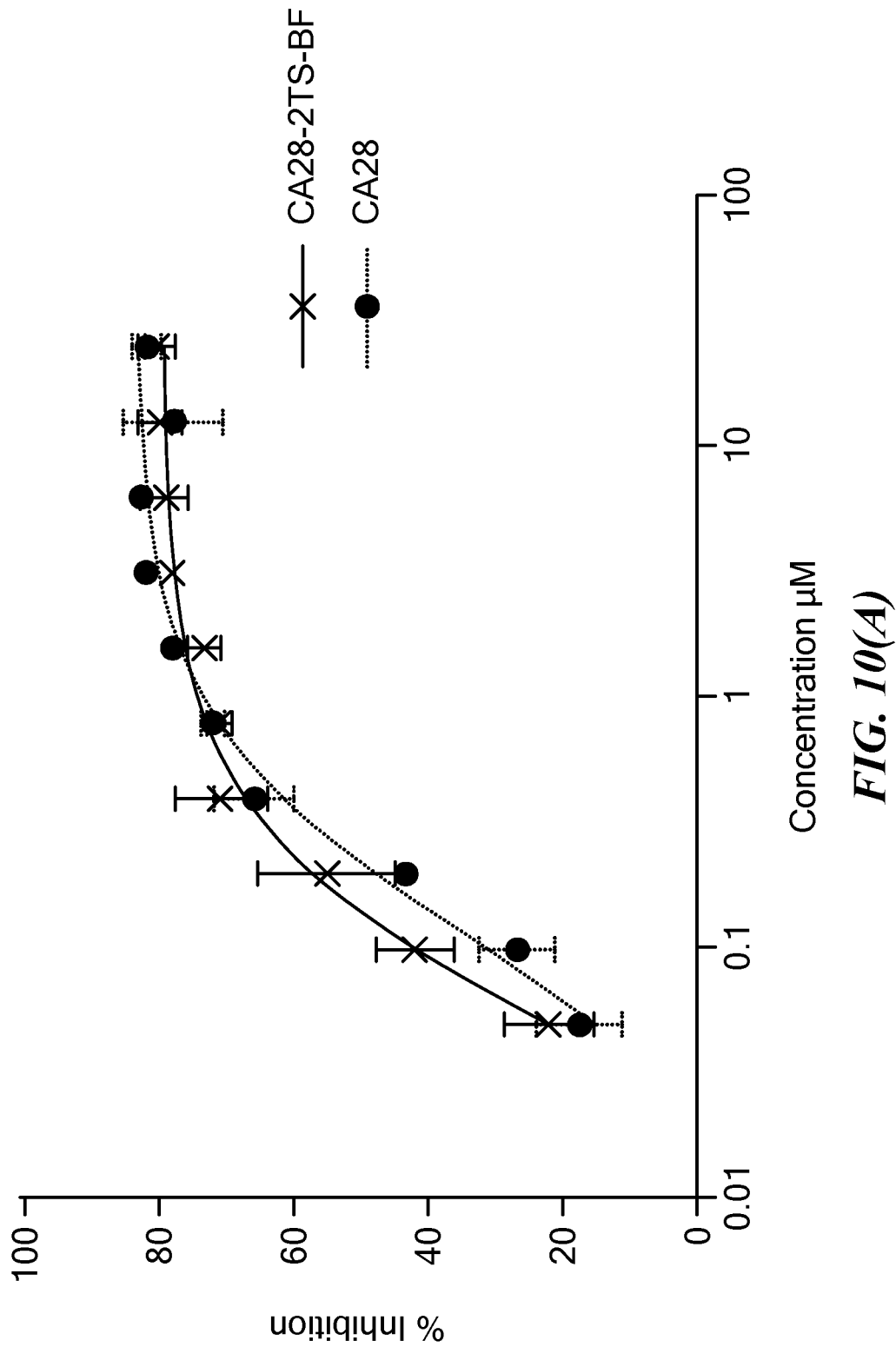
FIGS. 10(A) and 10(B) presents plots that show percent complement activation inhibiting activity of CA28 and bifunctionalized long-acting compstatin analog, CA28-2TS-BF, as a function of compound concentration (micromoles). (A) Classical pathway inhibition by CA28 (circles, red) and CA28-2TS-BF (crosses, blue). (B) Alternative pathway inhibition. CA28 (circles, red) and CA28-2TS-BF (crosses, blue).
Figure 10B:
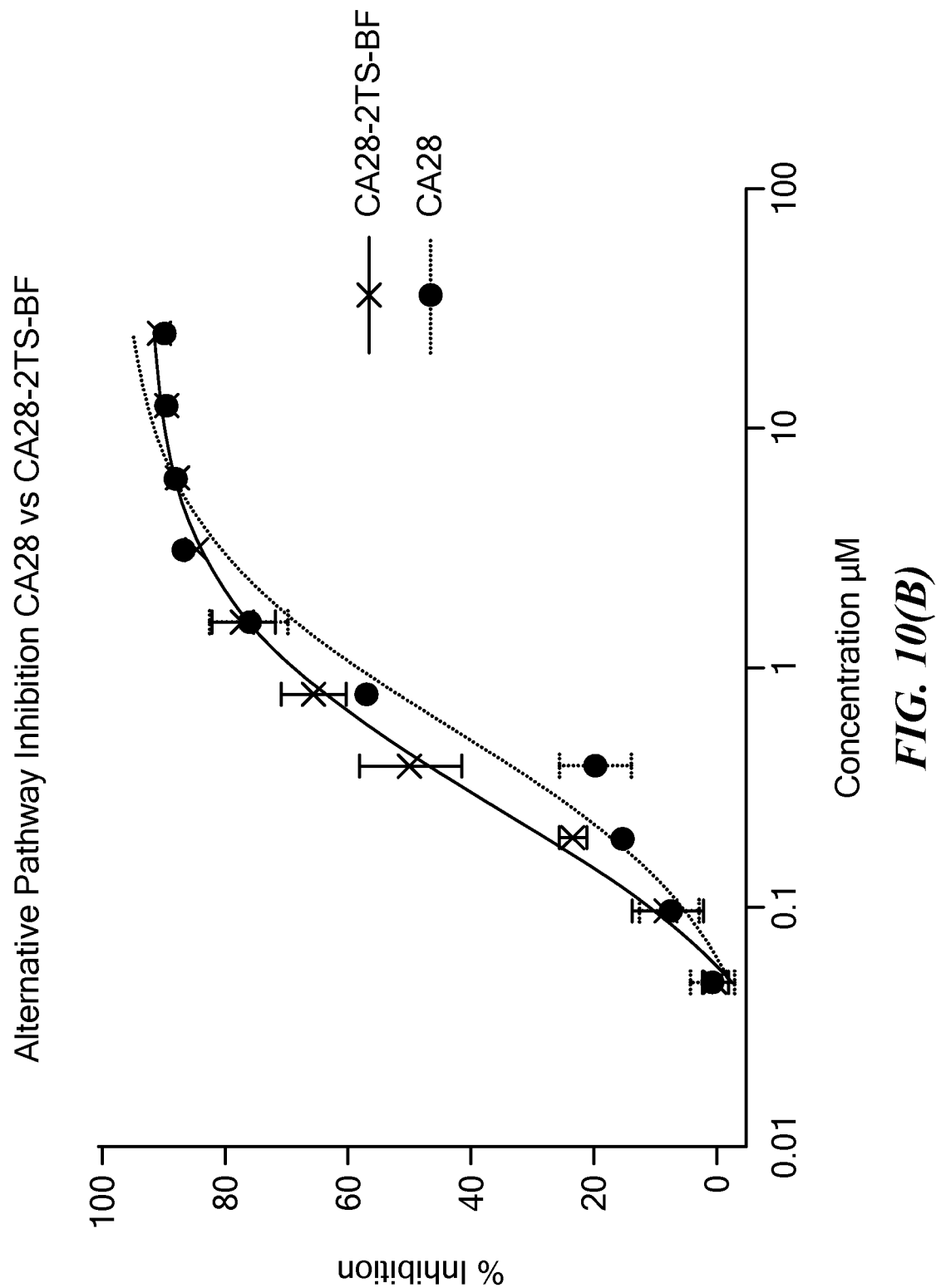
Figure 10C:
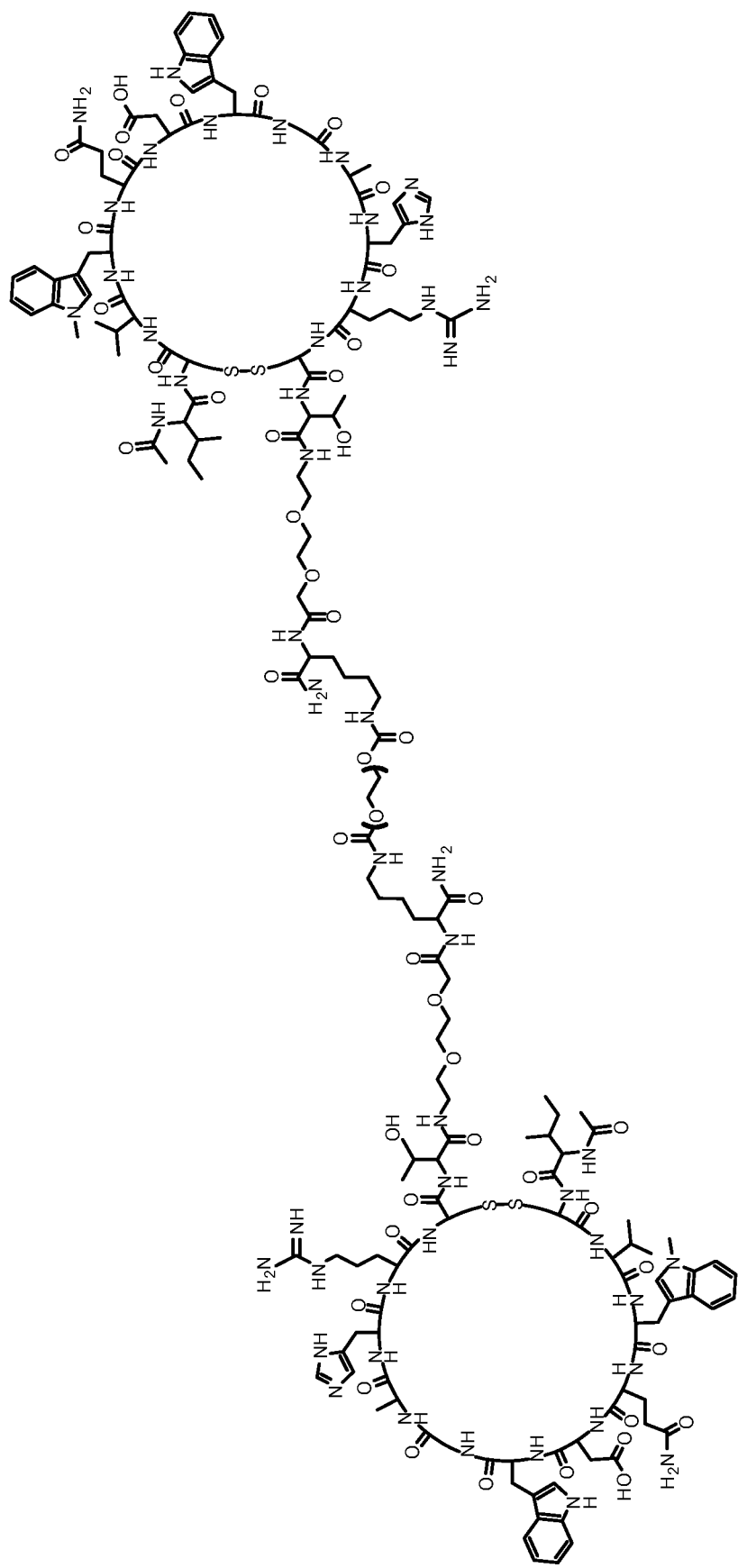
FIG. 10(C) (assuming a PEG moiety of 40 kD) shows the structure of CA28-2TS-BF.

FIG. 10(A) shows percent inhibition of classical complement activation inhibiting activity by CA28 and CA28-2TS-BF as a function of molar concentration of the compounds. FIG. 10(B) shows percent inhibition of alternative complement activation inhibiting activity by CA28 and CA28-2TS-BF as a function of molar concentration of the compounds. Raw data are tabulated in Table 9 below (4 replicates of each condition). Based on the inhibition curves shown in the figures and underlying data, the complement inhibiting activity of CA28-2TS-BF is at least as great as that of CA28 on a molar basis within the experimental error of the assay. These results further confirm the suitability of long-acting compstatin analogs described herein, e.g., for therapeutic purposes.

TABLE 9

| AP Inhibition | | | | | | | | |
|---|---|---|---|---|---|---|---|---|
| Conc uM | CA28 | | | | % Inhibition | | CA28-2TS-BF | |
| 25 | 90.07908 | 89.9353 | 90.65421 | 89.21639 | 90.25768 | 91.10484 | 90.68126 | 90.96365 |
| 12.5 | 88.92883 | 89.21639 | 89.21639 | 90.94177 | 90.11649 | 89.12814 | 89.26933 | 88.56336 |
| 6.25 | 87.05967 | 89.07261 | 86.20992 | 86.64127 | 88.28098 | 87.29263 | 67.43382 | 87.43382 |
| 3.125 | 85.62186 | 87.49101 | 87.49101 | 86.77211 | 84.04518 | 84.46877 | 85.17473 | 85.03353 |
| 1.5625 | 70.81236 | 81.30841 | 82.02732 | 70.38102 | 77.40911 | 69.5023 | 79.80939 | 81.08012 |
| 0.78125 | | 58.01582 | 55.57153 | 57.15313 | 61.73668 | 66.39605 | 72.74974 | 61.3131 |
| 0.390625 | 16.04458 | 12.4371 | 23.65205 | 24.94608 | 56.79492 | 44.9347 | 56.65372 | 40.69691 |
| 0.1953 | 15.02516 | | 15.31273 | 15.31273 | 22.34381 | 23.89693 | 26.01483 | 20.6495 |
| 0.09765 | 2.803741 | 14.30625 | 6.685844 | 5.823158 | 13.87222 | 6.953766 | 10.62479 | 0.3176955 |
| 0.0488 | −1.365921 | 5.679367 | 0.790802 | −2.803734 | 0.6000748 | 2.012009 | 0.3176956 | −2.929749 |
| 0 | −2.803734 | −1.509697 | 1.078362 | 3.235085 | 0.6000748 | 7.094963 | 2.153198 | −0.5294724 |
| 25 | 83.69539 | 79.90365 | | 81.00482 | 82.09877 | | 81.32716 | 77.31482 |
| 12.5 | 78.66483 | 67.24019 | 81.69305 | 83.75774 | 83.48766 | 80.70988 | 78.54939 | 76.08025 |
| 6.25 | 84.58362 | 84.03304 | 80.45423 | 81.28011 | 81.94444 | 78.39507 | 79.93827 | 74.84568 |

TABLE 9-continued

AP Inhibition

| Conc uM | CA28 | | | | % Inhibition | | CA28-2TS-BF | |
|---|---|---|---|---|---|---|---|---|
| 3.125 | 83.62009 | 81.59305 | 79.90365 | 81.8307 | 79.93827 | 77.9321 | 77.46913 | 76.69753 |
| 1.5625 | 76.04955 | 76.60014 | 79.76601 | 78.94012 | 71.60493 | 70.52469 | 74.63703 | 75.61728 |
| 0.78125 | 71.50723 | 69.85547 | 73.98486 | 72.33311 | 72.37654 | 68.20988 | 72.0679 | 71.14198 |
| 0.390625 | 58.64377 | 72.05782 | 66.89195 | 63.11081 | 79.16666 | 70.37037 | 71.2963 | 62.19136 |
| 0.1953 | 42.60152 | 44.39091 | | | 66.51234 | | 47.68519 | 50.92593 |
| 0.09765 | 24.7075 | 24.15682 | 23.05575 | 35.03098 | 41.66667 | 35.03086 | 48.91975 | 42.12963 |
| 0.0488 | 15.7605 | 12.59464 | 15.20992 | 27.04749 | 12.50001 | 26.23457 | 26.23457 | 23.61111 |
| 0 | −20.99105 | 7.088783 | 12.04405 | 1.858231 | 5.09259 | −0.1543198 | −0.9259262 | −4.012352 |

Example 17

Pharmacokinetic Properties of Long-Acting Compstatin Analog Administered by the Intravenous or Subcutaneous Route This Example describes determination of pharmacokinetic parameters of long-acting compstatin analog CA28-2TS-BF following administration to Cynomolgus monkeys with a single intravenous (IV) injection, single subcutaneous administration, or with once daily subcutaneous administration for seven days. CA28-2TS-BF was synthesized using a reactive bifunctional PEG of the TS type in terms of the NHS carboxylate attachment chemistry, which was linked to two molecules of CA28-AEEAc-Lys via the primary amine of the lysine side chain.

Dosing and Sample Collection

CA28-2TS-BF was administered to Cynomolgous monkeys at time 0 via intravenous injection into the saphenous vein or via single subcutaneous injection or repeat subcutaneous injection (once daily, for seven days). Six non-naïve female Cynomolgus monkeys, age 2-5 years, ranging in weight from 2.6 to 3.9 kilograms, were used in this study (three per group). The animals were healthy at the start of the trial. The study was not blinded. Animals were supplied with water ad libitum and a commercial diet twice daily prior to initiation of the study. Food was supplied to the animals per facility SOP prior to the study. Animals were not fasted. Animals were dosed at 7 mg/kg via intravenous or subcutaneous administration at time 0 on the appropriate day(s). Dosing solution concentration was 3.5 mg/mL for IV administration and 25 mg/mL for subcutaneous administration. Dosing volume was 2 mL/kg for IV administration and 0.28 mL/kg for subcutaneous administration. A size 23G3/4 gauge needle was used for subcutaneous administration. The compound was administered in 5% dextrose in water.

Blood specimens (~0.5-1 mL) were collected from the femoral vein at the following timepoints: Day 1: Pre-dose, 5 min, 15 min, 30 min, 1 hour (h), 4 h, 8 h. Days 2-9:0 min. Day 15: Final sample based on Day 1 dosing. Each blood sample was collected from the monkey's femoral vein via direct venipuncture and placed into a red top serum tube containing no anticoagulant, and kept at room temperature for at least 30 minutes. Blood samples were centrifuged at a temperature of 4° C. at 3000×g for 5 minutes. Samples were maintained chilled throughout processing. Serum samples were collected after centrifiigation and placed into sample tubes. Samples were stored in a freezer set to maintain −60° C. to −80° C. Serum samples and leftover dosing solutions were shipped frozen on dry ice for analysis.

The site of each subcutaneous administration was observed to see how fast the injection volume was absorbed and also to see if the formulation left behind a lump or fully went away. The dose sites for the animals receiving subcutaneous injections were observed in the evening of each dosing day. The dose site did not appear to have a lump and was fully absorbed by that time based on visual inspection. All animals were observed twice daily and showed normal activity throughout the study. No compound-related abnormalities were noted in the animals throughout the study.

Sample Analysis. Plasma samples obtained as described above were analyzed by LC/MS/MS leveraging CID (collision induced degradation) similarly to the method described in Example 3.

Results.

Serum concentrations vs time for CA28-2TS-BF when administered IV or subcutaneously as described above are plotted in FIG. 11. The data points represent all PEGylated CA28 compound detected. CA28 data shown on FIG. 11 are historical data obtained in a previous study in which CA28 was administered intravenously to Cynomolgus monkeys. In that study, CA28 was detected in samples using HPLC/MS.

A peak serum concentration of about 500 micrograms/mL was achieved by subcutaneous administration of CA28-2TS-BF once daily for 7 days. The terminal half-life of CA28-2TS-BF was approximately 8 days when administered either IV or by single subcutaneous injection. Raw data are provided in Tables 10(A) (IV administration) and 10(B) (subcutaneous administration) below. (In FIG. 11 and Tables 10(A) and 10(B), the day of dosing is considered day 0).

TABLE 10(A)

| Time (days) | CA28 (IV) 200 mg/kg | CA28-2TS-BF (single dose IV) 7 mg/kg | | |
|---|---|---|---|---|
| 0.0035 | | 232 | 190 | 214 |
| 0.01 | | 216 | 190 | 209 |
| 0.02 | 34 | 221 | 177 | 199 |
| 0.042 | 17 | 211 | 175 | 183 |
| 0.167 | 9 | 190 | 152 | 185 |
| 0.333 | 5 | 212 | 191 | 154 |
| 1 | 1.5 | 180 | 130 | 150 |
| 2 | | 141 | 116 | 126 |
| 3 | | 128 | 98.7 | 113 |
| 4 | | 114 | 89.1 | 95.8 |
| 5 | | 105 | 75 | 87.1 |
| 6 | | 95.1 | 67 | 74.4 |
| 7 | | 83.3 | 61.4 | 69.9 |
| 8 | | 86 | 52.8 | 68.4 |
| 14 | | 51 | 30.8 | 39.7 |

TABLE 10(B)

| Time (days) | CA28-2TS-BF (single dose SC) 7 mg/kg | | | CA28-2TS-BF (7 × day SC) 7 mg/kg/day | | |
|---|---|---|---|---|---|---|
| 0.0035 | BQL | BQL | BQL | BQL | BQL | BQL |
| 0.01 | 1.42 | BQL | 1.7 | BQL | BQL | BQL |
| 0.02 | 3.55 | 1.64 | 3.8 | BQL | BQL | BQL |
| 0.042 | 6.1 | 3.46 | 7.05 | 2.32 | 1.14 | 2.44 |
| 0.167 | 15 | 12.2 | 20.6 | 14.7 | 5.76 | 12.1 |

TABLE 10(B)-continued

| Time (days) | CA28-2TS-BF (single dose SC) 7 mg/kg | | | CA28-2TS-BF (7 × day SC) 7 mg/kg/day | | |
|---|---|---|---|---|---|---|
| 0.333 | 25 | 25.8 | 32.9 | 32.9 | 18 | 25.8 |
| 1 | 70 | 76.5 | 76 | 80.5 | 80 | 66.5 |
| 2 | 107 | 101 | 96.6 | 196 | 185 | 169 |
| 3 | 111 | 103 | 99.8 | 391 | 286 | 292 |
| 4 | 108 | 98.9 | 99.5 | 455 | 377 | 405 |
| 5 | 99.4 | 97.6 | 101 | 427 | 404 | 486 |
| 6 | 86.8 | 87 | 81.6 | 490 | 483 | 568 |
| 7 | 75.2 | 83.2 | 78.6 | 607 | 502 | 564 |
| 8 | 67.5 | 73.4 | 72.2 | 495 | 461 | 570 |
| 14 | 38.3 | 44.5 | 40.7 | 322 | 298 | 397 |

BQL = below quantification limit

As noted above, CA28-2TS-BF was synthesized using a reactive bifunctional PEG of the TS type, resulting in formation of a carbamate after reaction with the primary amine of lysine. CA28-2GS-BF was synthesized using a reactive bifunctional PEG of the GS type in terms of the NHS carboxylate attachment chemistry, resulting in formation of an amide after reaction with the primary amine of lysine. The compound also contains an ester linkage, which is absent in CA28-2TS-BF. It is notable that the terminal half-life of about 8 days achieved with CA28-2TS-BF in this experiment was considerably greater than that of CA28-2GS-BF, which was found to have a half-life of about 5 days in a similar experiment (see Example 8).

Example 18

Compstatin Analogs Inhibit C3 Deposition on Red Blood Cells of PNH Patients and Protects Against Complement-Mediated Lysis A modified Ham's test was performed to assess the ability of compstatin analogs to protect PNH RBCs from complement-mediated lysis. RBCs from a patient with PNH were exposed to acidified human serum (as a source of complement components) and magnesium ($Mg^{2+}$, needed for alternative pathway activation) in the absence of complement inhibitors or in the presence of varying amounts of compstatin analogs CA28 or CA28-2GS-BF. Exposure to heat inactivated human serum was used as a control representing no significant complement-mediated lysis as complement is inactivated by heat. Exposure to acidified human serum and magnesium ($Mg^{2+}$) in the absence of complement inhibitors (pane labeled $Mg^{2+}$) was used as a control representing maximum lysis.

Following incubation, cells were stained with antibodies to CD59 and C3d. CD59 level permitted the classification of the PNH RBCs as Type I, Type II, or Type III. Staining for C3d, a product of C3 activation and cleavage was used as a marker of C3 and C3 activation product deposition (loading). Flow cytometric analysis was performed to assess CD59 and C3d on RBC surfaces and to quantify the percentages of Type I, Type II, and Type III cells present in various samples.

Figure 12A:
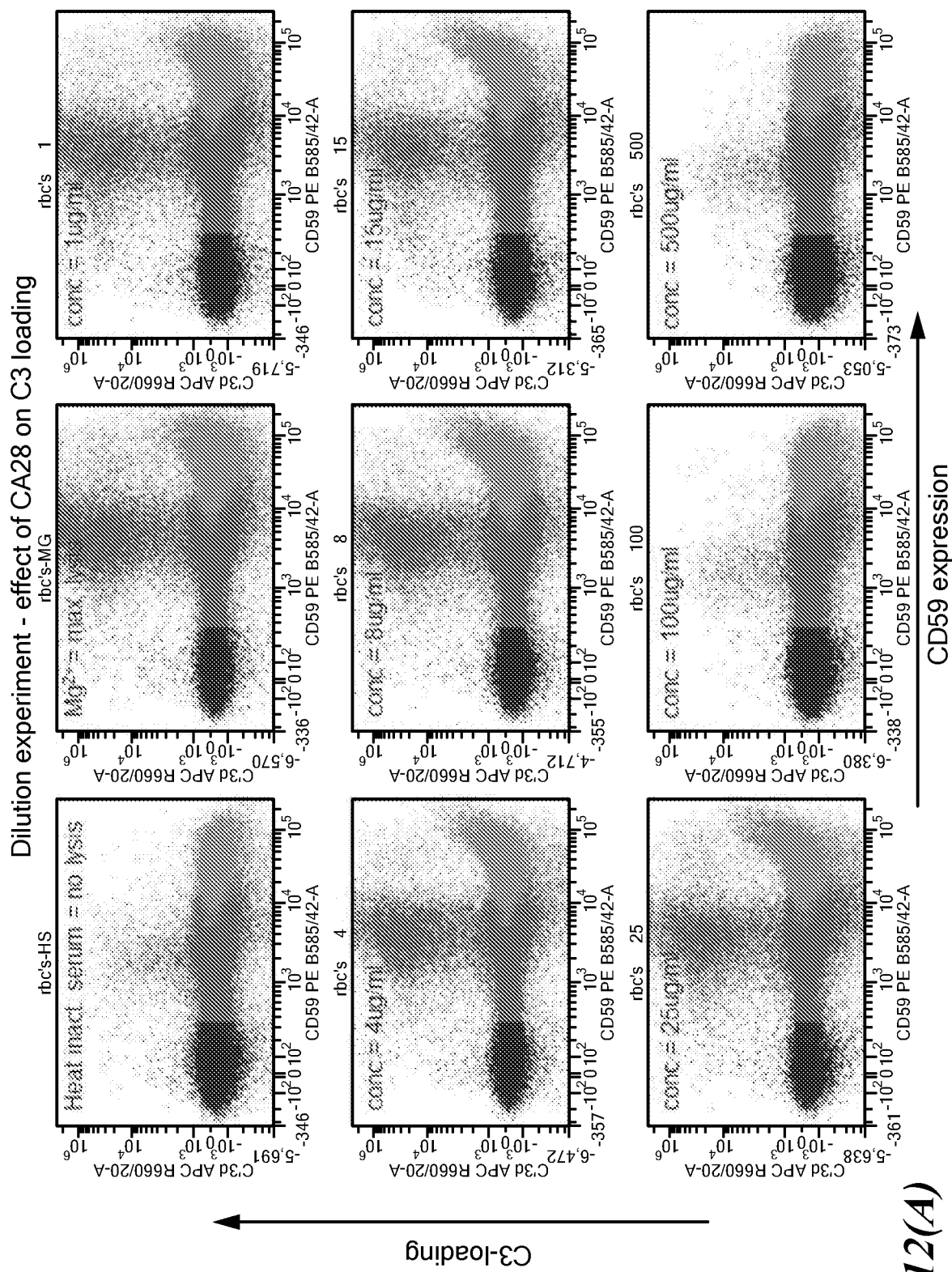
FIG. 12 shows flow cytometric analysis of C3 deposition on red blood cells from a patient with PNH, which were exposed to activated complement in a modified Ham's test. (A) Results of a dilution experiment demonstrating the effect of CA28 on C3 deposition are shown. (B) Results of a dilution experiment demonstrating the effect of CA28-2GS-BF on C3 deposition are shown. Compound concentrations used are shown on and above each panel.
Figure 12B:
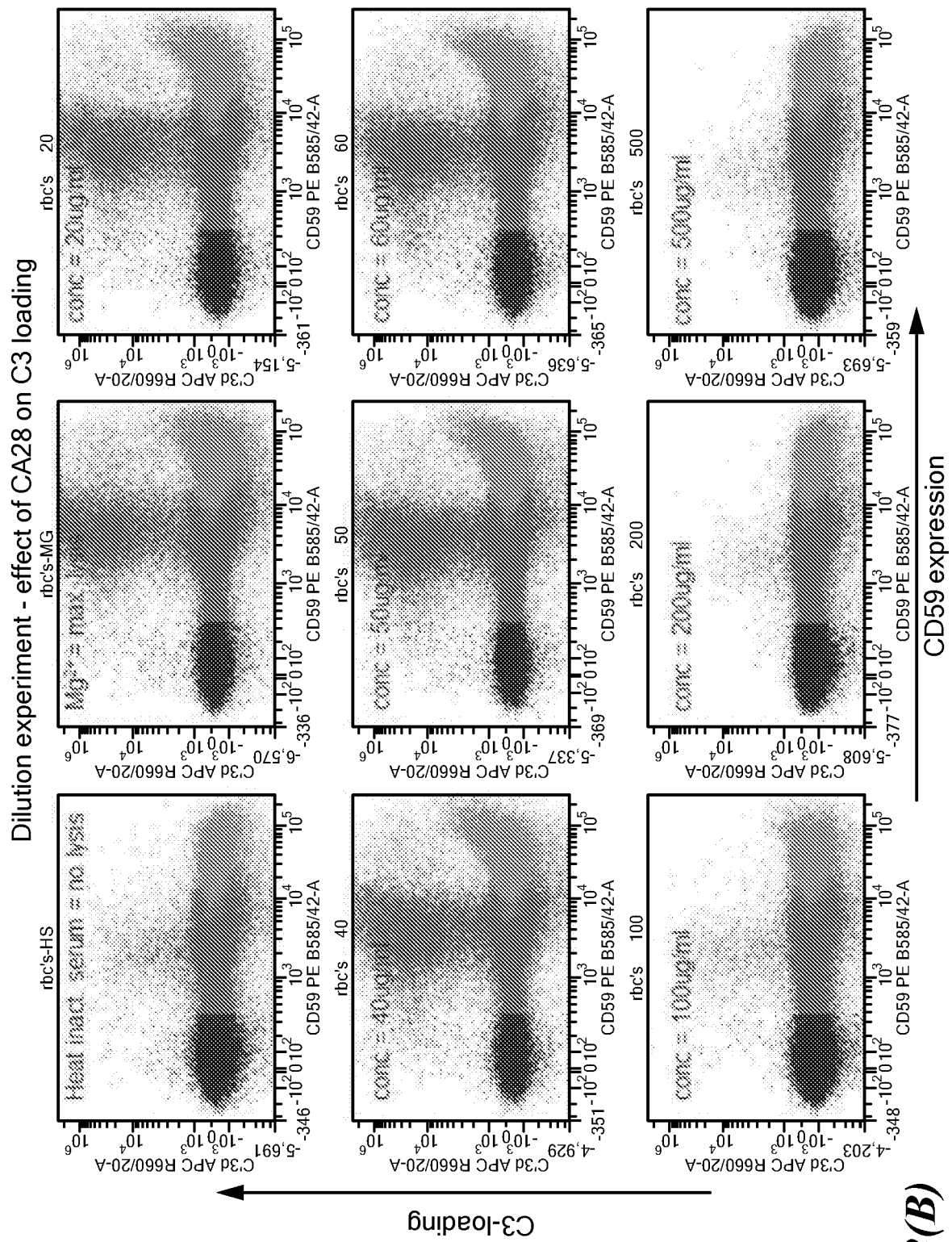

Results of a dilution experiment demonstrating the effect of different concentrations of CA28 on C3 deposition and cell percentages are shown in FIG. 12(A). Results of a dilution experiment demonstrating the effect of different concentrations CA28-2GS-BF on C3 deposition and cell percentages are shown in FIG. 12(B). The results are presented quantitatively in Table 11 below. Type I cells (shown in orange in FIG. 12) have normal levels of CD59. Type III cells (shown in blue in FIG. 12) have essentially no detectable CD59. These cells are very susceptible to complement-mediated lysis. Type II cells (shown in purple in FIG. 12) have reduced levels of CD59 as compared with normal or Type I cells and have an intermediate sensitivity to complement-mediated lysis. In the presence of complement activation Type III cells rapidly lyse. Reduction in or absence of lysis may be evidenced by an increased presence of Type III cells, as is evident as a higher percentage of Type III cells in the no lysis panel compared with the panel in (presence of $Mg^{2+}$ (max. lysis)) in both FIGS. 12(A) and 12(B). In other words, there are relatively fewer Type III cells in the positive control than in the negative control. Type II cells may eventually lyse in the presence of activated complement but can accumulate a considerable amount of C3 activation products such as C3d before they do so. Reduction in or absence of lysis may be evidenced by increased levels of C3 or C3 activation products on Type II cells, as is evident by comparing the level of C3d on Type II cells in the no lysis panel with the level of C3d on Type II cells in the max. lysis panel in both FIGS. 12(A) and 12(B). In other words, there is more C3d on cells in the max. lysis panel than in the no lysis panel. Type I cells have functional CD59, so they deactivate convertase and therefore do not accumulate as much C3d as Type II cells. However, the amount of C3d they accumulate can be used as a surrogate indicator for the amount of lysis of the more vulnerable cells (Type II and III). Thus, reduced C3d on Type I cells is indicative of protection against lysis. A shift in the relative percentages of Type I, II, and III cells from the percentages present in the max. lysis control panels ($Mg^{2+}$) towards the percentages present in the no lysis control panels (heat inactivated serum) is indicative of protection against complement-mediated lysis. These percentages are shown in the table below. The column labeled % C'3 in Table 11 refers to the percentage of cells deemed "positive" for presence of C3 and C3 activation products ("C3 loading"). As can be seen in FIGS. 12(A) and (B) and Table 11, CA28 and CA28-2GS-BF demonstrated similar protection of PNH red cell lysis over the concentrations tested, with virtually no C3 loading on PNH red cells at 100 micrograms/ml compound or higher concentrations. Note that the percentages of Type III, II, and I cells in the presence of 100 ug/ml or more compstatin analog were essentially the same as in the no lysis control, indicating complete protection from complement-mediated lysis as determined by this assay. Concentrations below 100 ug/ml but above 60 ug/ml, e.g., at least 70 ug/ml, at least 80 mg/ml, or at least 90 ug/ml, but below 100 ug/ml were not tested in this experiment but may also provide significant protection. 100 micrograms/ml CA28-2GS-BF represents a concentration of about 2.5 micromolar, which is readily achievable in vivo as described herein.

TABLE 11

Percentages and C3 loading of Type I, II, and III PNH RBCs in the absence or presence of compstatin analogs (concentrations in micrograms/ml are shown)

| | Type III % | % C3 | Type II % | % C3 | Type I % | % C3 |
|---|---|---|---|---|---|---|
| Heat activated (no lysis) | 37.09 | 0.29 | 51.79 | 1.22 | 11.12 | 0.09 |
| Magnesium added (maximum lysis) | 15.75 | 0.96 | 64.7 | 13.48 | 19.55 | 3.2 |
| CA28 1 | 19.42 | 1.2 | 64.81 | 10.06 | 15.77 | 1.7 |
| CA28 4 | 18.43 | 0.83 | 64.9 | 10.42 | 16.66 | 1.76 |
| CA28 8 | 17.83 | 0.7 | 66 | 11.12 | 16.17 | 1.66 |
| CA28 15 | 22.11 | 0.98 | 62.9 | 8.63 | 15 | 1.93 |

TABLE 11-continued

Percentages and C3 loading of Type I, II, and III PNH RBCs in the absence or presence of compstatin analogs (concentrations in micrograms/ml are shown)

|  | Type III % | % C3 | Type II % | % C3 | Type I % | % C3 |
|---|---|---|---|---|---|---|
| CA28 25 | 20.53 | 0.75 | 64.51 | 9.3 | 14.96 | 1.84 |
| CA28 100 | 37.96 | 0.1 | 51.5 | 0.92 | 10.64 | 0.08 |
| CA28 500 | 37.29 | 0.09 | 52.06 | 0.63 | 10.64 | 0.14 |
| CA28-2GS-BF 20 | 19.19 | 0.99 | 65.35 | 12.28 | 15.46 | 2.19 |
| CA28-2GS-BF 40 | 15.15 | 1.21 | 68.96 | 15.12 | 15.89 | 2.84 |
| CA28-2GS-BF 50 | 13.87 | 1.29 | 69.46 | 15.94 | 16.67 | 2.26 |
| CA28-2GS-BF 60 | 17.94 | 1.44 | 66.97 | 13.04 | 15.09 | 2.05 |
| CA28-2GS-BF 100 | 35.32 | 0.11 | 53.93 | 0.86 | 10.75 | 0.07 |
| CA28-2GS-BF 200 | 37.43 | 0.02 | 51.99 | 0.26 | 10.59 | 0.02 |
| CA28-2GS-BF 500 | 37.87 | 0.05 | 51.87 | 0.3 | 10.26 | 0.04 |

Example 19

Figure 13:
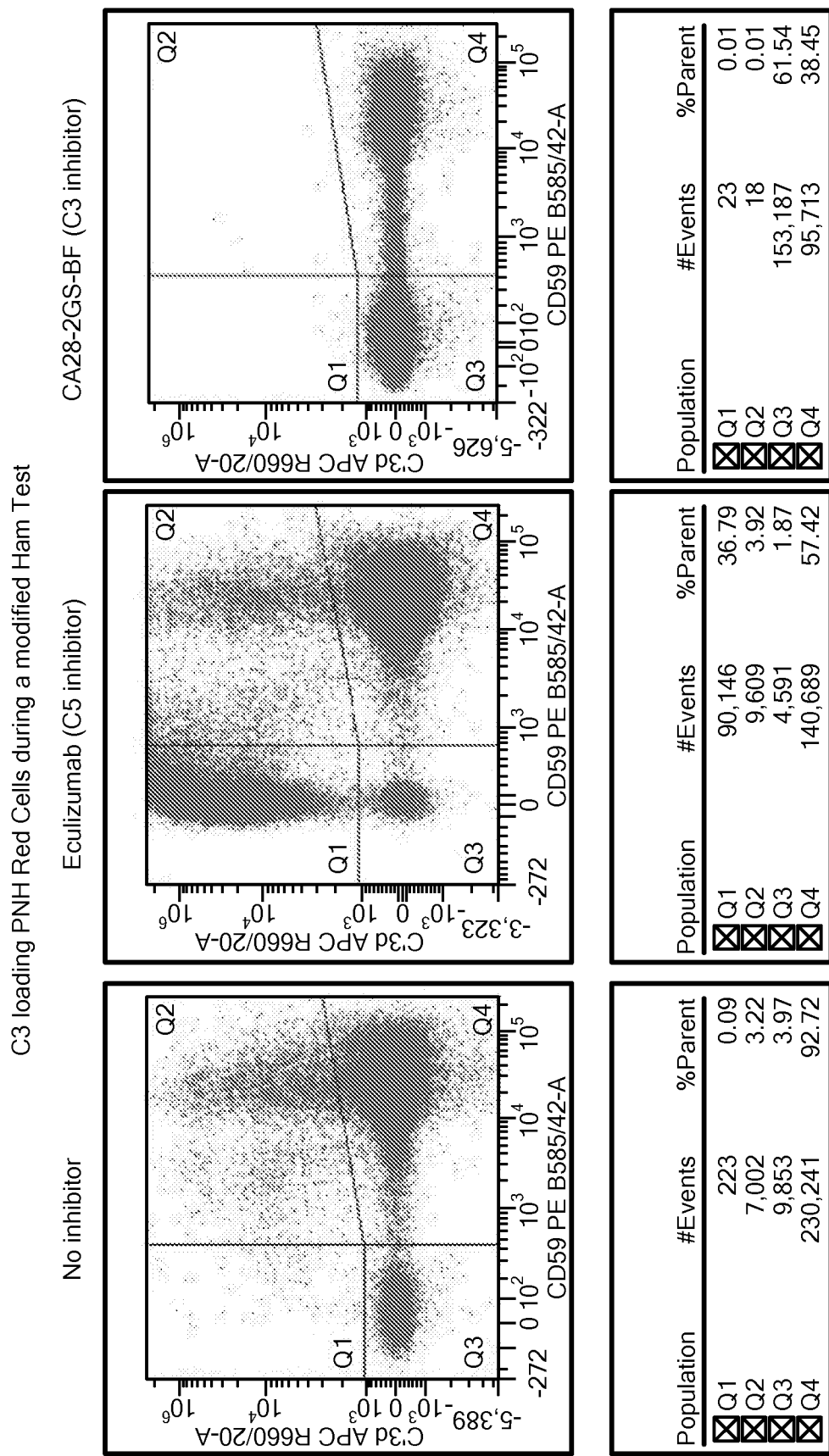
FIG. 13 shows flow cytometric analysis of C3 deposition on red blood cells from a patient with PNH, which were exposed to activated complement in a modified Ham's test in the absence of complement inhibitors (left panel), in the presence of anti-C5 monoclonal antibody eculizumab (middle panel) and in the presence of CA28-2GS-BF (right panel).

Effect of Compstatin Analog and Soliris on C3 Deposition on Red Blood Cells from PNH Patient A similar experiment to that described in Example 18 was performed to further demonstrate the protective effect of compstatin analog CA28-2GS-BF and compare it with that of anti-C5 antibody Soliris. A modified Ham's assay as in Example 18 was performed using PNH RBCs incubated in the presence of activated complement either in the absence of complement inhibitor (left panel) or in the presence of Soliris (middle panel) or CA28-2GS-BF (50 ug/ml) (right panel). Flow cytometry was performed after antibody staining using antibodies against CD59 and C3d. Results are shown in FIG. 13. In this figure, quadrant 1 (Q1) and quadrant 3 (Q3) represent Type III cells. Quadrant 2 (Q2) and quadrant 4 (Q4) represent Types I and II cells. Q1 and Q2 represent cells with a significant and abnormally high amount of C3 activation product (e.g., C3d) deposition. Q3 and Q4 represent cells without significant C3d deposition or somewhat elevated level (right portion of Q4) but less so than Q2 cells. The percentages of cells in the different quadrants is presented below each panel in FIG. 13 and in Table 12 below.

TABLE 12

|  | No Inhibitor | | Eculizumab | | CA28-2GS-BF | |
|---|---|---|---|---|---|---|
| Population | # Events | % Parent | # Events | % Parent | # Events | % Parent |
| Q1 | 233 | 0.09 | 90,146 | 36.79 | 23 | 0.01 |
| Q2 | 7,992 | 3.22 | 9,609 | 3.92 | 18 | 0.01 |
| Q3 | 9,853 | 3.97 | 4,591 | 1.87 | 153,187 | 61.54 |
| Q4 | 230,241 | 92.72 | 140,689 | 57.42 | 95,713 | 38.45 |

As can be seen, in the absence of inhibitors the great majority of cells lie in Q4 (Type I or Type II with low levels of C3 activation product deposition). Type III cells would have mainly been lysed, so their percentages (Q1 and Q3) are low. Q2 cells that accumulate C3 deposition products eventually lyse, so their number stays relatively low. In the presence of eculizumab, Type III cells are protected from lysis at least initially, but accumulate C3 activation products (e.g., C3d) as shown by the high percentage of Q1 cells as compared with the no inhibitor panel (36.79% vs 0.09%). The relative proportion of Q2+Q4 cells (Type I and II) is lower as a result of the increased survival of Type III cells. However, it is evident that significant deposition of C3 activation products (e.g., C3d) occurs on Type III cells, which may lead eventually to lysis or to clearance (in vivo). PNH RBCs treated with CA28-2GS-BF (right panel) exhibit essentially no deposition of C3d regardless of whether they are Type I, II, or III, in contrast to the results with eculizumab. The percentage of cells in Q1 and Q2 is negligible. There is a dramatic increase in the percentage of Type III cells (61.55%) as compared with results with no inhibitor or with eculizumab, indicating (together with the lack of C3d deposition) enhanced protection from lysis by CA28-2GS-BF.

Example 20

Phase 1 Clinical Trials of a Long-Acting Compstatin Analog in Healthy Subjects

Two Phase 1, randomized, double-blind, placebo-controlled clinical trials of a long-acting compstatin analog comprising a 40 kD linear PEG and two compstatin analog moieties (one linked to each end of the linear PEG), each comprising a peptide having the amino acid sequence of SEQ ID NO: 28 extended at its C-terminus by a moiety comprising AEEAc-Lys for attachment of the PEG moiety were initiated to assess safety, tolerability, pharmacokinetics and pharmacodynamics: a single ascending dose (SAD) trial and a multiple ascending dose (MAD) trial. This compound is referred to for convenience as LACA-40 in Examples 20-26. In the single ascending dose trial, healthy subjects are randomized into one of six cohorts at doses ranging from 45 mg to 1440 mg (45, 90, 180, 360, 720, or 1440 mg) in 5% dextrose. LACA-40 is administered by subcutaneous injection on the first day of the trial, followed by either 29 or 43 days of monitoring depending on dosing level. Each cohort includes 4 subjects who receive the drug and 1 or 2 subjects who receive placebo. In the multiple ascending dose trial, LACA-40 is administered by subcutaneous injection to healthy subjects daily for 28 consecutive days followed by 56 days of monitoring after last dosing. Subjects participate in one of four cohorts at doses ranging from 30 mg to 270 mg/day (30, 90, 180, or 270 mg/day). Each cohort includes 4 subjects who receive the drug and 1 subject who receives placebo. Safety is assessed by intensive clinical monitoring. Serial blood sampling is performed for the determination of LACA-40 concentrations in serum. Blood samples are also obtained to determine relevant markers of complement activity (C3, CH50 and AP50). Additional relevant PD markers (intact C3, iC3b, C3a, C4a and C5a) are measured in latter cohorts. Prior to multiple dosing, subjects receive *Neisseria meningitides, Streptococcus pneumoniae*, and *Haemophilus influenzae* Type B (Hib) vaccinations.

Results

When a total of 24 healthy subjects had received single doses of LACA-40 at doses up to 1440 mg in the Phase 1 single ascending dose trial, and a total of 16 healthy subjects had received multiple doses of LACA-40 for 28 consecutive days at doses up to 270 mg/day in the multiple ascending dose trial, 11 healthy subjects had received either single or multiple administrations of a placebo in the trials, and analysis revealed that LACA-40 was well tolerated in both trials with no serious adverse events or treatment emergent adverse events leading to study drug discontinuation or severe adverse events reported. In addition, no safety signals of clinical relevance were observed on review of laboratory data, vital signs, physical examinations or electrocardiogram results from either trial.

The pharmacokinetics of LACA-40 were in line with expectations derived from preclinical data, with little inter-subject variability observed.

In the multiple ascending dose trial, it was observed that the plasma concentration of LACA-40 increased linearly with dose, reaching maximum concentration between day 14 and 28. Serum concentrations were close to steady state after 28 days of daily dosing.

In both trials, a dose-dependent increase in C3 was observed that is indicative of LACA-40 binding to C3.

In the single ascending dose study, a reduction in alternative pathway-mediated hemolytic activity (AP50) was seen following a single dose of 1440 mg LACA-40.

Figure 14:
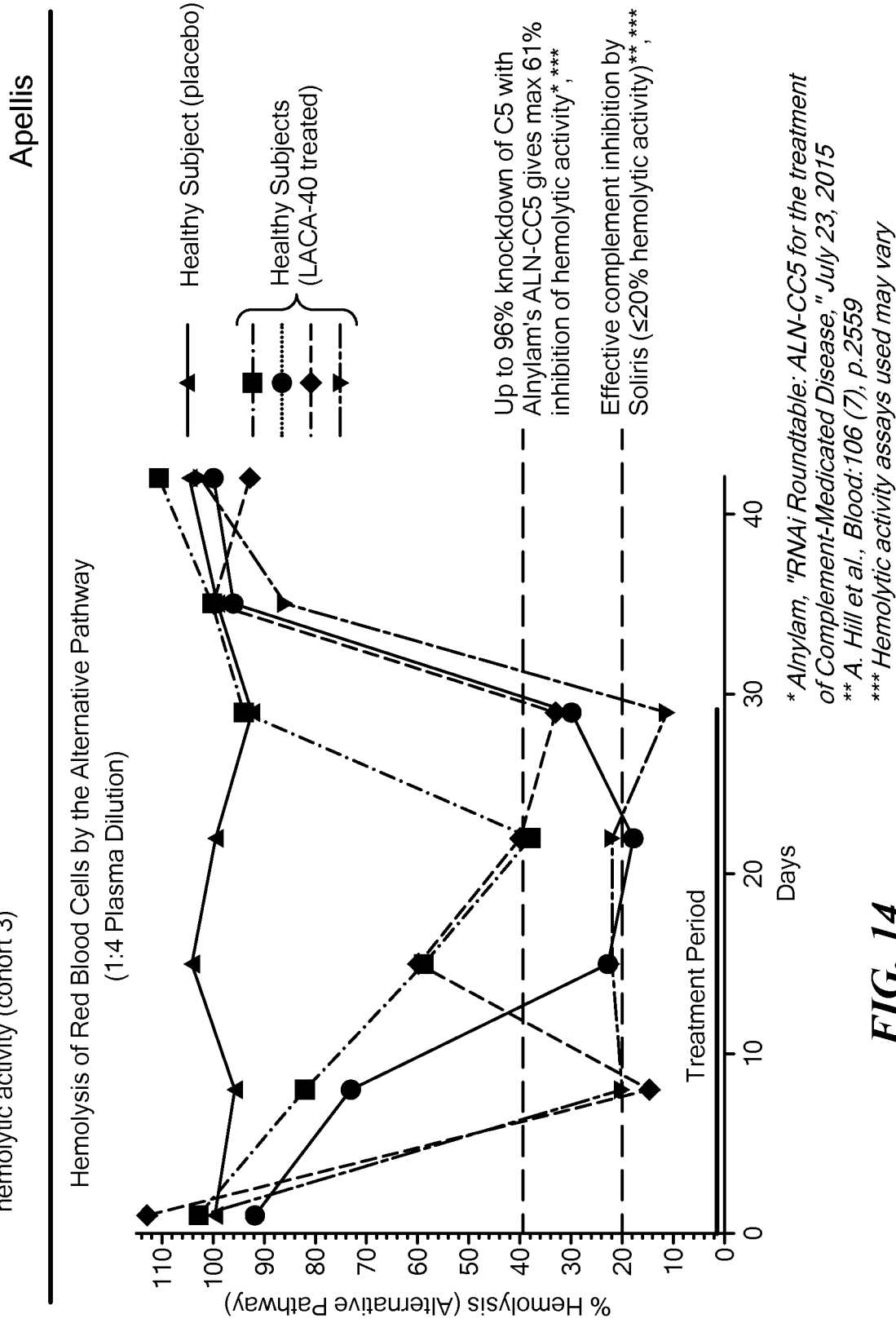
FIG. 14 shows a plot of ex vivo serum-induced hemolysis observed in a multiple ascending dose trial of a long-acting compstatin analog comprising a 40 kD PEG in healthy subjects.

In the third cohort of the multiple ascending dose trial of LACA-40, at a dose level of 180 mg/day, reduction of ex vivo serum-induced hemolysis was observed as early as seven days after initiation of treatment, continued for the duration of treatment, and reached a maximum of more than 80% in two of the four subjects and of more than 60% in the other two subjects (FIG. 14). In the fourth cohort of the multiple ascending dose trial of LACA-40, at a dose level of 270 mg/day, reduction of ex vivo serum-induced hemolysis was observed as early as seven days after initiation of treatment, continued for the duration of treatment, and reached a maximum of more than 80% in three of four subjects. The fourth subject is an outlier and exhibited a reduction of approximately 40% versus baseline.

Percent inhibition of ex vivo serum-induced hemolysis was determined based on a standard assay for hemolysis of rabbit erythrocytes when complement is activated by the alternative pathway (AP). Rabbit erythrocytes are spontaneous activators of the human AP. The assay makes use of the fact that when rabbit erythrocytes are incubated in serum with the addition of EGTA to chelate $Ca^{2+}$ (to inhibit complement activation by the classical and lectin pathways), the AP convertase is formed, resulting in the activation of C3 and subsequent lysis of the erythrocytes, which can be detected by detecting free hemoglobin by spectrophotometry. It is noted that this assay likely underestimates the actual percent inhibition of hemolysis because the negative control sample lacks serum, whereas serum is present in the samples from the subjects and contributes baseline absorbance in these samples.

It is worth noting that, in clinical trials of eculizumab in PNH patients, a complement inhibitor that binds to C5, 80% inhibition of ex vivo serum-induced hemolysis (using serum from PNH patients) was shown to be of considerable benefit in the treatment of PNH (Hillmen, P., et al., N Engl J Med 2004; 350:552-9). The present Example therefore confirms that pharmacologically relevant levels of complement inhibition were achieved at least at the 180 mg/day dose of LACA-40. The present Example further confirms that pharmacological doses of LACA-40 were safe and well tolerated, that LACA-40's pharmacokinetic/pharmacodynamic (PK/PD) profile supports daily SC administration, and that daily LACA-40 doses of 180 mg and 270 mg significantly reduced hemolytic activity as early as seven days after the start of dosing, and this inhibition was maintained through the dosing period.

In one aspect, PK data from these studies has been used to develop a PK/PD model, which may be used to aid dose selection in PNH patients or other patients to whom LACA-40 is administered.

The present disclosure contemplates that lower doses of LACA-40 may also be effective in PNH. For example, the ex vivo serum-induced hemolysis assay only measures lysis by MAC, reflecting intravascular hemolysis. LACA-40 (and certain other compounds described herein) protect cells from MAC and also from opsonization by C3 fragments, e.g., C3b, which is a cause of extravascular hemolysis and potential dysfunction that is not ameliorated by eculizumab. Therefore, without wishing to be bound by any particular theory, the present disclosure teaches that efficacy in treatment of PNH may be achieved in some embodiments even with doses that are lower than would be required to inhibit 80% of ex vivo serum-induced hemolysis, at least in part due to inhibition of extravascular hemolysis.

Thus, among other things, the present Example demonstrates that efficacious effects can be achieved with subcutaneous dosing (e.g., daily subcutaneous dosing for a relevant period of time, for example for at least one day, 2 days, 3 days, 4 days, 5 days, 6 days, 1 week, 2 weeks, 3 weeks, 4 weeks or more) of a long-acting compstatin analog comprising a 40 kD linear PEG and two compstatin analog moieties. The present Example specifically demonstrates efficacious effects achieved with a 180 mg/day daily dose, and specifically contemplates both higher and lower doses may well be desirable in appropriate circumstances. The present Example also specifically demonstrates efficacious effects achieved with a 270 mg/day daily dose, and specifically contemplates both higher and lower doses may well be desirable in appropriate circumstances.

Furthermore, in light of the particular demonstration of efficacious results achieved with provided dosing regimens for an LACA-40, the present Example, confirms the particular utility of long-acting compstatin analogs, and particularly of analogs comprising at least two compstatin analog moieties and/or of analogs comprising a PEG moiety with a molecular weight of approximately 40 kD (e.g., within the range of about 10 kD to about 50 kD, including specifically with a molecular weight of about 20 kD, 30 kD, 40 kD, etc), in such regimens.

Alternatively or additionally, the present Example demonstrates the particular utility of long-acting compstatin analogs having a total molecular weight no greater than about 50 kD in dosing regimens as described herein (see above).

Example 21

Phase Ib Clinical Trial of LACA-40 in Subjects with PNH

A Phase Ib single and multiple ascending dose clinical trial of LACA-40 was initiated to assess the safety, tolerability, PK and PD of LACA-40 in conjunction with eculizumab (Soliris) in adult patients with PNH. In this clinical trial, subcutaneous doses of LACA-40 in 5% dextrose are administered to patients with PNH, all of whom are on concurrent eculizumab therapy. To participate in the trial, patients must be at least 18 years of age, weigh greater than 55 kg, have been on treatment with eculizumab for at least 3 months, have a hemoglobin <10 g/dL at screening or have received at least one transfusion within 12 months prior to screening, have a platelet count of >30,000/$mm^3$, and an absolute neutrophil count >500 cells/µL. Prior to dosing, all subjects commence prophylactic oral antibiotics and receive vaccination against *Neisseria meningitides*. Subjects in cohorts 3 and 4 are also vaccinated against *Streptococcus pneumoniae* and *Haemophilus influenzae* Type B (Hib).

Each of the first two cohorts is composed of two patients who receive a single dose of LACA-40 followed by at least 28 days of monitoring. If the single dose is concluded to be well tolerated following this period of monitoring, the patient then receives a regimen of daily subcutaneous doses of LACA-40 for an additional 28 consecutive days. The third and fourth cohorts are composed of two and six patients, respectively, who receive daily subcutaneous doses of LACA-40 for 28 consecutive days. The doses studied are as follows:

Cohort 1: Single SC dose of 25 mg LACA-40 and repeated SC doses of 5 mg/day
Cohort 2: Single SC dose of 50 mg LACA-40 and repeated SC doses of 30 mg/day
Cohort 3: Repeated SC doses of 180 mg/day LACA-40
Cohort 4: Repeated SC doses of 270 mg/day LACA-40

Safety was assessed through clinical monitoring and all medication administered by qualified nurses at the subjects' home or in the clinic. Serial serum blood samples were collected for the determination of LACA-40 concentrations. Pharmacodynamic (PD) activity and signals of efficacy were assessed including lactate dehydrogenase (LDH), hemoglobin levels, RBC PNH clone distribution, transfusion requirements, complement levels, C3 fragment deposition on RBCs and reticulocytes.

Results

When the first three cohorts had completed their dosing, analysis revealed that LACA-40 had been well tolerated with one severe adverse event reported, which was considered unlikely to be related to administration of LACA-40.

When two subjects had completed dosing with a pharmacologically active dose of 180 mg, both had shown clinical improvement and relevant changes in blood biomarkers. Hemoglobin levels increased in both subjects during the first two weeks of treatment and remained stable until the end of treatment on day 28. LDH was stable at ~1.5×ULN in one subject and was reduced from 1.5×ULN to within the normal range in the other subject. The ratio of PNH Type III (CD59 Negative) RBCs approximately doubled in both subjects, increasing from 22.3% to 52% and 32.5% to 62.5% from day 1 to day 29, respectively. RBC transfusion requirements also reduced during the dosing period compared to recent historical data. No treatment-related serious adverse events had been reported and there had been no treatment related adverse events leading to discontinuation. Dosing proceeded to cohort 4 (270 mg daily).

When three subjects had completed 28 days of dosing with SC LACA-40 270 mg/day, all three subjects showed similar clinical improvement associated with relevant changes in blood biomarkers. Hb levels increased, LDH levels decreased, reticulocytes decreased, and the percentage of PNH Type III RBCs increased. Based on assessment of the risk/benefit profile, a protocol amendment to allow uninterrupted continued dosing in the 270 mg/day cohort for an additional 56 days for a total of 84 days treatment in addition to ongoing eculizumab therapy was approved. None of the three subjects had required a RBC transfusion since starting treatment with LACA-40.

These data confirm that pharmacological doses of LACA-40 are safe and well tolerated in subjects with PNH and daily SC dosing with LACA-40 will provide sustained inhibition of hemolytic activity in PNH patients. These data further confirm that inhibition of C3 provides clinical benefit to subjects with PNH who have a suboptimal response to anti-C5 treatment (e.g., eculizumab treatment).

The present disclosure thus contemplates subcutaneous dosing (e.g., daily subcutaneous dosing for a relevant period of time, for example for at least one day, 2 days, 3 days, 4 days, 5 days, 6 days, 1 week, 2 weeks, 3 weeks, 4 weeks or more, e.g., continuing for months or years) of a long-acting compstatin analog comprising a 40 kD linear PEG and two compstatin analog moieties, whether as a sole treatment or in combination with other therapy (e.g., eculizumab therapy).

Example 22

Phase 1b Clinical Trial of LACA-40 in PNH Patients

A Phase Ib open-label clinical trial of LACA-40 in treatment-naïve patients with PNH is performed to assess the safety, PK, PD and preliminary efficacy of repeated doses of LACA-40. Male and female patients diagnosed with hemolytic PNH are eligible. Subjects are required to have had a blood transfusion in the prior 12 months and lactate dehydrogenase (LDH) levels >2 times the upper limit of normal (ULN). Prior to dosing, subjects are vaccinated against *Neisseria meningitides, Streptococcus pneumoniae* and *Haemophilus influenzae* Type B (Hib) and commence prophylactic oral antibiotics. Doses of LACA-40 in 5% dextrose are administered by subcutaneous injection for at least 28 days and up to 84 consecutive days. (Treatment-naïve in this context refers to patients who have not previously been treated with a complement inhibitor.) Two cohorts of 3 patients each are enrolled. Doses of 180 mg/day for the first cohort and 270 mg/day for the second cohort are tested. The doses are administered in a volume of 1.8 ml either as a single daily injection or as 2 daily injections of 0.9 ml. The primary efficacy endpoint for the trial is measurement of LDH level as an indicator of intravascular hemolysis. Other relevant markers of efficacy measured include hemoglobin, RBC PNH clone distribution, total hemolytic complement activity (CH50), alternative pathway-mediated hemolytic activity (AP50), transfusion requirements, reticulocyte count, and deposition of C3 fragments on blood cells (as an indicator of potential for extravascular hemolysis). C3 fragments deposition measurement is performed by flow cytometry, e.g., as described above. An antibody that cross reacts with C3b, C3c, and C3d is used.

Results

Cohort 1

After completion of cohort 1, two subjects had received doses of 180 mg of LACA-40 for 28 days and one subject withdrew consent due a reaction after the first dose. Marked reduction in LDH levels, from 2078 U/L to 1082 U/L and 1325 U/L to 709 U/L (normal 100-250 U/L) from day 1 to day 29, respectively, were observed in both subjects who received 28 days of treatment. Neither subject achieved the criteria for continuation into part 2.

Screening hemoglobin (Hb) levels were below 80 g/L and both subjects received transfusions in the 3 weeks prior to dosing with LACA-40. Hb levels were maintained above 80 g/L in both subjects and neither required a transfusion during the dosing period. Both subjects received transfusions within about 4 weeks of stopping treatment with LACA-40.

The fraction of PNH type III (CD59 Negative) RBCs approximately tripled in both subjects, increasing from 5.1% and 13.4% on day 1 to 17.4% and 37.6% on day 29, respectively.

In both subjects who completed 28 days of dosing, LACA-40 appeared to be safe and well tolerated. The third subject developed nausea, vomiting and a rash 5-6 hours after receiving the 1st dose of LACA-40. This event was reported as a serious adverse event possibly related to LACA-40. To support continuation in the study, this reaction was further investigated with in-vitro cell reactivity testing and a skin prick test with LACA-40 and PEG 40 kD. Testing concluded that there was no evidence of T-cell activation and the skin test was negative. Therefore it was considered medically safe for the subject to re-enter the study. The subject, however, withdrew consent for personal reasons.

Cohort 2

After two subjects treated with 270 mg/day LACA-40 administered by SC injection had completed the 28-day treatment period both subjects demonstrated notable reductions in LDH levels to within 2× the upper limit of normal and increases in the percent of PNH Type III RBCs. Subjects in this cohort were eligible to continue receiving daily LACA-40 following review of all data if a clinical benefit was observed and if requested by the investigator. Both subjects treated met the pre-determined criteria to continue dosing to 84 days. One subject left the study for personal reasons. The other subject continued dosing and continued to show a sustained reduction in LDH when tested on day 57. Dosing of the next subject in cohort 2 is pending.

In summary, LACA-40 administered daily was safe and well tolerated and led to a sustained suppression of hemolysis in patients with PNH who were not receiving eculizumab.

Additionally, the present disclosure specifically provides certain insights relating particularly to certain desirable characteristics of devices (e.g., needle gauge, needle bore diameter and/or wall thickness, etc) particularly useful for delivery of certain LACA compositions, including specifically certain LACA-40 compositions as described herein (see above).

Example 23

Preclinical Studies of Intravitreal LACA-40

Preclinical studies in monkeys were performed to assess the safety and pharmacology of LACA-40 when injected intravitreally. Intravitreally administered LACA-40 in cynomolgus monkeys is distributed into the blood stream then further distributed and/or slowly eliminated from the body. The results of toxicokinetic analyses of vitreal and serum concentrations of LACA-40 after repeated intravitreal injections over the course of nine months at doses up to 24.8 mg/eye in 5% dextrose in volumes of either 50 or 100 µL/eye indicated that there was little intraocular or serum accumulation of the drug over multiple injections. In addition, a full toxicological review, including ophthalmological assessment by indirect and slit lamp, spectral domain optical coherence tomography, electroretinography, and tonometry and histopathological examinations of both eyes and of approximately 50 additional tissues from each monkey revealed no evidence of LACA-40-mediated changes at any of the doses tested.

Assessment of the pharmacokinetic profile of a single intravitreal dose of LACA-40 (10 mg/eye in both eyes) in monkeys revealed a vitreal half-life of approximately 3.2 days. After intravitreal injection, serum concentrations of LACA-40 increased until post-dose Day 7 then decreased with an apparent half-life of 10.4 days.

Among other things, the present disclosure contemplates dosing regimens for a long-acting compstatin analog comprising a 40 kD linear PEG and two compstatin analog moieties in which timing of individual doses is specifically selected to ensure a desired PK pattern in light of the half life for the LACA-40, as described herein.

Example 24

Phase 1b Single Ascending Dose Clinical Trial of LACA-40 in Subjects with AMD

A Phase 1 open label, single ascending dose clinical trial of LACA-40 in patients with wet AMD and receiving anti-VEGF therapy (specifically, Lucentis®, Eylea® or Avastin®), was initiated to assess safety, tolerability and PK of LACA-40. In this trial, patients receive a single dose of LACA-40 by intravitreal injection followed by 113 days of monitoring. It was originally planned to enroll nine patients in the trial, in three cohorts of three patients each, at doses of 5 mg, 10 mg and 20 mg of LACA-40 in 5% dextrose in a volume of 100 microliters. After enrollment of all three cohorts was completed, the third cohort was expanded from three patients to a total of 12 patients. LACA-40 was well tolerated in the initial nine patients, and no serious adverse events were reported.

The present disclosure provides dosing regimens in accordance with which a long-acting compstatin analog comprising a 40 kD linear PEG and two compstatin analog moieties is administered by intravitreal injection. In some embodiments, a long-acting compstatin analog comprising a 40 kD linear PEG and two compstatin analog moieties is administered as sole therapy; in some embodiments, it is administered in combination with another therapy (e.g., anti-VEGF therapy), so that the patient is simultaneously exposed to both.

The present Example specifically describes and supports dosing regimens under which a long-acting compstatin analog comprising a 40 kD linear PEG and two compstatin analog moieties is administered by intravitreal injection to subjects who are receiving VEGF therapy. In some embodiments, subjects treated with both anti-VEGF therapy and therapy with a LACA-40 receive doses of an anti-VEGF agent at intervals longer that those utilized for otherwise comparable subjects not receiving therapy with the LACA-40. A variety of anti-VEGF agents have been developed (reviewed, for example, in Lanzetta Br J Opthamol 97:1497, 2013). For example, reported dosing regimens for certain anti-VEGF agents include intravitreal injections of ranibizumab 0.5 mg or bevacizumab 1.25 mg administered every 4 weeks (q4) or PRN; in some embodiments, such regimens serve as appropriate reference regimens with respect to which anti-VEGF combination therapy regimens as described herein are assessed In light of the disclosure provided herein, including in this Example, those skilled in the art would appreciate that provided are certain combination therapy regimens, for example, in accordance with which each of a LACA-40 and an anti-VEGF agent is administered intravitreally; in some embodiments, the LACA-40 and anti-VEGF may be administered together in a single injection for certain (though not necessarily all) doses. In some embodiments, fewer doses of the anti-VEGF doses are administered in a selected period of time than are administered absent administration of the LACA-40

Example 25

Phase 2 Single Ascending Dose Clinical Trial of LACA-40 in Subjects with Geographic Atrophy A randomized, single-masked, sham-controlled clinical trial of LACA-40 in patients with GA is conducted. Approximately 240 patients are enrolled in the trial. Patients in the trial have a diagnosis of GA of the macula secondary to age-related macular degeneration, confirmed within 14 days prior to randomization by the central reading center using Fundus Autofluorescence images, as well as the following criteria: Total GA area must be ≥2.5 mm² and ≤17.5 mm² (1 and 7 disk areas [DA] respectively), determined by screening images of FAF.

Patients are randomized in a 2:2:1:1 manner to receive LACA-40 monthly, LACA-40 every other month, sham injection monthly or sham injection every other month. Patients in the LACA-40 arms receive a dose of 15 mg of LACA-40, injected into the vitreous humor in a 0.1 cc volume, monthly or every other month for 12 months followed by six months of monitoring after the end of treatment. In the sham-injection cohorts, patients receive a simulated injection. The safety, tolerability, PK, and evidence of activity of multiple intravitreal injections of LACA-40 in patients with GA in at least one eye are assessed. The primary efficacy endpoint is change in GA lesion size from baseline to month 12. The trial is designed to detect a reduction of at least 30% in lesion size growth between the LACA-40 arms and the sham-controlled arms from baseline to month 12. The primary safety endpoint is the number and severity of local and systemic treatment emergent adverse events Example 26

Phase 2 Single Ascending Dose Clinical Trial of LACA-40 in Subjects with Intermediate AMD A randomized, single-masked, sham-controlled clinical trial of LACA-40 in patients with intermediate AMD is conducted. Patients in the trial have a diagnosis of intermediate age-related macular degeneration. An aim of the trial is to assess whether LACA-40 can forestall the progression from intermediate AMD to GA or wet AMD Patients are randomized in a 2:2:1:1 manner to receive LACA-40 monthly, LACA-40 every other month, sham injection monthly or sham injection every other month. Patients in the LACA-40 arms receive a dose of 15 mg of LACA-40, injected into the vitreous humor in a 0.1 cc volume, monthly or every other month for at least 12 months followed by six months of monitoring after the end of treatment. In the sham-injection cohorts, patients receive a simulated injection. The safety, tolerability and evidence of activity of multiple intravitreal injections of LACA-40 in patients with intermediate AMD in at least one eye are assessed. Efficacy endpoints include the incidence of progression from intermediate AMD to GA and/or wet AMD, with a decreased incidence in patients treated with LACA-40 relative to patients who receive sham injections representing evidence of efficacy, and the change in the number and/or volume of high risk drusen and total drusen number and/or volume. A greater reduction in number, volume, and/or growth rate of drusen in patients treated with LACA-40 relative to patients who receive sham injections represents evidence of efficacy, The primary safety endpoint is the number and severity of local and systemic treatment emergent adverse events.

Example 27

Preclinical Studies of Inhaled CA28

Inhalation studies of single dose or repeated dosing were conducted in dog and cynomolgus monkey. There were no drug-related findings in any animals at the highest inhaled doses tested. These doses were 25 mg/kg/d in a 7 day repeated dose study in the dog, 80 mg/kg in a single dose study in the monkey, and 30 mg/kg/day in a 14 day repeated dose in the monkey.

An *Ascaris suum* challenge model was utilized to investigate the pharmacological effect of CA28 in vivo in cynomolgus monkeys as compared to corticosteroids. Doses of 20 mg/day or 15 mg/kg/d (for 14 consecutive days) of nebulized CA28 had a pharmacological effect in controlling the levels of inflammatory cytokines in the lungs (as measured in broncheoalveolar lavage fluid) after allergen challenge, both dining the 14 day treatment period and 28 days after cessation of treatment, after washout of the drug.

Example 28

Phase 1 Single and Multiple Ascending Dose Clinical Trial of Inhaled CA28 in Healthy Subjects A Phase 1 open-label, randomized, placebo-controlled, single and multiple ascending dose clinical trial of daily nebulized formulation of a compstatin analog (CA28) was conducted to assess safety, tolerability and PK of single and multiple inhaled doses of the drug in healthy volunteers. CA28 solution in (2% glycerol) or placebo (2% glycerol) was administered via a PARI LC Sprint® jet nebulizer with interrupter, driven by a PARI TurboBOY® S compressor. In the single ascending dose part of the trial, 16 subjects were enrolled in four cohorts of four subjects each. These subjects were administered a single dose of CA28 at doses ranging from 20 mg to 350 mg (20, 60, 150 or 350 mg) and monitored for 14 days after treatment. In this part of the trial, CA-28 was well tolerated and no serious adverse events were reported.

Four subjects were enrolled in the first cohort of the multiple ascending dose part of the trial. These subjects were to receive 14 consecutive days of treatment with a 60 mg/day dose of the drug. However, following nine days of treatment with the 60 mg/day dose, one subject developed signs and symptoms consistent with a potential bacterial infection that was considered to be possibly related to the pharmacology of the drug. The trial was paused and subsequently resumed, with subjects receiving 30 mg/day. Another subject developed signs and symptoms consistent with a potential bacterial infection that was considered to be possibly related to the pharmacology of the drug after 10 days of treatment at the 30 mg/day dose. The trial was then terminated.

Both subjects responded within hours to first-line antibiotic treatment, which is indicative of bacterial pathogenesis. In this trial, subjects were vaccinated against *Neisseria meningitides* and closely monitored for signs of infections. While the bacterial cultures were all negative, it is believed that *Haemophilus influenzae* or *Streptococcus pneumoniae* might have been implicated in the episodes of fever that were observed because C3 deficient individuals are known to be at increased risk of infection with *Neisseria meningitidis, Haemophilus influenzae* and *Streptococcus pneumoniae*. Vaccines against these three pathogens are available, and it is believed that the risk of infection can be addressed by vaccination, potentially with addition of prophylactic antibiotics (e.g., penicillin V).

Example 29

Pharmacokinetic (PK) Model for LACA-40

Figure 15:
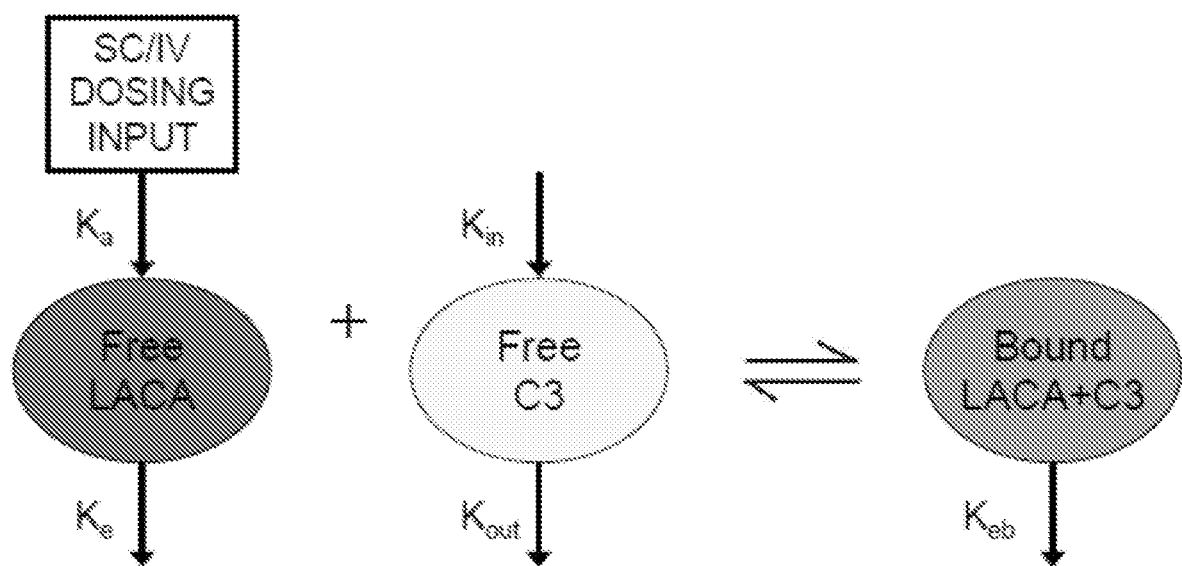
FIG. 15 shows a schematic diagram of a target-mediated drug disposition (TMDD) model.
Figure 16:
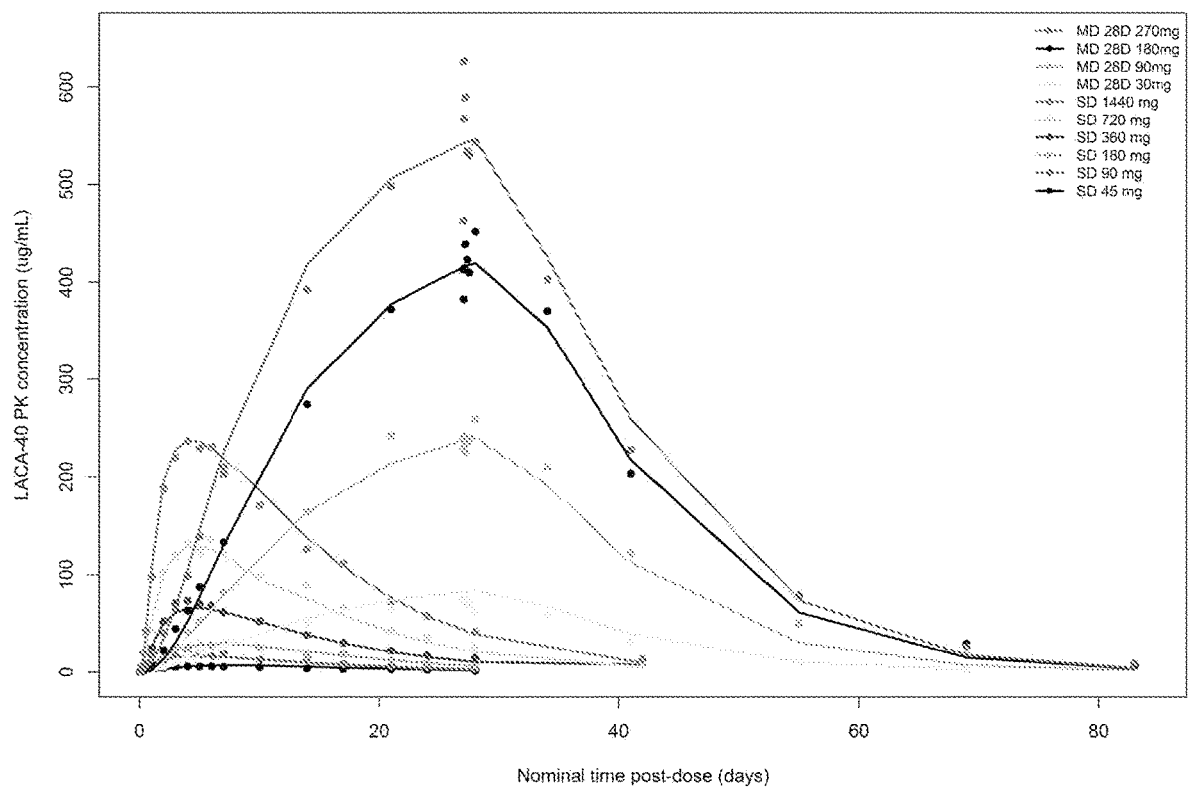
FIG. 16 shows LACA-40 observed and predicted serum concentrations over nominal time post-dose split by dosing regimen for both the single dose (SD) and 28 day multiple dose (MD, once daily) study in healthy subjects. The solid circles represent the observed mean PK concentrations at respective nominal time points overlaid with the TMDD model predictions represented with a solid line. Each dosing regimen is represented by a different color. LACA-40 was administered subcutaneously
Figure 17:
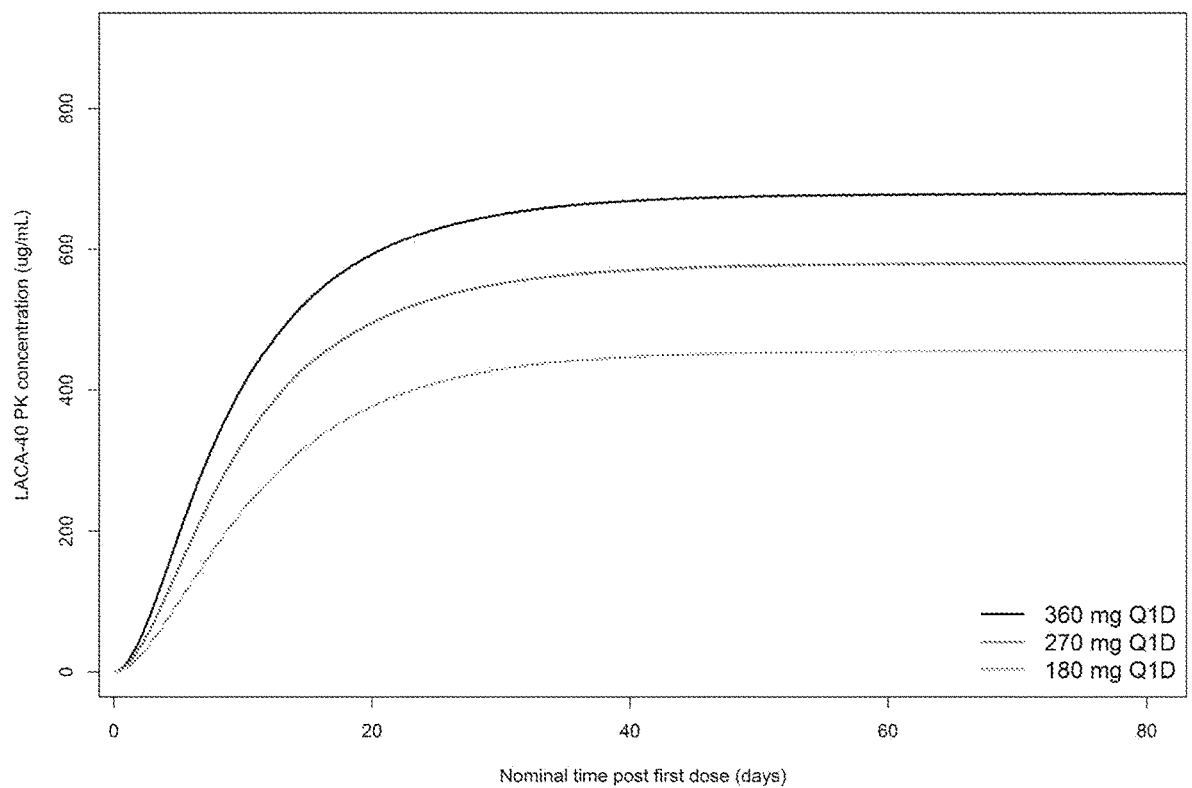
FIG. 17 shows the predicted trough PK serum concentrations over nominal time post-dose after multiple daily (Q1D) subcutaneous (SC) administration of LACA-40 at three dose levels; 180, 270 and 360 mg Q1D. The model predictions were based on the TMDD model.
Figure 18:
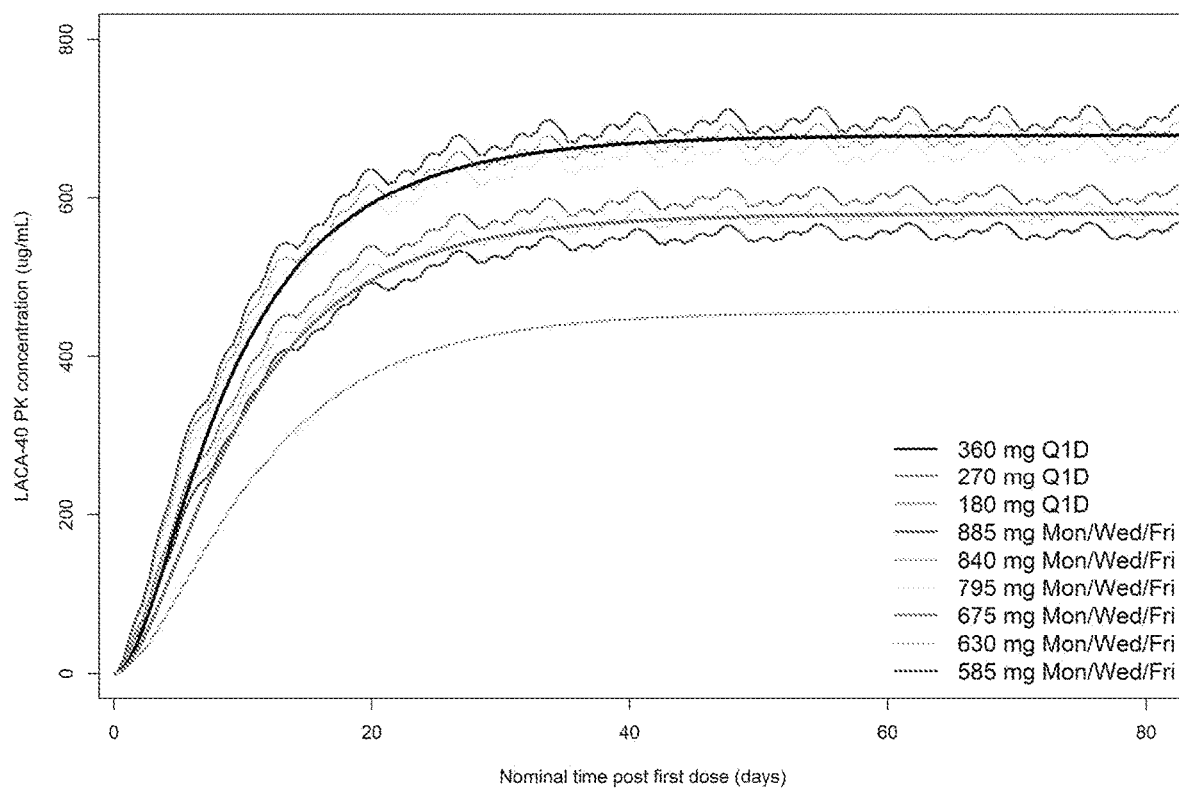
FIG. 18 shows the predicted trough PK serum concentrations over nominal time post-dose after multiple daily (Q1D) and thrice weekly (Mon/Wed/Fri) SC administration of various doses of LACA-40. Each dosing regimen is represented by a different colored line and model predictions were based on the TMDD model.
Figure 19:
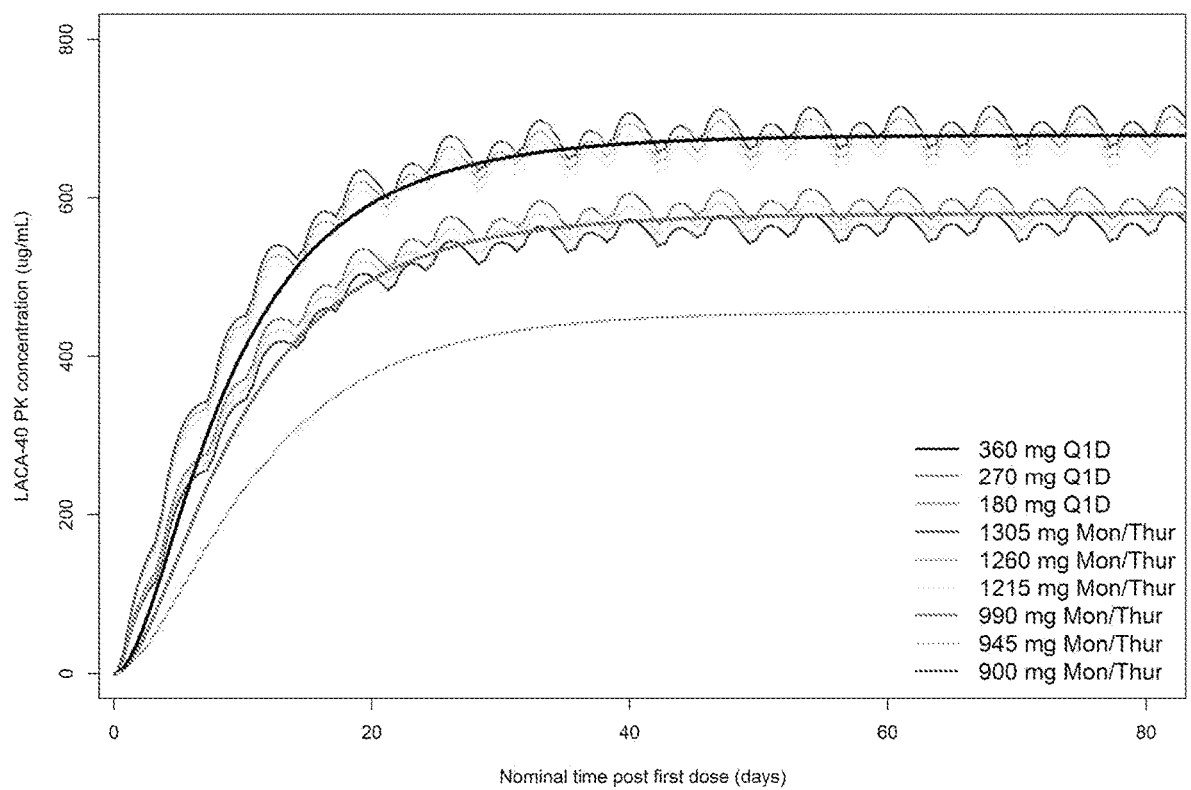
FIG. 19 shows the predicted trough PK serum concentrations over nominal time post-dose after multiple daily (Q1D) and twice weekly (Mon/Thur) SC administration of various doses of LACA-40. Each dosing regimen is represented by a different colored line and model predictions were based on the TMDD model.
Figure 20:
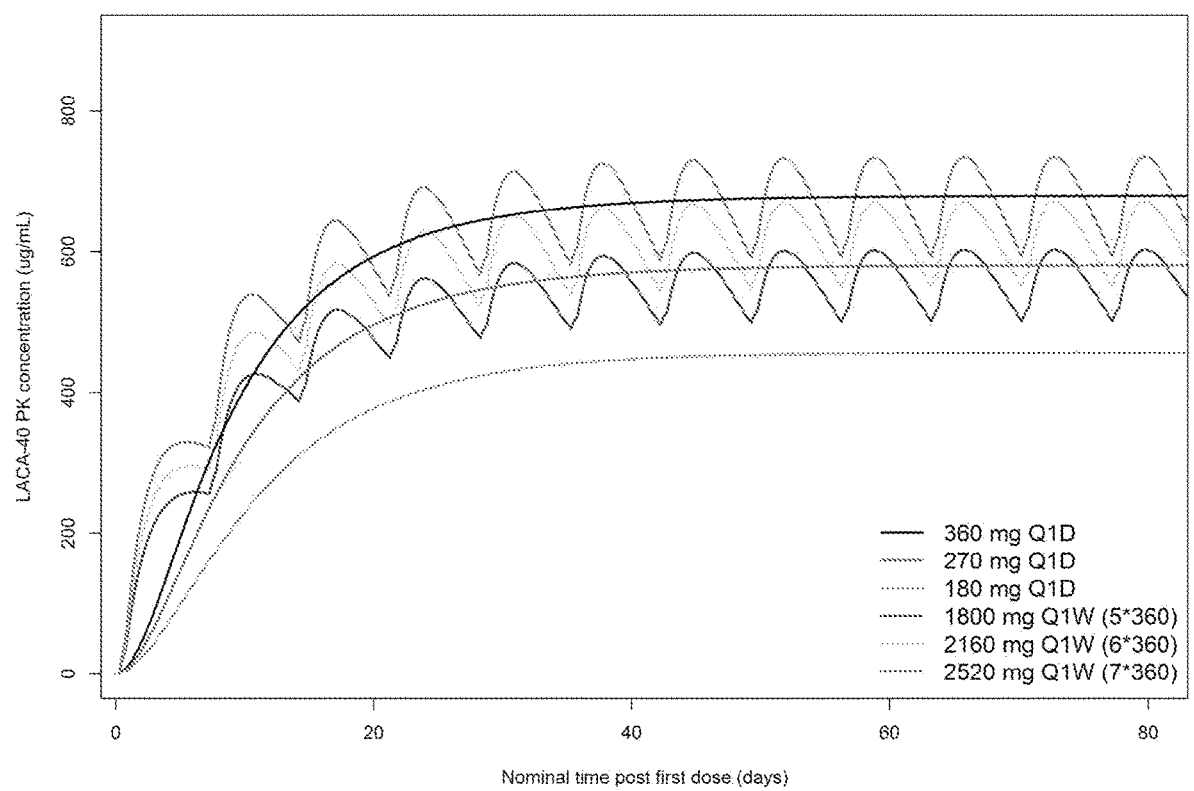
FIG. 20 shows the predicted trough PK serum concentrations over nominal time post-dose after multiple daily (Q1D) and once weekly (Q1W) SC administration of various doses of LACA-40. Each dosing regimen is represented by a different colored line and model predictions were based on the TMDD model.
Figure 21:
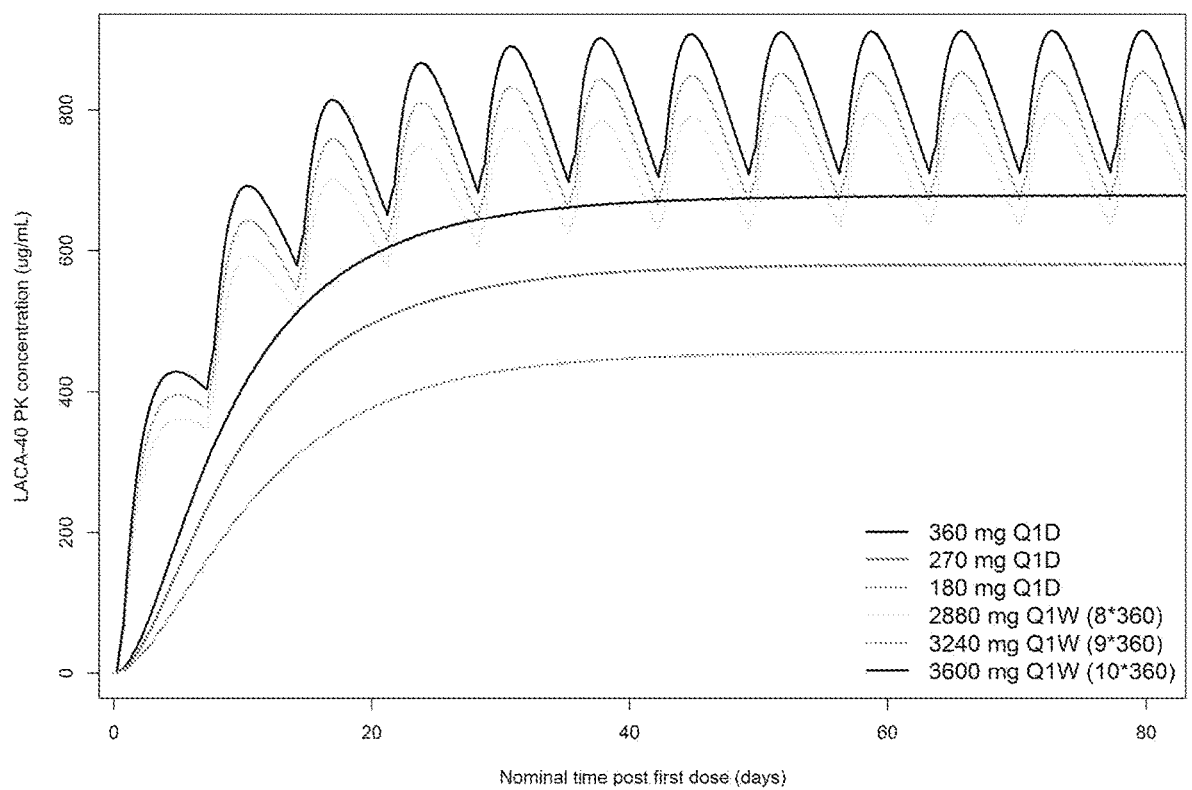
FIG. 21 shows the predicted trough PK serum concentrations over nominal time post-dose after multiple daily (Q1D) and once weekly (Q1W) SC administration of various doses of LACA-40. Each dosing regimen is represented by a different colored line and model predictions were based on the TMDD model.

LACA-40 is a potent and selective inhibitor of complement C3. Its high binding affinity influences both the disposition of LACA-40 and its target, complement C3, as demonstrated by the dose-dependent increase in complement C3 observed in the single ascending dose and multiple ascending dose studies in healthy subjects described above (Example 20). A family of pharmacokinetic (PK) models that describes this interdependence between drug and its target is known as Target Mediated Drug Disposition (TMDD) (Levy, G: Pharmacologic target-mediated drug disposition. *Clin. Pharmacol. Ther.* (1994) 56: 248-252). A schematic diagram of the model is presented in FIG. 15. The data from the completed single ascending dose and multiple ascending dose studies of LACA-40 in healthy subjects described in Example 20 was used to develop a TMDD model for LACA-40. The LACA-40 PK together with the impact of binding to complement C3 was well described using TMDD (QSS approximation, Mager D E, Jusko W J: General pharmacokinetic model for drugs exhibiting target mediated drug disposition. *J. Pharmacokinet. Pharmacodyn.* (2001) 28: 507-532). FIG. 16 shows the LACA-40 observed and predicted serum concentrations over nominal time post-dose split by dosing regimen for both the single dose (SD) and 28 day multiple dose (MD, once daily) study in healthy subject s. The figure demonstrates that the TMDD model provides a good model fit across time, dose and regimen The TMDD model was used to predict LACA-40 trough serum concentrations for daily administration of 180 mg, 270 mg, or 360 mg (FIG. 17) and to predict LACA-40 serum concentration for various different dose levels assuming thrice weekly, twice weekly, or weekly administration. Model predictions are depicted in FIGS. 18 and 19 (for thrice weekly and twice weekly doses, respectively) and in FIGS. 20 and 21 (for weekly administration). All presented predicted values are based on the model estimates from the TMDD, these are normally termed "typical value" and can be considered equivalent to the median.

Example 30

Pharmacokinetic and Pharmacodynamic Studies of Various Therapeutic Regimens

A double-blind, randomized Phase I clinical study was initiated to assess the safety, tolerability, PK and PD of different LACA-40 dosing regimens in healthy volunteers. This study includes three or more cohorts dosed as described in the following Tables 13-15.

TABLE 13

Dosing Regimens and Dosing Details

| | |
|---|---|
| Cohort 1: | Daily SC doses of 360 mg LACA-40 or matching placebo for a total of 28 doses during the 28-day dosing period |
| Cohort 2: | Twice per week SC doses of 1,300 mg LACA-40 or matching placebo for a total of 8 doses during the 28-day dosing period |
| Cohort 3: | Once per week SC doses of 2,600 mg LACA-40 or matching placebo for a total of 4 doses during the 28-day dosing period |
| Cohort 4: (Optional) | SC doses of LACA-40 (exact dose and dose frequency to be determined) or matching placebo during the 28-day dosing period |

Subjects received *Neisseria meningitides, Streptococcus pneumoniae,* and *Haemophilus influenzae* Type B (Hib) vaccinations prior to first dosing.

Participants in cohort 1 and cohort 2 were randomized according to a 4:1 randomization ratio, so that four participants received LACA-40 and one participant received placebo. Cohort 3 included two Sentinels randomized on a 1:1 ratio, with one participant receiving LACA-40 and the other participant receiving placebo; followed by four participants randomized on a 3:1 ratio, with three participants receiving LACA-40 and 1 participant receiving placebo. The number of participants and the randomization ratio for cohort 4 (which is an optional cohort) are to be determined.

TABLE 14

Dosing Specifications per Cohort

| | Dose | Volume per dose (mL) | Pump | Infusion Rate | Expected Infusion Time |
|---|---|---|---|---|---|
| Cohort 1 | 360 mg LACA-40 (n = 4) or placebo (n = 1) daily. | 10 mL | Crono Super PID | 0.33 mL/min | 30 min |
| Cohort 2 | 1300 mg LACA-40 (n = 4) or placebo (n = 1) twice a week | 20 mL | Freedom Edge | ~1 mL/min* (starting rate) | 20-70 min |
| Cohort 3 (Sentinels) | 2600 mg LACA-40 (n = 1) or placebo (n = 1) once a week | 40 mL | Freedom Edge | ~1 mL/min* (starting rate) | ~40-140 min |
| Cohort 3 (Remainders) | 2600 mg LACA-40 (n = 3) or placebo (n = 1) once a week | 40 mL | Freedom Edge | ~1 mL/min* (starting rate) | ~40-140 min |
| Cohort 4 | TBD | TBD | TBD | TBD | TBD |

*Actual infusion rate was typically ~0.5 mL/min on average

LACA-40 solution at a concentration of 36 mg/ml was used for cohort 1. LACA-40 solution at a concentration of 65 mg/ml was used for cohorts 2 and 3. In each case the compound was provided in acetate-buffered sorbitol solution at pH 5.0. LACA-40 or placebo was administered daily for 28 days to subjects in cohort 1 using a Neria™ infusion set with 29G needle. LACA-40 or placebo was administered to subjects in cohort 2 using RM-F2400 (LACA-40) and RM-F60 (placebo) Precision Flow rate tubing set and High Flo 24G 9 mm single-needle. LACA-40 or placebo was administered to subjects in cohort 3 using RM-F2400 (LACA-40) and RM-F60 (placebo) Precision Flow rate tubing set and High Flo 24G 9 mm single-needle or two-needle set. For cohort 3, 40 mL was delivered using two syringes, with the second syringe being connected to the same infusing tubing immediately once the first syringe was empty. The dosing schedules and planned administration sites for cohorts 1, 2, and 3 are set forth in the table below, where "Quadrant" refers to abdominal quadrant.

TABLE 15

Dosing Details

| | Administration sites* |
|---|---|
| Cohort 1 | |
| Day 1, 5, 9, 13, 17, 21, 25 | Upper right Quadrant |
| Day 2, 6, 10, 14, 18, 22, 26 | Upper Left Quadrant |
| Day 3, 7, 11, 15, 19, 23, 27 | Lower Right Quadrant |
| Day 4, 8, 12, 16, 20, 24, 28 | Lower Left Quadrant |
| Cohort 2 | |
| Day 1, 15 | Upper right Quadrant |
| Day 4, 18 | Upper Left Quadrant |
| Day 8, 22 | Lower Right Quadrant |
| Day 11, 25 | Lower Left Quadrant |
| Cohort 3 | |
| Day 1 | Upper right Quadrant |
| Day 8 | Upper Left Quadrant |
| Day 15 | Lower Right Quadrant |
| Day 22 | Lower Left Quadrant |

*If required, any quadrant other than the one used for the last infusion could be used as the administration site.

All medication was administered at the study location and subjects remained in the clinic until Day 35. Safety was assessed through clinical monitoring, including infusion site assessments. Serial serum blood samples were collected for the determination of LACA-40 concentrations.

Results

When the first three cohorts had completed dosing, analysis indicated that LACA-40 was safe and generally well tolerated.

Figure 22:
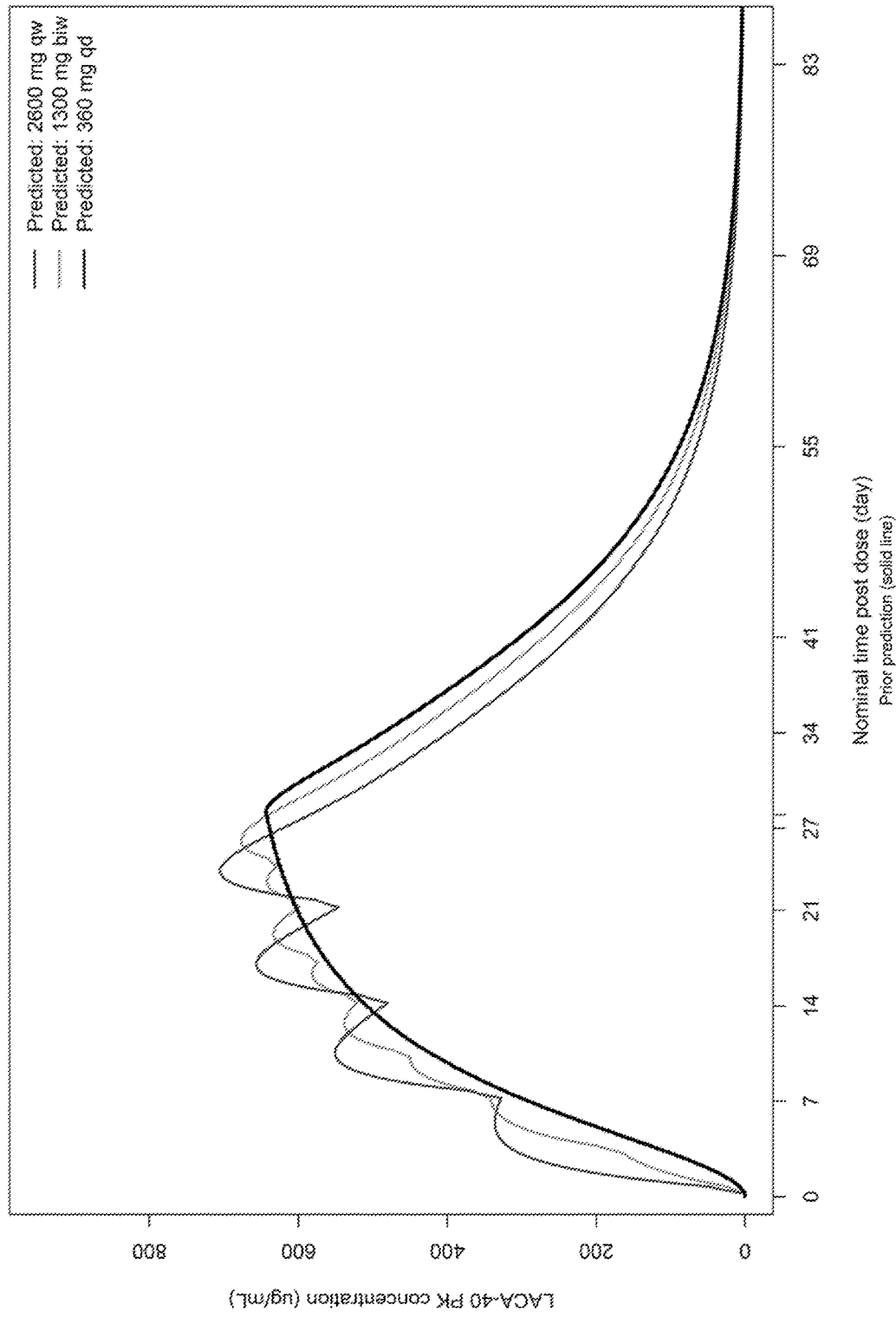
FIG. 22 shows the predicted serum concentrations over nominal time post-dose after multiple daily (qd), twice weekly (biw), or once weekly (qw) SC administration of various doses of LACA-40 over a 28 day dosing period, corresponding to dosing regimens for cohorts 1, 2, and 3 in the clinical study described in Example 30. Each dosing regimen is represented by a different colored line and model predictions were based on the TMDD model. For the twice weekly regimen, the plot reflects dosing at alternate 3 and 4 day intervals (i.e. dosing on days 1, 4, 8, 11, 15, 18, 22, and 25).
Figure 23:
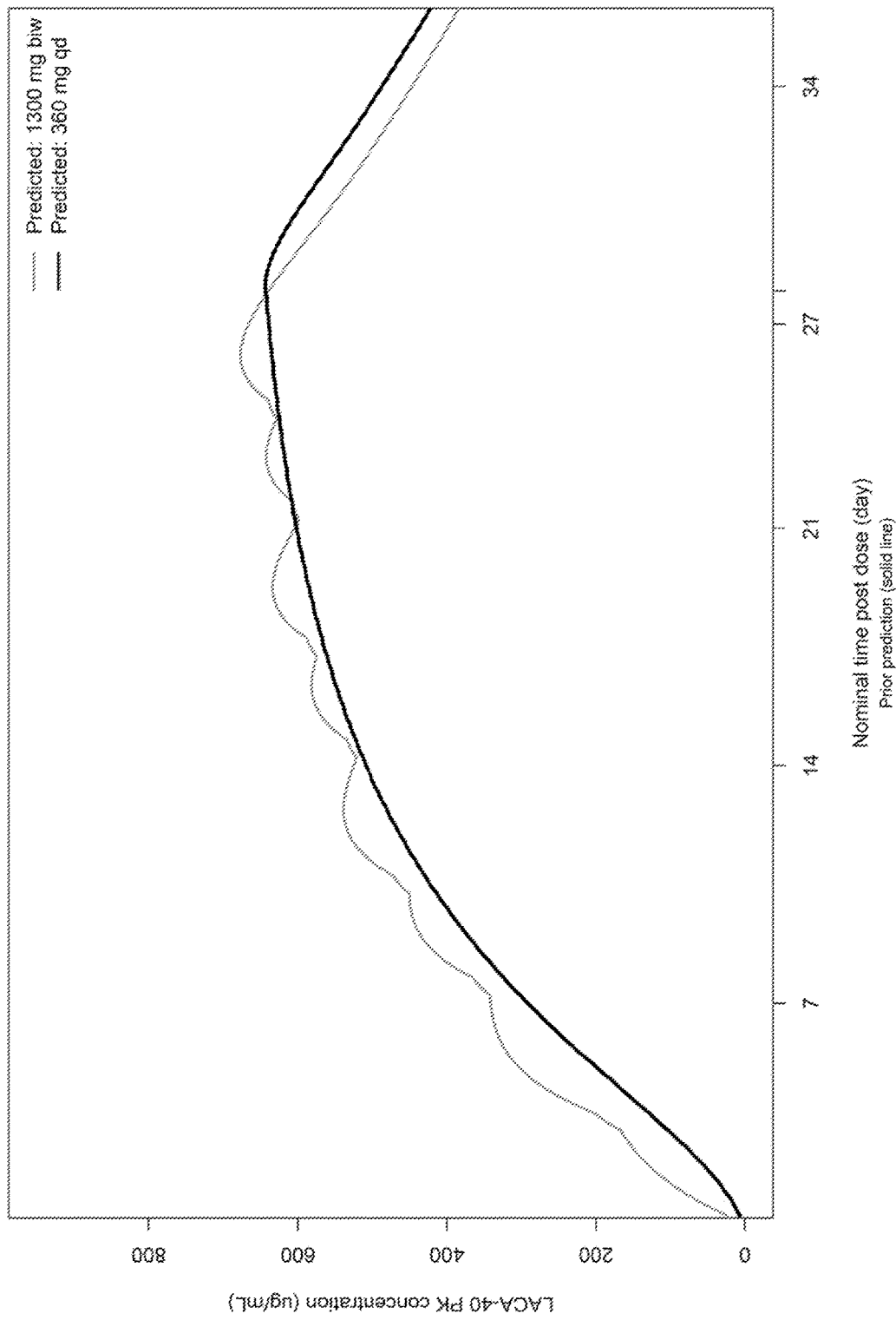
FIG. 23 shows an expanded view of predictions up to day 35 for LACA-40 concentrations depicted in FIG. 22 for daily and twice weekly administration over a 28 day period.
Figure 24:
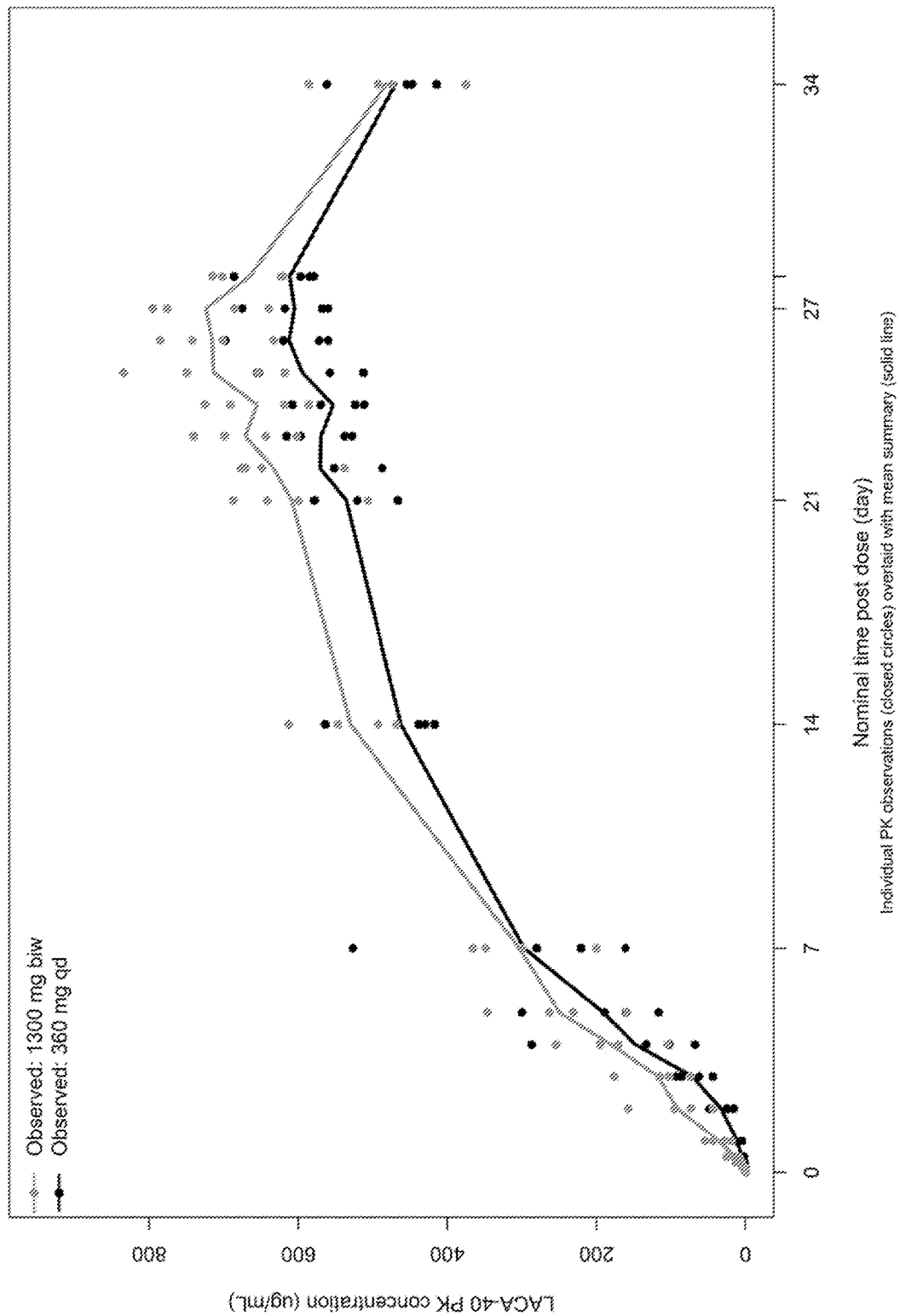
FIG. 24 shows plots of individual and mean summary observed LACA-40 serum concentrations for Cohorts 1 and 2 in the clinical study described in Example 30.
Figure 25:
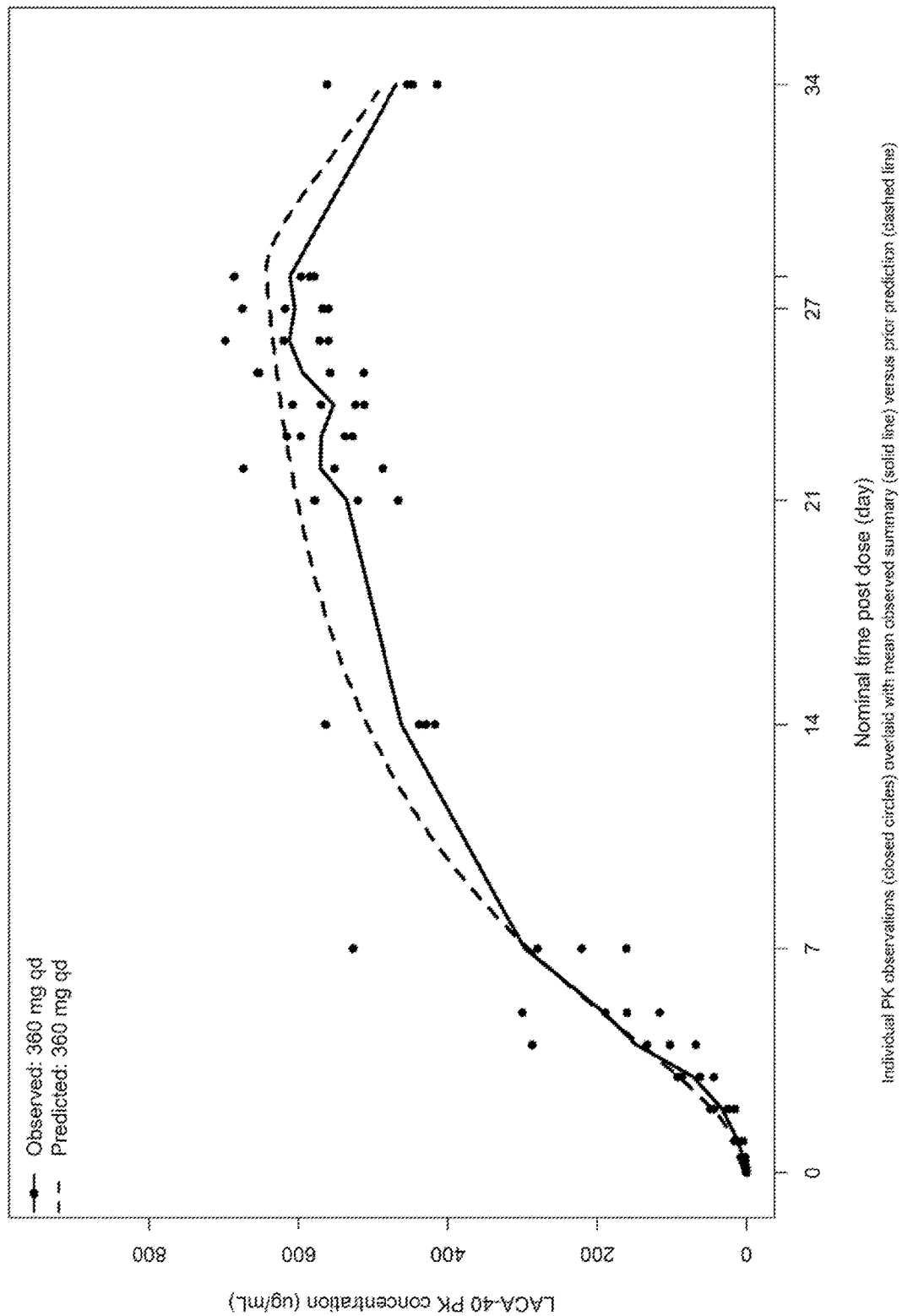
FIG. 25 shows plots of individual and mean summary observed LACA-40 serum concentrations for Cohort 1 in the clinical study described in Example 30 and predicted serum concentrations for this dosing regimen based on the TMDD model.
Figure 26:
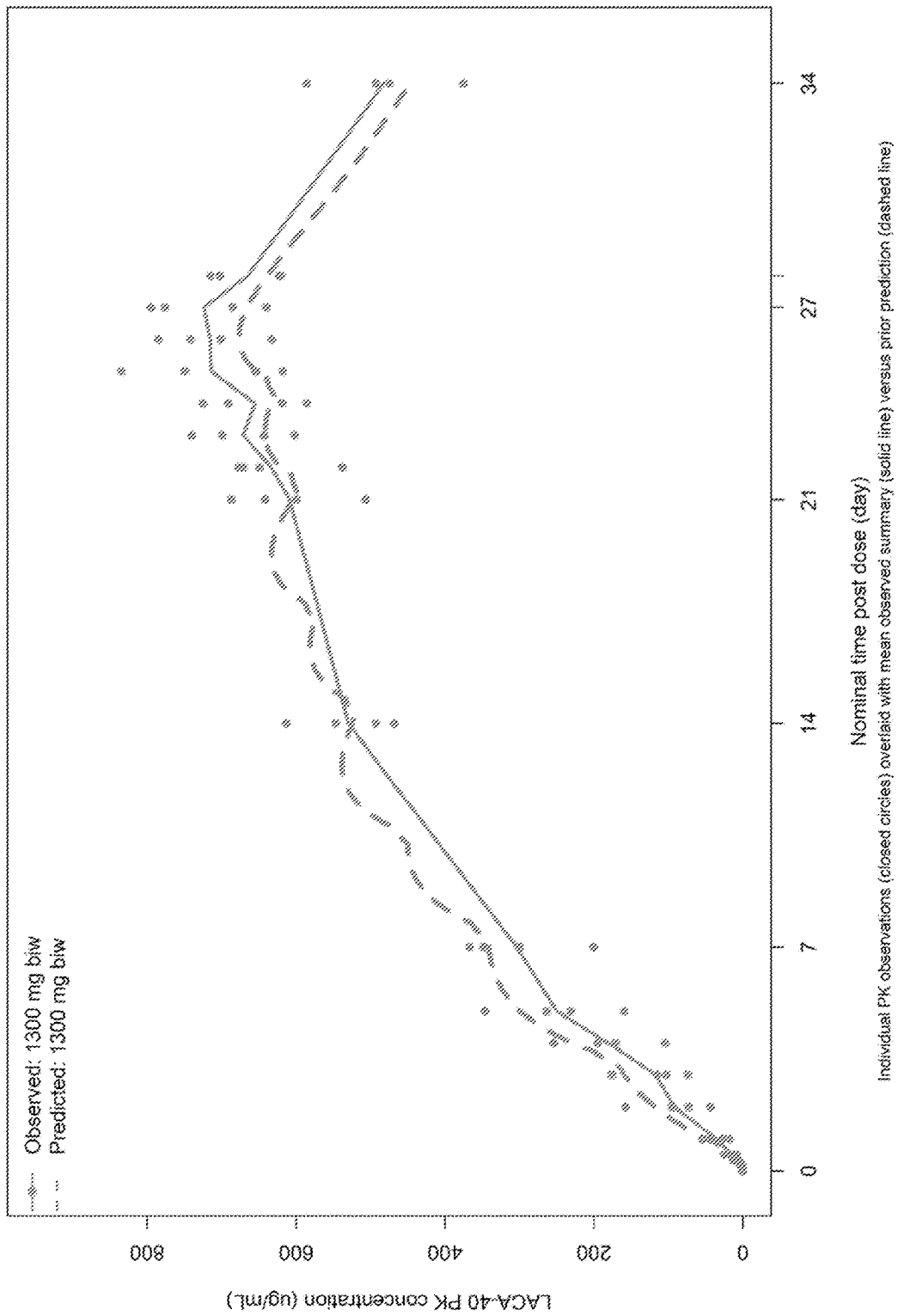
FIG. 26 shows plots of individual and mean summary observed LACA-40 serum concentrations for Cohort 2 in the clinical study described in Example 30 and predicted serum concentrations for this dosing regimen based on the TMDD model.
Figure 27:
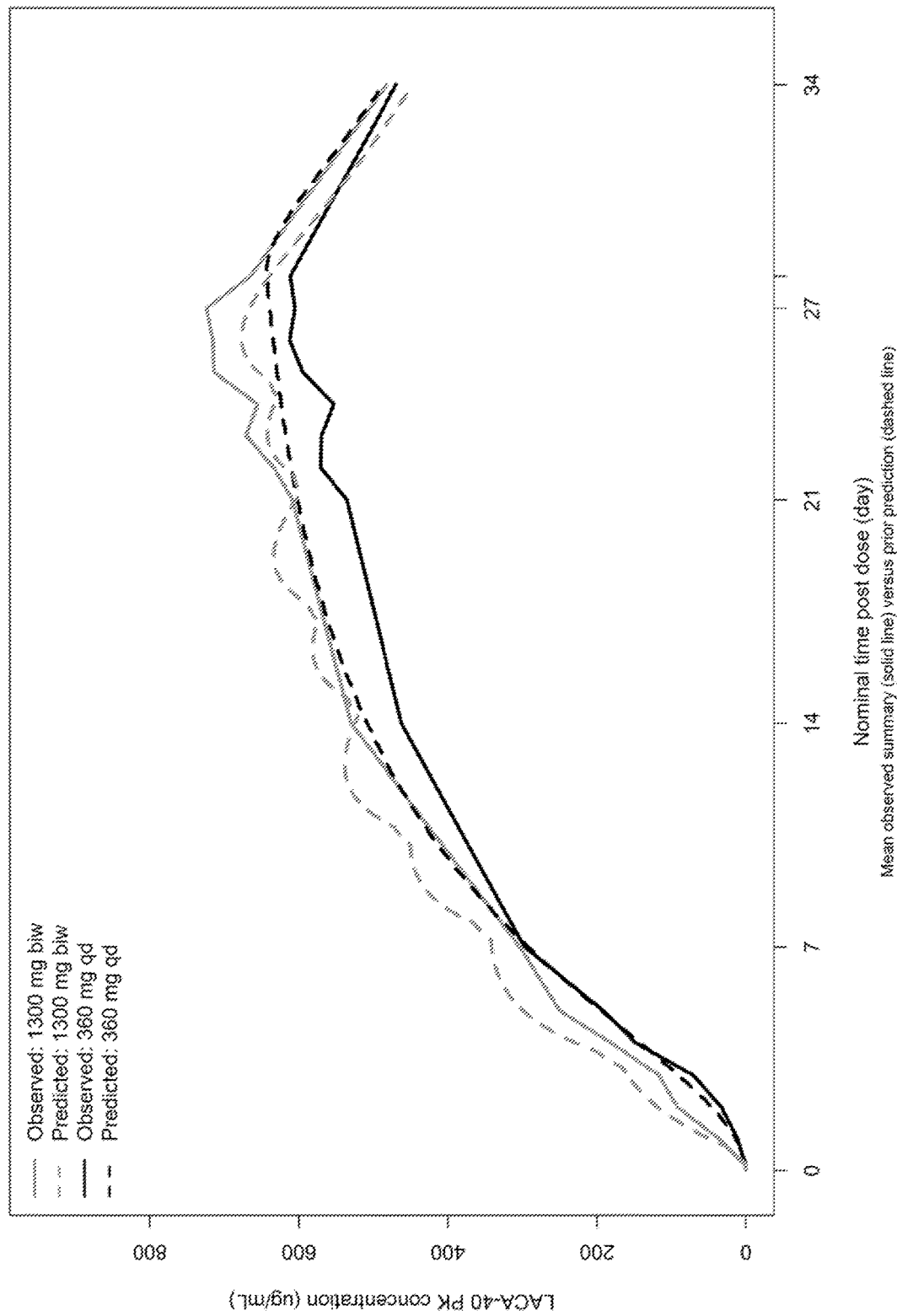
FIG. 27 shows plots of mean summary observed LACA-40 serum concentrations for Cohorts 1 and 2 in the clinical study described in Example 30 and predicted serum concentrations for these dosing regimens based on the TMDD model. The plots further demonstrate that the observed PK data is consistent with predictions from the TMDD model.
Figure 28:
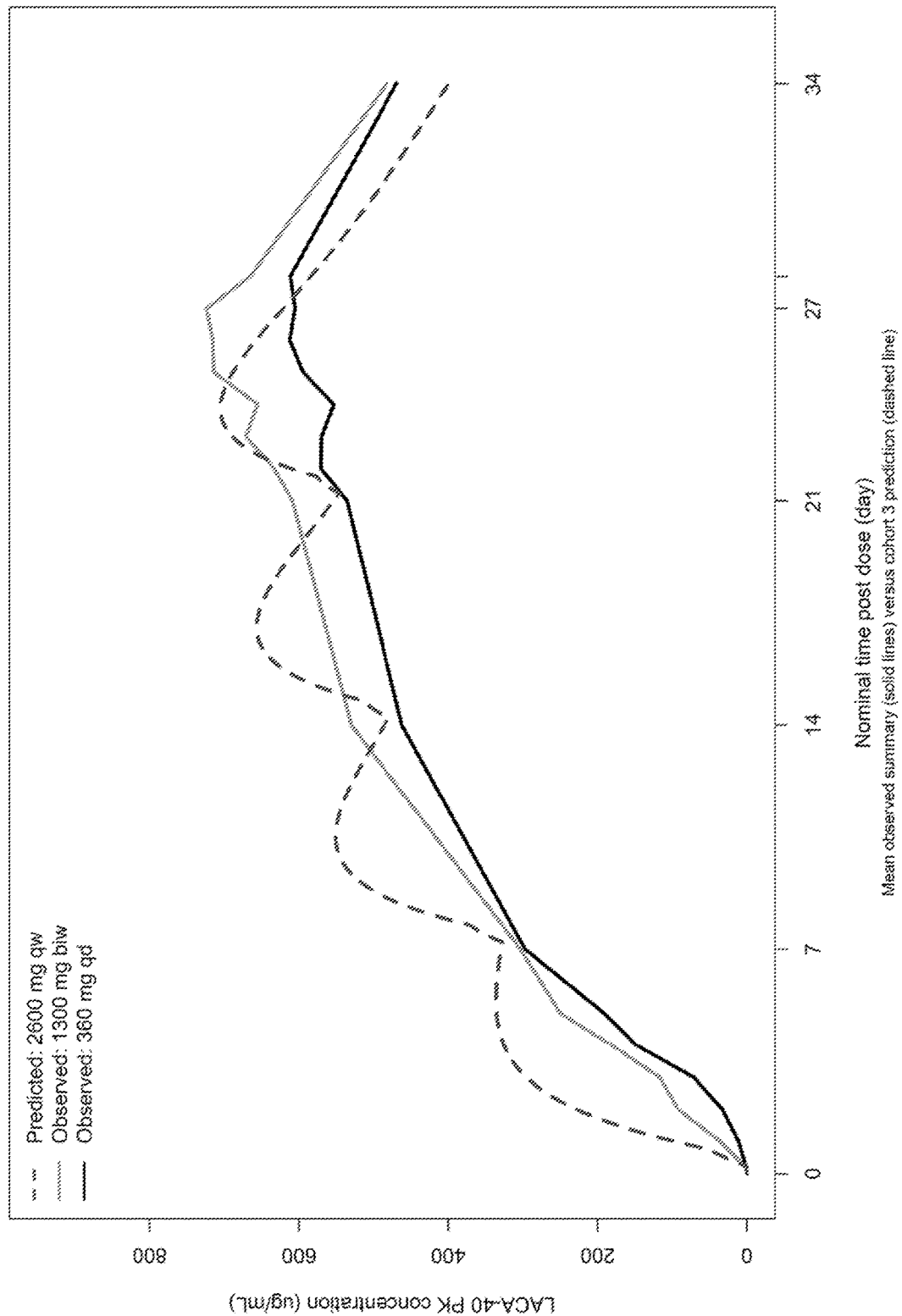
FIG. 28 shows mean summary observed LACA-40 serum concentrations for Cohorts 1 and 2 in the clinical study described in Example 30 and predicted serum concentrations for Cohort 3 based on the TMDD model.

PK data from cohorts 1 and 2 were analyzed and compared with predictions from the TMDD model described above. FIGS. 22 and 23 are plots showing the predictions. Individual and mean summary observed PK data for cohorts 1 and 2 are presented in FIG. 24. The cohort 1 (360 mg/d) observed PK data was consistent with TMDD model predictions (FIG. 25). The observed PK data for cohort 1 at later time-points was slightly lower than predicted by the model but was well within expected variability/tolerance (FIG. 25). Cohort 2 (1300 mg twice weekly) observed PK data was highly consistent with prediction from the TMDD model (FIG. 26). There was some indication at later time-points of slightly higher observed PK, but well within expected variability/tolerance (e.g., given subject and study-to-study variation, number of subjects, etc.). The mean observed data for cohorts 1 and 2 are presented in FIG. 27 without individual data, in order to allow better visualization and further demonstrate that the observed PK data is consistent with predictions. FIG. 28 shows observed summary PK data from cohorts 1 and 2 overlaid with cohort 3 prediction. The following Table 16 shows observed and predicted Cmax and area under the curve (AUC) over 35 days (816 hours) for cohorts 1 and 2 and predicted values for cohort 3. Compared with results from a previous study with 270 mg qd SC dosing (Cmax: 670 ug/mL) this shows that the PK exposure in the 360 mg qd cohort in this study was lower than expected but within the expected variability/tolerance (e.g., given subject and study-to-study variation, number of subjects, etc.). The observed 1300 mg biw Cmax was higher than predicted; driven by one subject with a $C_{max}$ of 835 ug/mL.

TABLE 16

Observed and Predicted PK Parameters

| | Observed | | Predicted | |
|---|---|---|---|---|
| | $C_{max}$ | $AUC_{0-816}$ | $C_{max}$ | $AUC_{0-816}$ |
| Cohort 1: 360 mg qd (28 days) | 629 | 343300 | 691 | 386938 |
| Cohort 2: 1300 mg biw (8 doses) | 749 | 387900 | 714 | 393577 |
| Cohort 3: 2600 mg qw (4 doses) | | | 760 | 373066 |

The data in this Example further confirm that pharmacologically relevant doses of LACA-40 administered via subcutaneous infusion are safe and well tolerated and demonstrate that LACA-40 is compatible with administration via subcutaneous infusion using various pump devices and with less frequent dosing than the daily administration that was used in prior studies involving subcutaneous administration. The data further confirm the ability of the TMDD pharmacokinetic model described above to accurately predict relevant LACA-40 PK parameters for different dosing regimens, e.g., dosing regimens with dosing intervals longer than a day (e.g., twice weekly).

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of administering the composition according to any of the methods disclosed herein, and methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods of treating a subject can include a step of providing a subject in need of such treatment (e.g., a subject who has had, or is at increased risk of having, a disease), a step of diagnosing a subject as having a disease and/or a step of selecting a subject for treatment with a cell-reactive compstatin analog. Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc. Discussion of various diseases, disorders, and conditions under various headings herein is for convenience and is not intended to limit the invention.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention may be explicitly excluded from the claims even if such exclusion is not set forth explicitly herein. For example, any compstatin analog, functional group, linking portion, clearance-reducing moiety, disease, or indication can be explicitly excluded.

We claim:

1. A method of treating a subject in need of treatment of a complement-mediated disorder comprising administering a long-acting compstatin analog (LACA) to the subject subcutaneously according to a dosing schedule in which about 1080 mg of the LACA is administered thrice weekly, every three days, twice weekly, or weekly,
    wherein the LACA comprises a clearance-reducing moiety attached to two compstatin analog moieties, wherein each compstatin analog moiety comprises a cyclic peptide comprising an amino acid sequence as set forth in SEQ ID NO: 28 extended by a lysine residue or a sequence comprising a lysine residue at the N-terminus, C-terminus, or both, wherein the lysine residue is separated from the cyclic portion of the peptide by a spacer comprising 8-amino-3,6-dioxaoctanoic acid (AEEAc);
    wherein the clearance reducing moiety comprises the polymer,
    wherein each end of the polymer is linked to one of the compstatin analog moieties by way of a carbamate, and
    wherein the polymer is PEG having an average molecular weight of about 40 kD.

2. The method of claim 1, wherein the LACA is administered weekly.

3. The method of claim 1, wherein the LACA is administered twice weekly.

4. The method of claim 1, wherein the LACA is administered thrice weekly.

5. The method of claim 1, wherein the LACA is administered every three days.

6. The method of claim 1, wherein the complement-mediated disorder is hemolytic anemia, Paroxysmal Nocturnal Hemoglobinuria (PNH), myasthenia gravis, glomerulonephritis, NMO, polyneuropathy, nephropathy, or vasculitis.

7. The method of claim 1, wherein the complement-mediated disorder is PNH.

8. A unit dose of a LACA, wherein the unit dose is for subcutaneous administration and wherein the amount of the unit dose is about 1080 mg,
    wherein the LACA comprises a clearance-reducing moiety attached to two compstatin analog moieties, wherein each compstatin analog moiety comprises a cyclic peptide comprising an amino acid sequence as set forth in SEQ ID NO: 28 extended by a lysine residue or a sequence comprising a lysine residue at the N-terminus, C-terminus, or both, wherein the lysine residue is separated from the cyclic portion of the peptide by a spacer comprising 8-amino-3,6-dioxaoctanoic acid (AEEAc);
    wherein the clearance reducing moiety comprises the polymer,
    wherein each end of the polymer is linked to one of the compstatin analog moieties by way of a carbamate, and
    wherein the polymer is PEG having an average molecular weight of about 40 kD.

9. The unit dose of claim 8, wherein the unit dose is for subcutaneous administration every three days.

10. The unit dose of claim 8, wherein the unit dose is for twice weekly subcutaneous administration.

11. The unit dose of claim 8, wherein the unit dose is for twice weekly subcutaneous administration.

12. The unit dose of claim 8, wherein the unit dose is for thrice weekly subcutaneous administration.

13. The unit dose of claim 8, further comprising a pharmaceutically acceptable carrier.

14. A syringe or container comprising the unit dose of claim 8.

15. A method of treating a subject in need of treatment for a complement-mediated disorder, the method comprising administering the unit dose of claim 8 to the subject subcutaneously.

16. The method of claim 15, wherein the unit dose is administered using a syringe pump.

17. The method of claim 15, wherein the unit dose is administered using an on-body delivery device.

18. The method of claim 15, wherein the unit dose is administered three times per week.

19. The method of claim 15, wherein the unit dose is administered twice weekly.

20. The method of claim 15, wherein the complement-mediated disorder is hemolytic anemia, Paroxysmal Nocturnal Hemoglobinuria (PNH), myasthenia gravis, glomerulonephritis, NMO, polyneuropathy, nephropathy, or vasculitis.

21. The method of claim 15, wherein the complement-mediated disorder is PNH.

22. The method according to claim 1, wherein the LACA comprises the compound having a structure

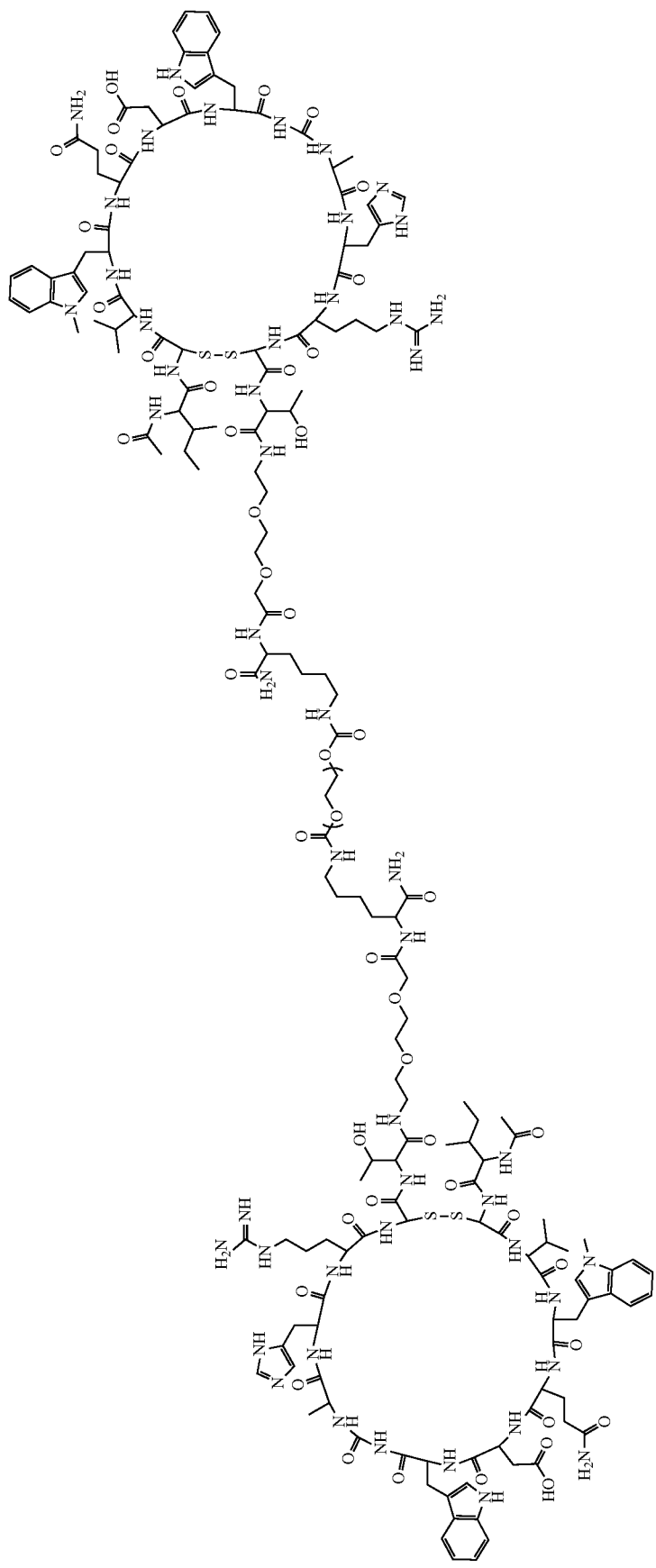

wherein the polymer is PEG having an average molecular weight of about 40 kD.

23. The unit dose according to claim 8, wherein the LACA comprises the compound having a structure

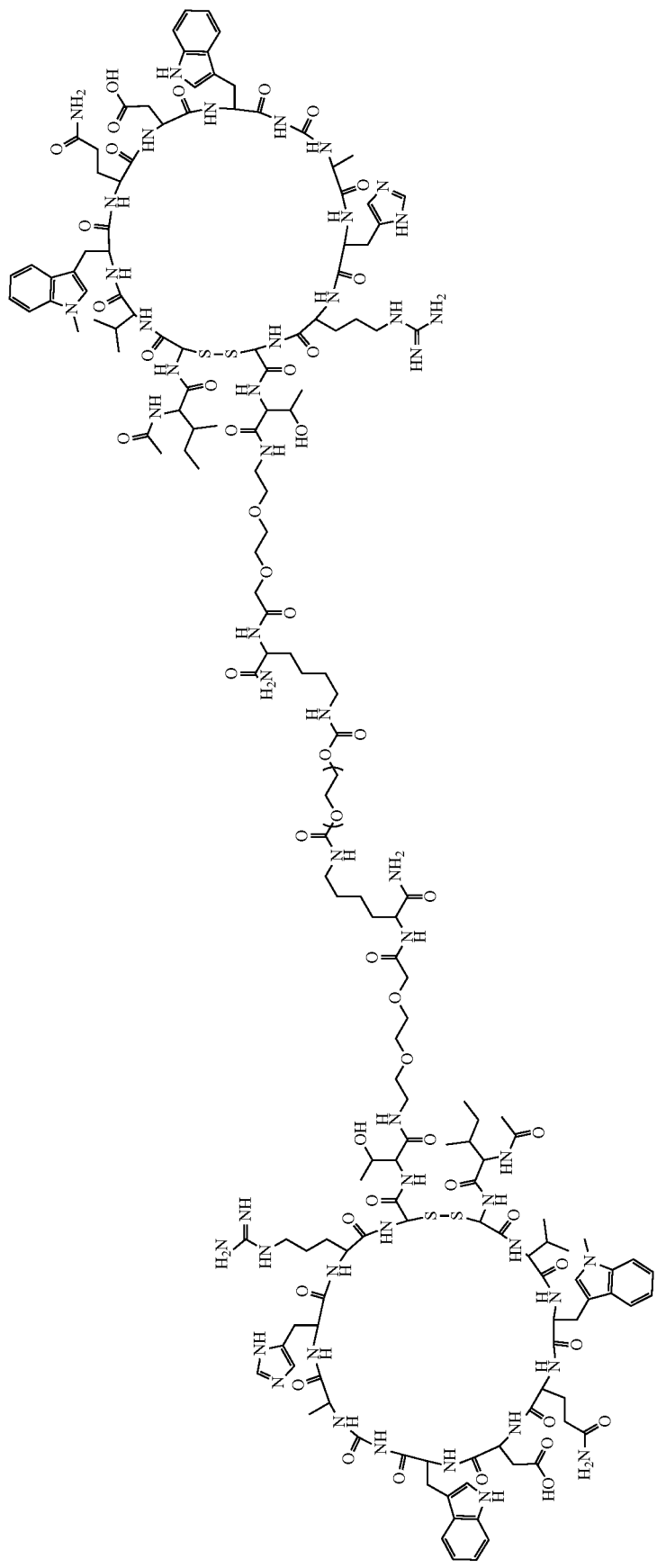

wherein the polymer is PEG having an average molecular weight of about 40 kD.

24. The method according to claim 15, wherein the LACA comprises the compound having a structure

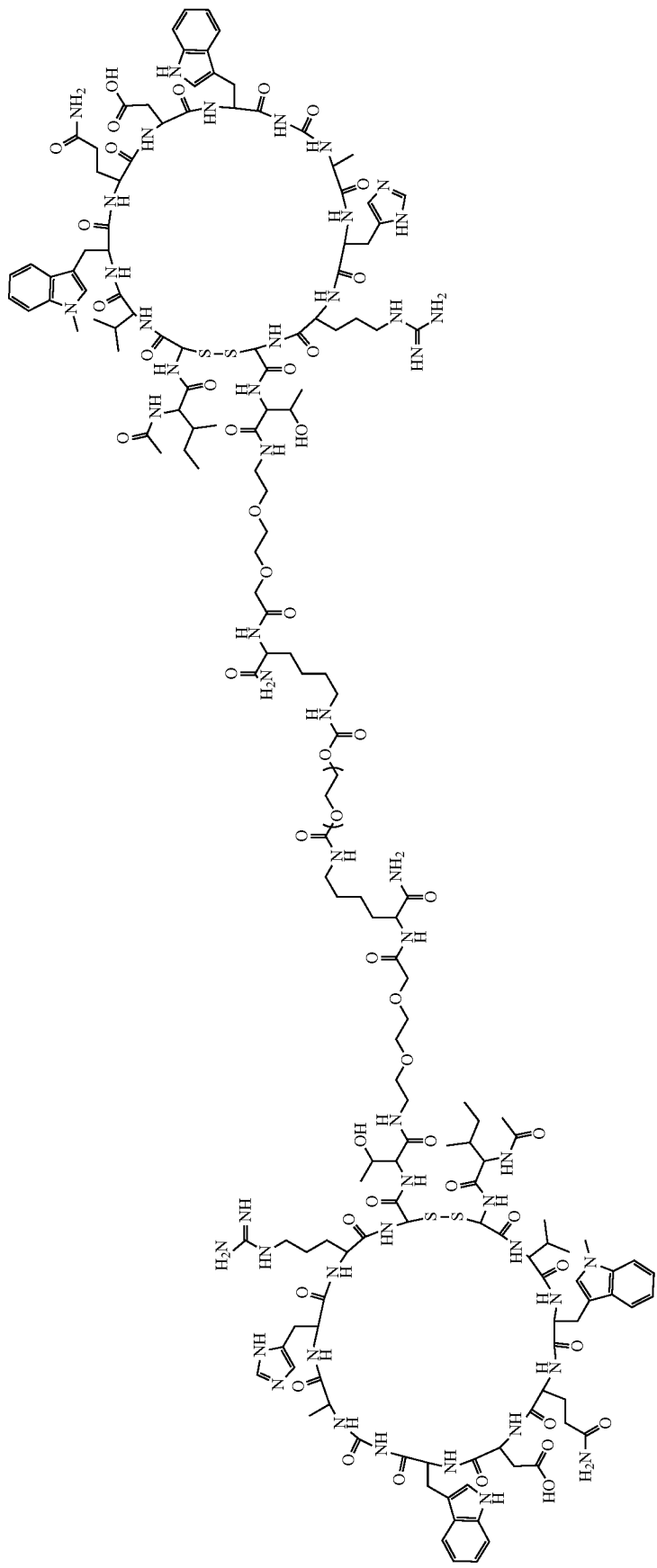

wherein the polymer is PEG having an average molecular weight of about 40 kD.

* * * * *